United States Patent
Nomura et al.

(10) Patent No.: US 10,807,951 B2
(45) Date of Patent: Oct. 20, 2020

(54) MTORC1 MODULATORS

(71) Applicant: THE REGENTS OF THE UNIVERSITY OF CALIFORNIA, Oakland, CA (US)

(72) Inventors: Daniel K. Nomura, Walnut Creek, CA (US); Roberto Zoncu, San Francisco, CA (US); Allison M. Roberts, Kensington, CA (US); Kelvin F. Cho, San Francisco, CA (US); Yik Sham Clive Chung, Berkeley, CA (US); Hijai Shin, Albany, CA (US); Benjamin Croze, Lafayette, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/159,380

(22) Filed: Oct. 12, 2018

(65) Prior Publication Data

US 2019/0112268 A1    Apr. 18, 2019

Related U.S. Application Data

(60) Provisional application No. 62/645,365, filed on Mar. 20, 2018, provisional application No. 62/639,431, filed on Mar. 6, 2018, provisional application No. 62/572,234, filed on Oct. 13, 2017.

(51) Int. Cl.

| | | |
|---|---|---|
| *C07D 209/12* | (2006.01) | |
| *C07D 209/08* | (2006.01) | |
| *A61K 31/00* | (2006.01) | |
| *A61P 25/28* | (2006.01) | |
| *A61P 3/10* | (2006.01) | |
| *A61P 25/16* | (2006.01) | |
| *A61P 35/00* | (2006.01) | |
| *A61K 47/64* | (2017.01) | |

(52) U.S. Cl.
CPC ............ *C07D 209/08* (2013.01); *A61K 31/00* (2013.01); *A61P 3/10* (2018.01); *A61P 25/16* (2018.01); *A61P 25/28* (2018.01); *A61P 35/00* (2018.01); *A61K 47/64* (2017.08)

(58) Field of Classification Search
CPC .................................................... C07D 209/12
See application file for complete search history.

(56) References Cited

U.S. PATENT DOCUMENTS

| | | | |
|---|---|---|---|
| 3,679,701 A * | 7/1972 | Hester, Jr. ............ | C07D 209/08 548/490 |
| 3,818,010 A * | 6/1974 | Richter ................. | C07D 209/08 514/307 |
| 4,526,932 A | 7/1985 | Imazaki et al. | |
| 4,598,156 A | 7/1986 | Martin | |
| 6,872,574 B2 | 3/2005 | Cravatt et al. | |
| 7,348,437 B2 | 3/2008 | Cravatt et al. | |
| 8,940,497 B2 | 1/2015 | Cravatt et al. | |
| 2003/0143648 A1 | 7/2003 | Cravatt et al. | |
| 2016/0252509 A1 | 9/2016 | Cravatt et al. | |
| 2016/0282369 A1 | 9/2016 | Cravatt et al. | |
| 2017/0115303 A1 | 4/2017 | Cravatt et al. | |
| 2018/0372751 A1 | 12/2018 | Cravatt et al. | |
| 2019/0290778 A1 | 9/2019 | Nomura et al. | |

FOREIGN PATENT DOCUMENTS

| | | |
|---|---|---|
| WO | WO-02/14273 A1 | 2/2002 |
| WO | WO-2010/150837 A1 | 12/2010 |
| WO | WO-2013/042006 A1 | 3/2013 |
| WO | WO-2014/040555 A1 | 3/2014 |
| WO | WO-2015/006492 A1 | 1/2015 |
| WO | WO-2015/177279 A1 | 11/2015 |
| WO | WO-2016/065226 A1 | 4/2016 |
| WO | WO-2016/065226 A8 | 4/2016 |
| WO | WO-2016/065236 A1 | 4/2016 |
| WO | WO-2018/136555 A2 | 7/2018 |
| WO | WO-2018/136555 A3 | 7/2018 |
| WO | WO-2019/067733 A1 | 4/2019 |
| WO | WO-2019/191526 A1 | 10/2019 |

OTHER PUBLICATIONS

Yokoe et al. (Iyo Kizai Kenkyusho Hokoku (Tokyo Ika Shika Daigaku) (1972), 6, 18-23 ). Abstract.*
Backus, K.M. et al. (Jun. 23, 2016, e-published Jun. 15, 2016). "Proteome-wide covalent ligand discovery in native biological systems," *Nature* 534(7608):570-574.
Bar-Peled, L. et al. (May 31, 2013). "A Tumor suppressor complex with GAP activity for the Rag GTPases that signal amino acid sufficiency to mTORC1," *Science* 340(6136):1100-1106.
Bateman, L.A. et al. (Jun. 29, 2017). "Chemoproteomics-enabled covalent ligand screen reveals a cysteine hotspot in reticulon 4 that impairs ER morphology and cancer pathogenicity," *Chem Commun (Camb)* 53(53):7234-7237.
Benjamin, D. et al. (Oct. 31, 2011). "Rapamycin passes the torch: a new generation of mTOR inhibitors," *Nat Rev Drug Discov* 10(11):868-880.
Berg, T. et al. (Mar. 19, 2002, e-published Mar. 12, 2002). "Small-molecule antagonists of Myc/Max dimerization inhibit Myc-induced transformation of chicken embryo fibroblasts," *PNAS USA* 99(6):3830-3835.
Berge, S.M. et al. (Jan. 1977). "Pharmaceutical salts," *J Pharm Sci* 66(11):1-19.
Brown, E.J. et al. (Jun. 30, 1994). "A mammalian protein targeted by G1-arresting rapamycin-receptor complex," *Nature* 369(6483)756-758.
Castellano, B.M. et al. (Mar. 24, 2017). "Lysosomal cholesterol activates mTORC1 via an SLC38A9-Niemann-Pick C1 signaling complex," *Science* 355(6331):1306-1311.

(Continued)

*Primary Examiner* — Bruck Kifle
(74) *Attorney, Agent, or Firm* — Mintz, Levin, Cohn, Ferris, Glovsky and Popeo, P.C.; Doris Lee

(57) ABSTRACT

Provided herein, inter alia, are methods and compounds for inhibiting mTORC1 and for treating diseases associated with mTORC1 activity.

10 Claims, 20 Drawing Sheets

Specification includes a Sequence Listing.

(56) References Cited

OTHER PUBLICATIONS

Dearaujo, M. et al. (Oct. 20, 2017, e-published Sep. 21, 2017). "Crystal structure of the human lysosomal mTORC1 scaffold complex and its impact on signaling," *Science* 358(6361):377-381.
Devaraj, N.K. (Aug. 22, 2018, e-published Jul. 23, 2018). "The Future of Bioorthogonal Chemistry," *ACS Cent Sci* 4(8):952-959.
Dimalta, C. et al. (Jun. 16, 2017). "Transcriptional activation of RagD GTPase controls mTORC1 and promotes cancer growth," *Science* 356(6343):1188-1192.
Dixon, S.J. et al. (May 2010). "Drug discovery: engineering drug combinations," *Nat Chem Biol* 6(5):318-319.
Efeyan, A. et al. (Sep. 2012, e-published Jun. 28, 2012). "Amino acids and mTORC1: from lysosomes to disease," *Trends Mol Med* 18(9):524-533.
Feldman, M.E. et al. (Feb. 10, 2009). "Active-site inhibitors of mTOR target rapamycin-resistant outputs of mTORC1 and mTORC2," *PLoS Biol* 7(2):e38.
Feldman, M.E. et al. (2010). "New inhibitors of the PI3K-Akt-mTOR pathway: insights into mTOR signaling from a new generation of Tor Kinase Domain Inhibitors (TORKinibs)," *Curr Top Microbiol Immunol* 347(241-262).
Grabiner, B.C. et al. (May 2014, e-published Mar. 14, 2014). "A diverse array of cancer-associated MTOR mutations are hyperactivating and can predict rapamycin sensitivity," *Cancer Discov* 4(5):554-563.
Guertin, D.A. et al. (Jul. 2007). "Defining the role of mTOR in cancer," *Cancer Cell* 12(1):9-22.
Gul, S. et al. (Dec. 2014, e-published Nov. 6, 2014). "Protein-protein interaction modulator drug discovery: past efforts and future opportunities using a rich source of low- and high-throughput screening assays," *Expert Opin Drug Discov* 9(12):1393-1404.
Hamdi, A. et al. (Feb. 2012, e-published Nov. 28, 2011). "Yeast two-hybrid methods and their applications in drug discovery," *Trends Pharmacol Sci* 33(2):109-118.
Heeres, J.T. et al. (Aug. 2011, e-published Dec. 7, 2010). "High-throughput screening for modulators of protein-protein interactions: use of photonic crystal biosensors and complementary technologies," *Chem Soc Rev* 40(8):4398-4410.
Heitman, J. et al. (Aug. 23, 1991). "Targets for cell cycle arrest by the immunosuppressant rapamycin in yeast," *Science* 253(5022):905-909.
Hoelder, S. et al. (Apr. 2012, e-published Mar. 3, 2012). "Discovery of small molecule cancer drugs: successes, challenges and opportunities," *Mol Oncol* 6(2):155-176.
Hurley, J.H. et al. (Jun. 20, 2017, e-published Mar. 15, 2017). "Mechanisms of Autophagy Initiation," *Annu Rev Biochem* 86:225-244.
International Search Report dated Feb. 8, 2019, for PCT/US2018/55692, filed Oct. 12, 2018, 7 pages.
Johnson, S.C. et al. (Jan. 17, 2013). "mTOR is a key modulator of ageing and age-related disease," *Nature* 493(7432):338-345.
Kang, S.A. et al. (Jul. 26, 2013). "mTORC1 phosphorylation sites encode their sensitivity to starvation and rapamycin," *Science* 341(6144):1236566.
Kim, E. et al. (Aug. 2008, e-published Jul. 6, 2008). "Regulation of TORC1 by Rag GTPases in nutrient response," *Nat Cell Biol* 10(8):935-945.
Komatsu, M. et al. (Jun. 15, 2006, e-published Apr. 19, 2006). "Loss of autophagy in the central nervous system causes neurodegeneration in mice," *Nature* 441(7095):880-884.
Lamming, D.W. et al. (Mar. 30, 2012). "Rapamycin-induced insulin resistance is mediated by mTORC2 loss and uncoupled from longevity," *Science* 335(6076):1638-1643.
Laplante, M. et al. (Dec. 1, 2009). "An emerging role of mTOR in lipid biosynthesis," *Curr Biol* 19(22):R1046-1052.
Laplante, M. et al. (2012). "DEPTOR cell-autonomously promotes adipogenesis, and its expression is associated with obesity," *Cell Metab* 16(2):202-212.
Laplante, M. et al. (Apr. 13, 2012). "mTOR signaling in growth control and disease," *Cell* 149(2):274-293.
Okosun, J. et al. (Feb. 2016, e-published Dec. 21, 2015). "Recurrent mTORC1-activating RRAGC mutations in follicular lymphoma," *Nat Genet* 8(2):183-188.
Patterson, D.M. et al. (Mar. 21, 2014, e-published Jan. 30, 2014). "Finding the right (bioorthogonal) chemistry," *ACS Chem Biol* 9(3):592-605.
Perera, R.M. et al. (Oct. 6, 2016, e-published Aug. 3, 2016). "The Lysosome as a Regulatory Hub," *Annu Rev Cell Dev Biol* 32:223-253.
Peterson, T.R. et al. (Aug. 5, 2011). "mTOR complex 1 regulates lipin 1 localization to control the SREBP pathway," *Cell* 146(3):408-420.
Ravikumar, B. et al. (Jun. 2004, e-published May 16, 2004). "Inhibition of mTOR induces autophagy and reduces toxicity of polyglutamine expansions in fly and mouse models of Huntington disease," *Nat Genet* 36(6):585-595.
Roberts, A.M. et al. (Feb. 2017, e-published Aug. 26, 2016). "Activity-based protein profiling for mapping and pharmacologically interrogating proteome-wide ligandable hotspots," Curr Opin Biotechnol 43:25-33.
Roberts, A.M. et al. (Apr. 21, 2017 e-published Feb. 15, 2017). "Chemoproteomic Screening of Covalent Ligands Reveals UBA5 as a Novel Pancreatic Cancer Target," *ACS Chem Biol* 12(4):899-904.
Rodrik-Outmezguine V.S. et al. (Jun. 9, 2016, e-published May 18, 2016). "Overcoming mTOR resistance mutations with a new-generation mTOR inhibitor," *Nature* 534(7606):272-276.
Sabatini, D.M. et al. (Jul. 15, 1994). "RAFT1: a mammalian protein that binds to FKBP12 in a rapamycin-dependent fashion and is homologous to yeast TORs," *Cell* 78(10):35-43.
Sahu, N. et al. (Nov. 8, 2016, e-published Sep. 8, 2016). "Proline Starvation Induces Unresolved ER Stress and Hinders mTORC1-Dependent Tumorigenesis," *Cell Metab* 24(5):753-761.
Sancak, Y. et al. (Jun. 2008, e-published May 22, 2008). "The Rag GTPases bind raptor and mediate amino acid signaling to mTORC1," *Science* 320(5882):1496-1501.
Sancak, Y. et al. (Apr. 16, 2010, e-published Apr. 8, 2010). "Ragulator-Rag complex targets mTORC1 to the lysosomal surface and is necessary for its activation by amino acids," *Cell* 141(2):290-303.
Sarbassov, D.D. et al. (Apr. 21, 2006, e-published Apr. 6, 2006). "Prolonged rapamycin treatment inhibits mTORC2 assembly and Akt/PKB," *Mol Cell* 22(2):159-168.
Saxton, R.A. et al. (Apr. 6, 2017). "mTOR Signaling in Growth, Metabolism, and Disease," *Cell* 168:960-976.
Settembre, C. et al. (Jan. 1, 2008, e-published Oct. 3, 2007). "A block of autophagy in lysosomal storage disorders," *Hum Mol Genet* 17(1):119-129.
Tang, X.J. et al. (Mar. 27, 2015, e-published Feb. 18, 2015). "Efficient Cu-catalyzed atom transfer radical addition reactions of fluoroalkylsulfonyl chlorides with electron-deficient alkenes induced by visible light," *Angew Chem Int Ed Engl* 54(14):4246-4249.
Thoreen, C.C. et al. (Mar. 20, 2009, e-published Jan. 15, 2009). "An ATP-competitive mammalian target of rapamycin inhibitor reveals rapamycin-resistant functions of mTORC1," *J Biol Chem* 284(12):8023-8032.
Wander, S.A. et al. (Apr. 2011, e-published Apr. 1, 2011). "Next-generation mTOR inhibitors in clinical oncology: how pathway complexity informs therapeutic strategy," *J Clin Invest* 121(4):1231-1241.
Written Opinion dated Feb. 8, 2019, for PCT/US2018/55692, filed Oct. 12, 2018, 5 pages.
Zoncu, R. et al. (Nov. 4, 2011). "mTORC1 senses lysosomal amino acids through an inside-out mechanism that requires the vacuolar H(+)-ATPase," *Science* 334(6056):678-683.
Zoncu, R. et al. (Jan. 2011, e-published Dec. 15, 2010). "mTOR: from growth signal integration to cancer, diabetes and ageing," *Nat Rev Mol Cell Biol* 12(10):21-35.

* cited by examiner

YP-1-44

CC-2-11          CC-1-44

MTORC1 MODULATORS

CROSS-REFERENCES TO RELATED APPLICATIONS

This application claims the benefit of U.S. Provisional Application No. 62/572,234, filed Oct. 13, 2017; U.S. Provisional Application No. 62/639,431, filed Mar. 6, 2018; and U.S. Provisional Application No. 62/645,365, filed Mar. 20, 2018, which are incorporated herein by reference in their entirety and for all purposes.

STATEMENT AS TO RIGHTS TO INVENTIONS MADE UNDER FEDERALLY SPONSORED RESEARCH AND DEVELOPMENT

This invention was made with government support under grants CA172668 and CA195761 awarded by the National Institutes of Health. The government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 052103-511001US_Sequence_Listing_ST25.txt, created Oct. 12, 2018, 24,539 bytes, machine format IBM-PC, MS Windows operating system, is hereby incorporated by reference.

BACKGROUND

Overwhelming evidence indicates that aberrant activity of a multiprotein complex known as mechanistic Target of Rapamycin Complex 1 (mTORC1) underlies the growth advantage that many cancer types display over the surrounding healthy tissue. Current therapeutic investigations in cancer and other mTORC1-related diseases suffer from limitations and significant side effects, including high toxicity and metabolic imbalance. Thus, renewed efforts must be directed toward identifying new ways to block mTORC1 selectively and safely. Disclosed herein, inter alia, are solutions to these and other problems in the art.

BRIEF SUMMARY

Described herein, inter alia, is the development of a mTORC1 Complex-Selective Inhibitor using Chemoproteomics-Enabled Covalent Ligand Screening to Reveal Disruptors of Protein-Protein Interactions.

In an aspect is provided a compound having the formula:

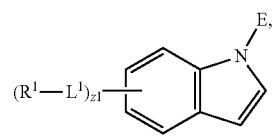

(I)

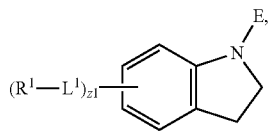

(VI)

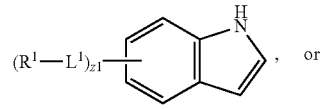

(XI)

, or

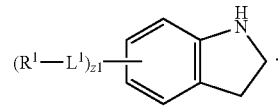

(XXI)

$L^1$ is independently a bond, —S(O)$_2$—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

$R^1$ is independently halogen, —CX$^1_3$, —CHX$^1_2$, —CH$_2$X$^1$, —OCX$^1_3$, —OCH$_2$X$^1$, —OCHX$^1_2$, —CN, —SO$_{n1}$R$^{1D}$, —SO$_{v1}$NR$^{1A}$R$^{1B}$, —NHC(O)NR$^{1A}$R$^{1B}$, —N(O)$_{m1}$, —NR$^{1A}$R$^{1B}$, —C(O)R$^{1C}$, —C(O)—OR$^{1C}$, —C(O)NR$^{1A}$R$^{1B}$, —OR$^{1D}$, —NR$^{1A}$SO$_2$R$^{1D}$, —NR$^{1A}$C(O)R$^{1C}$, —NR$^{1A}$C(O)OR$^{1C}$, —NR$^{1A}$OR$^{1C}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent -L$^1$-R$^1$ substituents may optionally be joined to form a substituted or unsubstituted cycloalkyl, substituted or unsubstituted heterocycloalkyl, substituted or unsubstituted aryl, or substituted or unsubstituted heteroaryl.

E is an electrophilic moiety.

Each $R^{1A}$, $R^{1B}$, $R^{1C}$, and $R^{1D}$ is independently hydrogen, —CX$_3$, —CHX$_2$, —CH$_2$X, —CN, —OH, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl.

Each X and $X^1$ is independently —F, —Cl, —Br, or —I. n1 is independently an integer from 0 to 4. m1 and v1 are independently 1 or 2. z1 is independently an integer from 0 to 8.

In another aspect is provided a pharmaceutical composition including a compound described herein and a pharmaceutically acceptable excipient.

In an aspect is provided a method for treating cancer, the method including administering to a subject in need thereof a therapeutically effective amount of a compound described herein.

In an aspect is provided a method for treating a neurodegenerative disease, the method including administering to a subject in need thereof a therapeutically effective amount of a compound described herein.

In an aspect is provided a method for treating a metabolic disease, the method including administering to a subject in need thereof a therapeutically effective amount of a compound described herein.

In an aspect is provided a method of reducing the level of activity of mTORC1, the method including contacting the mTORC1 with a compound described herein.

In an aspect is provided a method of reducing the level of activity of a LAMTOR protein, the method including contacting the LAMTOR protein with a compound described herein.

In an aspect is provided a LAMTOR5 protein covalently bonded to a compound described herein.

In an aspect is provided a LAMTOR5 protein covalently bonded to a fragment of a compound described herein.

BRIEF DESCRIPTION OF THE DRAWINGS

(FIG. 1A) Assay design. Protein A, fused to a red fluorescent protein (small oval with "A" in the figure) is attached to the surface of agarose beads via affinity interactions (i.e. a FLAG tag on the protein bound by an anti-FLAG antibody on the bead surface). The protein A-coated bead is then incubated with protein B, which binds to A and is fused to a green fluorescent protein (circle with "B" in the figure). Thus, the A-B interaction is reconstituted on the surface of the bead. In the presence of a drug that disrupts the A-B interaction, protein B detaches and disperses in the surrounding buffer solution, whereas protein A remains attached to the bead. (FIG. 1B) Calibration. Beads coated with an antibody against the FLAG tag (unlabeled) were incubated with FLAG-tagged and GFP-tagged RagB (a member of the Rag GTPase complex). Due to antibody-tag interaction, FLAG-GFP-RagB is captured to the surface of the bead. The beads were subsequently incubated with increasing concentrations of free FLAGx3 peptide, which competes for the binding of the antibody to FLAG-GFP-RagB. Thus, FLAG-GFP-RagB becomes progressively more dispersed from the bead surface. Intensity plots at the bottom show how the fluorescence signal decreases on the bead surface and increases in the buffer solution with increasing FLAGx3 peptide concentration. (FIG. 1C) High throughput implementation. Beads harboring A-B complexes are seeded in microplates containing a library of compounds. After an incubation time, microplates are imaged with an automated microscope by tiling together multiple visual fields per well. Individual visual fields are magnified and analyzed as shown in (FIG. 1B).

(FIG. 2A) Screening of a sub-library of cysteine-reactive compounds. Rag-Lamtor interaction is scored as GFP/RFP ratio. Compounds that disrupt the interaction are shown by dark bars, negative controls are in grey. The order of the columns is as follows, beginning from the leftmost column: DMSO, FGFP, compound A1, compound A2, compound A3, compound A4, compound A5, compound A6, compound A7, compound A8, DMSO, FGFP, compound A9, compound A10, compound A11, compound A12, compound A13, compound A14, compound A15, compound A16, DMSO, FGFP, compound A17, compound A18, compound A19, compound A20, compound A21, compound A22, compound A23, compound A24, DMSO, FGFP, compound A25, YP 1-44, compound A26, compound A27, compound A28, compound A29, compound A30, DMSO, FGFP, compound A31, compound A32, compound A33, compound A34, compound A35, compound A36, compound A37, DMSO, FGFP, and compound A38. The top hit, YP1-44, is indicated with an arrow. (FIG. 2B) Structure of the top hit, YP1-44. (FIG. 2C) Schematic of the Lamtor-Rag GTPase-mTORC1 complexes at the lysosomal surface. (FIG. 2D) Representative images from the screen in (FIG. 2A), showing dispersion of the GFP-RagB signal from RFP-Ragulator coated beads by YP1-44 but not 2 control compounds. In the leftmost column, free GFP in place of GFP-RagB provides a control for non-specific binding. (FIG. 2E) Quantification of the GFP/RFP ratios from the images in (FIG. 2D). (FIG. 2F) Dose-response curve for YP1-44 in visual IP experiments.

(FIG. 3A) mTORC1 recruitment assay. (top) in amino acid-starved HeLa cells, mTORC1 is dispersed in the cytoplasm and is not present on LAMP2-positive lysosomes both in control- and YP1-44-treated cells. (bottom) amino acid treatment causes mTORC1 localization to lysosomes in DMSO-treated cells, whereas mTORC1 recruitment fails in cells treated with 50 μM YP1-44 (FIG. 3B) YP1-44 causes dispersion of RagC from LAMP2-positive lysosomes. HeLa cells were incubated with 50 μM YP1-44 for 1 h and subjected to immunofluorescence staining for endogenous RagC and LAMP2. (FIG. 3C) YP1-44 causes dispersion of RagA from LAMP2-positive lysosomes. HeLa cells were incubated with 50 μM YP1-44 for 1 h and subjected to immunofluorescence staining for endogenous RagA and LAMP2. (FIG. 3D) YP1-44 suppresses mTORC1 activation by amino acids. Cells were subjected to the indicated treatments, followed by lysis and immunoblotting for the indicated phospho-proteins and total proteins, all of which are mTORC1 substrates.

(FIG. 4A) Workflow of using competitive isoTOP-ABPP platforms to map the druggable hotspot targeted by a lead covalent ligand using reconstituted proteins from the TORC1 complex. (FIG. 4B) IsoTOP-ABPP analysis of YP 1-44. We pretreated human purified mTORC1, Rag GTPase and Lamtor complexes (5 micrograms each) with DMSO vehicle or YP 1-44 (50 μM) prior to labeling with IA-alkyne (100 μM). Isotopically light (for control) or heavy (for YP 1-44-treated) biotin-azide tags bearing a TEV protease recognition peptide were appended to probe-labeled proteins by CuAAC and control and treated proteomes were combined in a 1:1 ratio. Probe-labeled proteins were avidin-enriched, tryptically digested, and probe-modified peptides were eluted by TEV protease and analyzed by LC-LC/MS/MS. Probe-modified peptide sequences were derived from ms2 spectra and light to heavy ratios for analyzed peptides were quantified using corresponding ms1 signal intensities. We identified two probe-modified peptides in LAMTOR5. LAMTOR5 C23 showed an isotopic ratio >3. Shown on the right panel is the ms1 signal intensity for the probe-modified isotopically light and heavy peptide that includes C23. (FIG. 4B) shows average isotopic ratios from n=4.

(FIG. 5A) Gel-based ABPP analysis of Hela cell proteome IA-alkyne cysteine-reactivity revealed YP 1-44 non-selectivity at 100 μM and above. (FIG. 5B) Structures of representative analogs of YP 1-44. (FIG. 5C) gel-based ABPP analysis of lead compound CC 1-44 against IA-alkyne labeling of LAMTOR5 pure protein. (FIG. 5D) gel-based ABPP analysis of Hela cell proteome IA-alkyne cysteine-reactivity showing CC 1-44 selectivity at up to 1 mM. (FIG. 5E) mTORC1 signaling in Hela cells treated with YP 1-44 and analogs. (FIG. 5F) p-AKT signaling in Hela cells treated with YP 1-44 and analogs.

(FIG. 6A) Visual IP experiment monitoring binding of GFP-RagB to RFP-tagged, bead-bound Lamtor complex. Whereas YP 1-44 causes RagB dissociation from Lamtor, CC 1-44 does not. (FIG. 6B) Immunofluorescence for endogenous RagA and LAMP2 in HEK- 293A cells treated with DMSO, YP 1-44 or CC 1-44 for 2 h. Whereas YP 1-44 causes RagA dissociation from Lamtor, CC 1-44 treatment results in increased RagA clustering on lysosomes. (FIG. 6C) Immunofluorescence for endogenous mTOR and LAMP2 in HEK-293A cells treated with DMSO or CC 1-44 for 2 h. CC 1-44 treatment induces dissociation of mTOR from lysosomes. (FIG. 6D) Immunoblotting for autophagic markers LC3b and p62 from HEK-293A cells treated with DMSO (lane 1) or CC 1-44 (lane 3) for 2 h. Increase in the LC3b band and disappearance of the p62 band in the CC 1-44 sample indicates activation of autophagy. Samples treated with the vacuolar H+ATPase inhibitor Bafilomycin A (lanes 2 and 4) provide an indication of total autophagic flux, which is also increased by CC 1-44 treatment.

(FIG. 8A) Structures of CC 2-11 and CC 1-44. CC 2-11 bears an alkyne group on a separate ring from the cysteine-reactive warhead. The presence of the alkyne group enables us to directly label the modified target protein (e.g. Lamtor5) with biotin or rhodamine groups, either in gels or in complex proteomes. (FIG. 8B) In preliminary experiments with purified Lamtor-Rag complexes, CC 2-11 enables rhodamine labeling of a 28 KDa band corresponding to Lamtor5, and the signal competes by incubation with excess unlabeled CC 1-44. Thus, CC 2-11 allows precise mapping of the target cysteines as well as accurate identification of the off-targets.

(FIG. 9A) initial YP 1-44 analogs and their relative potency against IA-alkyne labeling of pure human LAMTOR5 protein visualized by gel-based ABPP (a). Protein expression levels were also ascertained by silver staining (b). (FIG. 9B) Gel-based ABPP IA-alkyne cysteine-reactivity analysis of YP 1-44 analogs against Rag-Ragulator complex proteins (a). Protein expression levels were also ascertained by silver staining (b). (FIG. 9C) Hela whole cell proteome gel-based ABPP analysis of IA-alkyne cysteine-reactivity with YP 1-44 analogs (a). Protein expression levels were also ascertained by silver staining (b).

DETAILED DESCRIPTION

I. Definitions

Figure 1A:
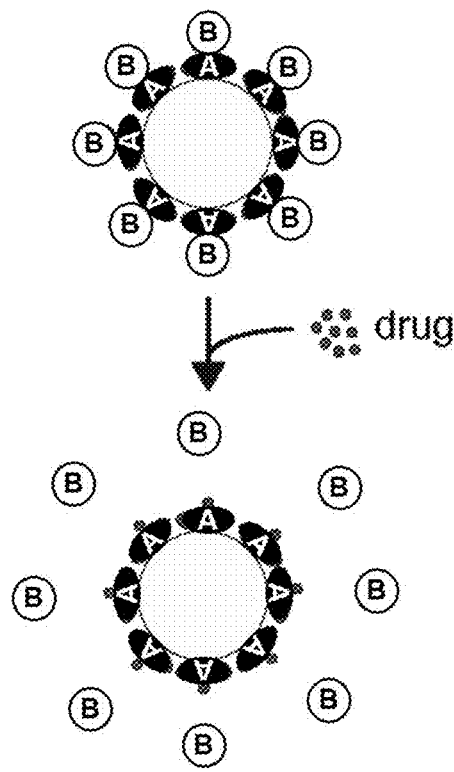
FIGS. 1A-1C. Visual-IP technology to identify inhibitors of protein-protein interaction.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., C$_1$-C$_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—S—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$C(O)_2$R'— represents both —$C(O)_2$R'— and —R'$C(O)_2$—. As described above, heteroalkyl groups, as used herein, include those groups that are attached to the remainder of the molecule through a heteroatom, such as —C(O)R', —C(O)NR', —NR'R", —OR', —SR', and/or —$SO_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "⌇" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

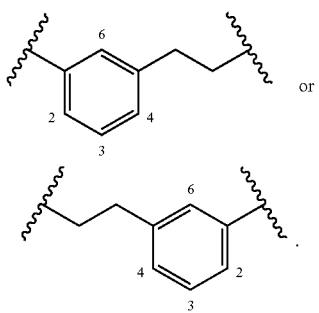

An alkylarylene moiety may be substituted (e.g. with a substituent group) on the alkylene moiety or the arylene linker (e.g. at carbons 2, 3, 4, or 6) with halogen, oxo, —N₃, —CF₃, —CCl₃, —CBr₃, —CI₃, —CN, —CHO, —OH, —NH₂, —COOH, —CONH₂, —NO₂, —SH, —SO₂CH₃—SO₃H, —OSO₃H, —SO₂NH₂, —NHNH₂, —ONH₂, —NHC(O)NHNH₂, substituted or unsubstituted C₁-C₅ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO₂R', —CONR'R", —OC(O)NR'R", —NR"C(O)R', —NR'—C(O)NR"R'", —NR"C(O)₂R', —NR—C(NR'R"R'")=NR"", —NR—C(NR'R")=NR'", —S(O)R', —S(O)₂R', —S(O)₂NR'R", —NRSO₂R', —NR'NR"R'", —ONR'R", —NR'C(O)NR"NR'"R"", —CN, —NO₂, —NR'SO₂R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF₃ and —CH₂CF₃) and acyl (e.g., —C(O)CH₃, —C(O)CF₃, —C(O)CH₂OCH₃, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO₂R', —CONR'R", —OC(O)NR'R", —NR"C(O)R', —NR'—C(O)NR"R'", —NR"C(O)₂R', —NR—C(NR'R"R'")=NR"", —NR—C(NR'R")=NR'", —S(O)R', —S(O)₂R', —S(O)₂NR'R", —NRSO₂R', —NR'NR"R'", —ONR'R", —NR'C(O)NR"NR'"R"", —CN, —NO₂, —R', —N₃, —CH(Ph)₂, fluoro(C₁-C₄)alkoxy, and fluoro(C₁-C₄)alkyl, —NR'SO₂R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl, heteroalkyl, cycloalkyl, heterocycloalkyl, aryl, heteroaryl, substituted with at least one substituent selected from:

(i) oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl, heteroalkyl, cycloalkyl, heterocycloalkyl, aryl, heteroaryl, substituted with at least one substituent selected from:

(a) oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCH Cl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl, heteroalkyl, cycloalkyl, heterocycloalkyl, aryl, heteroaryl, substituted with at least one substituent selected from: oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted phenyl, and each substituted or unsubstituted heteroaryl is a substituted or unsubstituted 5 to 6 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^{3}$H), iodine-125 ($^{125}$I), or carbon-14 ($^{14}$C). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

As used herein, the term "bioconjugate reactive moiety" and "bioconjugate reactive group" refers to a moiety or group capable of forming a bioconjugate linker (e.g., covalent linker) as a result of the association between atoms or molecules of bioconjugate reactive groups. The association can be direct or indirect. For example, a conjugate between a first bioconjugate reactive group (e.g., —NH2, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g. a first linker of second linker), or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, bioconjugates or bioconjugate linkers are formed using bioconjugate chemistry (i.e. the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g. a sulfhydryl). In embodiments, the first bioconjugate reactive group (e.g., haloacetyl moiety) is covalently attached to the second bioconjugate reactive group (e.g. a sulfhydryl). In embodiments, the first bioconjugate reactive group (e.g., pyridyl moiety) is covalently attached to the second bioconjugate reactive group (e.g. a sulfhydryl). In embodiments, the first bioconjugate reactive group (e.g., —N-hydroxysuccinimide moiety) is covalently attached to the second bioconjugate reactive group (e.g. an amine). In embodiments, the first bioconjugate reactive group (e.g., maleimide moiety) is covalently attached to the second bioconjugate reactive group (e.g. a sulfhydryl). In embodiments, the first bioconjugate reactive group (e.g., -sulfo-N-hydroxysuccinimide moiety) is covalently attached to the second bioconjugate reactive group (e.g. an amine). Additional bioconjugate reactive moieties are described in detail in Patterson et al (ACS Chem. Biol. 2014, 9, 592-605) and Deveraj ACS Cent. Sci. 2018, 4, 952-959, both of which are incorporated herein by reference in their entirety for all purposes.

Useful bioconjugate reactive moieties used for bioconjugate chemistries herein include, for example: (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc. (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups which are capable of participating in Diels-Alder reactions such as, for example, maleimido or maleimide groups; (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, to form sulfonamides; (g) thiol groups, which can be converted to disulfides, reacted with acyl halides, or bonded to metals such as gold, or react with maleimides; (h) amine or sulfhydryl groups (e.g., present in cysteine), which can be, for example, acylated, alkylated or oxidized; (i) alkenes, which can undergo, for example, cycloadditions, acylation, Michael addition, etc; (j) epoxides, which can react with, for example, amines and hydroxyl compounds; (k) phosphoramidites and other standard functional groups useful in nucleic acid synthesis; (l) metal silicon oxide bonding; (m) metal bonding to reactive phosphorus groups (e.g. phosphines) to form, for example, phosphate diester bonds; (n) azides coupled to alkynes using copper catalyzed cycloaddition click chemistry; (o) biotin conjugate can react with avidin or strepavidin to form a avidin-biotin complex or streptavidin-biotin complex. The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present disclosure contain both basic and acidic functionalities that allow the compounds to be converted into either base or acid addition salts.

Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present disclosure provides compounds, which are in a prodrug form. Prodrugs of the compounds described herein are those compounds that readily undergo chemical changes under physiological conditions to provide the compounds of the present disclosure. Prodrugs of the compounds described herein may be converted in vivo after administration. Additionally, prodrugs can be converted to the compounds of the present disclosure by chemical or biochemical methods in an ex vivo environment, such as, for example, when contacted with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A polypeptide, or a cell is "recombinant" when it is artificial or engineered, or derived from or contains an artificial or engineered protein or nucleic acid (e.g. nonnatural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

The term "co-administer" is meant that a composition described herein is administered at the same time, just prior to, or just after the administration of one or more additional therapies. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered transdermally, by a topical route, or formulated as applicator sticks, solutions, suspensions, emulsions, gels, creams, ointments, pastes, jellies, paints, powders, and aerosols.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms (e.g., ocular pain, seeing halos around lights, red eye, very high intraocular pressure), fully or partially remove the disease's underlying cause, shorten a disease's duration, or do a combination of these things.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. In embodiments, the treating or treatment is no prophylactic treatment.

The term "prevent" refers to a decrease in the occurrence of disease symptoms in a patient. As indicated above, the prevention may be complete (no detectable symptoms) or partial, such that fewer symptoms are observed than would likely occur absent treatment.

An "effective amount" is an amount sufficient for a compound to accomplish a stated purpose relative to the absence of the compound (e.g. achieve the effect for which it is administered, treat a disease, reduce enzyme activity, increase enzyme activity, reduce signaling pathway, reduce one or more symptoms of a disease or condition (e.g. reduce signaling pathway stimulated by mTORC1, reduce the signaling pathway activity of mTORC1). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity (e.g. signaling pathway) of a protein in the absence of a compound as described herein (including embodiments, examples, figures, or Tables).

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a protein or enzyme (e.g. mTORC1). In some embodiments contacting includes allowing a compound described herein to interact with a protein or enzyme that is involved in a signaling pathway.

As defined herein, the term "inhibition", "inhibit", "inhibiting" and the like in reference to a protein-inhibitor interaction means negatively affecting (e.g. decreasing) the activity or function of the protein (e.g. decreasing the signaling pathway stimulated by mTORC1), relative to the activity or function of the protein in the absence of the inhibitor. In some embodiments inhibition refers to reduction of a disease or symptoms of disease. In some embodiments, inhibition refers to a reduction in the activity of a signal transduction pathway or signaling pathway (e.g. reduction of a pathway involving mTORC1). Thus, inhibition includes, at least in part, partially or totally blocking stimulation, decreasing, preventing, or delaying activation, or inactivating, desensitizing, or down-regulating the signaling pathway or enzymatic activity or the amount of a protein (e.g. mTORC1).

The term "modulator" refers to a composition that increases or decreases the level of a target molecule or the function of a target molecule or the physical state of the target of the molecule (e.g. a target may be mTORC1) relative to the absence of the composition.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

"Disease" or "condition" refer to a state of being or health status of a patient or subject capable of being treated with the compounds or methods provided herein. In some embodiments, the disease is a disease related to (e.g. caused by) a mTORC1. In some embodiments, the disease is a disease related to (e.g. caused by) a mTORC1 signaling pathway activity. Examples of diseases, disorders, or conditions include, but are not limited to cancer. Examples of diseases, disorders, or conditions include, but are not limited to MYH-associated polyposis. In some instances, "disease" or "condition" refers to cancer. In some instances, "disease" or "condition" refers to MYH-associated polyposis. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma.

As used herein, the term "cancer" refers to all types of cancer, neoplasm or malignant tumors found in mammals (e.g. humans), including leukemias, lymphomas, carcinomas and sarcomas. Exemplary cancers that may be treated with a compound or method provided herein include brain cancer, glioma, glioblastoma, neuroblastoma, prostate cancer, colorectal cancer, pancreatic cancer, Medulloblastoma, melanoma, cervical cancer, gastric cancer, ovarian cancer, lung cancer, cancer of the head, Hodgkin's Disease, and Non-Hodgkin's Lymphomas. Exemplary cancers that may be treated with a compound or method provided herein include cancer of the thyroid, endocrine system, brain, breast, cervix, colon, head & neck, liver, kidney, lung, ovary, pancreas, rectum, stomach, and uterus. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

As used herein, the term "lymphoma" refers to a group of cancers affecting hematopoietic and lymphoid tissues. It begins in lymphocytes, the blood cells that are found primarily in lymph nodes, spleen, thymus, and bone marrow. Two main types of lymphoma are non-Hodgkin lymphoma and Hodgkin's disease. Hodgkin's disease represents approximately 15% of all diagnosed lymphomas. This is a cancer associated with Reed-Stemberg malignant B lymphocytes. Non-Hodgkin's lymphomas (NHL) can be classified based on the rate at which cancer grows and the type of cells involved. There are aggressive (high grade) and indolent (low grade) types of NHL. Based on the type of cells involved, there are B-cell and T-cell NHLs. Exemplary B-cell lymphomas that may be treated with a compound or method provided herein include, but are not limited to, small lymphocytic lymphoma, Mantle cell lymphoma, follicular lymphoma, marginal zone lymphoma, extranodal (MALT) lymphoma, nodal (monocytoid B-cell) lymphoma, splenic lymphoma, diffuse large cell B-lymphoma, Burkitt's lymphoma, lymphoblastic lymphoma, immunoblastic large cell lymphoma, or precursor B-lymphoblastic lymphoma. Exemplary T-cell lymphomas that may be treated with a compound or method provided herein include, but are not limited to, cunateous T-cell lymphoma, peripheral T-cell lymphoma, anaplastic large cell lymphoma, mycosis fungoides, and precursor T-lymphoblastic lymphoma.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

As used herein, the term "autoimmune disease" refers to a disease or condition in which a subject's immune system has an aberrant immune response against a substance that does not normally elicit an immune response in a healthy subject. Examples of autoimmune diseases that may be treated with a compound, pharmaceutical composition, or method described herein include Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal or neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, or Wegener's granulomatosis (i.e., Granulomatosis with Polyangiitis (GPA).

As used herein, the term "neurodegenerative disease" or "neurodegenerative disorder" refers to a disease or condition in which the function of a subject's nervous system becomes impaired. Examples of neurodegenerative diseases that may be treated with a compound, pharmaceutical composition, or method described herein include Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, chronic fatigue syndrome, Cockayne syndrome, Corticobasal degeneration, Creutzfeldt-Jakob disease, frontotemporal dementia, Gerstmann-Straiussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, myalgic encephalomyelitis, Narcolepsy, Neuroborreliosis, Parkinson's disease, Pelizaeus-Merzbacher Disease, Pick's disease, Primary lateral sclerosis, Prion diseases, Refsum's disease, Sandhoffs disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, progressive supranuclear palsy, or Tabes dorsalis.

As used herein, the term "metabolic disease" or "metabolic disorder" refers to a disease or condition in which a subject's metabolism or metabolic system (e.g., function of storing or utilizing energy) becomes impaired. Examples of metabolic diseases that may be treated with a compound, pharmaceutical composition, or method described herein include diabetes (e.g., type I or type II), obesity, metabolic syndrome, or a mitochondrial disease (e.g., dysfunction of mitochondria or aberrant mitochondrial function).

"mTORC1 associated cancer" (also referred to herein as "mTORC1 related cancer") refers to a cancer caused by aberrant mTORC1 activity or signaling. Other cancers that are associated with aberrant activity of mTORC1 are well known in the art and determining such cancers are within the skill of a person of skill in the art.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present disclosure, should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

The term "administer (or administering) a mTORC1 inhibitor" means administering a compound that inhibits the activity or level (e.g. amount) or level of a signaling pathway of mTORC1 to a subject. Administration may include, without being limited by mechanism, allowing sufficient time for the mTORC1 inhibitor to reduce the activity of one or more mTORC1 component proteins or for the mTORC1 inhibitor to reduce one or more symptoms of a disease (e.g. cancer, wherein the mTORC1 inhibitor may arrest the cell cycle, slow the cell cycle, reduce DNA replication, reduce cell replication, reduce cell growth, reduce metastasis, or cause cell death).

The compounds described herein can be used in combination with one another, with other active agents known to be useful in treating a disease associated with cells expressing mTORC1, or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

As a non-limiting example, the compounds described herein can be co-administered with conventional chemotherapeutic agents including alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, methotrexate, leucovorin, capecitabine, cytarabine, floxuridine, fludarabine, gemcitabine, pemetrexed, raltitrexed, etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin, etc.), and the like.

The compounds described herein can also be co-administered with conventional hormonal therapeutic agents including, but not limited to, steroids (e.g., dexamethasone), finasteride, aromatase inhibitors, tamoxifen, and gonadotropin-releasing hormone agonists (GnRH) such as goserelin.

Additionally, the compounds described herein can be co-administered with conventional immunotherapeutic agents including, but not limited to, immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), and radioimmunotherapy (e.g., anti-CD20 monoclonal antibody conjugated to $^{111}$In, $^{90}$Y, or $^{131}$I, etc.).

In a further embodiment, the compounds described herein can be co-administered with conventional radiotherapeutic agents including, but not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

In therapeutic use for the treatment of cancer, compound utilized in the pharmaceutical compositions of the present invention may be administered at the initial dosage of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound or drug being employed. For example, dosages can be empirically determined considering the type and stage of cancer diagnosed in a particular patient. The dose administered to a patient, in the context of the present invention, should be sufficient to affect a beneficial therapeutic response in the patient over time. The size of the dose will also be determined by the existence, nature, and extent of any adverse side-effects that accompany the administration of a compound in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

The compounds described herein can be used in combination with one another, with other active agents known to be useful in treating cancer or with adjunctive agents that may not be effective alone, but may contribute to the efficacy of the active agent.

The term "associated" or "associated with" in the context of a substance or substance activity or function associated with a disease (e.g. a protein associated disease, a cancer associated with aberrant mTORC1 activity, mTORC1 associated cancer, mutant mTORC1 associated cancer, activated mTORC1 associated cancer) means that the disease (e.g. cancer) is caused by (in whole or in part), or a symptom of the disease is caused by (in whole or inpart) the substance or substance activity or function. For example, a cancer associated with aberrant mTORC1 activity or function may be a cancer that results (entirely or partially) from aberrant mTORC1 activity or function (e.g. enzyme activity, protein-protein interaction, signaling pathway) or a cancer wherein a particular symptom of the disease is caused (entirely or partially) by aberrant mTORC1 activity or function. As used herein, what is described as being associated with a disease, if a causative agent, could be a target for treatment of the disease. For example, a cancer associated with aberrant mTORC1 activity or function or an mTORC1 associated cancer, may be treated with a mTORC1 modulator or mTORC1 inhibitor, in the instance where increased mTORC1 activity or function (e.g. signaling pathway activity) causes the cancer.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

"Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer.

"Anti-cancer agent" and "anticancer agent" are used in accordance with their plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflomithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras famesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1;

sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflomithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta *Medica*), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, lso-eleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

The term "electrophilic" as used herein refers to a chemical group that is capable of accepting electron density. An "electrophilic substituent", "electrophilic chemical moiety", or "electrophic moiety" refers to an electron-poor chemical group, substitutent, or moiety (monovalent chemical group), which may react with an electron-donating group, such as a nucleophile, by accepting an electron pair or electron density to form a bond. In some embodiments, the electrophilic substituent of the compound is capable of reacting with a cysteine residue. In some embodiments, the electrophilic substituent is capable of forming a covalent bond with a cysteine residue (e.g., mTORC1 cysteine residue, LAMTOR cysteine residue, LAMTOR5 cysteine residue) and may be referred to as a "covalent cysteine modifier moiety" or "covalent cysteine modifier substituent". The covalent bond formed between the electrophilic substituent and the sulfhydryl group of the cysteine may be a reversible or irreversible bond.

"Nucleophilic" as used herein refers to a chemical group that is capable of donating electron density.

The term "LAMTOR5" or "late endosomal/lysosomal adaptor, MAPK and MTOR Activator 5" or "HBXIP" or "HBx-interacting protein" refers to one or more of the family of human LAMTOR proteins. The term "LAMTOR5" refers to the nucleotide sequences or proteins of human LAMTOR5 (SEQ ID NO: 1). The term "LAMTOR5" includes both the wild-type form of the nucleotide sequences or proteins as well as any mutants thereof. In some embodiments, "LAMTOR5" is wild-type LAMTOR5. In some embodiments, "LAMTOR5" is one or more mutant forms. The term "LAMTOR5" XYZ refers to a nucleotide sequence or protein of a mutant LAMTOR5 wherein the Y numbered amino acid of LAMTOR5 that has an X amino acid in the wildtype instead has a Z amino acid in the mutant. In some embodiments LAMTOR5 refers to Entrez 10542, UniProt O43504, RefSeq mRNA NM_006402, or RefSeq protein NP_006393. In some embodiments LAMTOR5 refers to NM_006402.2. In some embodiments LAMTOR5 refers to NP 006393.2. In some embodiments LAMTOR5 refers to gi:5454170. In some embodiments LAMTOR5 refers to UniProt A0A0C4DGV4, RefSeq mRNA NM_006402, or RefSeq protein NP_006393. In embodiments, LAMTOR5 has the sequence:

```
                                         (SEQ ID NO: 1)
MEPGAGHLDGHRAGSPSLRQALCDGSAVMFSSKERGRCTVINFVPLEAPL

RSTPRSRQVTEACGGEGRAVPLGSEPEWSVGGMEATLEQHLEDTMKNPSI

VGVLCTDSQGLNLGCRGTLSDEHAGVISVLAQQAAKLTSDPTDIPVVCLE

SDNGNIMIQKHDGITVAVHKMAS
```

The term "Ragulator complex" as used herein refers to a complex having guanine nucleotide exchange factor activity for Rag GTPases (e.g., RagA, RagB, RagC, RagD, RagA/B dimer, RagC/D dimer, RagA/B-RagC/D heterodimeric GTPase). In embodiments, the Ragulator complex includes LAMTOR1 (c11ORF59), LAMTOR2 (ROBLD3), LAMTOR3 (MAP2KIIP1, MAPKSP1), LAMTOR4 (C7orf59), and/or LAMTOR5 (HBXIP) proteins.

The term "mTOR" refers to the protein "mechanistic target of rapamycin (serine/threonine kinase)" or "mammalian target of rapamycin". The term "mTOR" may refer to the nucleotide sequence or protein sequence of human mTOR (e.g., Entrez 2475, Uniprot P42345, RefSeq NM_004958, or RefSeq NP_004949) (SEQ ID NO:2). The term "mTOR" includes both the wild-type form of the nucleotide sequences or proteins as well as any mutants thereof. In some embodiments, "mTOR" is wild-type mTOR. In some embodiments, "mTOR" is one or more mutant forms. The term "mTOR" XYZ refers to a nucleotide sequence or protein of a mutant mTOR wherein the Y numbered amino acid of mTOR that normally has an X amino acid in the wildtype, instead has a Z amino acid in the mutant. In embodiments, an mTOR is the human mTOR. In embodiments, the mTOR has the nucleotide sequence corresponding to reference number GI:206725550. In embodiments, the mTOR has the nucleotide sequence corresponding to RefSeq NM_004958.3. In embodiments, the mTOR has the protein sequence corresponding to reference number GI:4826730. In embodiments, the mTOR has the protein sequence corresponding to RefSeq NP_004949.1. In embodiments, the mTOR has the following amino acid sequence:

(SEQ ID NO: 2)

MLGTGPAAATTAATTSSNVSVLQQFASGLKSRNEETRAKAAKELQHYVTMELREMSQEES
TRFYDQLNHHIFELVSSSDANERKGGILAIASLIGVEGGNATRIGRFANYLRNLLPSNDP
VVMEMASKAIGRLAMAGDTFTAEYVEFEVKRALEWLGADRNEGRRHAAVLVLRELAISVP
TFFFQQVQPFFDNIFVAVWDPKQAIREGAVAALRACLILTTQREPKEMQKPQWYRHTFEE
AEKGFDETLAKEKGMNRDDRIHGALLILNELVRISSMEGERLREEMEEITQQQLVHDKYC
KDLMGFGTKPRHITPFTSFQAVQPQQSNALVGLLGYSSHQGLMGFGTSPSPAKSTLVESR
CCRDLMEEKFDQVCQWVLKCRNSKNSLIQMTILNLLPRLAAFRPSAFTDTQYLQDTMNHV
LSCVKKEKERTAAFQALGLLSVAVRSEFKVYLPRVLDIIRAALPPKDFAHKRQKAMQVDA
TVFTCISMLARAMGPGIQQDIKELLEPMLAVGLSPALTAVLYDLSRQIPQLKKDIQDGLL
KMLSLVLMHKPLRHPGMPKGLAHQLASPGLTTLPEASDVGSITLALRTLGSFEFEGHSLT
QFVRHCADHFLNSEHKEIRMEAARTCSRLLTPSIHLISGHAHVVSQTAVQVVADVLSKLL
VVGITDPDPDIRYCVLASLDERFDAHLAQAENLQALFVALNDQVFEIRELAICTVGRLSS
MNPAFVMPFLRKMLIQILTELEHSGIGRIKEQSARMLGHLVSNAPRLIRPYMEPILKALI
LKLKDPDPDPNPGVINNVLATIGELAQVSGLEMRKWVDELFIIIMDMLQDSSLLAKRQVA
LWTLGQLVASTGYVVEPYRKYPTLLEVLLNFLKTEQNQGTRREAIRVLGLLGALDPYKHK
VNIGMIDQSRDASAVSLSESKSSQDSSDYSTSEMLVNMGNLPLDEFYPAVSMVALMRIFR
DQSLSHHHTMVVQAITFIFKSLGLKCVQFLPQVMPTFLNVIRVCDGAIREFLFQQLGMLV
SFVKSHIRPYMDEIVTLMREFWVMNTSIQSTIILLIEQIVVALGGEFKLYLPQLIPHMLR
VFMHDNSPGRIVSIKLLAAIQLFGANLDDYLHLLLPPIVKLFDAPEAPLPSRKAALETVD
RLTESLDFTDYASRIIHPIVRTLDQSPELRSTAMDTLSSLVFQLGKKYQIFIPMVNKVLV
RHRINHQRYDVLICRIVKGYTLADEEEDPLIYQHRMLRSGQGDALASGPVETGPMKKLHV
STINLQKAWGAARRVSKDDWLEWLRRLSLELLKDSSSPSLRSCWALAQAYNPMARDLFNA
AFVSCWSELNEDQQDELIRSIELALTSQDIAEVTQTLLNLAEFMEHSDKGPLPLRDDNGI
VLLGERAAKCRAYAKALHYKELEFQKGPTPAILESLISINNKLQQPEAAAGVLEYAMKHF
GELEIQATWYEKLHEWEDALVAYDKKMDTNKDDPELMLGRMRCLEALGEWGQLHQQCCEK
WTLVNDETQAKMARMAAAAAWGLGQWDSMEEYTCMIPRDTHDGAFYRAVLALHQDLFSLA
QQCIDKARDLLDAELTAMAGESYSRAYGAMVSCHMLSELEEVIQYKLVPERREIIRQIWW
ERLQGCQRIVEDWQKILMVRSLVVSPHEDMRTWLKYASLCGKSGRLALAHKTLVLLLGVD
PSRQLDHPLPTVHPQVTYAYMKNMWKSARKIDAFQHMQHFVQTMQQQAQHAIATEDQQHK
QELHKLMARCFLKLGEWQLNLQGINESTIPKVLQYYSAATEHDRSWYKAWHAWAVMNFEA
VLHYKHQNQARDEKKKLRHASGANITNATTAATTAATATTTASTEGSNSESEAESTENSP
TPSPLQKKVTEDLSKTLLMYTVPAVQGFFRSISLSRGNNLQDTLRVLTLWFDYGHWPDVN
EALVEGVKAIQIDTWLQVIPQLIARIDTPRPLVGRLIHQLLTDIGRYHPQALIYPLTVAS
KSTTTARHNAANKILKNMCEHSNTLVQQAMMVSEELIRVAILWHEMWHEGLEEASRLYFG
ERNVKGMFEVLEPLHAMMERGPQTLKETSFNQAYGRDLMEAQEWCRKYMKSGNVKDLTQA
WDLYYHVFRRISKQLPQLTSLELQYVSPKLLMCRDLELAVPGTYDPNQPIIRIQSIAPSL
QVITSKQRPRKLTLMGSNGHEFVFLLKGHEDLRQDERVMQLFGLVNTLLANDPTSLRKNL
SIQRYAVIPLSTNSGLIGWVPHCDTLHALIRDYREKKKILLNIEHRIMLRMAPDYDHLTL
MQKVEVFEHAVNNTAGDDLAKLLWLKSPSSEVWFDRRTNYTRSLAVMSMVGYILGLGDRH
PSNLMLDRLSGKILHIDFGDCFEVAMTREKFPEKIPFRLTRMLTNAMEVTGLDGNYRITC

-continued

```
HTVMEVLREHKDSVMAVLEAFVYDPLLNWRLMDTNTKGNKRSRTRTDSYSAGQSVEILDG

VELGEPAHKKTGTTVPESIHSFIGDGLVKPEALNKKAIQIINRVRDKLTGRDFSHDDTLD

VPTQVELLIKQATSHENLCQCYIGWCPFW
```

The term "mTORC1" refers to the protein complex including mTOR and Raptor (regulatory-associated protein of mTOR). mTORC1 may also include MLST8 (mammalian lethal with SEC13 protein 8), PRAS40, and/or DEPTOR. mTORC1 may function as a nutrient/energy/redox sensor and regulator of protein synthesis. The term "mTORC1 pathway" or "mTORC1 signal transduction pathway" refers to a cellular pathway including mTORC1. An mTORC1 pathway includes the pathway components upstream and downstream from mTORC1. An mTORC1 pathway is a signaling pathway that is modulated by modulation of mTORC1 activity. In embodiments, an mTORC1 pathway is a signaling pathway that is modulated by modulation of mTORC1 activity but not by modulation of mTORC2 activity. In embodiments, an mTORC1 pathway is a signaling pathway that is modulated to a greater extent by modulation of mTORC1 activity than by modulation of mTORC2 activity.

The term "mTORC2" refers to the protein complex including mTOR and RICTOR (rapamycin-insensitive companion of mTOR). mTORC2 may also include G(3L, mSIN1 (mammalian stress-activated protein kinase interacting protein 1), Protor 1/2, DEPTOR, TTI1, and/or TEL2. mTORC2 may regulate cellular metabolism and the cytoskeleton. The term "mTORC2 pathway" or "mTORC2 signal transduction pathway" refers to a cellular pathway including mTORC2. An mTORC2 pathway includes the pathway components upstream and downstream from mTORC2. An mTORC2 pathway is a signaling pathway that is modulated by modulation of mTORC2 activity. In embodiments, an mTORC2 pathway is a signaling pathway that is modulated by modulation of mTORC2 activity but not by modulation of mTORC1 activity. In embodiments, an mTORC2 pathway is a signaling pathway that is modulated to a greater extent by modulation of mTORC2 activity than by modulation of mTORC1 activity.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propogated to other signaling pathway components. For example, binding of a mTORC1 (e.g., LAMTOR5 component) with a compound as described herein may result in a change in one or more protein-protein interactions of the mTORC1 (e.g., with a lysosome) or LAMTOR5 (e.g., with the Ragulator complex or with a Rag GTPase) or interactions between the mTORC1 and a membrane (e.g., of a lysosome), resulting in changes in cell growth, proliferation, or survival.

An amino acid residue in a protein "corresponds" to a given residue when it occupies the same essential structural position within the protein as the given residue. For example, a selected residue in a selected protein corresponds to C23 of human LAMTOR5, SEQ ID NO: 1, when the selected residue occupies the same essential spatial or other structural relationship as C23 in human LAMTOR5 having SEQ ID NO: 1. In some embodiments, where a selected protein is aligned for maximum homology with the human LAMTOR5 protein of SEQ ID NO: 1, the position in the aligned selected protein aligning with C23 is said to correspond to C23 of SEQ ID NO: 1. Instead of a primary sequence alignment, a three dimensional structural alignment can also be used, e.g., where the structure of the selected protein is aligned for maximum correspondence with the human LAMTOR5 protein of SEQ ID NO: 1 and the overall structures compared. In this case, an amino acid that occupies the same essential position as C23 of SEQ ID NO: 1 in the structural model is said to correspond to the C23 residue. Another example is wherein a selected residue in a selected protein corresponds to C23 in human LAMTOR5 (e.g., (SEQ ID NO: 1)) when the selected residue (e.g., cysteine residue) occupies essential the same sequence, spatial, or other structural position within the protein as C23 in human LAMTOR5, having the sequence SEQ ID NO: 1. For example, a selected residue in a selected protein corresponds to C148 of human LAMTOR5 having the sequence of SEQ ID NO: 1, when the selected residue occupies the same essential spatial or other structural relationship as C148 in human LAMTOR5 of SEQ ID NO: 1. In some embodiments, where a selected protein is aligned for maximum homology with the human LAMTOR5 protein of sequence SEQ ID NO: 1, the position in the aligned selected protein aligning with C148 of SEQ ID NO: 1, is said to correspond to C148. Instead of a primary sequence alignment, a three dimensional structural alignment can also be used, e.g., where the structure of the selected protein is aligned for maximum correspondence with the human LAMTOR5 protein, having the sequence SEQ ID NO: 1, and the overall structures compared. In this case, an amino acid that occupies the same essential position as C148 of SEQ ID NO: 1 in the structural model is said to correspond to the C148 residue. Another example is wherein a selected residue in a selected protein corresponds to C148 in human LAMTOR5 (e.g., (SEQ ID NO: 1)) when the selected residue (e.g., cysteine residue) occupies essentially the same sequence, spatial, or other structural position within the protein as C148 in human LAMTOR5 having the sequence SEQ ID NO: 1.

II. Compounds

In an aspect is provided a compound having the formula:

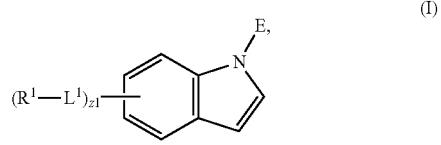

(I)

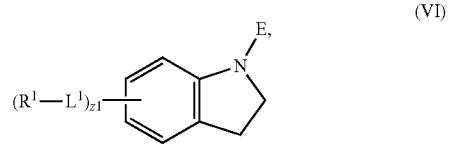

(VI)

-continued

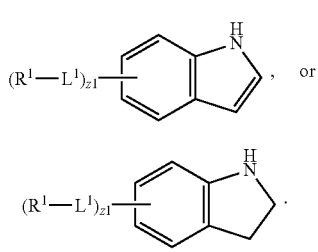

In embodiments, the compound has the formula:

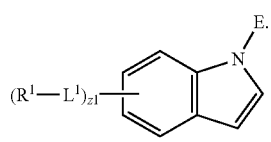

In embodiments, the compound has the formula:

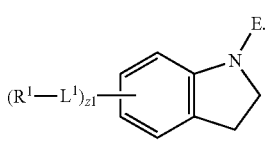

In embodiments, the compound has the formula:

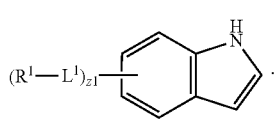

In embodiments, the compound has the formula:

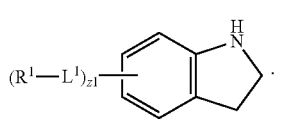

$L^1$ is independently a bond, —S(O)$_2$—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

$R^1$ is independently halogen, —CX$^1_3$, —CHX$^1_2$, —CH$_2$X$^1$, —OCX$^1_3$, —OCH$_2$X$^1$, —OCHX$^1_2$, —CN, —SO$_{n1}$R$^{1D}$, —SO$_{v1}$NR$^{1A}$R$^{1B}$, —NHC(O)NR$^{1A}$R$^{1B}$, —N(O)$_{m1}$, —NR$^{1A}$R$^{1B}$, —C(O)R$^{1C}$, —C(O)—OR$^{1C}$, —C(O)NR$^{1A}$R$^{1B}$, —OR$^{1D}$, —NR$^{1A}$SO$_2$R$^{1D}$, —NR$^{1A}$C(O)R$^{1C}$, —NR$^{1A}$C(O)OR$^{1C}$, —NR$^{1A}$OR$^{1C}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent -L$^1$-R$^1$ substituents may optionally be joined to form a substituted or unsubstituted cycloalkyl, substituted or unsubstituted heterocycloalkyl, substituted or unsubstituted aryl, or substituted or unsubstituted heteroaryl.

E is an electrophilic moiety.

Each R$^{1A}$, R$^{1B}$, R$^{1C}$, and R$^{1D}$ is independently hydrogen, —CX$_3$, —CHX$_2$, —CH$_2$X, —CN, —OH, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1A}$ and R$^{1B}$ substituents bonded to the same nitrogen atom may optionally be joined to form a substituted or unsubstituted heterocycloalkyl or substituted or unsubstituted heteroaryl.

Each X and X$^1$ is independently —F, —Cl, —Br, or —I. n1 is independently an integer from 0 to 4. m1 and v1 are independently 1 or 2. z1 is independently an integer from 0 to 6.

In an embodiment, the compound has the formula:

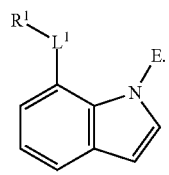

R$^1$, L, and E are as described herein, including in embodiments.

In an embodiment, the compound has the formula:

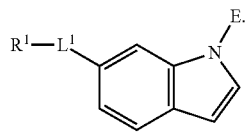

R$^1$, L$^1$, and E are as described herein, including in embodiments.

In an embodiment, the compound has the formula:

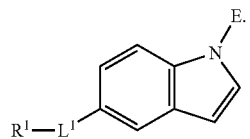

R$^1$, L$^1$, and E are as described herein, including in embodiments.

In an embodiment, the compound has the formula:

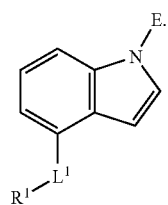
(Id)

$R^1$, $L^1$, and E are as described herein, including in embodiments.

In an embodiment, the compound has the formula:

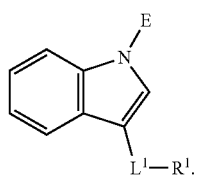
(Ie)

$R^1$, $L^1$, and E are as described herein, including in embodiments.

In an embodiment, the compound has the formula:

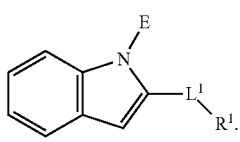
(If)

$R^1$, $L^1$, and E are as described herein, including in embodiments.

In an embodiment, the compound has the formula:

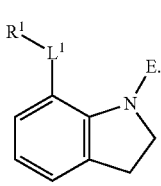
(VIa)

$R^1$, $L^1$, and E are as described herein, including in embodiments.

In an embodiment, the compound has the formula:

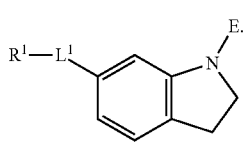
(VIb)

$R^1$, $L^1$, and E are as described herein, including in embodiments.

In an embodiment, the compound has the formula:

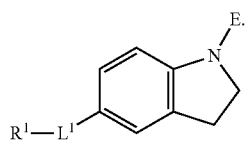
(VIc)

$R^1$, $L^1$, and E are as described herein, including in embodiments.

In an embodiment, the compound has the formula:

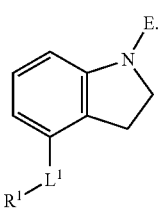
(VId)

$R^1$, $L^1$, and E are as described herein, including in embodiments.

In an embodiment, the compound has the formula:

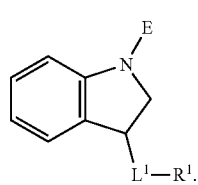
(VIe)

$R^1$, $L^1$, and E are as described herein, including in embodiments.

In an embodiment, the compound has the formula:

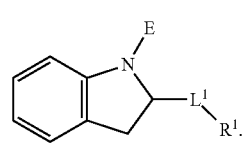
(VIf)

$R^1$, $L^1$, and E are as described herein, including in embodiments.

In an embodiment, the compound has the formula:

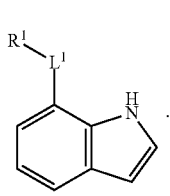
(XIa)

$R^1$ and $L^1$ are as described herein, including in embodiments.

In an embodiment, the compound has the formula:

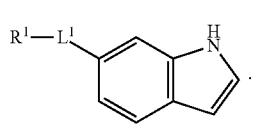
(XIb)

$R^1$ and $L^1$ are as described herein, including in embodiments.

In an embodiment, the compound has the formula:

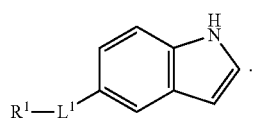
(XIc)

$R^1$, $L^1$, and E are as described herein, including in embodiments.

In an embodiment, the compound has the formula:

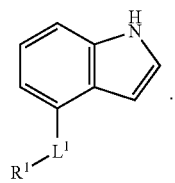
(XId)

$R^1$ and $L^1$ are as described herein, including in embodiments.

In an embodiment, the compound has the formula:

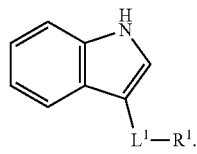
(XIe)

$R^1$ and $L^1$ are as described herein, including in embodiments.

In an embodiment, the compound has the formula:

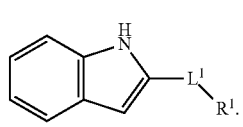
(XIf)

$R^1$ and $L^1$ are as described herein, including in embodiments.

In an embodiment, the compound has the formula:

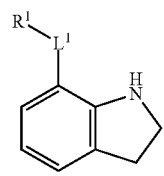
(XXIa)

$R^1$ and $L^1$ are as described herein, including in embodiments.

In an embodiment, the compound has the formula:

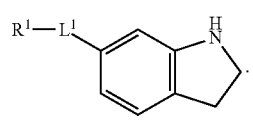
(XXIb)

$R^1$ and $L^1$ are as described herein, including in embodiments.

In an embodiment, the compound has the formula:

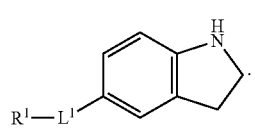
(XXIc)

$R^1$ and $L^1$ are as described herein, including in embodiments.

In an embodiment, the compound has the formula:

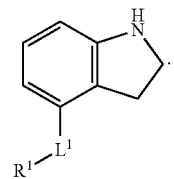
(XXId)

$R^1$ and $L^1$ are as described herein, including in embodiments.

In an embodiment, the compound has the formula:

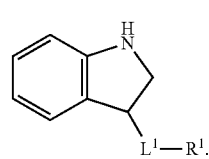
(XXIe)

$R^1$ and $L^1$ are as described herein, including in embodiments.

In an embodiment, the compound has the formula:

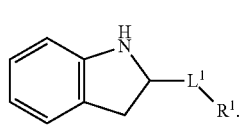
(XXIf)

$R^1$ and $L^1$ are as described herein, including in embodiments.

In embodiments, the compound has the formula:

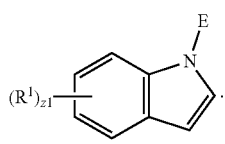
(II)

$R^1$ and E are as described herein, including in embodiments.

In embodiments, the compound has the formula:

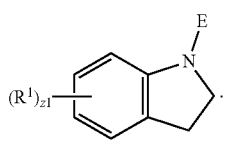
(VII)

$R^1$ and E are as described herein, including in embodiments.

In embodiments, the compound has the formula:

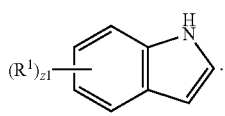
(XII)

$R^1$ is as described herein, including in embodiments.

In embodiments, the compound has the formula:

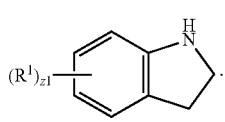
(XXII)

$R^1$ is as described herein, including in embodiments.

In embodiments, z1 is 2. In embodiments, z1 is 3. In embodiments, z1 is 0. In embodiments, z1 is 1. In embodiments, z1 is 4. In embodiments, z1 is 5. In embodiments, z1 is 6.

In embodiments, the compound has the formula:

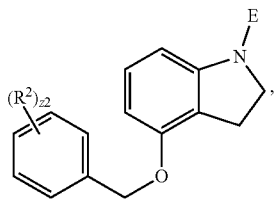

wherein E and $R^2$ are as described herein. The symbol z2 is an integer from 0 to 5. In embodiments, z2 is 0. In embodiments, z2 is 1. In embodiments, z2 is 2 In embodiments, z2 is 3. In embodiments, z2 is 4. In embodiments, z2 is 5.

In embodiments, the compound has the formula:

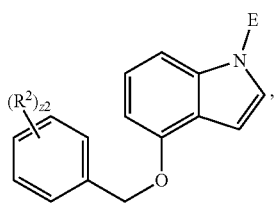

wherein E, z2, and $R^2$ are as described herein.

In embodiments, the compound has the formula:

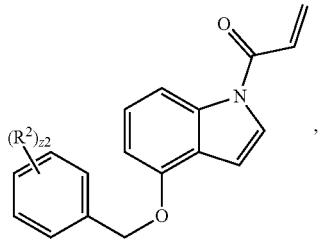

wherein z2 and $R^2$ are as described herein.

In embodiments, the compound has the formula:

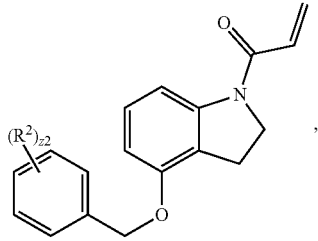

wherein z2 and $R^2$ are as described herein.

In embodiments, the compound has the formula:

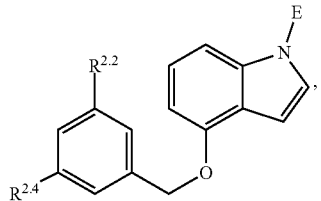

wherein E is as described herein and $R^{2.2}$ and $R^{2.4}$ are each $R^2$ at a fixed position on the attached ring. $R^{2.2}$ and $R^{2.4}$ are each independently a moiety equal to $R^2$ described herein, including in any aspect, embodiment, example, figure, or claim. For example, in embodiments, $R^{2.2}$ is independently oxo, halogen, —$CX^2_3$, —$CHX^2_2$, —$CH_2X^2$, —$OCX^2_3$, —$OCH_2X^2$, —$OCHX^2_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, a bioconjugate linker, a detectable moiety, $R^3$-substituted or unsubstituted alkyl (e.g., $C_1$-$C_8$, $C_1$-$C_6$, $C_1$-$C_4$, or $C_1$-$C_2$), $R^3$-substituted or unsubstituted heteroalkyl (e.g., 2 to 8 membered, 2 to 6 membered, 4 to 6 membered, 2 to 3 membered, or 4 to 5 membered), $R^3$-substituted or unsubstituted cycloalkyl (e.g., $C_3$-$C_8$, $C_3$-$C_6$, $C_4$-$C_6$, or $C_5$-$C_6$), $R^3$-substituted or unsubstituted heterocycloalkyl (e.g., 3 to 8 membered, 3 to 6 membered, 4 to 6 membered, 4 to 5 membered, or 5 to 6 membered), $R^3$-substituted or unsubstituted aryl (e.g., $C_6$-$C_{10}$ or phenyl), or $R^3$-substituted or unsubstituted heteroaryl (e.g., 5 to 10 membered, 5 to 9 membered, or 5 to 6 membered). Likewise, in embodiments, $R^{2.4}$ is independently oxo, halogen, —$CX^2_3$, —$CHX^2_2$, —$CH_2X^2$, —$OCX^2_3$, —$OCH_2X^2$, —$OCHX^2_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$N_3$, a bioconjugate linker, a detectable moiety, $R^3$-substituted or unsubstituted alkyl (e.g., $C_1$-$C_8$, $C_1$-$C_6$, $C_1$-$C_4$, or $C_1$-$C_2$), $R^3$-substituted or unsubstituted heteroalkyl (e.g., 2 to 8 membered, 2 to 6 membered, 4 to 6 membered, 2 to 3 membered, or 4 to 5 membered), $R^3$-substituted or unsubstituted cycloalkyl (e.g., $C_3$-$C_8$, $C_3$-$C_6$, $C_4$-$C_6$, or $C_5$-$C_6$), $R^3$-substituted or unsubstituted heterocycloalkyl (e.g., 3 to 8 membered, 3 to 6 membered, 4 to 6 membered, 4 to 5 membered, or 5 to 6 membered), $R^3$-substituted or unsubstituted aryl (e.g., $C_6$-$C_{10}$ or phenyl), or $R^3$-substituted or unsubstituted heteroaryl (e.g., 5 to 10 membered, 5 to 9 membered, or 5 to 6 membered).

In embodiments, the compound has the formula:

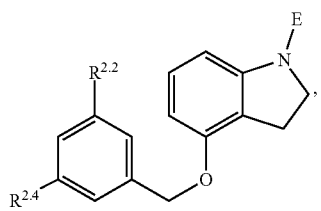

wherein E is as described herein. and $R^{2.2}$ and $R^{2.4}$ are described herein (e.g., are each independently a moiety equal to $R^2$), including in any aspect, embodiment, figure, or claim.

In embodiments, the compound has the formula:

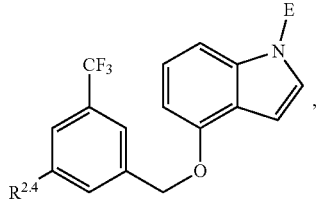

wherein $R^{2.4}$ is as described herein, including in any aspect, embodiment, example, figure, or claim.

In embodiments, the compound has the formula:

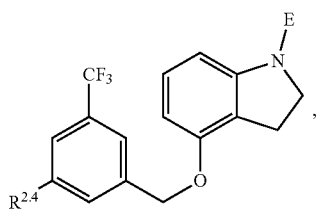

wherein $R^{2.4}$, wherein $R^{2.4}$ is as described herein, including in any aspect, embodiment, example, figure, or claim.

In embodiments, the compound has the formula:

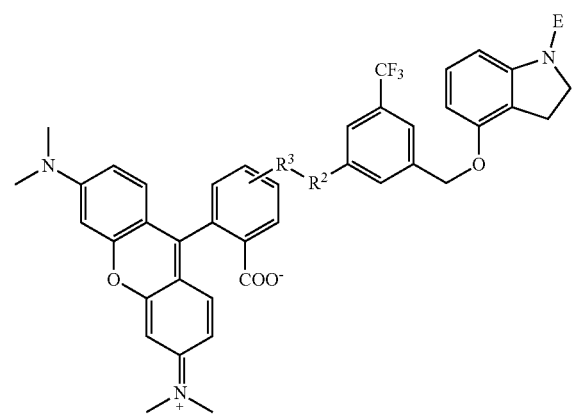

wherein $R^2$ and $R^3$ are as described herein, including in any aspect, embodiment, example, figure, or claim.

In embodiments, $R^1$ is independently halogen, —$CX^1_3$, —$CHX^1_2$, —$CH_2X^1$, —$OCX^1_3$, —$OCH_2X^1$, —$OCHX^1_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^1$ is independently halogen, —$CX^1_3$, —$CHX^1_2$, —$CH_2X^1$, —$OCX^1_3$, —$OCH_2X^1$, —$OCHX^1_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, substituted or unsubstituted $C_1$-$C_6$ alkyl, substituted or unsubstituted 2 to 6 membered heteroalkyl, substituted or unsubstituted $C_3$-$C_8$ cycloalkyl, substituted or unsubstituted 3 to 8 membered heterocycloalkyl, substituted or unsubstituted phenyl, or substituted or unsubstituted 5 to 6 membered heteroaryl. In embodiments, $R^1$ is independently halogen, —$CX^1_3$, —$CHX^1_2$, —$CH_2X^1$, —OH, —SH, —$OCX^1_3$, —$OCHX^1_2$, —$OCH_2X^1$, —$CH_3$, —$CH_2CH_3$, —$OCH_3$, —$OCH_2CH_3$, —$SCH_3$, or —$SCH_2CH_3$. In embodiments, $R^1$ is independently halogen, —$CX^1_3$, —$CHX^1_2$, —$CH_2X^1$, —OH, —SH, —$OCX^1_3$, —$OCHX^1_2$, —$OCH_2X^1$, —$CH_3$, —$CH_2CH_3$, —$OCH_3$, —$OCH_2CH_3$, —$SCH_3$, or —$SCH_2CH_3$. In embodiments, $R^1$ is substituted or unsubstituted $C_1$-$C_6$ alkyl. In embodiments, $R^1$ is substituted or unsubstituted 2 to 6 membered heteroalkyl. In embodiments, $R^1$ is substituted or unsubstituted $C_3$-$C_8$ cycloalkyl. In embodiments, $R^1$ is substituted or unsubstituted 3 to 8 membered heterocycloalkyl. In embodiments, $R^1$ is substituted or unsubstituted phenyl. In embodiments, $R^1$ is substituted or unsubstituted 5 to 6 membered heteroaryl. In embodiments, $R^1$ is independently halogen. In embodiments, $R^1$ is independently —$CX^1_3$. In embodiments, $R^1$ is independently —$CHX^1_2$. In embodiments, $R^1$ is independently —$CH_2X^1$. In embodiments, $R^1$ is independently —$OCX^1_3$. In embodiments, $R^1$ is independently —$OCH_2X^1$. In embodiments, $R^1$ is independently —$OCHX^1_2$. In embodiments, $R^1$ is independently —$OCH_2X^1$. In embodiments, $R^1$ is independently —CN. In embodiments, $R^1$ is independently —$SO_{n1}R^{1D}$. In embodiments, $R^1$ is independently —$SO_vNR^{1A}R^{1B}$. In embodiments, $R^1$ is independently —$NHC(O)NR^{1A}R^{1B}$. In embodiments, $R^1$ is independently —$N(O)_{m1}$. In embodiments, $R^1$ is independently —$NR^{1A}R^{1B}$. In embodiments, $R^1$ is independently —$C(O)R^{1C}$. In embodiments, $R^1$ is independently —$C(O)OR^{1C}$. In embodiments, $R^1$ is independently —$C(O)NR^{1A}R^{1B}$. In embodiments, $R^1$ is independently —$OR^{1D}$. In embodiments, $R^1$ is independently —$NR^{1A}SO_2R^{1D}$. In embodiments, $R^1$ is independently —$NR^{1A}C(O)R^{1C}$. In embodiments, $R^1$ is independently —$NR^{1A}C(O)OR^{1C}$. In embodiments, $R^1$ is independently —$NR^{1A}OR^{1C}$. In embodiments, $R^1$ is independently —OH. In embodiments, $R^1$ is independently —$NH_2$. In embodiments, $R^1$ is independently —COOH. In embodiments, $R^1$ is independently —$CONH_2$. In embodiments, $R^1$ is independently —$NO_2$. In embodiments, $R^1$ is independently —SH. In embodiments, $R^1$ is independently —$CF_3$. In embodiments, $R^1$ is independently —$CHF_2$. In embodiments, $R^1$ is independently —$CH_2F$. In embodiments, $R^1$ is independently —$OCF_3$. In embodiments, $R^1$ is independently —$OCH_2F$. In embodiments, $R^1$ is independently —$OCHF_2$. In embodiments, $R^1$ is independently —$OCH_3$. In embodiments, $R^1$ is independently —$OCH_2CH_3$. In embodiments, $R^1$ is independently —$OCH_2CH_2CH_3$. In embodiments, $R^1$ is independently —$OCH(CH_3)_2$. In embodiments, $R^1$ is independently —$OC(CH_3)_3$. In embodiments, $R^1$ is independently —$SCH_3$. In embodiments, $R^1$ is independently —$SCH_2CH_3$. In embodiments, $R^1$ is independently —$SCH_2CH_2CH_3$. In embodiments, $R^1$ is independently —$SCH(CH_3)_2$. In embodiments, $R^1$ is independently —$SC(CH_3)_3$. In embodiments, $R^1$ is independently —$CH_3$. In embodiments, $R^1$ is independently —$CH_2CH_3$. In embodiments, $R^1$ is independently —$CH_2CH_2CH_3$. In embodiments, $R^1$ is independently —$CH(CH_3)_2$. In embodiments, $R^1$ is independently —$C(CH_3)_3$. In embodiments, $R^1$ is independently —F. In embodiments, $R^1$ is independently —Cl. In embodiments, $R^1$ is independently —Br. In embodiments, $R^1$ is independently —I.

In embodiments, $R^1$ is independently halogen, —$CX^1_3$, —CN, —OH, —$NH_2$, —COOH, —$CONH_2$, —$NO_2$, —SH, —$OCX^1_3$, —$OCHX^1_2$, —$OCH_2X^1$, —$CHX^1_2$, —$CH_2X^1$, substituted or unsubstituted $C_1$-$C_8$ alkyl, or substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted phenyl, or substituted or unsubstituted 5 to 6 membered heteroaryl. In embodiments, $R^1$ is independently halogen, —$CX^1_3$, —CN, unsubstituted $C_1$-$C_4$ alkyl, or unsubstituted 2 to 4 membered heteroalkyl. In embodiments, $R^1$ is independently unsubstituted methyl, unsubstituted ethyl, unsubstituted isopropyl, or unsubstituted tert-butyl. In embodiments, $R^1$ is independently unsubstituted methyl. In embodiments, $R^1$ is independently unsubstituted ethyl. In embodiments, $R^1$ is independently unsubstituted propyl. In embodiments, $R^1$ is independently unsubstituted n-propyl. In embodiments, $R^1$ is independently unsubstituted isopropyl. In embodiments, $R^1$ is independently unsubstituted butyl. In embodiments, $R^1$ is independently unsubstituted n-butyl. In embodiments, $R^1$ is independently unsubstituted isobutyl. In embodiments, $R^1$ is independently unsubstituted tert-butyl. In embodiments, $R^1$ is independently unsubstituted pentyl. In embodiments, $R^1$ is independently unsubstituted hexyl. In embodiments, $R^1$ is independently unsubstituted heptyl. In embodiments, $R^1$ is independently unsubstituted octyl. In embodiments, $R^1$ is independently —$CF_3$. In embodiments, $R^1$ is independently —$CCl_3$. In embodiments, $R^1$ is independently unsubstituted phenyl. In embodiments, $R^1$ is independently unsubstituted pyridyl. In embodiments, $R^1$ is independently halogen. In embodiments, $R^1$ is independently —CN. In embodiments, $R^1$ is independently —OH. In embodiments, $R^1$ is independently —$NH_2$. In embodiments, $R^1$ is independently —COOH. In embodiments, $R^1$ is independently —$CONH_2$. In embodiments, $R^1$ is independently —$NO_2$. In embodiments, $R^1$ is independently —SH. In embodiments, $R^1$ is independently —$SO_3H$. In embodiments, $R^1$ is independently —$SO_4H$. In embodiments, $R^1$ is independently —$SO_2NH_2$. In embodiments, $R^1$ is independently —$NHNH_2$. In embodiments, $R^1$ is independently —$ONH_2$. In embodiments, $R^1$ is independently —$NHC(O)NHNH_2$. In embodiments, $R^1$ is independently —$NHC(O)NH_2$. In embodiments, $R^1$ is independently —$NHSO_2H$. In embodiments, $R^1$ is independently —NHC(O)H. In embodiments, $R^1$ is independently —NHC(O)OH. In embodiments, $R^1$ is independently —NHOH. In embodiments, $R^1$ is independently substituted or unsubstituted alkyl. In embodiments, $R^1$ is independently substituted or unsubstituted heteroalkyl. In embodiments, $R^1$ is independently substituted or unsubstituted cycloalkyl. In embodiments, $R^1$ is independently substituted or unsubstituted heterocycloalkyl. In embodiments, $R^1$ is independently substituted or unsubstituted aryl. In embodiments, $R^1$ is independently substituted or unsubstituted heteroaryl. In embodiments, $R^1$ is independently substituted alkyl. In embodiments, $R^1$ is independently substituted heteroalkyl. In embodiments, $R^1$ is independently substituted cycloalkyl. In embodiments, $R^1$ is independently substituted heterocycloalkyl. In embodiments, $R^1$ is independently substituted aryl. In embodiments, $R^1$ is independently substituted heteroaryl. In embodiments, $R^1$ is independently unsubstituted alkyl. In embodiments, $R^1$ is independently unsubstituted heteroalkyl. In embodiments, $R^1$ is independently unsubstituted cycloalkyl. In embodiments, $R^1$ is independently unsubstituted heterocycloalkyl. In embodiments, $R^1$ is independently unsubstituted aryl. In embodiments, $R^1$ is independently unsubstituted heteroaryl. In embodiments, $R^1$ is independently substituted or unsubstituted $C_1$-$C_8$ alkyl. In embodiments, $R^1$ is independently substituted or unsubstituted 2 to 8 membered heteroalkyl. In embodiments, $R^1$ is independently substituted or unsubstituted $C_3$-$C_8$ cycloalkyl. In embodiments, $R^1$ is independently substituted or unsubstituted 3 to 8 membered heterocycloalkyl. In embodiments, $R^1$ is independently substituted or unsubstituted $C_6$-$C_{10}$ aryl. In embodiments, $R^1$ is independently substituted or unsubstituted 5 to 10 membered heteroaryl. In embodiments, $R^1$ is independently substituted $C_1$-$C_8$ alkyl. In embodiments, $R^1$ is independently substituted 2 to 8 membered heteroalkyl. In embodiments, $R^1$ is independently substituted $C_3$-$C_8$ cycloalkyl. In embodiments, $R^1$ is independently substituted 3 to 8 membered heterocycloalkyl. In embodiments, $R^1$ is independently substituted $C_6$-$C_{10}$ aryl. In embodiments, $R^1$ is independently substituted 5 to 10 membered heteroaryl. In embodiments, $R^1$ is independently unsubstituted $C_1$-$C_8$ alkyl. In embodiments, $R^1$ is independently unsubstituted 2 to 8 membered heteroalkyl. In embodiments, $R^1$ is independently unsubstituted $C_3$-$C_8$ cycloalkyl. In embodiments, $R^1$ is independently unsubstituted 3 to 8 membered heterocycloalkyl. In embodiments, $R^1$ is independently unsubstituted $C_6$-$C_{10}$ aryl. In embodiments, $R^1$ is independently unsubstituted 5 to 10 membered heteroaryl. In embodiments, $R^1$ is independently substituted or unsubstituted $C_1$-$C_4$ alkyl. In embodiments, $R^1$ is independently substituted or unsubstituted 2 to 4 membered heteroalkyl. In embodiments, $R^1$ is independently substituted or unsubstituted $C_3$-$C_6$ cycloalkyl. In embodiments, $R^1$ is independently substituted or unsubstituted 3 to 6 membered heterocycloalkyl. In embodiments, $R^1$ is independently substituted or unsubstituted phenyl. In embodiments, $R^1$ is independently substituted or unsubstituted 5 to 6 membered heteroaryl. In embodiments, $R^1$ is independently substituted $C_1$-$C_4$ alkyl. In embodiments, $R^1$ is independently substituted 2 to 4 membered heteroalkyl. In embodiments, $R^1$ is independently substituted $C_3$-$C_6$ cycloalkyl. In embodiments, $R^1$ is independently substituted 3 to 6 membered heterocycloalkyl. In embodiments, $R^1$ is independently substituted phenyl. In embodiments, $R^1$ is independently substituted 5 to 6 membered heteroaryl. In embodiments, $R^1$ is independently unsubstituted $C_1$-$C_4$ alkyl. In embodiments, $R^1$ is independently unsubstituted 2 to 4 membered heteroalkyl. In embodiments, $R^1$ is independently unsubstituted $C_3$-$C_6$ cycloalkyl. In embodiments, $R^1$ is independently unsubstituted 3 to 6 membered heterocycloalkyl. In embodiments, $R^1$ is independently unsubstituted phenyl. In embodiments, $R^1$ is independently unsubstituted 5 to 6 membered heteroaryl.

In embodiments, two adjacent -$L^1$-$R^1$ substituents are joined to form a substituted or unsubstituted cycloalkyl, substituted or unsubstituted heterocycloalkyl, substituted or unsubstituted aryl, or substituted or unsubstituted heteroaryl. In embodiments, two adjacent -$L^1$-$R^1$ substituents are joined to form a substituted or unsubstituted cycloalkyl. In embodiments, two adjacent -$L^1$-$R^1$ substituents are joined to form a substituted or unsubstituted heterocycloalkyl. In embodiments, two adjacent -$L^1$-$R^1$ substituents are joined to form a substituted or unsubstituted aryl. In embodiments, two adjacent $R^1$ substituents are joined to form a substituted or unsubstituted heteroaryl. In embodiments, two adjacent -$L^1$-$R^1$ substituents are joined to form a substituted or unsubstituted $C_3$-$C_8$ cycloalkyl. In embodiments, two adjacent -$L^1$-$R^1$ substituents are joined to form a substituted or unsubstituted 3 to 8 membered heterocycloalkyl. In embodiments, two adjacent -$L^1$-$R^1$ substituents are joined to form a substituted or unsubstituted $C_6$-$C_{10}$ aryl. In embodiments, two adjacent -$L^1$-$R^1$ substituents are joined to form a substituted or unsubstituted 5 to 10 membered heteroaryl. In embodiments, two adjacent $R^1$ substituents are joined to form a substituted or unsubstituted $C_3$-$C_6$ cycloalkyl. In embodiments, two adjacent -$L^1$-$R^1$ substituents are joined to form a substituted or unsubstituted 3 to 6 membered heterocycloalkyl. In embodiments, two adjacent -$L^1$-$R^1$ substituents are joined to form a substituted or unsubstituted phenyl. In embodiments, two adjacent -$L^1$-$R^1$ substituents are joined to form a substituted or unsubstituted 5 to 6 membered heteroaryl. It will be understood that when two adjacent $L^1$ substituents are a bond, two adjacent -$L^1$-$R^1$ substituents that are joined are equivalent to two adjacent —$R^1$ substituents being joined and may be depicted as such in a formula.

In embodiments, $R^{1A}$ is independently hydrogen. In embodiments, $R^{1A}$ is independently —$CX^{1A}_3$. In embodiments, $R^{1A}$ is independently —$CHX^{1A}_2$. In embodiments, $R^{1A}$ is independently —$CH_2X^{1A}$. In embodiments, $R^{1A}$ is independently —CN. In embodiments, $R^{1A}$ is independently —COOH. In embodiments, $R^{1A}$ is independently —$CONH_2$. In embodiments, $X^{1A}$ is independently —F, —Cl, —Br, or —I.

In embodiments, $R^{1A}$ is independently substituted or unsubstituted alkyl (e.g., $C_1$-$C_8$, $C_1$-$C_6$, $C_1$-$C_4$, or $C_1$-$C_2$). In embodiments, $R^{1A}$ is independently substituted alkyl (e.g., $C_1$-$C_8$, $C_1$-$C_6$, $C_1$-$C_4$, or $C_1$-$C_2$). In embodiments, $R^{1A}$ is independently unsubstituted alkyl (e.g., $C_1$-$C_8$, $C_1$-$C_6$, $C_1$-$C_4$, or $C_1$-$C_2$). In embodiments, $R^{1A}$ is independently unsubstituted methyl. In embodiments, $R^{1A}$ is independently unsubstituted ethyl. In embodiments, $R^{1A}$ is independently unsubstituted propyl. In embodiments, $R^{1A}$ is independently unsubstituted isopropyl. In embodiments, $R^{1A}$ is independently unsubstituted tert-butyl. In embodiments, $R^{1A}$ is independently substituted or unsubstituted heteroalkyl (e.g., 2 to 8 membered, 2 to 6 membered, 4 to 6 membered, 2 to 3 membered, or 4 to 5 membered). In embodiments, $R^{1A}$ is independently substituted heteroalkyl (e.g., 2 to 8 membered, 2 to 6 membered, 4 to 6 membered, 2 to 3 membered, or 4 to 5 membered). In embodiments, $R^{1A}$ is independently unsubstituted heteroalkyl (e.g., 2 to 8 membered, 2 to 6 membered, 4 to 6 membered, 2 to 3 membered, or 4 to 5 membered). In embodiments, $R^{1A}$ is independently substituted or unsubstituted cycloalkyl (e.g., $C_3$-$C_8$, $C_3$-$C_6$, $C_4$-$C_6$, or $C_5$-$C_6$). In embodiments, $R^{1A}$ is independently substituted cycloalkyl (e.g., $C_3$-$C_8$, $C_3$-$C_6$, $C_4$-$C_6$, or $C_5$-$C_6$). In embodiments, $R^{1A}$ is independently unsubstituted cycloalkyl (e.g., $C_3$-$C_8$, $C_3$-$C_6$, $C_4$-$C_6$, or $C_5$-$C_6$). In embodiments, $R^{1A}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{1A}$ is independently substituted heterocycloalkyl (e.g., 3 to 8 membered, 3 to 6 membered, 4 to 6 membered, 4 to 5 membered, or 5 to 6 membered). In embodiments, $R^{1A}$ is independently unsubstituted heterocycloalkyl (e.g., 3 to 8 membered, 3 to 6 membered, 4 to 6 membered, 4 to 5 membered, or 5 to 6 membered). In embodiments, $R^{1A}$ is independently substituted or unsubstituted aryl (e.g., $C_6$-$C_{10}$ or phenyl). In embodiments, $R^{1A}$ is independently substituted aryl (e.g., $C_6$-$C_{10}$ or phenyl). In embodiments, $R^{1A}$ is independently unsubstituted aryl (e.g., $C_6$-$C_{10}$ or phenyl). In embodiments, $R^{1A}$ is independently substituted or unsubstituted heteroaryl (e.g., 5 to 10 membered, 5 to 9 membered, or 5 to 6 membered). In embodiments, $R^{1A}$ is independently substituted heteroaryl (e.g., 5 to 10 membered, 5 to 9 membered, or 5 to 6 membered). In embodiments, $R^{1A}$ is independently unsubstituted heteroaryl (e.g., 5 to 10 membered, 5 to 9 membered, or 5 to 6 membered).

In embodiments, $R^{1B}$ is independently hydrogen. In embodiments, $R^{1B}$ is independently —$CX^{1B}_3$. In embodiments, $R^{1B}$ is independently —CHX$^{1B}$$_2$. In embodiments, $R^{1B}$ is independently —CH$_2$X$^{1B}$. In embodiments, $R^{1B}$ is independently —CN. In embodiments, $R^{1B}$ is independently —COOH. In embodiments, $R^{1B}$ is independently —CONH$_2$. In embodiments, X$^{1B}$ is independently —F, —Cl, —Br, or —I.

In embodiments, $R^{1B}$ is independently substituted or unsubstituted alkyl (e.g., C$_1$-C$_8$, C$_1$-C$_6$, C$_1$-C$_4$, or C$_1$-C$_2$). In embodiments, $R^{1B}$ is independently substituted alkyl (e.g., C$_1$-C$_8$, C$_1$-C$_6$, C$_1$-C$_4$, or C$_1$-C$_2$). In embodiments, $R^{1B}$ is independently unsubstituted alkyl (e.g., C$_1$-C$_8$, C$_1$-C$_6$, C$_1$-C$_4$, or C$_1$-C$_2$). In embodiments, $R^{1B}$ is independently unsubstituted methyl. In embodiments, $R^{1B}$ is independently unsubstituted ethyl. In embodiments, $R^{1B}$ is independently unsubstituted propyl. In embodiments, $R^{1B}$ is independently unsubstituted isopropyl. In embodiments, $R^{1B}$ is independently unsubstituted tert-butyl. In embodiments, $R^{1B}$ is independently substituted or unsubstituted heteroalkyl (e.g., 2 to 8 membered, 2 to 6 membered, 4 to 6 membered, 2 to 3 membered, or 4 to 5 membered). In embodiments, $R^{1B}$ is independently substituted heteroalkyl (e.g., 2 to 8 membered, 2 to 6 membered, 4 to 6 membered, 2 to 3 membered, or 4 to 5 membered). In embodiments, $R^{1B}$ is independently unsubstituted heteroalkyl (e.g., 2 to 8 membered, 2 to 6 membered, 4 to 6 membered, 2 to 3 membered, or 4 to 5 membered). In embodiments, $R^{1B}$ is independently substituted or unsubstituted cycloalkyl (e.g., C$_3$-C$_8$, C$_3$-C$_6$, C$_4$-C$_6$, or C$_5$-C$_6$). In embodiments, $R^{1B}$ is independently substituted cycloalkyl (e.g., C$_3$-C$_8$, C$_3$-C$_6$, C$_4$-C$_6$, or C$_5$-C$_6$). In embodiments, $R^{1B}$ is independently unsubstituted cycloalkyl (e.g., C$_3$-C$_8$, C$_3$-C$_6$, C$_4$-C$_6$, or C$_5$-C$_6$). In embodiments, $R^{1B}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{1B}$ is independently substituted heterocycloalkyl (e.g., 3 to 8 membered, 3 to 6 membered, 4 to 6 membered, 4 to 5 membered, or 5 to 6 membered). In embodiments, $R^{1B}$ is independently unsubstituted heterocycloalkyl (e.g., 3 to 8 membered, 3 to 6 membered, 4 to 6 membered, 4 to 5 membered, or 5 to 6 membered). In embodiments, $R^{1B}$ is independently substituted or unsubstituted aryl (e.g., C$_6$-C$_{10}$ or phenyl). In embodiments, $R^{1B}$ is independently substituted aryl (e.g., C$_6$-C$_{10}$ or phenyl). In embodiments, $R^{1B}$ is independently unsubstituted aryl (e.g., C$_6$-C$_{10}$ or phenyl). In embodiments, $R^{1B}$ is independently substituted or unsubstituted heteroaryl (e.g., 5 to 10 membered, 5 to 9 membered, or 5 to 6 membered). In embodiments, $R^{1B}$ is independently substituted heteroaryl (e.g., 5 to 10 membered, 5 to 9 membered, or 5 to 6 membered). In embodiments, $R^{1B}$ is independently unsubstituted heteroaryl (e.g., 5 to 10 membered, 5 to 9 membered, or 5 to 6 membered).

In embodiments, $R^{1A}$ and $R^{1B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered). In embodiments, $R^{1A}$ and $R^{1B}$ substituents bonded to the same nitrogen atom may be joined to form a substituted heterocycloalkyl (e.g., 3 to 8 membered, 3 to 6 membered, 4 to 6 membered, 4 to 5 membered, or 5 to 6 membered). In embodiments, $R^{1A}$ and $R^{1B}$ substituents bonded to the same nitrogen atom may be joined to form an unsubstituted heterocycloalkyl (e.g., 3 to 8 membered, 3 to 6 membered, 4 to 6 membered, 4 to 5 membered, or 5 to 6 membered). In embodiments, $R^{1A}$ and $R^{1B}$ substituents bonded to the same nitrogen atom may be joined to form a substituted or unsubstituted heteroaryl (e.g., 5 to 10 membered, 5 to 9 membered, or 5 to 6 membered). In embodiments, $R^{1A}$ and $R^{1B}$ substituents bonded to the same nitrogen atom may be joined to form a substituted heteroaryl (e.g., 5 to 10 membered, 5 to 9 membered, or 5 to 6 membered). In embodiments, $R^{1A}$ and $R^{1B}$ substituents bonded to the same nitrogen atom may be joined to form an unsubstituted heteroaryl (e.g., 5 to 10 membered, 5 to 9 membered, or 5 to 6 membered).

In embodiments, $R^{1C}$ is independently hydrogen. In embodiments, $R^{1C}$ is independently —CX$^1$C$_3$. In embodiments, $R^{1C}$ is independently —CHX$^1$C$_2$. In embodiments, $R^{1C}$ is independently —CH$_2$X$^1$c. In embodiments, $R^{1C}$ is independently —CN. In embodiments, $R^{1C}$ is independently —COOH. In embodiments, $R^{1C}$ is independently —CONH$_2$. In embodiments, X$^1$c is independently —F, —Cl, —Br, or —I.

In embodiments, $R^{1C}$ is independently substituted or unsubstituted alkyl (e.g., C$_1$-C$_8$, C$_1$-C$_6$, C$_1$-C$_4$, or C$_1$-C$_2$). In embodiments, $R^{1C}$ is independently substituted alkyl (e.g., C$_1$-C$_8$, C$_1$-C$_6$, C$_1$-C$_4$, or C$_1$-C$_2$). In embodiments, $R^{1C}$ is independently unsubstituted alkyl (e.g., C$_1$-C$_8$, C$_1$-C$_6$, C$_1$-C$_4$, or C$_1$-C$_2$). In embodiments, $R^{1C}$ is independently unsubstituted methyl. In embodiments, $R^{1C}$ is independently unsubstituted ethyl. In embodiments, $R^{1C}$ is independently unsubstituted propyl. In embodiments, $R^{1C}$ is independently unsubstituted isopropyl. In embodiments, $R^{1C}$ is independently unsubstituted tert-butyl. In embodiments, $R^{1C}$ is independently substituted or unsubstituted heteroalkyl (e.g., 2 to 8 membered, 2 to 6 membered, 4 to 6 membered, 2 to 3 membered, or 4 to 5 membered). In embodiments, $R^{1C}$ is independently substituted heteroalkyl (e.g., 2 to 8 membered, 2 to 6 membered, 4 to 6 membered, 2 to 3 membered, or 4 to 5 membered). In embodiments, $R^{1C}$ is independently unsubstituted heteroalkyl (e.g., 2 to 8 membered, 2 to 6 membered, 4 to 6 membered, 2 to 3 membered, or 4 to 5 membered). In embodiments, $R^{1C}$ is independently substituted or unsubstituted cycloalkyl (e.g., C$_3$-C$_8$, C$_3$-C$_6$, C$_4$-C$_6$, or C$_5$-C$_6$). In embodiments, $R^{1C}$ is independently substituted cycloalkyl (e.g., C$_3$-C$_8$, C$_3$-C$_6$, C$_4$-C$_6$, or C$_5$-C$_6$). In embodiments, $R^{1C}$ is independently unsubstituted cycloalkyl (e.g., C$_3$-C$_8$, C$_3$-C$_6$, C$_4$-C$_6$, or C$_5$-C$_6$). In embodiments, $R^{1C}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{1C}$ is independently substituted heterocycloalkyl (e.g., 3 to 8 membered, 3 to 6 membered, 4 to 6 membered, 4 to 5 membered, or 5 to 6 membered). In embodiments, $R^{1C}$ is independently unsubstituted heterocycloalkyl (e.g., 3 to 8 membered, 3 to 6 membered, 4 to 6 membered, 4 to 5 membered, or 5 to 6 membered). In embodiments, $R^{1C}$ is independently substituted or unsubstituted aryl (e.g., C$_6$-C$_{10}$ or phenyl). In embodiments, $R^{1C}$ is independently substituted aryl (e.g., C$_6$-C$_{10}$ or phenyl). In embodiments, $R^{1C}$ is independently unsubstituted aryl (e.g., C$_6$-C$_{10}$ or phenyl). In embodiments, $R^{1C}$ is independently substituted or unsubstituted heteroaryl (e.g., 5 to 10 membered, 5 to 9 membered, or 5 to 6 membered). In embodiments, $R^{1C}$ is independently substituted heteroaryl (e.g., 5 to 10 membered, 5 to 9 membered, or 5 to 6 membered). In embodiments, $R^{1C}$ is independently unsubstituted heteroaryl (e.g., 5 to 10 membered, 5 to 9 membered, or 5 to 6 membered).

In embodiments, $R^{1D}$ is independently hydrogen. In embodiments, $R^{1D}$ is independently —CX$^{1D}$$_3$. In embodiments, $R^{1D}$ is independently —CHX$^{1D2}$. In embodiments, $R^{1D}$ is independently —CH$_2$X$^{1D}$. In embodiments, $R^{1D}$ is independently —CN. In embodiments, $R^{1D}$ is independently —COOH. In embodiments, $R^{1D}$ is independently —CONH$_2$. In embodiments, $X^{1D}$ is independently —F, —Cl, —Br, or —I.

In embodiments, $R^{1D}$ is independently substituted or unsubstituted alkyl (e.g., $C_1$-$C_8$, $C_1$-$C_6$, $C_1$-$C_4$, or $C_1$-$C_2$). In embodiments, $R^{1D}$ is independently substituted alkyl (e.g., $C_1$-$C_8$, $C_1$-$C_6$, $C_1$-$C_4$, or $C_1$-$C_2$). In embodiments, $R^{1D}$ is independently unsubstituted alkyl (e.g., $C_1$-$C_8$, $C_1$-$C_6$, $C_1$-$C_4$, or $C_1$-$C_2$). In embodiments, $R^{1D}$ is independently unsubstituted methyl. In embodiments, $R^{1D}$ is independently unsubstituted ethyl. In embodiments, $R^{1D}$ is independently unsubstituted propyl. In embodiments, $R^{1D}$ is independently unsubstituted isopropyl. In embodiments, $R^{1D}$ is independently unsubstituted tert-butyl. In embodiments, $R^{1D}$ is independently substituted or unsubstituted heteroalkyl (e.g., 2 to 8 membered, 2 to 6 membered, 4 to 6 membered, 2 to 3 membered, or 4 to 5 membered). In embodiments, $R^{1D}$ is independently substituted heteroalkyl (e.g., 2 to 8 membered, 2 to 6 membered, 4 to 6 membered, 2 to 3 membered, or 4 to 5 membered). In embodiments, $R^{1D}$ is independently unsubstituted heteroalkyl (e.g., 2 to 8 membered, 2 to 6 membered, 4 to 6 membered, 2 to 3 membered, or 4 to 5 membered). In embodiments, $R^{1D}$ is independently substituted or unsubstituted cycloalkyl (e.g., $C_3$-$C_8$, $C_3$-$C_6$, $C_4$-$C_6$, or $C_5$-$C_6$). In embodiments, $R^{1D}$ is independently substituted cycloalkyl (e.g., $C_3$-$C_8$, $C_3$-$C_6$, $C_4$-$C_6$, or $C_5$-$C_6$). In embodiments, $R^{1D}$ is independently unsubstituted cycloalkyl (e.g., $C_3$-$C_8$, $C_3$-$C_6$, $C_4$-$C_6$, or $C_5$-$C_6$). In embodiments, $R^{1D}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{1D}$ is independently substituted heterocycloalkyl (e.g., 3 to 8 membered, 3 to 6 membered, 4 to 6 membered, 4 to 5 membered, or 5 to 6 membered). In embodiments, $R^{1D}$ is independently unsubstituted heterocycloalkyl (e.g., 3 to 8 membered, 3 to 6 membered, 4 to 6 membered, 4 to 5 membered, or 5 to 6 membered). In embodiments, $R^{1D}$ is independently substituted or unsubstituted aryl (e.g., $C_6$-$C_{10}$ or phenyl). In embodiments, $R^{1D}$ is independently substituted aryl (e.g., $C_6$-$C_{10}$ or phenyl). In embodiments, $R^{1D}$ is independently unsubstituted aryl (e.g., $C_6$-$C_{10}$ or phenyl). In embodiments, $R^{1D}$ is independently substituted or unsubstituted heteroaryl (e.g., 5 to 10 membered, 5 to 9 membered, or 5 to 6 membered). In embodiments, $R^{1D}$ is independently substituted heteroaryl (e.g., 5 to 10 membered, 5 to 9 membered, or 5 to 6 membered). In embodiments, $R^{1D}$ is independently unsubstituted heteroaryl (e.g., 5 to 10 membered, 5 to 9 membered, or 5 to 6 membered).

In embodiments, $R^1$ is independently halogen, —$CX^1_3$, —$CHX^1_2$, —$CH_2X^1$, —$OCX^1_3$, —$OCH_2X^1$, —$OCHX^1_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, $R^2$-substituted or unsubstituted alkyl (e.g., $C_1$-$C_8$, $C_1$-$C_6$, $C_1$-$C_4$, or $C_1$-$C_2$), $R^2$-substituted or unsubstituted heteroalkyl (e.g., 2 to 8 membered, 2 to 6 membered, 4 to 6 membered, 2 to 3 membered, or 4 to 5 membered), $R^2$-substituted or unsubstituted cycloalkyl (e.g., $C_3$-$C_8$, $C_3$-$C_6$, $C_4$-$C_6$, or $C_5$-$C_6$), $R^2$-substituted or unsubstituted heterocycloalkyl (e.g., 3 to 8 membered, 3 to 6 membered, 4 to 6 membered, 4 to 5 membered, or 5 to 6 membered), $R^2$-substituted or unsubstituted aryl (e.g., $C_6$-$C_{10}$ or phenyl), or $R^2$-substituted or unsubstituted heteroaryl (e.g., 5 to 10 membered, 5 to 9 membered, or 5 to 6 membered). In embodiments, $R^1$ is independently unsubstituted methyl. In embodiments, $R^1$ is independently unsubstituted ethyl. In embodiments, $R^1$ is independently $R^2$-substituted 2 membered heteroalkyl. In embodiments, $R^1$ is independently $R^2$-substituted methoxy.

In embodiments, two adjacent -$L^1$-$R^1$ substituents are joined to form a $R^2$-substituted or unsubstituted cycloalkyl (e.g., $C_3$-$C_8$, $C_3$-$C_6$, $C_4$-$C_6$, or $C_5$-$C_6$), $R^2$-substituted or unsubstituted heterocycloalkyl (e.g., 3 to 8 membered, 3 to 6 membered, 4 to 6 membered, 4 to 5 membered, or 5 to 6 membered), $R^2$-substituted or unsubstituted aryl (e.g., $C_6$-$C_{10}$ or phenyl), or $R^2$-substituted or unsubstituted heteroaryl (e.g., 5 to 10 membered, 5 to 9 membered, or 5 to 6 membered). In embodiments, two adjacent -$L^1$-$R^1$ substituents are joined to form an unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). In embodiments, two adjacent -$L^1$-$R^1$ substituents are joined to form a $R^2$-substituted cycloalkyl (e.g., $C_3$-$C_8$, $C_3$-$C_6$, $C_4$-$C_6$, or $C_5$-$C_6$). In embodiments, two adjacent -$L^1$-$R^1$ substituents are joined to form a $R^2$-substituted heterocycloalkyl (e.g., 3 to 8 membered, 3 to 6 membered, 4 to 6 membered, 4 to 5 membered, or 5 to 6 membered). In embodiments, two adjacent -$L^1$-$R^1$ substituents are joined to form a $R^2$-substituted aryl (e.g., $C_6$-$C_{10}$ or phenyl). In embodiments, two adjacent -$L^1$-$R^1$ substituents are joined to form a $R^2$-substituted heteroaryl (e.g., 5 to 10 membered, 5 to 9 membered, or 5 to 6 membered). In embodiments, two adjacent -$L^1$-$R^1$ substituents are joined to form an unsubstituted cycloalkyl (e.g., $C_3$-$C_8$, $C_3$-$C_6$, $C_4$-$C_6$, or $C_5$-$C_6$). In embodiments, two adjacent -$L^1$-$R^1$ substituents are joined to form an unsubstituted heterocycloalkyl (e.g., 3 to 8 membered, 3 to 6 membered, 4 to 6 membered, 4 to 5 membered, or 5 to 6 membered). In embodiments, two adjacent -$L^1$-$R^1$ substituents are joined to form an unsubstituted aryl (e.g., $C_6$-$C_{10}$ or phenyl). In embodiments, two adjacent -$L^1$-$R^1$ substituents are joined to form an unsubstituted heteroaryl (e.g., 5 to 10 membered, 5 to 9 membered, or 5 to 6 membered).

In embodiments, two adjacent $R^1$ substituents are joined to form a $R^2$-substituted or unsubstituted cycloalkyl (e.g., $C_3$-$C_8$, $C_3$-$C_6$, $C_4$-$C_6$, or $C_5$-$C_6$), $R^2$-substituted or unsubstituted heterocycloalkyl (e.g., 3 to 8 membered, 3 to 6 membered, 4 to 6 membered, 4 to 5 membered, or 5 to 6 membered), $R^2$-substituted or unsubstituted aryl (e.g., $C_6$-$C_{10}$ or phenyl), or $R^2$-substituted or unsubstituted heteroaryl (e.g., 5 to 10 membered, 5 to 9 membered, or 5 to 6 membered). In embodiments, two adjacent $R^1$ substituents are joined to form an unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). In embodiments, two adjacent $R^1$ substituents are joined to form a $R^2$-substituted cycloalkyl (e.g., $C_3$-$C_8$, $C_3$-$C_6$, $C_4$-$C_6$, or $C_5$-$C_6$). In embodiments, two adjacent $R^1$ substituents are joined to form a $R^2$-substituted heterocycloalkyl (e.g., 3 to 8 membered, 3 to 6 membered, 4 to 6 membered, 4 to 5 membered, or 5 to 6 membered). In embodiments, two adjacent $R^1$ substituents are joined to form a $R^2$-substituted aryl (e.g., $C_6$-$C_{10}$ or phenyl). In embodiments, two adjacent $R^1$ substituents are joined to form a $R^2$-substituted heteroaryl (e.g., 5 to 10 membered, 5 to 9 membered, or 5 to 6 membered). In embodiments, two adjacent $R^1$ substituents are joined to form an unsubstituted cycloalkyl (e.g., $C_3$-$C_8$, $C_3$-$C_6$, $C_4$-$C_6$, or $C_5$-$C_6$). In embodiments, two adjacent $R^1$ substituents are joined to form an unsubstituted heterocycloalkyl (e.g., 3 to 8 membered, 3 to 6 membered, 4 to 6 membered, 4 to 5 membered, or 5 to 6 membered). In embodiments, two adjacent $R^1$ substituents are joined to form an unsubstituted aryl (e.g., $C_6$-$C_{10}$ or phenyl). In embodiments, two adjacent $R^1$ substituents are joined to form an unsubstituted heteroaryl (e.g., 5 to 10 membered, 5 to 9 membered, or 5 to 6 membered).

$R^2$ is independently oxo, halogen, —$CX^2_3$, —$CHX^2_2$, —$CH_2X^2$, —$OCX^2_3$, —$OCH_2X^2$, —$OCHX^2_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$N_3$, a bioconjugate linker, a detectable moiety, $R^3$-substituted or unsubstituted alkyl (e.g., $C_1$-$C_8$, $C_1$-$C_6$, $C_1$-$C_4$, or $C_1$-$C_2$), $R^3$-substituted or unsubstituted heteroalkyl (e.g., 2 to 8 membered, 2 to 6 membered, 4 to 6 membered, 2 to 3 membered, or 4 to 5 membered), $R^3$-substituted or unsubstituted cycloalkyl (e.g., $C_3$-$C_8$, $C_3$-$C_6$, $C_4$-$C_6$, or $C_5$-$C_6$), $R^3$-substituted or unsubstituted heterocycloalkyl (e.g., 3 to 8 membered, 3 to 6 membered, 4 to 6 membered, 4 to 5 membered, or 5 to 6 membered), $R^3$-substituted or unsubstituted aryl (e.g., $C_6$-$C_{10}$ or phenyl), or $R^3$-substituted or unsubstituted heteroaryl (e.g., 5 to 10 membered, 5 to 9 membered, or 5 to 6 membered).

In embodiments, $R^2$ is independently oxo, halogen, —$CX^2_3$, —$CHX^2_2$, —$CH_2X^2$, —$OCX^2_3$, —$OCH_2X^2$, —$OCHX^2_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$N_3$, $R^3$-substituted or unsubstituted alkyl (e.g., $C_1$-$C_8$, $C_1$-$C_6$, $C_1$-$C_4$, or $C_1$-$C_2$), $R^3$-substituted or unsubstituted heteroalkyl (e.g., 2 to 8 membered, 2 to 6 membered, 4 to 6 membered, 2 to 3 membered, or 4 to 5 membered), $R^3$-substituted or unsubstituted cycloalkyl (e.g., $C_3$-$C_8$, $C_3$-$C_6$, $C_4$-$C_6$, or $C_5$-$C_6$), $R^3$-substituted or unsubstituted heterocycloalkyl (e.g., 3 to 8 membered, 3 to 6 membered, 4 to 6 membered, 4 to 5 membered, or 5 to 6 membered), $R^3$-substituted or unsubstituted aryl (e.g., $C_6$-$C_{10}$ or phenyl), or $R^3$-substituted or unsubstituted heteroaryl (e.g., 5 to 10 membered, 5 to 9 membered, or 5 to 6 membered).

In embodiments, $R^2$ is independently oxo, halogen, —$CX^2_3$, —$CHX^2_2$, —$CH_2X^2$, —$OCX^2_3$, —$OCH_2X^2$, —$OCHX^2_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, a bioconjugate linker, a detectable moiety, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^2$ is independently —F, —Cl, —Br, or —I. In embodiments, $R^2$ is independently unsubstituted methyl. In embodiments, $R^2$ is independently unsubstituted ethyl. In embodiments, $R^2$ is independently unsubstituted ethynyl. In embodiments, $R^2$ is independently $R^3$-substituted ethynyl. In embodiments, $R^2$ is independently unsubstituted phenyl. In embodiments, $R^2$ is independently $R^3$-substituted phenyl. In embodiments, $R^2$ is independently a detectable moiety. In embodiments, $R^2$ is independently a monovalent rhodamine. In embodiments, $R^2$ is independently a bioconjugate linker (e.g., a covalent linker resulting from a reaction between two bioconjugate reactive moieties, for example $R^2$ may be a covalent linker (e.g., a divalent triazole) resulting from a reaction between an azide and an alkynyl).

$R^3$ is independently oxo, halogen, —$CX^3_3$, —$CHX^3_2$, —$CH_2X^3$, —$OCX^3_3$, —$OCH_2X^3$, —$OCHX^3_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$N_3$, a bioconjugate linker, a detectable moiety, $R^4$-substituted or unsubstituted alkyl (e.g., $C_1$-$C_8$, $C_1$-$C_6$, $C_1$-$C_4$, or $C_1$-$C_2$), $R^4$-substituted or unsubstituted heteroalkyl (e.g., 2 to 8 membered, 2 to 6 membered, 4 to 6 membered, 2 to 3 membered, or 4 to 5 membered), $R^4$-substituted or unsubstituted cycloalkyl (e.g., $C_3$-$C_8$, $C_3$-$C_6$, $C_4$-$C_6$, or $C_5$-$C_6$), $R^4$-substituted or unsubstituted heterocycloalkyl (e.g., 3 to 8 membered, 3 to 6 membered, 4 to 6 membered, 4 to 5 membered, or 5 to 6 membered), $R^4$-substituted or unsubstituted aryl (e.g., $C_6$-$C_{10}$ or phenyl), or $R^4$-substituted or unsubstituted heteroaryl (e.g., 5 to 10 membered, 5 to 9 membered, or 5 to 6 membered).

In embodiments, $R^3$ is independently oxo, halogen, —$CX^3_3$, —$CHX^3_2$, —$CH_2X^3$, —$OCX^3_3$, —$OCH_2X^3$, —$OCHX^3_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$N_3$, $R^4$-substituted or unsubstituted alkyl (e.g., $C_1$-$C_8$, $C_1$-$C_6$, $C_1$-$C_4$, or $C_1$-$C_2$), $R^4$-substituted or unsubstituted heteroalkyl (e.g., 2 to 8 membered, 2 to 6 membered, 4 to 6 membered, 2 to 3 membered, or 4 to 5 membered), $R^4$-substituted or unsubstituted cycloalkyl (e.g., $C_3$-$C_8$, $C_3$-$C_6$, $C_4$-$C_6$, or $C_5$-$C_6$), $R^4$-substituted or unsubstituted heterocycloalkyl (e.g., 3 to 8 membered, 3 to 6 membered, 4 to 6 membered, 4 to 5 membered, or 5 to 6 membered), $R^4$-substituted or unsubstituted aryl (e.g., $C_6$-$C_{10}$ or phenyl), or $R^4$-substituted or unsubstituted heteroaryl (e.g., 5 to 10 membered, 5 to 9 membered, or 5 to 6 membered).

In embodiments, $R^3$ is independently oxo, halogen, —$CX^3_3$, —$CHX^3_2$, —$CH_2X^3$, —$OCX^3_3$, —$OCH_2X^3$, —$OCHX^3_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, a bioconjugate linker, a detectable moiety, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^3$ is independently —F, —Cl, —Br, or —I. In embodiments, $R^3$ is independently unsubstituted methyl. In embodiments, $R^3$ is independently unsubstituted ethyl. In embodiments, $R^3$ is independently $R^4$-substituted ethynyl. In embodiments, $R^3$ is independently unsubstituted ethynyl. In embodiments, $R^3$ is independently —$CF_3$. In embodiments, $R^3$ is independently —F. In embodiments, $R^3$ is independently —CN. In embodiments, $R^3$ is independently —$NO_2$. In embodiments, $R^3$ is independently a detectable moiety. In embodiments, $R^3$ is independently a monovalent rhodamine. In embodiments, $R^3$ is independently a bioconjugate linker (e.g., a covalent linker resulting from a reaction between two bioconjugate reactive moieties, for example $R^3$ may be a covalent linker (e.g., a divalent triazole) resulting from a reaction between an azide and an alkynyl).

$R^4$ is independently oxo, halogen, —$CX^4_3$, —$CHX^4_2$, —$CH_2X^4$, —$OCX^4_3$, —$OCH_2X^4$, —$OCHX^4_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, a detectable moiety, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^4$ is independently —F, —Cl, —Br, or —I. In embodiments, $R^4$ is independently unsubstituted methyl. In embodiments, $R^4$ is independently unsubstituted ethyl. In embodiments, $R^4$ is independently a detectable moiety. In embodiments, $R^4$ is independently a monovalent rhodamine.

In embodiments, n1 is 0. In embodiments, n1 is 1. In embodiments, n1 is 2. In embodiments, n1 is 3. In embodiments, n1 is 4. In embodiments, m1 is 1. In embodiments, m1 is 2. In embodiments, v1 is 1. In embodiments, v1 is 2.

In embodiments, $R^1$ is independently halogen, —$CX^1_3$, —$CHX^1_2$, —$CH_2X^1$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^1_3$, —$OCHX^1_2$, —$OCH_2X^1$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent -$L^1$-$R^1$ substituents may optionally be joined to form a substituted or unsubstituted cycloalkyl, substituted or unsubstituted heterocycloalkyl, substituted or unsubstituted aryl, or substituted or unsubstituted heteroaryl. In embodiments, $R^1$ is independently halogen, —$CX^1_3$, —$CHX^1_2$, —$CH_2X^1$, —CN, —OH, —$NH_2$, —COOH, —$CONH_2$, —$NO_2$, —SH, —$OCX^1_3$, —$OCHX^1_2$, —$OCH_2X^1$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^1$ is independently halogen, —$CX^1_3$, —$CHX^1_2$, —$CH_2X^1$, —CN, —OH, —$NH_2$, —COOH, —$CONH_2$, —$NO_2$, —SH, —$OCX^1_3$, —$OCHX^1_2$, —$OCH_2X^1$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^1$ is independently —CN. In embodiments, $R^1$ is independently unsubstituted isopropyl. In embodiments, $R^1$ is independently halogen. In embodiments, $R^1$ is independently —F. In embodiments, $R^1$ is independently —Cl. In embodiments, $R^1$ is independently —$OCH_3$. In embodiments, $R^1$ is independently unsubstituted cyclohexyl. In embodiments, $R^1$ is independently unsubstituted phenyl. In embodiments, $R^1$ is independently —$CF_3$. In embodiments, $R^1$ is independently —$NO_2$. In embodiments, $R^1$ is independently unsubstituted naphthalenyl. In embodiments, $R^1$ is independently unsubstituted 1-naphthalenyl. In embodiments, $R^1$ is independently unsubstituted 2-naphthalenyl. In embodiments, $R^1$ is independently —$OCF_3$. In embodiments, $R^1$ is independently —$OCHF_2$. In embodiments, $R^1$ is independently —$OCH_2F$. In embodiments, $R^1$ is independently unsubstituted cyclopropyl. In embodiments, $R^1$ is independently unsubstituted cyclobutyl. In embodiments, $R^1$ is independently unsubstituted cyclopentyl. In embodiments, $R^1$ is independently unsubstituted sec-butyl. In embodiments, $R^1$ is independently unsubstituted 2-butyl. In embodiments, $R^1$ is independently —CH($CH_3$)($CH_2CH_3$). In embodiments, $R^1$ is independently —$CH_2CF_3$. In embodiments, $R^1$ is independently —$CH_2CX^1_3$. In embodiments, $R^1$ is independently —CH($CH_3$)($OCH_3$). In embodiments, $R^1$ is independently unsubstituted butyl. In embodiments, $R^1$ is independently unsubstituted n-butyl. In embodiments, $R^1$ is independently unsubstituted n-pentyl. In embodiments, $R^1$ is independently unsubstituted n-hexyl. In embodiments, $R^1$ is independently unsubstituted n-heptyl. In embodiments, $R^1$ is independently unsubstituted n-octyl. In embodiments, $R^1$ is independently unsubstituted 1-pentyl. In embodiments, $R^1$ is independently unsubstituted 1-hexyl. In embodiments, $R^1$ is independently unsubstituted 1-heptyl. In embodiments, $R^1$ is independently unsubstituted 1-octyl. In embodiments, $R^1$ is independently —Br. In embodiments, $R^1$ is independently —$CH_3$. In embodiments, $R^1$ is independently —OCH($CH_3$)$_2$.

In embodiments, $R^1$ is independently halogen, —$CX^1_3$, —$CHX^1_2$, —$CH_2X^1$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^1_3$, —$OCHX^1_2$, —$OCH_2X^1$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent -$L^1$-$R^1$ substituents may optionally be joined to form a substituted or unsubstituted cycloalkyl, substituted or unsubstituted heterocycloalkyl, substituted or unsubstituted aryl, or substituted or unsubstituted heteroaryl. In embodiments, $R^1$ is independently halogen, —$CX^1_3$, —$CHX^1_2$, —$CH_2X^1$, —CN, —OH, —$NH_2$, —COOH, —$CONH_2$, —$NO_2$, —SH, —$OCX^1_3$, —$OCHX^1_2$, —$OCH_2X^1$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^1$ is independently halogen, —$CX^1_3$, —$CHX^1_2$, —$CH_2X^1$, —CN, —OH, —$NH_2$, —COOH, —$CONH_2$, —$NO_2$, —SH, —$OCX^1_3$, —$OCHX^1_2$, —$OCH_2X^1$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^1$ is independently halogen, —$CF_3$, —OH, —SH, —$NHC(O)CH_3$, —$OCH_3$, —$SCH_3$,

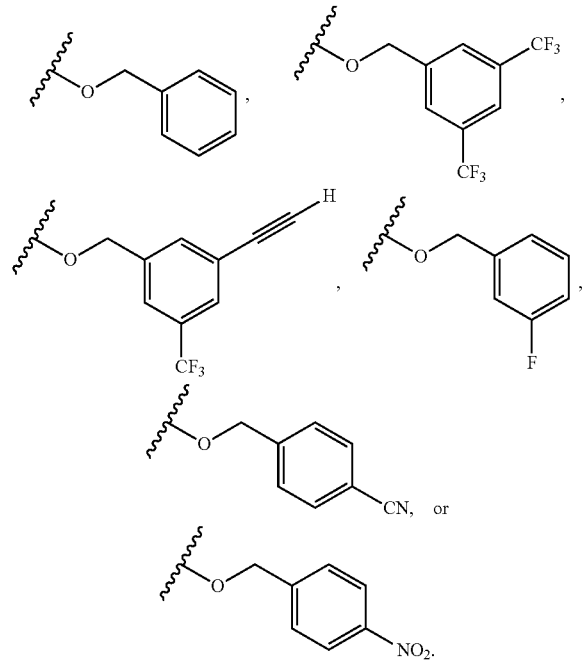

In embodiments, $L^1$ is a bond, —$S(O)_2$—, —NH—, —O—, —S—, —C(O)—, —C(O)NH—, —NHC(O)—, —NHC(O)NH—, —C(O)O—, —OC(O)—, substituted (e.g., substituted with a substituent group, a size-limited substituent group, or lower substituent group) or unsubstituted alkylene (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkylene (e.g., 2 to 8 membered, 2 to 6 membered, or 2 to 4 membered), substituted (e.g., substituted with a substituent group, a size-limited substituent group, or lower substituent group) or unsubstituted cycloalkylene (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkylene (e.g., 3 to 8 membered, 3 to 6 membered, or 5 to 6 membered), substituted (e.g., substituted with a substituent group, a size-limited substituent group, or lower substituent group) or unsubstituted arylene (e.g., $C_6$-$C_{10}$, $C_{10}$, or phenylene), or substituted (e.g., substituted with a substituent group, a size-limited substituent group, or lower substituent group) or unsubstituted heteroarylene (e.g., 5 to 10 membered, 5 to 9 membered, or 5 to 6 membered). In embodiments, $L^1$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene. In embodiments, $L^1$ is a bond, —$S(O)_2$—, —NH—, —O—, —S—, —C(O)—, —C(O)NH—, —NHC(O)—, —NHC(O)NH—, —C(O)O—, —OC(O)—, substituted or unsubstituted alkylene, or substituted or unsubstituted heteroalkylene. In embodiments, $L^1$ is a bond, —O—, —C(O)—, —S—, —NH—, —NHC(O)—, —C(O)NH—, unsubstituted $C_1$-$C_4$ alkylene, or unsubstituted 2 to 4 membered heteroalkylene. In embodiments, $L^1$ is a bond. In embodiments, $L^1$ is —$OCH_2$—. In embodiments, $L^1$ is —NHC(O)—. In embodiments, $L^1$ is —S—. In embodiments, $L^1$ is —O—.

In embodiments, $L^1$ is a bond, —$S(O)_2$—, —NH—, —O—, —S—, —C(O)—, —C(O)NH—, —NHC(O)—, —NHC(O)NH—, —C(O)O—, —OC(O)—, $R^{10}$-substituted or unsubstituted alkylene (e.g., $C_1$-$C_8$ alkylene, $C_1$-$C_6$ alkylene, or $C_1$-$C_4$ alkylene), $R^{10}$-substituted or unsubstituted heteroalkylene (e.g., 2 to 8 membered heteroalkylene, 2 to 6 membered heteroalkylene, or 2 to 4 membered heteroalkylene), $R^{10}$-substituted or unsubstituted cycloalkylene (e.g., $C_3$-$C_8$ cycloalkylene, $C_3$-$C_6$ cycloalkylene, or $C_5$-$C_6$ cycloalkylene), $R^{10}$-substituted or unsubstituted heterocycloalkylene (e.g., 3 to 8 membered heterocycloalkylene, 3 to 6 membered heterocycloalkylene, or 5 to 6 membered heterocycloalkylene), $R^{10}$-substituted or unsubstituted arylene (e.g., $C_6$-$C_{10}$ arylene, $C_{10}$ arylene, or phenylene), or $R^{10}$-substituted or unsubstituted heteroarylene (e.g., 5 to 10 membered heteroarylene, 5 to 9 membered heteroarylene, or 5 to 6 membered heteroarylene).

In embodiments, $L^1$ is a bond, —$S(O)_2$—, —NH—, —O—, —S—, —C(O)—, —C(O)NH—, —NHC(O)—, —NHC(O)NH—, —C(O)O—, —OC(O)—, unsubstituted alkylene (e.g., $C_1$-$C_8$ alkylene, $C_1$-$C_6$ alkylene, or $C_1$-$C_4$ alkylene), unsubstituted heteroalkylene (e.g., 2 to 8 membered heteroalkylene, 2 to 6 membered heteroalkylene, or 2 to 4 membered heteroalkylene), unsubstituted cycloalkylene (e.g., $C_3$-$C_8$ cycloalkylene, $C_3$-$C_6$ cycloalkylene, or $C_5$-$C_6$ cycloalkylene), unsubstituted heterocycloalkylene (e.g., 3 to 8 membered heterocycloalkylene, 3 to 6 membered heterocycloalkylene, or 5 to 6 membered heterocycloalkylene), unsubstituted arylene (e.g., $C_6$-$C_{10}$ arylene, $C_{10}$ arylene, or phenylene), or unsubstituted heteroarylene (e.g., 5 to 10 membered heteroarylene, 5 to 9 membered heteroarylene, or 5 to 6 membered heteroarylene).

In embodiments, $L^1$ is $R^{10}$-substituted or unsubstituted methylene. In embodiments, $L^1$ is $R^{10}$-substituted or unsubstituted $C_2$ alkylene. In embodiments, $L^1$ is $R^{10}$-substituted or unsubstituted $C_3$ alkylene. In embodiments, $L^1$ is $R^{10}$-substituted or unsubstituted $C_4$ alkylene. In embodiments, $L^1$ is $R^{10}$-substituted or unsubstituted $C_5$ alkylene. In embodiments, $L^1$ is $R^{10}$-substituted or unsubstituted $C_6$ alkylene. In embodiments, $L^1$ is $R^{10}$-substituted or unsubstituted $C_7$ alkylene. In embodiments, $L^1$ is $R^{10}$-substituted or unsubstituted $C_8$ alkylene. In embodiments, $L^1$ is $R^{10}$-substituted methylene. In embodiments, $L^1$ is $R^{10}$-substituted $C_2$ alkylene. In embodiments, $L^1$ is $R^{10}$-substituted $C_3$ alkylene. In embodiments, $L^1$ is $R^{10}$-substituted $C_4$ alkylene. In embodiments, $L^1$ is $R^{10}$-substituted $C_5$ alkylene. In embodiments, $L^1$ is $R^{10}$-substituted $C_6$ alkylene. In embodiments, $L^1$ is $R^{10}$-substituted $C_7$ alkylene. In embodiments, $L^1$ is $R^{10}$-substituted $C_8$ alkylene. In embodiments, $L^1$ is an unsubstituted methylene. In embodiments, $L^1$ is an unsubstituted $C_2$ alkylene. In embodiments, $L^1$ is an unsubstituted $C_3$ alkylene. In embodiments, $L^1$ is an unsubstituted $C_4$ alkylene. In embodiments, $L^1$ is an unsubstituted $C_8$ alkylene. In embodiments, $L^1$ is an unsubstituted $C_6$ alkylene. In embodiments, $L^1$ is an unsubstituted $C_7$ alkylene. In embodiments, $L^1$ is an unsubstituted $C_8$ alkylene.

In embodiments, $L^1$ is $R^{10}$-substituted or unsubstituted 2 to 8 membered heteroalkylene. In embodiments, $L^1$ is $R^{10}$-substituted 2 to 8 membered heteroalkylene. In embodiments, $L^1$ is unsubstituted 2 to 8 membered heteroalkylene. In embodiments, $L^1$ is $R^{10}$-substituted or unsubstituted 2 membered heteroalkylene. In embodiments, $L^1$ is $R^{10}$-substituted 2 membered heteroalkylene. In embodiments, $L^1$ is unsubstituted 2 membered heteroalkylene. In embodiments, $L^1$ is $R^{10}$-substituted or unsubstituted 3 membered heteroalkylene. In embodiments, $L^1$ is $R^{10}$-substituted 3 membered heteroalkylene. In embodiments, $L^1$ is unsubstituted 3 membered heteroalkylene. In embodiments, $L^1$ is $R^{10}$-substituted or unsubstituted 4 membered heteroalkylene. In embodiments, $L^1$ is $R^{10}$-substituted 4 membered heteroalkylene. In embodiments, $L^1$ is unsubstituted 4 membered heteroalkylene. In embodiments, $L^1$ is $R^{10}$-substituted or unsubstituted 5 membered heteroalkylene. In embodiments, $L^1$ is $R^{10}$-substituted 5 membered heteroalkylene. In embodiments, $L^1$ is unsubstituted 5 membered heteroalkylene. In embodiments, $L^1$ is $R^{10}$-substituted or unsubstituted 6 membered heteroalkylene. In embodiments, $L^1$ is $R^{10}$-substituted 6 membered heteroalkylene. In embodiments, $L^1$ is unsubstituted 6 membered heteroalkylene. In embodiments, $L^1$ is $R^{10}$-substituted or unsubstituted 7 membered heteroalkylene. In embodiments, $L^1$ is $R^{10}$-substituted 7 membered heteroalkylene. In embodiments, $L^1$ is unsubstituted 7 membered heteroalkylene.

$R^{10}$ is independently oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, X is independently —F. In embodiments, X is independently —Cl. In embodiments, X is independently —Br. In embodiments, X is independently —I. In embodiments, $X^1$ is independently —F. In embodiments, $X^1$ is independently —Cl. In embodiments, $X^1$ is independently —Br. In embodiments, $X^1$ is independently —I.

In embodiments, E is a covalent cysteine modifier moiety. In embodiments, E is

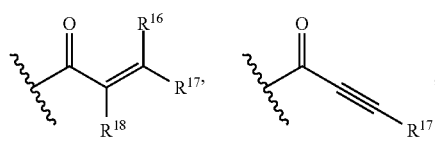

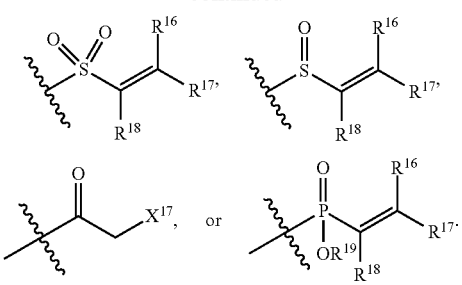

In embodiments, E is

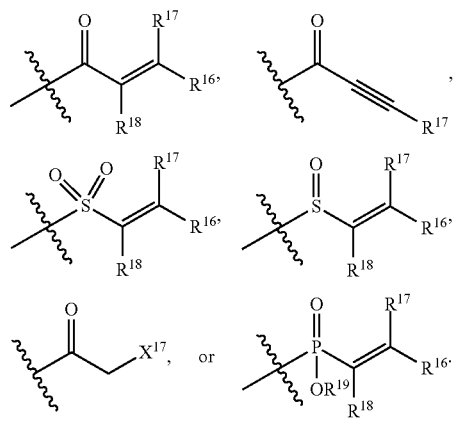

In embodiments, E is

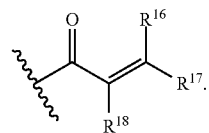

In embodiments, E is

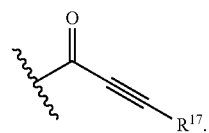

In embodiments, E is

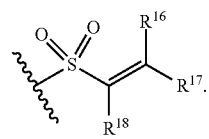

In embodiments, E is

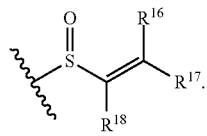

In embodiments, E is

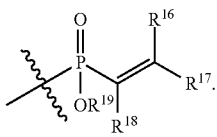

In embodiments, E is

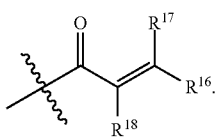

In embodiments, E is

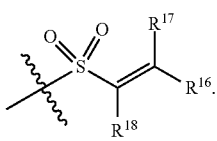

In embodiments, E is

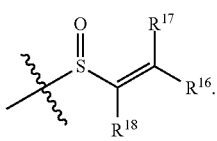

In embodiments, E is

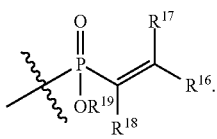

In embodiments, E is

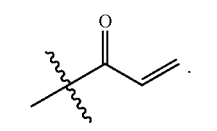 [SMILES: *C(=O)C=C]

In embodiments, E is

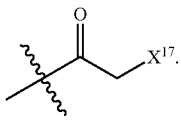

In embodiments, E is

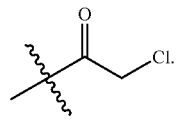 [SMILES: *C(=O)CCl]

In embodiments, E is:

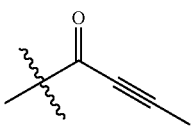

In embodiments, E is:

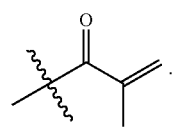 [SMILES: *C(=O)C(=C)C]

In embodiments, E is:

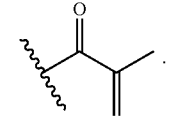 [SMILES: *C(=O)C(=C)C]

$R^{16}$ is independently hydrogen, halogen, $-CX^{16}_3$, $-CHX^{16}_2$, $-CH_2X^{16}$, $-CN$, $-SO_{n16}R^{16A}$, $-SO_{v16}NR^{16A}R^{16B}$, $-NHNR^{16A}R^{16B}$, $-ONR^{16A}R^{16B}$, $-NHC(O)NHNR^{16A}R^{16B}$, $-NHC(O)NR^{16A}R^{16B}$, $-N(O)_{m16}$, $-NR^{16A}R^{16B}$, $-C(O)R^{16A}$, $-C(O)-OR^{16A}$, $-C(O)NR^{16A}R^{16B}$, $-OR^{16A}$, $-NR^{16A}SO_2R^{16B}$, $-NR^{16A}C(O)R^{16B}$, $-NR^{16A}C(O)OR^{16B}$, $-NR^{16A}OR^{16B}$, $-OCX^{16}_3$, $-OCHX^{16}_2$, $-OCH_2X^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl.

$R^{17}$ is independently hydrogen, halogen, $CX^{17}_3$, $-CHX^{17}_2$, $-CH_2X^{17}$, $-CN$, $-SO_{n17}R^{17A}$, $-SO_{v17}NR^{17A}R^{17B}$, $-NHNR^{17A}R^{17B}$, $-ONR^{17A}R^{17B}$, $-NHC(O)NHNR^{17A}R^{17B}$, $-NHC(O)NR^{17A}R^{17B}$, $-N(O)_{m17}$, $-NR^{17A}R^{17B}$, $-C(O)R^{17A}$, $-C(O)-OR^{17A}$, $-C(O)NR^{17A}R^{17B}$, $-OR^{17A}$, $-NR^{17A}SO_2R^{17B}$, $-NR^{17A}C(O)R^{17B}$, $-NR^{17A}C(O)OR^{17B}$, $-NR^{17A}OR^{17B}$, $-OCX^{17}_3$, $-OCHX^{17}_2$, $-OCH_2X^{17}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl.

$R^{18}$ is independently hydrogen, halogen, $CX^{18}_3$, $-CHX^{18}_2$, $-CH_2X^{18}$, $-CN$, $-SO_{n18}R^{18A}$, $-SO_{v18}NR^{18A}R^{18B}$, $-NHNR^{18A}R^{18B}$, $-ONR^{18A}R^{18B}$, $-NHC(O)NHNR^{18A}R^{18B}$, $-NHC(O)NR^{18A}R^{18B}$, $-N(O)_{m18}$, $-NR^{18A}R^{18B}$, $-C(O)R^{18A}$, $-C(O)-OR^{18A}$, $-C(O)NR^{18A}R^{18B}$, $-OR^{18A}$, $-NR^{18A}SO_2R^{18B}$, $-NR^{18A}C(O)R^{18B}$, $-NR^{18A}C(O)OR^{18B}$, $-NR^{18A}OR^{18B}$, $-OCX^{18}_3$, $-OCHX^{18}_2$, $-OCH_2X^{18}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl.

$R^{19}$ is independently hydrogen, halogen, $CX^{19}_3$, $-CHX^{19}_2$, $-CH_2X^{19}$, $-CN$, $-SO_{n19}R^{19A}$, $-SO_{v19}NR^{19A}R^{19B}$, $-NHNR^{19A}R^{19B}$, $-ONR^{19A}R^{19B}$, $-NHC(O)NHNR^{19A}R^{19B}$, $-NHC(O)NR^{19A}R^{19B}$, $-N(O)_{m19}$, $-NR^{19A}R^{19B}$, $-C(O)R^{19A}$, $-C(O)-OR^{19A}$, $-C(O)NR^{19A}R^{19B}$, $-OR^{19A}$, $-NR^{19A}SO_2R^{19B}$, $-NR^{19A}C(O)R^{19B}$, $-NR^{19A}C(O)OR^{19B}$, $-NR^{19A}OR^{19B}$, $-OCX^{19}_3$, $-OCHX^{19}_2$, $-OCH_2X^{19}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl.

$R^{16A}$, $R^{16B}$, $R^{17A}$, $R^{17B}$, $R^{18A}$, $R^{18B}$, $R^{19A}$, and $R^{19B}$ are independently hydrogen, $-CX_3$, $-CHX_2$, $-CH_2X$, $-CN$, $-OH$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{16A}$ and $R^{16B}$ substituents bonded to the same nitrogen atom may optionally be joined to form a substituted or unsubstituted heterocycloalkyl or substituted or unsubstituted heteroaryl; $R^{17A}$ and $R^{17B}$ substituents bonded to the same nitrogen atom may optionally be joined to form a substituted or unsubstituted heterocycloalkyl or substituted or unsubstituted heteroaryl; $R^{18A}$ and $R^{18B}$ substituents bonded to the same nitrogen atom may optionally be joined to form a substituted or unsubstituted heterocycloalkyl or substituted or unsubstituted heteroaryl; $R^{19A}$ and $R^{19B}$ substituents bonded to the same nitrogen atom may optionally be joined to form a substituted or unsubstituted heterocycloalkyl or substituted or unsubstituted heteroaryl. X, $X^{16}$, $X^{17}$, $X^{18}$ and $X^{19}$ is independently $-F$, $-Cl$, $-Br$, or $-I$. The symbols n16, n17, n18, and n19 are independently an integer from 0 to 4. The symbols m16, m17, m18, m19, v16, v17, v18, and v19 are independently 1 or 2.

In embodiments, $R^{16}$ is independently hydrogen, halogen, $CX^{16}_3$, $-CHX^{16}_2$, $-CH_2X^{16}$, $-CN$, $-SO_{n16}R^{16D}$, $-SO_{v16}NR^{16A}R^{16B}$, $-NHNR^{16A}R^{16B}$, $-ONR^{16A}R^{16B}$, $-NHC(O)NHNR^{16A}R^{16B}$, $-NHC(O)NR^{16A}R^{16B}$, $-N(O)_{m16}$, $-NR^{16A}R^{16B}$, $-C(O)R^{16C}$, $-C(O)-OR^{16C}$, $-C(O)NR^{16A}R^{16B}$, $-OR^{16D}$, $-NR^{16A}SO_2R^{16D}$, $-NR^{16A}C(O)R^{16C}$, $-NR^{16A}C(O)OR^{16C}$, $-NR^{16A}OR^{16C}$, $-OCX^{16}_3$, $-OCHX^{16}_2$, $-OCH_2X^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. In embodiments, $R^{17}$ is independently hydrogen, halogen, $CX^{17}_3$, $-CHX^{17}_2$, $-CH_2X^{17}$, $-CN$, $-SO_{n17}R^{17D}$, $-SO_{v17}NR^{17A}R^{17B}$, $-NHNR^{17A}R^{17B}$, $-ONR^{17A}R^{17B}$, $-NHC=(O)NHNR^{17A}R^{17B}$, $-NHC(O)NR^{17A}R^{17B}$, $-N(O)_{m17}$, $-NR^{17A}R^{17B}$, $-C(O)R^{17C}$, $-C(O)-OR^{17C}$, $-C(O)NR^{17A}R^{17B}$, $-OR^{17D}$, $-NR^{17A}SO_2R^{17D}$, $-NR^{17A}C(O)R^{17C}$, $NR^{17A}C(O)OR^{17C}$, $-NR^{17A}OR^{17C}$, $-OCX^{17}_3$, $-OCHX^{17}_2$, $-OCH_2X^{17}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. In embodiments, $R^{18}$ is independently hydrogen, halogen, $CX^{18}_3$, $-CHX^{18}_2$, $-CH_2X^{18}$, $-CN$, $-SO_{n8}R^{18D}$, $-SO_{v18}NR^{18A}R^{18B}$, $-NHNR^{18A}R^{18B}$, $-ONR^{18A}R^{18B}$, $-NHC=(O)NHNR^{18A}R^{18B}$, $-NHC(O)NR^{18A}R^{18B}$, $-N(O)_{m18}$, $-NR^{18A}R^{18B}$, $-C(O)R^{18C}$, $-C(O)-OR^{18C}$, $-C(O)NR^{18A}R^{18B}$, $-OR^{18D}$, $-NR^{18A}SO_2R^{18D}$, $-NR^{18A}C(O)R^{18C}$, $-NR^{18A}C(O)OR^{18C}$, $-NR^{18A}OR^{18C}$, $-OCX^{18}_3$, $-OCHX^{18}_2$, $-OCH_2X^{18}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. In embodiments, $R^{19}$ is independently hydrogen, halogen, $CX^{19}_3$, $-CHX^{19}_2$, $-CH_2X^{19}$, $-CN$, $-SO_{n19}R^{19D}$, $-SO_{v19}NR^{19A}R^{19B}$, $-NHNR^{19A}R^{19B}$, $-ONR^{19A}R^{19B}$, $-NHC=(O)NHNR^{19A}R^{19B}$, $-NHC(O)NR^{19A}R^{19B}$, $-N(O)_{m19}$, $-NR^{19A}R^{19B}$, $-C(O)R^{19C}$, $-C(O)-OR^{19C}$, $-C(O)NR^{19A}R^{19B}$, $-OR^{19D}$, $-NR^{19A}SO_2R^{19D}$, $-NR^{19A}C(O)R^{19C}$, $-NR^{19A}C(O)OR^{19C}$, $-NR^{19A}OR^{19C}$, $-OCX^{19}_3$, $-OCHX^{19}_2$, $-OCH_2X^{19}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $R^{16A}$, $R^{16B}$, $R^{16C}$, $R^{16D}$, $R^{17A}$, $R^{17B}$, $R^{17C}$, $R^{17D}$, $R^{18A}$, $R^{18B}$, $R^{18C}$, $R^{18D}$, $R^{19A}$, $R^{19B}$, $R^{19C}$, $R^{19D}$, are independently hydrogen, halogen, $-CX_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX_3$, $-OCHX_2$, $-OCH_2X$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{16A}$ and $R^{16B}$ substituents bonded to the same nitrogen atom may optionally be joined to form a substituted or unsubstituted heterocycloalkyl or substituted or unsubstituted heteroaryl; $R^{17A}$ and $R^{17B}$ substituents bonded to the same nitrogen atom may optionally be joined to form a substituted or unsubstituted heterocycloalkyl or substituted or unsubstituted heteroaryl; $R^{18A}$ and $R^{18B}$ substituents bonded to the same nitrogen atom may optionally be joined to form a substituted or unsubstituted heterocycloalkyl or substituted or unsubstituted heteroaryl; $R^{19A}$ and $R^{19B}$ substituents bonded to the same nitrogen atom may optionally be joined to form a substituted or unsubstituted heterocycloalkyl or substituted or unsubstituted heteroaryl. Each X, $X^{16}$, $X^{17}$, $X^{18}$ and $X^{19}$ is independently $-F$, $-Cl$, $-Br$, or $-I$. The symbols n16, n17, n18, and n19 are independently an integer from 0 to 4. The symbols m16, m17, m18, m19, v16, v17, v18, and v19 are independently 1 or 2. In embodiments, $R^{18}$ is $-CN$. In embodiments, $R^{16}$ is unsubstituted methyl. In embodiments, $R^{17}$ is unsubstituted methyl. In embodiments, $R^{19}$ is unsubstituted methyl. In embodiments, $R^{18}$ is hydrogen. In embodiments, $R^{16}$ is hydrogen. In embodiments, $R^{17}$ is hydrogen. In embodiments, $R^{19}$ is hydrogen.

X may independently be —F. X may independently be —Cl. X may independently be —Br. X may independently be —I. $X^{16}$ may independently be —F. $X^{16}$ may independently be —Cl. $X^{16}$ may independently be —Br. $X^{16}$ may independently be —I. $X^{17}$ may independently be —F. $X^{17}$ may independently be —Cl. $X^{17}$ may independently be —Br. $X^{17}$ may independently be —I. $X^{18}$ may independently be —F. $X^{18}$ may independently be —Cl. $X^{18}$ may independently be —Br. $X^{18}$ may independently be —I. $X^{19}$ may independently be —F. $X^{19}$ may independently be —Cl. $X^{19}$ may independently be —Br. $X^{19}$ may independently be —I.

n16 may independently be 0. n16 may independently be 1. n16 may independently be 2. n16 may independently be 3. n16 may independently be 4. n17 may independently be 0. n17 may independently be 1. n17 may independently be 2. n17 may independently be 3. n17 may independently be 4. n18 may independently be 0. n18 may independently be 1. n18 may independently be 2. n18 may independently be 3. n18 may independently be 4. n19 may independently be 0. n19 may independently be 1. n19 may independently be 2. n19 may independently be 3. n19 may independently be 4.

v16 may independently be 1. v16 may independently be 2. v17 may independently be 1. v17 may independently be 2. v18 may independently be 1. v18 may independently be 2. v19 may independently be 1. v19 may independently be 2.

m16 may independently be 1. m16 may independently be 2. m17 may independently be 1. m17 may independently be 2. m18 may independently be 1. m18 may independently be 2. m19 may independently be 1. m19 may independently be 2.

In embodiments, $R^{16}$ is hydrogen. In embodiments, $R^{16}$ is halogen. In embodiments, $R^{16}$ is $CX^{16}_3$. In embodiments, $R^{16}$ is —$CHX^{16}_2$. In embodiments, $R^{16}$ is —$CH_2X^{16}$. In embodiments, $R^{16}$ is —CN. In embodiments, $R^{16}$ is —$SO_{n16}R^{16D}$. In embodiments, $R^{16}$ is —$SO_{v16}NR^{16A}R^{16B}$. In embodiments, $R^{16}$ is —$NHNR^{16A}R^{16B}$. In embodiments, $R^{16}$ is —$ONR^{16A}R^{16B}$. In embodiments, $R^{16}$ is —NHC(O)$NHNR^{16A}R^{16B}$. In embodiments, $R^{16}$ is —NHC(O)$NR^{16A}R^{16B}$. In embodiments, $R^{16}$ is —$N(O)_{m16}$. In embodiments, $R^{16}$ is —$NR^{16A}R^{16B}$. In embodiments, $R^{16}$ is —C(O)$R^{16C}$. In embodiments, $R^{16}$ is —C(O)—$OR^{16C}$. In embodiments, $R^{16}$ is —C(O)$NR^{16A}R^{16B}$. In embodiments, $R^{16}$ is —$OR^{16D}$. In embodiments, $R^{16}$ is —$NR^{16A}SO_2R^{16D}$. In embodiments, $R^{16}$ is —$NR^{16A}C(O)R^{16C}$. In embodiments, $R^{16}$ is —$NR^{16A}C(O)OR^{16C}$. In embodiments, $R^{16}$ is —$NR^{16A}OR^{16C}$. In embodiments, $R^{16}$ is —$OCX^{16}_3$. In embodiments, $R^{16}$ is —$OCHX^{16}_2$. In embodiments, $R^{16}$ is —$SO_{n16}R^{16A}$. In embodiments, $R^{16}$ is —$SO_{v16}NR^{16A}R^{16B}$. In embodiments, $R^{16}$ is —$NHNR^{16A}R^{16B}$. In embodiments, $R^{16}$ is —$ONR^{16A}R^{16B}$. In embodiments, $R^{16}$ is —NHC(O)$NHNR^{16A}R^{16B}$. In embodiments, $R^{16}$ is —NHC(O)$NR^{16A}R^{16B}$. In embodiments, $R^{16}$ is —C(O)$R^{16A}$. In embodiments, $R^{16}$ is —C(O)—$OR^{16A}$. In embodiments, $R^{16}$ is —C(O)$NR^{16A}R^{16B}$. In embodiments, $R^{16}$ is —$OR^{16A}$. In embodiments, $R^{16}$ is —$NR^{16A}SO_2R^{16B}$. In embodiments, $R^{16}$ is —$NR^{16A}C(O)R^{16B}$. In embodiments, $R^{16}$ is —$NR^{16A}C(O)OR^{16B}$. In embodiments, $R^{16}$ is —$NR^{16A}OR^{16B}$.

In embodiments, $R^{16}$ is substituted or unsubstituted alkyl. In embodiments, $R^{16}$ is substituted or unsubstituted heteroalkyl. In embodiments, $R^{16}$ is substituted or unsubstituted cycloalkyl. In embodiments, $R^{16}$ is substituted or unsubstituted heterocycloalkyl. In embodiments, $R^{16}$ is substituted or unsubstituted aryl. In embodiments, $R^{16}$ is substituted or unsubstituted heteroaryl. In embodiments, $R^{16}$ is substituted alkyl. In embodiments, $R^{16}$ is substituted heteroalkyl. In embodiments, $R^{16}$ is substituted cycloalkyl. In embodiments, $R^{16}$ is substituted heterocycloalkyl. In embodiments, $R^{16}$ is substituted aryl. In embodiments, $R^{16}$ is substituted heteroaryl. In embodiments, $R^{16}$ is unsubstituted alkyl. In embodiments, $R^{16}$ is unsubstituted heteroalkyl. In embodiments, $R^{16}$ is unsubstituted cycloalkyl. In embodiments, $R^{16}$ is unsubstituted heterocycloalkyl. In embodiments, $R^{16}$ is unsubstituted aryl. In embodiments, $R^{16}$ is unsubstituted heteroaryl. In embodiments, $R^{16}$ is unsubstituted methyl. In embodiments, $R^{16}$ is unsubstituted ethyl. In embodiments, $R^{16}$ is unsubstituted propyl. In embodiments, $R^{16}$ is unsubstituted isopropyl. In embodiments, $R^{16}$ is unsubstituted butyl. In embodiments, $R^{16}$ is unsubstituted tert-butyl. In embodiments, $R^{16}$ is —$CH_2Ph$. In embodiments, $R^{16}$ is independently halogen, —$CX^{16}_3$, —$CHX^{16}_2$, —$CH_2X^{16}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{16}_3$, —$OCHX^{16}_2$, substituted or unsubstituted $C_1$-$C_6$ alkyl, substituted or unsubstituted 2 to 6 membered heteroalkyl, substituted or unsubstituted $C_3$-$C_8$ cycloalkyl, substituted or unsubstituted 3 to 8 membered heterocycloalkyl, substituted or unsubstituted $C_6$ aryl, or substituted or unsubstituted 5 to 6 membered heteroaryl. In embodiments, $R^{16}$ is independently halogen, —$CX^{16}_3$, —$CHX^{16}_2$, —$CH_2X^{16}$, —OH, —SH, —COOH, —$OCX^{16}_3$, —$OCHX^{16}_2$, —$CH_3$, —$CH_2CH_3$, —$OCH_3$, —$OCH_2CH_3$, —$SCH_3$, or —$SCH_2CH_3$. In embodiments, $R^{16}$ is independently halogen or —$OCH_3$. In embodiments, $R^{16}$ is substituted or unsubstituted $C_1$-$C_6$ alkyl. In embodiments, $R^{16}$ is substituted or unsubstituted 2 to 6 membered heteroalkyl. In embodiments, $R^{16}$ is substituted or unsubstituted $C_3$-$C_8$ cycloalkyl. In embodiments, $R^{16}$ is substituted or unsubstituted 3 to 8 membered heterocycloalkyl. In embodiments, $R^{16}$ is substituted or unsubstituted $C_6$ aryl. In embodiments, $R^{16}$ is substituted or unsubstituted 5 to 6 membered heteroaryl. In embodiments, $R^{16}$ is independently halogen. In embodiments, $R^{16}$ is independently —$CX^{16}_3$. In embodiments, $R^{16}$ is independently —$CHX^{16}_2$. In embodiments, $R^{16}$ is independently —$CH_2X^{16}$. In embodiments, $R^{16}$ is independently —OH. In embodiments, $R^{16}$ is independently —SH. In embodiments, $R^{16}$ is independently —COOH. In embodiments, $R^{16}$ is independently —$OCX^{16}_3$. In embodiments, $R^{16}$ is independently —$OCHX^{16}_2$. In embodiments, $R^{16}$ is independently —$CH_3$. In embodiments, $R^{16}$ is independently —$CH_2CH_3$. In embodiments, $R^{16}$ is independently —$OCH_3$. In embodiments, $R^{16}$ is independently —$OCH_2CH_3$. In embodiments, $R^{16}$ is independently —$SCH_3$. In embodiments, $R^{16}$ is independently —$SCH_2CH_3$. In embodiments, $R^{16}$ is independently —Cl or —$OCH_3$. In embodiments, $R^{16}$ is independently halogen, —$CX^{16}_3$, —CN, —OH, —$NH_2$, —COOH, —$CONH_2$, —$NO_2$, —SH, —$OCX^{16}_3$, —$OCHX^{16}_2$, —$CHX^{16}_2$, —$CH_2X^{16}$, substituted or unsubstituted $C_1$-$C_8$ alkyl, or substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted phenyl, or substituted or unsubstituted 5 to 6 membered heteroaryl. In embodiments, $R^{16}$ is independently halogen, —$CX^{16}_3$, —CN, unsubstituted $C_1$-$C_4$ alkyl, or unsubstituted 2 to 4 membered heteroalkyl. In embodiments, $R^{16}$ is independently unsubstituted methyl, unsubstituted ethyl, unsubstituted isopropyl, or unsubstituted tert-butyl. In embodiments, $R^{16}$ is independently unsubstituted methyl. In embodiments, $R^{16}$ is independently unsubstituted ethyl. In embodiments, $R^{16}$ is independently unsubstituted propyl. In embodiments, $R^{16}$ is independently unsubstituted n-propyl. In embodiments, $R^{16}$ is independently unsubstituted isopropyl. In embodiments, $R^{16}$ is independently unsubstituted butyl. In embodiments, $R^{16}$ is independently unsubstituted n-butyl. In embodiments, $R^{16}$ is independently unsubstituted isobutyl. In embodiments, $R^{16}$ is independently unsubstituted tert-butyl. In embodiments, $R^{16}$ is independently unsubstituted pentyl. In embodiments, $R^{16}$ is independently unsubstituted hexyl. In embodiments, $R^{16}$ is independently unsubstituted heptyl. In embodiments, $R^{16}$ is independently unsubstituted octyl. In embodiments, $R^{16}$ is independently —F. In embodiments, $R^{16}$ is independently —Cl. In embodiments, $R^{16}$ is independently —Br. In embodiments, $R^{16}$ is independently —I. In embodiments, $R^{16}$ is independently unsubstituted methoxy. In embodiments, $R^{16}$ is independently unsubstituted ethoxy. In embodiments, $R^{16}$ is independently —$CF_3$. In embodiments, $R^{16}$ is independently —$CCl_3$. In embodiments, $R^{16}$ is an unsubstituted isopropyl. In embodiments, $R^{16}$ is an unsubstituted phenyl. In embodiments, $R^{16}$ is an unsubstituted pyridyl. In embodiments, $R^{16}$ is independently halogen. In embodiments, $R^{16}$ is independently —$CX^{16}_3$. In embodiments, $R^{16}$ is independently —$CHX^{16}_2$. In embodiments, $R^{16}$ is independently —$CH_2X^{16}$. In embodiments, $R^{16}$ is independently —CN. In embodiments, $R^{16}$ is independently —OH. In embodiments, $R^{16}$ is independently —$NH_2$. In embodiments, $R^{16}$ is independently —COOH. In embodiments, $R^{16}$ is independently —$CONH_2$. In embodiments, $R^{16}$ is independently —$NO_2$. In embodiments, $R^{16}$ is independently —SH. In embodiments, $R^{16}$ is independently —$SO_3H$. In embodiments, $R^{16}$ is independently —$SO_4H$. In embodiments, $R^{16}$ is independently —$SO_2NH_2$. In embodiments, $R^{16}$ is independently —$NHNH_2$. In embodiments, $R^{16}$ is independently —$ONH_2$. In embodiments, $R^{16}$ is independently —NHC(O)$NHNH_2$. In embodiments, $R^{16}$ is independently —NHC(O)$NH_2$. In embodiments, $R^{16}$ is independently —$NHSO_2H$. In embodiments, $R^{16}$ is independently —NHC(O)H. In embodiments, $R^{16}$ is independently —NHC(O)OH. In embodiments, $R^{16}$ is independently —NHOH. In embodiments, $R^{16}$ is independently —$OCX^{16}_3$. In embodiments, $R^{16}$ is independently —$OCHX^{16}_2$. In embodiments, $R^{16}$ is independently substituted or unsubstituted alkyl. In embodiments, $R^{16}$ is independently substituted or unsubstituted heteroalkyl. In embodiments, $R^{16}$ is independently substituted or unsubstituted cycloalkyl. In embodiments, $R^{16}$ is independently substituted or unsubstituted heterocycloalkyl. In embodiments, $R^{16}$ is independently substituted or unsubstituted aryl. In embodiments, $R^{16}$ is independently substituted or unsubstituted heteroaryl. In embodiments, $R^{16}$ is independently substituted alkyl. In embodiments, $R^{16}$ is independently substituted heteroalkyl. In embodiments, $R^{16}$ is independently substituted cycloalkyl. In embodiments, $R^{16}$ is independently substituted heterocycloalkyl. In embodiments, $R^{16}$ is independently substituted aryl. In embodiments, $R^{16}$ is independently substituted heteroaryl. In embodiments, $R^{16}$ is independently unsubstituted alkyl. In embodiments, $R^{16}$ is independently unsubstituted heteroalkyl. In embodiments, $R^{16}$ is independently unsubstituted cycloalkyl. In embodiments, $R^{16}$ is independently unsubstituted heterocycloalkyl. In embodiments, $R^{16}$ is independently unsubstituted aryl. In embodiments, $R^{16}$ is independently unsubstituted heteroaryl. In embodiments, $R^{16}$ is independently substituted or unsubstituted $C_1$-$C_8$ alkyl. In embodiments, $R^{16}$ is independently substituted or unsubstituted 2 to 8 membered heteroalkyl. In embodiments, $R^{16}$ is independently substituted or unsubstituted $C_3$-$C_8$ cycloalkyl. In embodiments, $R^{16}$ is independently substituted or unsubstituted 3 to 8 membered heterocycloalkyl. In embodiments, $R^{16}$ is independently substituted or unsubstituted $C_6$-$C_{10}$ aryl. In embodiments, $R^{16}$ is independently substituted or unsubstituted 5 to 10 membered heteroaryl. In embodiments, $R^{16}$ is independently substituted $C_1$-$C_8$ alkyl. In embodiments, $R^{16}$ is independently substituted 2 to 8 membered heteroalkyl. In embodiments, $R^{16}$ is independently substituted $C_3$-$C_8$ cycloalkyl. In embodiments, $R^{16}$ is independently substituted 3 to 8 membered heterocycloalkyl. In embodiments, $R^{16}$ is independently substituted $C_6$-$C_{10}$ aryl. In embodiments, $R^{16}$ is independently substituted 5 to 10 membered heteroaryl. In embodiments, $R^{16}$ is independently unsubstituted $C_1$-$C_8$ alkyl. In embodiments, $R^{16}$ is independently unsubstituted 2 to 8 membered heteroalkyl. In embodiments, $R^{16}$ is independently unsubstituted $C_3$-$C_8$ cycloalkyl. In embodiments, $R^{16}$ is independently unsubstituted 3 to 8 membered heterocycloalkyl. In embodiments, $R^{16}$ is independently unsubstituted $C_6$-$C_{10}$ aryl. In embodiments, $R^{16}$ is independently unsubstituted 5 to 10 membered heteroaryl. In embodiments, $R^{16}$ is independently substituted or unsubstituted $C_1$-$C_4$ alkyl. In embodiments, $R^{16}$ is independently substituted or unsubstituted 2 to 4 membered heteroalkyl. In embodiments, $R^{16}$ is independently substituted or unsubstituted $C_3$-$C_6$ cycloalkyl. In embodiments, $R^{16}$ is independently substituted or unsubstituted 3 to 6 membered heterocycloalkyl. In embodiments, $R^{16}$ is independently substituted or unsubstituted phenyl. In embodiments, $R^{16}$ is independently substituted or unsubstituted 5 to 6 membered heteroaryl. In embodiments, $R^{16}$ is independently substituted $C_1$-$C_4$ alkyl. In embodiments, $R^{16}$ is independently substituted 2 to 4 membered heteroalkyl. In embodiments, $R^{16}$ is independently substituted $C_3$-$C_6$ cycloalkyl. In embodiments, $R^{16}$ is independently substituted 3 to 6 membered heterocycloalkyl. In embodiments, $R^{16}$ is independently substituted phenyl. In embodiments, $R^{16}$ is independently substituted 5 to 6 membered heteroaryl. In embodiments, $R^{16}$ is independently unsubstituted $C_1$-$C_4$ alkyl. In embodiments, $R^{16}$ is independently unsubstituted 2 to 4 membered heteroalkyl. In embodiments, $R^{16}$ is independently unsubstituted $C_3$-$C_6$ cycloalkyl. In embodiments, $R^{16}$ is independently unsubstituted 3 to 6 membered heterocycloalkyl. In embodiments, $R^{16}$ is independently unsubstituted phenyl. In embodiments, $R^{16}$ is independently unsubstituted 5 to 6 membered heteroaryl.

In embodiments, $R^{16A}$ is hydrogen. In embodiments, $R^{16A}$ is —$CX_3$. In embodiments, $R^{16A}$ is —CN. In embodiments, $R^{16A}$ is —COOH. In embodiments, $R^{16A}$ is —$CONH_2$. In embodiments, $R^{16A}$ is —$CHX_2$. In embodiments, $R^{16A}$ is —$CH_2X$. In embodiments, $R^{16A}$ is unsubstituted methyl. In embodiments, $R^{16A}$ is unsubstituted ethyl. In embodiments, $R^{16A}$ is unsubstituted propyl. In embodiments, $R^{16A}$ is unsubstituted isopropyl. In embodiments, $R^{16A}$ is unsubstituted butyl. In embodiments, $R^{16A}$ is unsubstituted tert-butyl.

In embodiments, $R^{16B}$ is hydrogen. In embodiments, $R^{16B}$ is —$CX_3$. In embodiments, $R^{16B}$ is —CN. In embodiments, $R^{16B}$ is —COOH. In embodiments, $R^{16B}$ is —$CONH_2$. In embodiments, $R^{16B}$ is —$CHX_2$. In embodiments, $R^{16B}$ is —$CH_2X$. In embodiments, $R^{16B}$ is unsubstituted methyl. In embodiments, $R^{16B}$ is unsubstituted ethyl. In embodiments, $R^{16B}$ is unsubstituted propyl. In embodiments, $R^{16B}$ is unsubstituted isopropyl. In embodiments, $R^{16B}$ is unsubstituted butyl. In embodiments, $R^{16B}$ is unsubstituted tert-butyl.

In embodiments, $R^{16C}$ is hydrogen. In embodiments, $R^{16C}$ is —$CX_3$. In embodiments, $R^{16C}$ is —CN. In embodiments, $R^{16C}$ is —COOH. In embodiments, $R^{16C}$ is —$CONH_2$. In embodiments, $R^{16C}$ is —$CHX_2$. In embodiments, $R^{16C}$ is —$CH_2X$. In embodiments, $R^{16C}$ is unsubstituted methyl. In embodiments, $R^{16C}$ is unsubstituted ethyl. In embodiments, $R^{16C}$ is unsubstituted propyl. In embodiments, $R^{16C}$ is unsubstituted isopropyl. In embodiments, $R^{16C}$ is unsubstituted butyl. In embodiments, $R^{16C}$ is unsubstituted tert-butyl.

In embodiments, $R^{16D}$ is hydrogen. In embodiments, $R^{16D}$ is —$CX_3$. In embodiments, $R^{16D}$ is —CN. In embodiments, $R^{16D}$ is —COOH. In embodiments, $R^{16D}$ is —$CONH_2$. In embodiments, $R^{16D}$ is —$CHX_2$. In embodiments, $R^{16D}$ is —$CH_2X$. In embodiments, $R^{16D}$ is unsubstituted methyl. In embodiments, $R^{16D}$ is unsubstituted ethyl. In embodiments, $R^{16D}$ is unsubstituted propyl. In embodiments, $R^{16D}$ is unsubstituted isopropyl. In embodiments, $R^{16D}$ is unsubstituted butyl. In embodiments, $R^{16D}$ is unsubstituted tert-butyl.

In embodiments, $R^{16}$, $R^{16A}$, $R^{16B}$, $R^{16C}$, and $R^{16D}$ are each independently hydrogen, halogen, —$CF_3$, —$CI_3$, —$CI_3$, —$CBr_3$, —$CHF_2$, —$CHCl_2$, —$CHI_2$, —$CHBr_2$, —$OCH_2F$, —$OCH_2Cl$, —$OCH_2I$, —$OCH_2Br$, —$OCHF_2$, —$CHCl_2$, —$OCHI_2$, —$OCHBr_2$, —$OCF_3$, —$OCl_3$, —$OCI_3$, —$OCBr_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, $R^{75}$-substituted or unsubstituted alkyl (e.g., $C_1$-$C_8$, $C_1$-$C_6$, $C_1$-$C_4$, or $C_1$-$C_2$), $R^{75}$-substituted or unsubstituted heteroalkyl (e.g., 2 to 8 membered, 2 to 6 membered, 4 to 6 membered, 2 to 3 membered, or 4 to 5 membered), $R^{75}$-substituted or unsubstituted cycloalkyl (e.g., $C_3$-$C_8$, $C_3$-$C_6$, $C_4$-$C_6$, or $C_5$-$C_6$), $R^{75}$-substituted or unsubstituted heterocycloalkyl (e.g., 3 to 8 membered, 3 to 6 membered, 4 to 6 membered, 4 to 5 membered, or 5 to 6 membered), $R^{75}$-substituted or unsubstituted aryl (e.g., $C_6$-$C_{10}$ or phenyl), or $R^{75}$-substituted or unsubstituted heteroaryl (e.g., 5 to 10 membered, 5 to 9 membered, or 5 to 6 membered).

In embodiments, $R^{16}$, $R^{16A}$, $R^{16B}$, $R^{16C}$, and $R^{16D}$ are each independently hydrogen, halogen, —$CF_3$, —$CI_3$, —$CI_3$, —$CBr_3$, —$CHF_2$, —$CHCl_2$, —$CHI_2$, —$CHBr_2$, —$OCH_2F$, —$OCH_2Cl$, —$OCH_2I$, —$OCH_2Br$, —$OCHF_2$, —$CHCl_2$, —$OCHI_2$, —$OCHBr_2$, —$OCF_3$, —$OCl_3$, —$OCI_3$, —$OCBr_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). In embodiments, $R^{16}$, $R^{16A}$, $R^{16B}$, $R^{16C}$, and $R^{16D}$ are each independently hydrogen. In embodiments, $R^{16}$, $R^{16A}$, $R^{16B}$, $R^{16C}$, and $R^{16D}$ are each independently unsubstituted methyl. In embodiments, $R^{16}$, $R^{16A}$, $R^{16B}$, $R^{16C}$, and $R^{16D}$ are each independently unsubstituted ethyl.

$R^{75}$ is independently oxo, halogen, —$CX^{75}_3$, —$CHX^{75}_2$, —$CH_2X^{75}$, —$OCX^{75}_3$, —$OCH_2X^{75}$, —$OCHX^{75}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{75}$ is independently —F, —Cl, —Br, or —I. In embodiments, $R^{75}$ is independently unsubstituted methyl. In embodiments, $R^{75}$ is independently unsubstituted ethyl.

In embodiments, $R^{17}$ is hydrogen. In embodiments, $R^{17}$ is halogen. In embodiments, $R^{17}$ is $CX^{17}_3$. In embodiments, $R^{17}$ is —$CHX^{17}_2$. In embodiments, $R^{17}$ is —$CH_2X^{17}$. In embodiments, $R^{17}$ is —CN. In embodiments, $R^{17}$ is —$SO_{n17}R^{17D}$. In embodiments, $R^{17}$ is —$SO_{v17}NR^{17A}R^{17B}$. In embodiments, $R^{17}$ is —$NHNR^{17A}R^{17B}$. In embodiments, $R^{17}$ is —$ONR^{17A}R^{17B}$. In embodiments, $R^{17}$ is —NHC=(O)$NHNR^{17A}R^{17B}$. In embodiments, $R^{17}$ is —NHC(O) $NR^{17A}R^{17B}$. In embodiments, $R^{17}$ is —$N(O)_{m17}$. In embodiments, $R^{17}$ is —$NR^{17A}R^{17B}$. In embodiments, $R^{17}$ is —C(O) $R^{17C}$. In embodiments, $R^{17}$ is —C(O)—$OR^{17C}$. In embodiments, $R^{17}$ is —C(O)$NR^{17A}R^{17B}$. In embodiments, $R^{17}$ is —$OR^{17D}$. In embodiments, $R^{17}$ is —$NR^{17A}SO_2R^{17D}$. In embodiments, $R^{17}$ is —$NR^{17A}C(O)R^{17C}$. In embodiments, $R^{17}$ is —$NR^{17A}C(O)OR^{17C}$. In embodiments, $R^{17}$ is —$NR^{17A}OR^{17C}$. In embodiments, $R^{17}$ is —$OCX^{17}_3$. In embodiments, $R^{17}$ is —$OCHX^{17}_2$. In embodiments, $R^{17}$ is —$SO_{n17}R^{17A}$. In embodiments, $R^{17}$ is —$SO_{v17}NR^{17A}R^{17B}$. In embodiments, $R^{17}$ is —$NHNR^{17A}R^{17B}$. In embodiments, $R^{17}$ is —$ONR^{17A}R^{17B}$. In embodiments, $R^{17}$ is —NHC(O) $NHNR^{17A}R^{17B}$. In embodiments, $R^{17}$ is —NHC(O) $NR^{17A}R^{17B}$. In embodiments, $R^{17}$ is —$N(O)_{m17}$. In embodiments, $R^{17}$ is —$NR^{17A}R^{17B}$. In embodiments, $R^{17}$ is —C(O) $R^{17A}$. In embodiments, $R^{17}$ is —C(O)—$OR^{17A}$. In embodiments, $R^{17}$ is —C(O)$NR^{17A}R^{17B}$. In embodiments, $R^{17}$ is —$OR^{17A}$. In embodiments, $R^{17}$ is —$NR^{17A}SO_2R^{17B}$. In embodiments, $R^{17}$ is —$NR^{17A}C(O)R^{17B}$ In embodiments, $R^{17}$ is —$NR^{17A}C(O)OR^{17B}$. In embodiments, $R^{17}$ is —$NR^{17A}OR^{17B}$.

In embodiments, $R^{17}$ is substituted or unsubstituted alkyl. In embodiments, $R^{17}$ is substituted or unsubstituted heteroalkyl. In embodiments, $R^{17}$ is substituted or unsubstituted cycloalkyl. In embodiments, $R^{17}$ is substituted or unsubstituted heterocycloalkyl. In embodiments, $R^{17}$ is substituted or unsubstituted aryl. In embodiments, $R^{17}$ is substituted or unsubstituted heteroaryl. In embodiments, $R^{17}$ is substituted alkyl. In embodiments, $R^{17}$ is substituted heteroalkyl. In embodiments, $R^{17}$ is substituted cycloalkyl. In embodiments, $R^{17}$ is substituted heterocycloalkyl. In embodiments, $R^{17}$ is substituted aryl. In embodiments, $R^{17}$ is substituted heteroaryl. In embodiments, $R^{17}$ is unsubstituted alkyl. In embodiments, $R^{17}$ is unsubstituted heteroalkyl. In embodiments, $R^{17}$ is unsubstituted cycloalkyl. In embodiments, $R^{17}$ is unsubstituted heterocycloalkyl. In embodiments, $R^{17}$ is unsubstituted aryl. In embodiments, $R^{17}$ is unsubstituted heteroaryl. In embodiments, $R^{17}$ is unsubstituted methyl. In embodiments, $R^{17}$ is unsubstituted ethyl. In embodiments, $R^{17}$ is unsubstituted propyl. In embodiments, $R^{17}$ is unsubstituted isopropyl. In embodiments, $R^{17}$ is unsubstituted butyl. In embodiments, $R^{17}$ is unsubstituted tert-butyl. In embodiments, $R^{17}$ is —CH$_2$Ph.

In embodiments, $R^{17A}$ is hydrogen. In embodiments, $R^{17A}$ is —CX$_3$. In embodiments, $R^{17A}$ is —CN. In embodiments, $R^{17A}$ is —COOH. In embodiments, $R^{17A}$ is —CONH$_2$. In embodiments, $R^{17A}$ is —CHX$_2$. In embodiments, $R^{17A}$ is —CH$_2$X. In embodiments, $R^{17A}$ is unsubstituted methyl. In embodiments, $R^{17A}$ is unsubstituted ethyl. In embodiments, $R^{17A}$ is unsubstituted propyl. In embodiments, $R^{17A}$ is unsubstituted isopropyl. In embodiments, $R^{17A}$ is unsubstituted butyl. In embodiments, $R^{17A}$ is unsubstituted tert-butyl.

In embodiments, $R^{17B}$ is hydrogen. In embodiments, $R^{17B}$ is —CX$_3$. In embodiments, $R^{17B}$ is —CN. In embodiments, $R^{17B}$ is —COOH. In embodiments, $R^{17B}$ is —CONH$_2$. In embodiments, $R^{17B}$ is —CHX$_2$. In embodiments, $R^{17B}$ is —CH$_2$X. In embodiments, $R^{17B}$ is unsubstituted methyl. In embodiments, $R^{17B}$ is unsubstituted ethyl. In embodiments, $R^{17B}$ is unsubstituted propyl. In embodiments, $R^{17B}$ is unsubstituted isopropyl. In embodiments, $R^{17B}$ is unsubstituted butyl. In embodiments, $R^{17B}$ is unsubstituted tert-butyl.

In embodiments, $R^{17C}$ is hydrogen. In embodiments, $R^{17C}$ is —CX$_3$. In embodiments, $R^{17C}$ is —CN. In embodiments, $R^{17C}$ is —COOH. In embodiments, $R^{17C}$ is —CONH$_2$. In embodiments, $R^{17C}$ is —CHX$_2$. In embodiments, $R^{17C}$ is —CH$_2$X. In embodiments, $R^{17C}$ is unsubstituted methyl. In embodiments, $R^{17C}$ is unsubstituted ethyl. In embodiments, $R^{17C}$ is unsubstituted propyl. In embodiments, $R^{17C}$ is unsubstituted isopropyl. In embodiments, $R^{17C}$ is unsubstituted butyl. In embodiments, $R^{17C}$ is unsubstituted tert-butyl.

In embodiments, $R^{17D}$ is hydrogen. In embodiments, $R^{17D}$ is —CX$_3$. In embodiments, $R^{17D}$ is —CN. In embodiments, $R^{17D}$ is —COOH. In embodiments, $R^{17D}$ is —CONH$_2$. In embodiments, $R^{17D}$ is —CHX$_2$. In embodiments, $R^{17D}$ is —CH$_2$X. In embodiments, $R^{17D}$ is unsubstituted methyl. In embodiments, $R^{17D}$ is unsubstituted ethyl. In embodiments, $R^{17D}$ is unsubstituted propyl. In embodiments, $R^{17D}$ is unsubstituted isopropyl. In embodiments, $R^{17D}$ is unsubstituted butyl. In embodiments, $R^{17D}$ is unsubstituted tert-butyl.

In embodiments, $R^{17}$, $R^{17A}$, $R^{17B}$, $R^{17C}$, and $R^{17D}$ are each independently hydrogen, halogen, —CF$_3$, —CI$_3$, —CI$_3$, —CBr$_3$, —CHF$_2$, —CHCl$_2$, —CHI$_2$, —CHBr$_2$, —OCH$_2$F, —OCH$_2$Cl, —OCH$_2$I, —OCH$_2$Br, —OCHF$_2$, —CHCl$_2$, —OCHI$_2$, —OCHBr$_2$, —OCF$_3$, —OCl$_3$, —OCI$_3$, —OCBr$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O)NHNH$_2$, —NHC═(O) NH$_2$, —NHSO$_2$H, —NHC═(O)H, —NHC(O)—OH, —NHOH, $R^{76}$-substituted or unsubstituted alkyl (e.g., $C_1$-$C_8$, $C_1$-$C_6$, $C_1$-$C_4$, or $C_1$-$C_2$), $R^{76}$-substituted or unsubstituted heteroalkyl (e.g., 2 to 8 membered, 2 to 6 membered, 4 to 6 membered, 2 to 3 membered, or 4 to 5 membered), $R^{76}$-substituted or unsubstituted cycloalkyl (e.g., $C_3$-$C_8$, $C_3$-$C_6$, $C_4$-$C_6$, or $C_5$-$C_6$), $R^{76}$-substituted or unsubstituted heterocycloalkyl (e.g., 3 to 8 membered, 3 to 6 membered, 4 to 6 membered, 4 to 5 membered, or 5 to 6 membered), $R^{76}$-substituted or unsubstituted aryl (e.g., $C_6$-$C_{10}$ or phenyl), or $R^{76}$-substituted or unsubstituted heteroaryl (e.g., 5 to 10 membered, 5 to 9 membered, or 5 to 6 membered).

In embodiments, $R^{17}$, $R^{17A}$, $R^{17B}$, $R^{17C}$, and $R^{17D}$ are each independently hydrogen, halogen, —CF$_3$, —CI$_3$, —CI$_3$, —CBr$_3$, —CHF$_2$, —CHCl$_2$, —CHI$_2$, —CHBr$_2$, —OCH$_2$F, —OCH$_2$Cl, —OCH$_2$I, —OCH$_2$Br, —OCHF$_2$, —CHCl$_2$, —OCHI$_2$, —OCHBr$_2$, —OCF$_3$, —OCl$_3$, —OCI$_3$, —OCBr$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O)NHNH$_2$, —NHC═(O) NH$_2$, —NHSO$_2$H, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). In embodiments, $R^{17}$, $R^{17A}$, $R^{17B}$, $R^{17C}$, and $R^{17D}$ are each independently hydrogen. In embodiments, $R^{17}$, $R^{17A}$, $R^{17B}$, $R^{17C}$, and $R^{17D}$ are each independently unsubstituted methyl. In embodiments, $R^{17}$, $R^{17A}$, $R^{17B}$, $R^{17C}$, and $R^{17D}$ are each independently unsubstituted ethyl.

$R^{76}$ is independently oxo, halogen, —CX$^{76}_3$, —CHX$^{76}_2$, —CH$_2$X$^{76}$, —OCX$^{76}_3$, —OCH$_2$X$^{76}$, —OCHX$^{76}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O)NHNH$_2$, —NHC═(O) NH$_2$, —NHSO$_2$H, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{76}$ is independently —F, —Cl, —Br, or —I. In embodiments, $R^{76}$ is independently unsubstituted methyl. In embodiments, $R^{76}$ is independently unsubstituted ethyl.

In embodiments, $R^{18}$ is hydrogen. In embodiments, $R^{18}$ is halogen. In embodiments, $R^{18}$ is CX$^{18}_3$. In embodiments, $R^{18}$ is —CHX$^{18}_2$. In embodiments, $R^{18}$ is —CH$_2$X$^{18}$. In embodiments, $R^{18}$ is —CN. In embodiments, $R^{18}$ is —SO$_{n18}$R$^{18D}$. In embodiments, $R^{18}$ is —SO$_{v18}$NR$^{18A}$R$^{18B}$. In embodiments, $R^{18}$ is —NHNR$^{18A}$R$^{18B}$. In embodiments, $R^{18}$ is —ONR$^{18A}$R$^{18B}$. In embodiments, $R^{18}$ is —NHC═(O)NHNR$^{18A}$R$^{18B}$. In embodiments, $R^{18}$ is —NHC(O)NR$^{18A}$R$^{18B}$. In embodiments, $R^{18}$ is —N(O)$_{m8}$. In embodiments, $R^{18}$ is —NR$^{18A}$R$^{18B}$. In embodiments, $R^{18}$ is —C(O)R$^{18C}$. In embodiments, $R^{18}$ is —C(O)—OR$^{18C}$. In embodiments, $R^{18}$ is —C(O)NR$^{18A}$R$^{18B}$. In embodiments, $R^{18}$ is —OR$^{18D}$. In embodiments, $R^{18}$ is —NR$^{18A}$SO$_2$R$^{18D}$. In embodiments, $R^{18}$ is —NR$^{18A}$C(O)R$^{18C}$. In embodiments, $R^{18}$ is —NR$^{18A}$C(O)OR$^{18C}$. In embodiments, $R^{18}$ is —NR$^{18A}$OR$^{18C}$. In embodiments, $R^{18}$ is —OCX$^{18}_3$. In embodiments, $R^{18}$ is —OCHX$^{18}_2$. In embodiments, $R^{18}$ is —SO$_{n18}$R$^{18A}$. In embodiments, $R^{18}$ is —SO$_{v18}$NR$^{18A}$R$^{18B}$. In embodiments, $R^{18}$ is —NHNR$^{18A}$R$^{18B}$. In embodiments, $R^{18}$ is —ONR$^{18A}$R$^{18B}$. In embodiments, $R^{18}$ is —NHC(O) NHNR$^{18A}$R$^{18B}$. In embodiments, $R^{18}$ is —NHC(O) NR$^{18A}$R$^{18B}$. In embodiments, $R^{18}$ is —N(O)$_{m18}$. In embodiments, $R^{18}$ is —NR$^{18A}$R$^{18B}$. In embodiments, $R^8$ is —C(O) R$^{18A}$. In embodiments, $R^{18}$ is —C(O)—OR$^{18A}$. In embodiments, $R^{18}$ is —C(O)NR$^{18A}$R$^{18B}$. In embodiments, $R^{18}$ is —$OR^{18A}$. In embodiments, $R^{18}$ is —$NR^{18A}SO_2R^{18B}$. In embodiments, $R^{18}$ is —$NR^{18A}C(O)R^{18B}$ In embodiments, $R^{18}$ is —$NR^{18A}C(O)OR^{18B}$. In embodiments, $R^{18}$ is —$NR^{18A}OR^{18B}$.

In embodiments, $R^{18}$ is substituted or unsubstituted alkyl. In embodiments, $R^{18}$ is substituted or unsubstituted heteroalkyl. In embodiments, $R^{18}$ is substituted or unsubstituted cycloalkyl. In embodiments, $R^{18}$ is substituted or unsubstituted heterocycloalkyl. In embodiments, $R^{18}$ is substituted or unsubstituted aryl. In embodiments, $R^{18}$ is substituted or unsubstituted heteroaryl. In embodiments, $R^{18}$ is substituted alkyl. In embodiments, $R^{18}$ is substituted heteroalkyl. In embodiments, $R^{18}$ is substituted cycloalkyl. In embodiments, $R^{18}$ is substituted heterocycloalkyl. In embodiments, $R^{18}$ is substituted aryl. In embodiments, $R^8$ is substituted heteroaryl. In embodiments, $R^{18}$ is unsubstituted alkyl. In embodiments, $R^{18}$ is unsubstituted heteroalkyl. In embodiments, $R^{18}$ is unsubstituted cycloalkyl. In embodiments, $R^{18}$ is unsubstituted heterocycloalkyl. In embodiments, $R^{18}$ is unsubstituted aryl. In embodiments, $R^{18}$ is unsubstituted heteroaryl. In embodiments, $R^{18}$ is unsubstituted methyl. In embodiments, $R^{18}$ is unsubstituted ethyl. In embodiments, $R^{18}$ is unsubstituted propyl. In embodiments, $R^{18}$ is unsubstituted isopropyl. In embodiments, $R^{18}$ is unsubstituted butyl. In embodiments, $R^{18}$ is unsubstituted tert-butyl. In embodiments, $R^{18}$ is —$CH_2Ph$.

In embodiments, $R^{18A}$ is hydrogen. In embodiments, $R^{18A}$ is —$CX_3$. In embodiments, $R^{18A}$ is —CN. In embodiments, $R^{18A}$ is —COOH. In embodiments, $R^{18A}$ is —$CONH_2$. In embodiments, $R^{18A}$ is —$CHX_2$. In embodiments, $R^{18A}$ is —$CH_2X$. In embodiments, $R^{18A}$ is unsubstituted methyl. In embodiments, $R^{18A}$ is unsubstituted ethyl. In embodiments, $R^{18A}$ is unsubstituted propyl. In embodiments, $R^{18A}$ is unsubstituted isopropyl. In embodiments, $R^{18A}$ is unsubstituted butyl. In embodiments, $R^{18A}$ is unsubstituted tert-butyl.

In embodiments, $R^{18B}$ is hydrogen. In embodiments, $R^{18B}$ is —$CX_3$. In embodiments, $R^{18B}$ is —CN. In embodiments, $R^{18B}$ is —COOH. In embodiments, $R^{18B}$ is —$CONH_2$. In embodiments, $R^{18B}$ is —$CHX_2$. In embodiments, $R^{18B}$ is —$CH_2X$. In embodiments, $R^{18B}$ is unsubstituted methyl. In embodiments, $R^{18B}$ is unsubstituted ethyl. In embodiments, $R^{18B}$ is unsubstituted propyl. In embodiments, $R^{18B}$ is unsubstituted isopropyl. In embodiments, $R^{18B}$ is unsubstituted butyl. In embodiments, $R^{18B}$ is unsubstituted tert-butyl.

In embodiments, $R^{18C}$ is hydrogen. In embodiments, $R^{18C}$ is —$CX_3$. In embodiments, $R^{18C}$ is —CN. In embodiments, $R^{18C}$ is —COOH. In embodiments, $R^{18C}$ is —$CONH_2$. In embodiments, $R^{18C}$ is —$CHX_2$. In embodiments, $R^{18C}$ is —$CH_2X$. In embodiments, $R^{18C}$ is unsubstituted methyl. In embodiments, $R^{18C}$ is unsubstituted ethyl. In embodiments, $R^{18C}$ is unsubstituted propyl. In embodiments, $R^{18C}$ is unsubstituted isopropyl. In embodiments, $R^{18C}$ is unsubstituted butyl. In embodiments, $R^{18C}$ is unsubstituted tert-butyl.

In embodiments, $R^{18D}$ is hydrogen. In embodiments, $R^{18D}$ is —$CX_3$. In embodiments, $R^{18D}$ is —CN. In embodiments, $R^{18D}$ is —COOH. In embodiments, $R^{18D}$ is —$CONH_2$. In embodiments, $R^{18D}$ is —$CHX_2$. In embodiments, $R^{18D}$ is —$CH_2X$. In embodiments, $R^{18D}$ is unsubstituted methyl. In embodiments, $R^{18D}$ is unsubstituted ethyl. In embodiments, $R^{18D}$ is unsubstituted propyl. In embodiments, $R^{18D}$ is unsubstituted isopropyl. In embodiments, $R^{18D}$ is unsubstituted butyl. In embodiments, $R^{18D}$ is unsubstituted tert-butyl.

In embodiments, $R^{18}$, $R^{18A}$, $R^{18B}$, $R^{18C}$, and $R^{18D}$ are each independently hydrogen, halogen, —$CF_3$, —$CI_3$, —$CI_3$, —$CBr_3$, —$CHF_2$, —$CHCl_2$, —$CHI_2$, —$CHBr_2$, —$OCH_2F$, —$OCH_2Cl$, —$OCH_2I$, —$OCH_2Br$, —$OCHF_2$, —$CHCl_2$, —$OCHI_2$, —$OCHBr_2$, —$OCF_3$, —$OCl_3$, —$OCI_3$, —$OCBr_3$,
—CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, $R^{77}$-substituted or unsubstituted alkyl (e.g., $C_1$-$C_8$, $C_1$-$C_6$, $C_1$-$C_4$, or $C_1$-$C_2$), $R^{77}$-substituted or unsubstituted heteroalkyl (e.g., 2 to 8 membered, 2 to 6 membered, 4 to 6 membered, 2 to 3 membered, or 4 to 5 membered), $R^{77}$-substituted or unsubstituted cycloalkyl (e.g., $C_3$-$C_8$, $C_3$-$C_6$, $C_4$-$C_6$, or $C_5$-$C_6$), $R^{77}$-substituted or unsubstituted heterocycloalkyl (e.g., 3 to 8 membered, 3 to 6 membered, 4 to 6 membered, 4 to 5 membered, or 5 to 6 membered), $R^{77}$-substituted or unsubstituted aryl (e.g., $C_6$-$C_{10}$ or phenyl), or $R^{77}$-substituted or unsubstituted heteroaryl (e.g., 5 to 10 membered, 5 to 9 membered, or 5 to 6 membered).

In embodiments, $R^{18}$, $R^{18A}$, $R^{18B}$, $R^{18C}$, and $R^{18D}$ are each independently hydrogen, halogen, —$CF_3$, —$CI_3$, —$CI_3$, —$CBr_3$, —$CHF_2$, —$CHCl_2$, —$CHI_2$, —$CHBr_2$, —$OCH_2F$, —$OCH_2Cl$, —$OCH_2I$, —$OCH_2Br$, —$OCHF_2$, —$CHCl_2$, —$OCHI_2$, —$OCHBr_2$, —$OCF_3$, —$OCl_3$, —$OCI_3$, —$OCBr_3$,
—CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). In embodiments, $R^{18}$, $R^{18A}$, $R^{18B}$, $R^{18C}$, and $R^{18D}$ are each independently hydrogen. In embodiments, $R^{18}$, $R^{18A}$, $R^{18B}$, $R^{18C}$, and $R^{18D}$ are each independently unsubstituted methyl. In embodiments, $R^{18}$, $R^{18A}$, $R^{18B}$, $R^{18C}$, and $R^{18D}$ are each independently unsubstituted ethyl.

$R^{77}$ is independently oxo, halogen, —$CX^{77}_3$, —$CHX^{77}_2$, —$CH_2X^{77}$, —$OCX^{77}_3$, —$OCH_2X^{77}$, —$OCHX^{77}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{77}$ is independently —F, —Cl, —Br, or —I. In embodiments, $R^{77}$ is independently unsubstituted methyl. In embodiments, $R^{77}$ is independently unsubstituted ethyl.

In embodiments, $R^{19}$ is hydrogen. In embodiments, $R^{19}$ is halogen. In embodiments, $R^{19}$ is $CX^{19}_3$. In embodiments, $R^{19}$ is —$CHX^{19}_2$. In embodiments, $R^{19}$ is —$CH_2X^{19}$. In embodiments, $R^{19}$ is —CN. In embodiments, $R^{19}$ is —SO$_{n19}$R$^{19D}$. In embodiments, R$^{19}$ is —SO$_{v19}$NR$^{19A}$R$^{19B}$. In embodiments, R$^{19}$ is —NHNR$^{19A}$R$^{19B}$. In embodiments, R$^{19}$ is —ONR$^{19A}$R$^{19B}$. In embodiments, R$^{19}$ is —NHC(O)NHNR$^{19A}$R$^{19B}$. In embodiments, R$^{19}$ is —NHC(O)NR$^{19A}$R$^{19B}$. In embodiments, R$^{19}$ is —N(O)$_{m9}$. In embodiments, R$^{19}$ is —NR$^{19A}$R$^{19B}$. In embodiments, R$^{19}$ is —C(O)R$^{19C}$. In embodiments, R$^{19}$ is —C(O)—OR$^{19C}$. In embodiments, R$^{19}$ is —C(O)NR$^{19A}$R$^{19B}$. In embodiments, R$^{19}$ is —OR$^{19D}$. In embodiments, R$^{19}$ is —NR$^{19A}$SO$_2$R$^{19D}$. In embodiments, R$^{19}$ is —NR$^{19A}$C(O)R$^{19C}$. In embodiments, R$^{19}$ is —NR$^{19A}$C(O)OR$^{19C}$. In embodiments, R$^{19}$ is —NR$^{19A}$OR$^{19C}$. In embodiments, R$^{19}$ is —OCX$^{19}_3$. In embodiments, R$^{19}$ is —OCHX$^{19}_2$. In embodiments, R$^{19}$ is —SO$_{n19}$R$^{19A}$. In embodiments, R$^{19}$ is —SO$_{v19}$NR$^{19A}$R$^{19B}$. In embodiments, R$^{19}$ is —NHNR$^{19A}$R$^{19B}$. In embodiments, R$^{19}$ is —ONR$^{19A}$R$^{19B}$. In embodiments, R$^{19}$ is —NHC(O)NHNR$^{19A}$R$^{19B}$. In embodiments, R$^{19}$ is —NHC(O)NR$^{19A}$R$^{19B}$. In embodiments, R$^{19}$ is —N(O)$_{m19}$. In embodiments, R$^{19}$ is —NR$^{19A}$R$^{19B}$. In embodiments, R$^{19}$ is —C(O)R$^{19A}$. In embodiments, R$^{19}$ is —C(O)—OR$^{19A}$. In embodiments, R$^{19}$ is —C(O)NR$^{19A}$R$^{19B}$. In embodiments, R$^{19}$ is —OR$^{19A}$. In embodiments, R$^{19}$ is —NR$^{19A}$SO$_2$R$^{19B}$. In embodiments, R$^{19}$ is —NR$^{19A}$C(O)R$^{19B}$ In embodiments, R$^{19}$ is —NR$^{19A}$C(O)OR$^{19B}$. In embodiments, R$^{19}$ is —NR$^{19A}$OR$^{19B}$.

In embodiments, R$^{19}$ is substituted or unsubstituted alkyl. In embodiments, R$^{19}$ is substituted or unsubstituted heteroalkyl. In embodiments, R$^{19}$ is substituted or unsubstituted cycloalkyl. In embodiments, R$^{19}$ is substituted or unsubstituted heterocycloalkyl. In embodiments, R$^{19}$ is substituted or unsubstituted aryl. In embodiments, R$^{19}$ is substituted or unsubstituted heteroaryl. In embodiments, R$^{19}$ is substituted alkyl. In embodiments, R$^{19}$ is substituted heteroalkyl. In embodiments, R$^{19}$ is substituted cycloalkyl. In embodiments, R$^{19}$ is substituted heterocycloalkyl. In embodiments, R$^{19}$ is substituted aryl. In embodiments, R$^{19}$ is substituted heteroaryl. In embodiments, R$^{19}$ is unsubstituted alkyl. In embodiments, R$^{19}$ is unsubstituted heteroalkyl. In embodiments, R$^{19}$ is unsubstituted cycloalkyl. In embodiments, R$^{19}$ is unsubstituted heterocycloalkyl. In embodiments, R$^{19}$ is unsubstituted aryl. In embodiments, R$^{19}$ is unsubstituted heteroaryl. In embodiments, R$^{19}$ is unsubstituted methyl. In embodiments, R$^{19}$ is unsubstituted ethyl. In embodiments, R$^{19}$ is unsubstituted propyl. In embodiments, R$^{19}$ is unsubstituted isopropyl. In embodiments, R$^{19}$ is unsubstituted butyl. In embodiments, R$^{19}$ is unsubstituted tert-butyl. In embodiments, R$^{19}$ is —CH$_2$Ph.

In embodiments, R$^{19A}$ is hydrogen. In embodiments, R$^{19A}$ is —CX$_3$. In embodiments, R$^{19A}$ is —CN. In embodiments, R$^{19A}$ is —COOH. In embodiments, R$^{19A}$ is —CONH$_2$. In embodiments, R$^{19A}$ is —CHX$_2$. In embodiments, R$^{19A}$ is —CH$_2$X. In embodiments, R$^{19A}$ is unsubstituted methyl. In embodiments, R$^{19A}$ is unsubstituted ethyl. In embodiments, R$^{19A}$ is unsubstituted propyl. In embodiments, R$^{19A}$ is unsubstituted isopropyl. In embodiments, R$^{19A}$ is unsubstituted butyl. In embodiments, R$^{19A}$ is unsubstituted tert-butyl.

In embodiments, R$^{19B}$ is hydrogen. In embodiments, R$^{19B}$ is —CX$_3$. In embodiments, R$^{19B}$ is —CN. In embodiments, R$^{19B}$ is —COOH. In embodiments, R$^{19B}$ is —CONH$_2$. In embodiments, R$^{19B}$ is —CHX$_2$. In embodiments, R$^{19B}$ is —CH$_2$X. In embodiments, R$^{19B}$ is unsubstituted methyl. In embodiments, R$^{19B}$ is unsubstituted ethyl. In embodiments, R$^{19B}$ is unsubstituted propyl. In embodiments, R$^{19B}$ is unsubstituted isopropyl. In embodiments, R$^{19B}$ is unsubstituted butyl. In embodiments, R$^{19B}$ is unsubstituted tert-butyl.

In embodiments, R$^{19C}$ is hydrogen. In embodiments, R$^{19C}$ is —CX$_3$. In embodiments, R$^{19C}$ is —CN. In embodiments, R$^{19C}$ is —COOH. In embodiments, R$^{19C}$ is —CONH$_2$. In embodiments, R$^{19C}$ is —CHX$_2$. In embodiments, R$^{19C}$ is —CH$_2$X. In embodiments, R$^{19C}$ is unsubstituted methyl. In embodiments, R$^{19C}$ is unsubstituted ethyl. In embodiments, R$^{19C}$ is unsubstituted propyl. In embodiments, R$^{19C}$ is unsubstituted isopropyl. In embodiments, R$^{19C}$ is unsubstituted butyl. In embodiments, R$^{19C}$ is unsubstituted tert-butyl.

In embodiments, R$^{19D}$ is hydrogen. In embodiments, R$^{19D}$ is —CX$_3$. In embodiments, R$^{19D}$ is —CN. In embodiments, R$^{19D}$ is —COOH. In embodiments, R$^{19D}$ is —CONH$_2$. In embodiments, R$^{19D}$ is —CHX$_2$. In embodiments, R$^{19D}$ is —CH$_2$X. In embodiments, R$^{19D}$ is unsubstituted methyl. In embodiments, R$^{19D}$ is unsubstituted ethyl. In embodiments, R$^{19D}$ is unsubstituted propyl. In embodiments, R$^{19D}$ is unsubstituted isopropyl. In embodiments, R$^{19D}$ is unsubstituted butyl. In embodiments, R$^{19D}$ is unsubstituted tert-butyl.

In embodiments, R$^{19}$, R$^{19A}$, R$^{19B}$, R$^{19C}$, and R$^{19D}$ are each independently hydrogen, halogen, —CF$_3$, —CI$_3$, —CI$_3$, —CBr$_3$, —CHF$_2$, —CHCl$_2$, —CHI$_2$, —CHBr$_2$, —OCH$_2$F, —OCH$_2$Cl, —OCH$_2$I, —OCH$_2$Br, —OCHF$_2$, —CHCl$_2$, —OCHI$_2$, —OCHBr$_2$, —OCF$_3$, —OCl$_3$, —OCI$_3$, —OCBr$_3$,
—CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, R$^{78}$-substituted or unsubstituted alkyl (e.g., C$_1$-C$_8$, C$_1$-C$_6$, C$_1$-C$_4$, or C$_1$-C$_2$), R$^{78}$-substituted or unsubstituted heteroalkyl (e.g., 2 to 8 membered, 2 to 6 membered, 4 to 6 membered, 2 to 3 membered, or 4 to 5 membered), R$^{78}$-substituted or unsubstituted cycloalkyl (e.g., C$_3$-C$_8$, C$_3$-C$_6$, C$_4$-C$_6$, or C$_5$-C$_6$), R$^{78}$-substituted or unsubstituted heterocycloalkyl (e.g., 3 to 8 membered, 3 to 6 membered, 4 to 6 membered, 4 to 5 membered, or 5 to 6 membered), R$^{78}$-substituted or unsubstituted aryl (e.g., C$_6$-C$_{10}$ or phenyl), or R$^{78}$-substituted or unsubstituted heteroaryl (e.g., 5 to 10 membered, 5 to 9 membered, or 5 to 6 membered).

In embodiments, R$^{19}$, R$^{19A}$, R$^{19B}$, R$^{19C}$, and R$^{19D}$ are each independently hydrogen, halogen, —CF$_3$, —CI$_3$, —CI$_3$, —CBr$_3$, —CHF$_2$, —CHCl$_2$, —CHI$_2$, —CHBr$_2$, —OCH$_2$F, —OCH$_2$Cl, —OCH$_2$I, —OCH$_2$Br, —OCHF$_2$, —CHCl$_2$, —OCHI$_2$, —OCHBr$_2$, —OCF$_3$, —OCl$_3$, —OCI$_3$, —OCBr$_3$,
—CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered). In embodiments, R$^{19}$, R$^{19A}$, R$^{19B}$, R$^{19C}$, and R$^{19D}$ are each independently hydrogen. In embodiments, R$^{19}$, R$^{19A}$, R$^{19B}$, R$^{19C}$, and R$^{19D}$ are each independently unsubstituted methyl. In embodiments, R$^{19}$, R$^{19A}$, R$^{19B}$, R$^{19C}$, and R$^{19D}$ are each independently unsubstituted ethyl.

$R^{78}$ is independently oxo, halogen, $-CX^{78}_3$, $-CHX^{78}_2$, $-CH_2X^{78}$, $-OCX^{78}_3$, $-OCH_2X^{78}$, $-OCHX^{78}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{78}$ is independently $-F$, $-Cl$, $-Br$, or $-I$. In embodiments, $R^{78}$ is independently unsubstituted methyl. In embodiments, $R^{78}$ is independently unsubstituted ethyl.

In an embodiment, the compound has the formula:

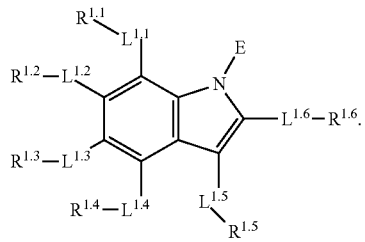

(III)

$R^{1.1}$, $R^{1.2}$, $R^{1.3}$, $R^{1.4}$, $R^{1.5}$, and $R^{1.6}$ are each independently hydrogen or a moiety equal to $R^1$, including any embodiment of $R^1$. $L^{1.1}$, $L^{1.2}$, $L^{1.3}$, $L^{1.4}$, $L^{1.5}$, and $L^{1.6}$ are each independently a moiety equal to $L^1$, including any embodiment of $L^1$. E is as described herein, including in embodiments.

In an embodiment, the compound has the formula:

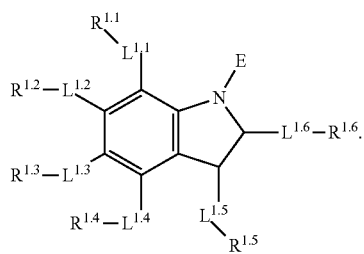

(VIII)

$R^{1.1}$, $R^{1.2}$, $R^{1.3}$, $R^{1.4}$, $R^{1.5}$, and $R^{1.6}$ are each independently hydrogen or a moiety equal to $R^1$, including any embodiment of $R^1$. $L^{1.1}$, $L^{1.2}$, $L^{1.3}$, $L^{1.4}$, $L^{1.5}$, and $L^{1.6}$ are each independently a moiety equal to $L^1$, including any embodiment of $L^1$. E is as described herein, including in embodiments.

In an embodiment, the compound has the formula:

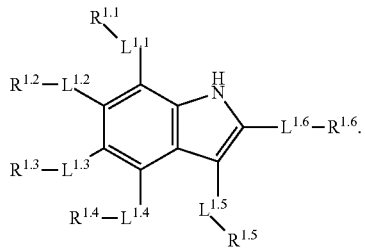

(XIII)

$R^{1.1}$, $R^{1.2}$, $R^{1.3}$, $R^{1.4}$, $R^{1.5}$, and $R^{1.6}$ are each independently hydrogen or a moiety equal to $R^1$, including any embodiment of $R^1$. $L^{1.1}$, $L^{1.2}$, $L^{1.3}$, $L^{1.4}$, $L^{1.5}$, and $L^{1.6}$ are each independently a moiety equal to $L^1$, including any embodiment of $L^1$. E is as described herein, including in embodiments.

In an embodiment, the compound has the formula:

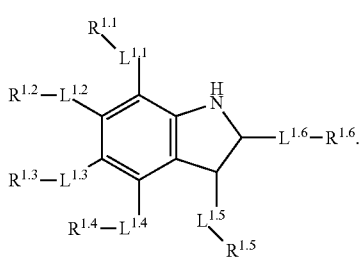

(XXIII)

$R^{1.1}$, $R^{1.2}$, $R^{1.3}$, $R^{1.4}$, $R^{1.5}$, and $R^{1.6}$ are each independently hydrogen or a moiety equal to $R^1$, including any embodiment of $R^1$. $L^{1.1}$, $L^{1.2}$, $L^{1.3}$, $L^{1.4}$, $L^{1.5}$, and $L^{1.6}$ are each independently a moiety equal to $L^1$, including any embodiment of $L^1$.

In an embodiment, the compound has the formula:

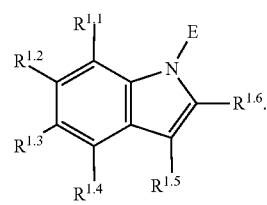

(IIIa)

$R^{1.1}$, $R^{1.2}$, $R^{1.3}$, $R^{1.4}$, $R^{1.5}$, and $R^{1.6}$, and E are as described herein, including in embodiments.

In an embodiment, the compound has the formula:

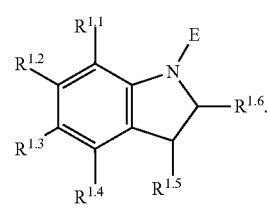

(VIIIa)

$R^{1.1}$, $R^{1.2}$, $R^{1.3}$, $R^{1.4}$, $R^{1.5}$, and $R^{1.6}$, and E are as described herein, including in embodiments.

In an embodiment, the compound has the formula:

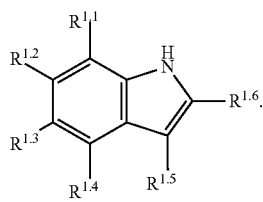

(XIIIa)

$R^{1.1}$, $R^{1.2}$, $R^{1.3}$, $R^{1.4}$, $R^{1.5}$, and $R^{1.6}$ are as described herein, including in embodiments.

In an embodiment, the compound has the formula:

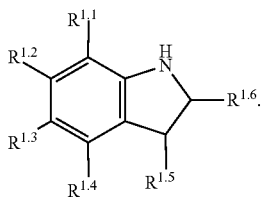

(XXIIIa)

$R^{1.1}$, $R^{1.2}$, $R^{1.3}$, $R^{1.4}$, $R^{1.5}$, and $R^{1.6}$ are as described herein, including in embodiments.

In embodiments, $R^{1.1}$ is independently hydrogen, halogen, $-CX^{1.1}_3$, $-CHX^{1.1}_2$, $-CH_2X^{1.1}$, $-CN$, $-OH$, $-NH_2$, $-COOH$, $-CONH_2$, $-NO_2$, $-SH$, $-OCX^{1.1}_3$, $-OCHX^{1.1}_2$, $-OCH_2X^{1.1}$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. $X^{1.1}$ is independently $-F$, $-Cl$, $-Br$, or $-I$. In embodiments, $R^{1.1}$ is independently hydrogen, halogen, $-CX^{1.1}_3$, $-CHX^{1.1}_2$, $-CH_2X^{1.1}$, $-CN$, $-OH$, $-NH_2$, $-COOH$, $-CONH_2$, $-NO_2$, $-SH$, $-OCX^{1.1}_3$, $-OCHX^{1.1}_2$, $-OCH_2X^{1.1}$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^{1.1}$ is independently $-OCH_3$. In embodiments, $R^{1.1}$ is independently unsubstituted phenyl. In embodiments, $R^{1.1}$ is independently $-CF_3$. In embodiments, $R^{1.1}$ is independently $-NO_2$. In embodiments, $R^{1.1}$ is independently $-OCF_3$. In embodiments, $R^{1.1}$ is independently $-OCHF_2$. In embodiments, $R^{1.1}$ is independently $-OCH_2F$. In embodiments, $R^{1.1}$ is independently halogen. In embodiments, $R^{1.1}$ is independently $-F$. In embodiments, $R^{1.1}$ is independently $-Cl$. In embodiments, $R^{1.1}$ is independently $-Br$. In embodiments, $R^{1.1}$ is independently $-I$. In embodiments, $R^{1.1}$ is independently $-CH_3$. In embodiments, $R^{1.1}$ is independently unsubstituted methyl. In embodiments, $R^{1.1}$ is independently unsubstituted ethyl. In embodiments, $R^{1.1}$ is independently unsubstituted propyl. In embodiments, $R^{1.1}$ is independently unsubstituted n-propyl. In embodiments, $R^{1.1}$ is independently unsubstituted isopropyl. In embodiments, $R^{1.1}$ is independently unsubstituted butyl. In embodiments, $R^{1.1}$ is independently unsubstituted n-butyl. In embodiments, $R^{1.1}$ is independently unsubstituted isobutyl. In embodiments, $R^{1.1}$ is independently unsubstituted tert-butyl. In embodiments, $R^{1.1}$ is independently unsubstituted pentyl. In embodiments, $R^{1.1}$ is independently unsubstituted hexyl. In embodiments, $R^{1.1}$ is independently unsubstituted heptyl. In embodiments, $R^{1.1}$ is independently unsubstituted octyl. In embodiments, $R^{1.1}$ is independently $-CX^{1.1}_3$. In embodiments, $R^{1.1}$ is independently $-CHX^{1.1}_2$. In embodiments, $R^{1.1}$ is independently $-CH_2X^{1.1}$. In embodiments, $R^{1.1}$ is independently $-CN$. In embodiments, $R^{1.1}$ is independently $-OH$. In embodiments, $R^{1.1}$ is independently $-NH_2$. In embodiments, $R^{1.1}$ is independently $-COOH$. In embodiments, $R^{1.1}$ is independently $-CONH_2$. In embodiments, $R^{1.1}$ is independently $-SH$. In embodiments, $R^{1.1}$ is independently $-OCX^{1.1}_3$. In embodiments, $R^{1.1}$ is independently $-OCHX^{1.1}_2$. In embodiments, $R^{1.1}$ is independently $-OCH_2X^{1.1}$. In embodiments, $R^{1.1}$ is independently unsubstituted $C_1$-$C_6$ alkyl. In embodiments, $R^{1.1}$ is independently unsubstituted 2 to 6 membered heteroalkyl. In embodiments, $R^{1.1}$ is independently unsubstituted $C_3$-$C_6$ cycloalkyl. In embodiments, $R^{1.1}$ is independently unsubstituted 3 to 6 membered heterocycloalkyl. In embodiments, $R^{1.1}$ is independently unsubstituted phenyl. In embodiments, $R^{1.1}$ is independently unsubstituted 5 to 6 membered heteroaryl. In embodiments, $R^{1.1}$ is independently $-NHC(O)CH_3$. In embodiments, $R^{1.1}$ is independently $-OCH_3$. In embodiments, $R^{1.1}$ is independently $-SCH_3$. In embodiments, $R^{1.1}$ is independently

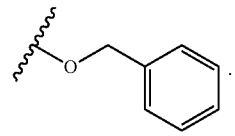 [SMILES: *OCc1ccccc1]

In embodiments, $R^{1.1}$ is independently

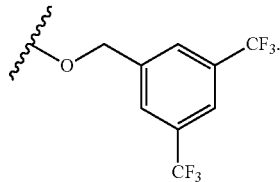 [SMILES: *OCc1cc(C(F)(F)F)cc(C(F)(F)F)c1]

In embodiments $R^{1.1}$ is independently

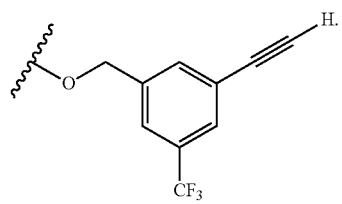

In embodiments, $R^{1.1}$ is independently

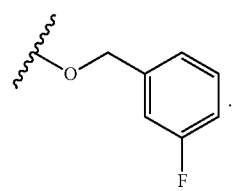 [SMILES: *OCc1cccc(F)c1]

In embodiments, $R^{1.1}$ is independently

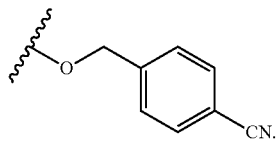 [SMILES: *OCc1ccc(C#N)cc1]

In embodiments, $R^{1.1}$ is independently

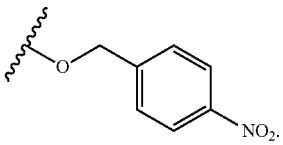 [SMILES: *OCc1ccc([N+](=O)[O-])cc1]

In embodiments, $R^{1.1}$ is independently hydrogen.

In embodiments, $L^{1.1}$ is a bond, —S(O)$_2$—, —NH—, —O—, —S—, —C(O)—, —C(O)NH—, —NHC(O)—, —NHC(O)NH—, —C(O)O—, —OC(O)—, substituted or unsubstituted alkylene (e.g., $C_1$-$C_8$, $C_1$-$C_6$, or $C_1$-$C_4$), substituted or unsubstituted heteroalkylene (e.g., 2 to 8 membered, 2 to 6 membered, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8 membered, 3 to 6 membered, or 5 to 6 membered), substituted or unsubstituted arylene (e.g., $C_6$-$C_{10}$, $C_{10}$, or phenylene), or substituted or unsubstituted heteroarylene (e.g., 5 to 10 membered, 5 to 9 membered, or 5 to 6 membered). In embodiments, $L^{1.1}$ is a bond, —S(O)$_2$—, —NH—, —O—, —S—, —C(O)—, —C(O)NH—, —NHC(O)—, —NHC(O)NH—, —C(O)O—, —OC(O)—, substituted or unsubstituted alkylene, or substituted or unsubstituted heteroalkylene. In embodiments, $L^{1.1}$ is a bond, —O—, —C(O)—, —S—, —NH—, —NHC(O)—, —C(O)NH—, unsubstituted $C_1$-$C_4$ alkylene, or unsubstituted 2 to 4 membered heteroalkylene. In embodiments, $L^{1.1}$ is a bond. In embodiments, $L^{1.1}$ is —OCH$_2$—. In embodiments, $L^{1.1}$ is —NHC(O)—. In embodiments, $L^{1.1}$ is —S—. In embodiments, $L^{1.1}$ is —O—.

In embodiments, $R^{1.2}$ is independently hydrogen, halogen, —CX$^{1.2}_3$, —CHX$^{1.2}_2$, —CH$_2$X$^{1.2}$, —CN, —OH, —NH$_2$, —COOH, —CONH$_2$, —NO$_2$, —SH, —OCX$^{1.2}_3$, —OCHX$^{1.2}_2$, —OCH$_2$X$^{1.2}$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. $X^{1.2}$ is independently —F, —Cl, —Br, or —I. In embodiments, $R^{1.2}$ is independently hydrogen, halogen, —CX$^{1.2}_3$, —CHX$^{1.2}_2$, —CH$_2$X$^{1.2}$, —CN, —OH, —NH$_2$, —COOH, —CONH$_2$, —NO$_2$, —SH, —OCX$^{1.2}_3$, —OCHX$^{1.2}_2$, —OCH$_2$X$^{1.2}$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^{1.2}$ is independently —OCH$_3$. In embodiments, $R^{1.2}$ is independently unsubstituted phenyl. In embodiments, $R^{1.2}$ is independently —CF$_3$. In embodiments, $R^{1.2}$ is independently —NO$_2$. In embodiments, $R^{1.2}$ is independently —OCF$_3$. In embodiments, $R^{1.2}$ is independently —OCHF$_2$. In embodiments, $R^{1.2}$ is independently —OCH$_2$F. In embodiments, $R^{1.2}$ is independently halogen. In embodiments, $R^{1.2}$ is independently —F. In embodiments, $R^{1.2}$ is independently —Cl. In embodiments, $R^{1.2}$ is independently —Br. In embodiments, $R^{1.2}$ is independently —I. In embodiments, $R^{1.2}$ is independently —CH$_3$. In embodiments, $R^{1.2}$ is independently unsubstituted methyl. In embodiments, $R^{1.2}$ is independently unsubstituted ethyl. In embodiments, $R^{1.2}$ is independently unsubstituted propyl. In embodiments, $R^{1.2}$ is independently unsubstituted n-propyl. In embodiments, $R^{1.2}$ is independently unsubstituted isopropyl. In embodiments, $R^{1.2}$ is independently unsubstituted butyl. In embodiments, $R^{1.2}$ is independently unsubstituted n-butyl. In embodiments, $R^{1.2}$ is independently unsubstituted isobutyl. In embodiments, $R^{1.2}$ is independently unsubstituted tert-butyl. In embodiments, $R^{1.2}$ is independently unsubstituted pentyl. In embodiments, $R^{1.2}$ is independently unsubstituted hexyl. In embodiments, $R^{1.2}$ is independently unsubstituted heptyl. In embodiments, $R^{1.2}$ is independently unsubstituted octyl. In embodiments, $R^{1.2}$ is independently —CX$^{1.2}_3$. In embodiments, $R^{1.2}$ is independently —CHX$^{1.2}_2$. In embodiments, $R^{1.2}$ is independently —CH$_2$X$^{1.2}$. In embodiments, $R^{1.2}$ is independently —CN. In embodiments, $R^{1.2}$ is independently —OH. In embodiments, $R^{1.2}$ is independently —NH$_2$. In embodiments, $R^{1.2}$ is independently —COOH. In embodiments, $R^{1.2}$ is independently —CONH$_2$. In embodiments, $R^{1.2}$ is independently —SH. In embodiments, $R^{1.2}$ is independently —OCX$^{1.2}_3$. In embodiments, $R^{1.2}$ is independently —OCHX$^{1.2}_2$. In embodiments, $R^{1.2}$ is independently —OCH$_2$X$^{1.2}$. In embodiments, $R^{1.2}$ is independently unsubstituted $C_1$-$C_6$ alkyl. In embodiments, $R^{1.2}$ is independently unsubstituted 2 to 6 membered heteroalkyl. In embodiments, $R^{1.2}$ is independently unsubstituted $C_3$-$C_6$ cycloalkyl. In embodiments, $R^{1.2}$ is independently unsubstituted 3 to 6 membered heterocycloalkyl. In embodiments, $R^{1.2}$ is independently unsubstituted phenyl. In embodiments, $R^{1.2}$ is independently unsubstituted 5 to 6 membered heteroaryl. In embodiments, $R^{1.2}$ is independently —NHC(O)CH$_3$. In embodiments, $R^{1.2}$ is independently —OCH$_3$. In embodiments, $R^{1.2}$ is independently —SCH$_3$. In embodiments, $R^{1.2}$ is independently

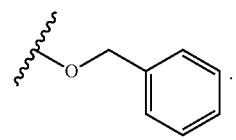 [SMILES: *OCc1ccccc1]

In embodiments, $R^{1.2}$ is independently

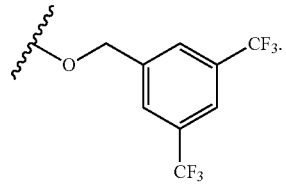 [SMILES: *OCc1cc(C(F)(F)F)cc(C(F)(F)F)c1]

In embodiments, $R^{1.2}$ is independently

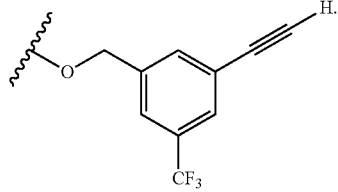

In embodiments, $R^{1.2}$ is independently

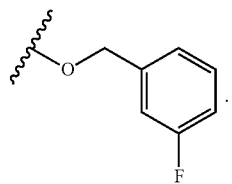 [SMILES: *OCc1cccc(F)c1]

In embodiments, $R^{1.2}$ is independently

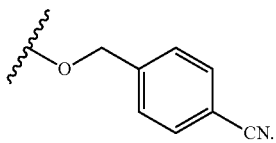 [SMILES: *OCc1ccc(C#N)cc1]

In embodiments, $R^{1.2}$ is independently

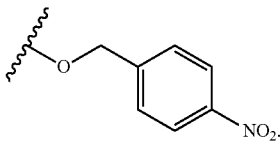 [SMILES: *OCc1ccc([N+](=O)[O-])cc1]

In embodiments, $R^{1.2}$ is independently a hydrogen.

In embodiments, $L^{1.2}$ is a bond, —S(O)$_2$—, —NH—, —O—, —S—, —C(O)—, —C(O)NH—, —NHC(O)—, —NHC(O)NH—, —C(O)O—, —OC(O)—, substituted or unsubstituted alkylene (e.g., $C_1$-$C_8$, $C_1$-$C_6$, or $C_1$-$C_4$), substituted or unsubstituted heteroalkylene (e.g., 2 to 8 membered, 2 to 6 membered, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8 membered, 3 to 6 membered, or 5 to 6 membered), substituted or unsubstituted arylene (e.g., $C_6$-$C_{10}$, $C_{10}$, or phenylene), or substituted or unsubstituted heteroarylene (e.g., 5 to 10 membered, 5 to 9 membered, or 5 to 6 membered). In embodiments, $L^{1.2}$ is a bond, —S(O)$_2$—, —NH—, —O—, —S—, —C(O)—, —C(O)NH—, —NHC(O)—, —NHC(O)NH—, —C(O)O—, —OC(O)—, substituted or unsubstituted alkylene, or substituted or unsubstituted heteroalkylene. In embodiments, $L^{1.2}$ is a bond, —O—, —C(O)—, —S—, —NH—, —NHC(O)—, —C(O)NH—, unsubstituted $C_1$-$C_4$ alkylene, or unsubstituted 2 to 4 membered heteroalkylene. In embodiments, $L^{1.2}$ is a bond. In embodiments, $L^{1.2}$ is —OCH$_2$—. In embodiments, $L^{1.2}$ is —NHC(O)—. In embodiments, $L^{1.2}$ is —S—. In embodiments, $L^{1.2}$ is —O—.

In embodiments, $R^{1.3}$ is independently hydrogen, halogen, —CX$^{1.3}_3$, —CHX$^{1.3}_2$, —CH$_2$X$^{1.3}$, —CN, —OH, —NH$_2$, —COOH, —CONH$_2$, —NO$_2$, —SH, —OCX$^{1.3}_3$, —OCHX$^{1.3}_2$, —OCH$_2$X$^{1.3}$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. $X^{1.3}$ is independently —F, —Cl, —Br, or —I. In embodiments, $R^{1.3}$ is independently hydrogen, halogen, —CX$^{1.3}_3$, —CHX$^{1.3}_2$, —CH$_2$X$^{1.3}$, —CN, —OH, —NH$_2$, —COOH, —CONH$_2$, —NO$_2$, —SH, —OCX$^{1.3}_3$, —OCHX$^{1.3}_2$, —OCH$_2$X$^{1.3}$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^{1.3}$ is independently —OCH$_3$. In embodiments, $R^{1.3}$ is independently unsubstituted phenyl. In embodiments, $R^{1.3}$ is independently —CF$_3$. In embodiments, $R^{1.3}$ is independently —NO$_2$. In embodiments, $R^{1.3}$ is independently —OCF$_3$. In embodiments, $R^{1.3}$ is independently —OCHF$_2$. In embodiments, $R^{1.3}$ is independently —OCH$_2$F. In embodiments, $R^{1.3}$ is independently halogen. In embodiments, $R^{1.3}$ is independently —F. In embodiments, $R^{1.3}$ is independently —Cl. In embodiments, $R^{1.3}$ is independently —Br. In embodiments, $R^{1.3}$ is independently —I. In embodiments, $R^{1.3}$ is independently —CH$_3$. In embodiments, $R^{1.3}$ is independently unsubstituted methyl. In embodiments, $R^{1.3}$ is independently unsubstituted ethyl. In embodiments, $R^{1.3}$ is independently unsubstituted propyl. In embodiments, $R^{1.3}$ is independently unsubstituted n-propyl. In embodiments, $R^{1.3}$ is independently unsubstituted isopropyl. In embodiments, $R^{1.3}$ is independently unsubstituted butyl. In embodiments, $R^{1.3}$ is independently unsubstituted n-butyl. In embodiments, $R^{1.3}$ is independently unsubstituted isobutyl. In embodiments, $R^{1.3}$ is independently unsubstituted tert-butyl. In embodiments, $R^{1.3}$ is independently unsubstituted pentyl. In embodiments, $R^{1.3}$ is independently unsubstituted hexyl. In embodiments, $R^{1.3}$ is independently unsubstituted heptyl. In embodiments, $R^{1.3}$ is independently unsubstituted octyl. In embodiments, $R^{1.3}$ is independently —CX$^{1.3}_3$. In embodiments, $R^{1.3}$ is independently —CHX$^{1.3}_2$. In embodiments, $R^{1.3}$ is independently —CH$_2$X$^{1.3}$. In embodiments, $R^{1.3}$ is independently —CN. In embodiments, $R^{1.3}$ is independently —OH. In embodiments, $R^{1.3}$ is independently —NH$_2$. In embodiments, $R^{1.3}$ is independently —COOH. In embodiments, $R^{1.3}$ is independently —CONH$_2$. In embodiments, $R^{1.3}$ is independently —SH. In embodiments, $R^{1.3}$ is independently —OCX$^{1.3}_3$. In embodiments, $R^{1.3}$ is independently —OCHX$^{1.3}_2$. In embodiments, $R^{1.3}$ is independently —OCH$_2$X$^{1.3}$. In embodiments, $R^{1.3}$ is independently unsubstituted $C_1$-$C_6$ alkyl. In embodiments, $R^{1.3}$ is independently unsubstituted 2 to 6 membered heteroalkyl. In embodiments, $R^{1.3}$ is independently unsubstituted $C_3$-$C_6$ cycloalkyl. In embodiments, $R^{1.3}$ is independently unsubstituted 3 to 6 membered heterocycloalkyl. In embodiments, $R^{1.3}$ is independently unsubstituted phenyl. In embodiments, $R^{1.3}$ is independently unsubstituted 5 to 6 membered heteroaryl. In embodiments, $R^{1.3}$ is independently —NHC(O)CH$_3$. In embodiments, $R^{1.3}$ is independently —OCH$_3$. In embodiments, $R^{1.3}$ is independently —SCH$_3$. In embodiments, $R^{1.3}$ is independently

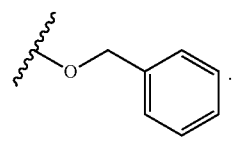 [SMILES: *OCc1ccccc1]

In embodiments, $R^{1.3}$ is independently

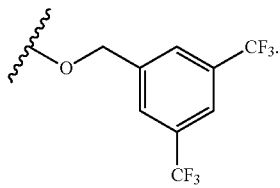

In embodiments, $R^{1.3}$ is independently

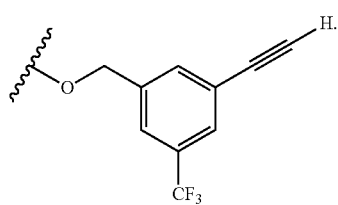

In embodiments, $R^{1.3}$ is independently

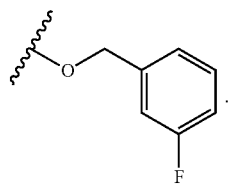

In embodiments, $R^{1.3}$ is independently

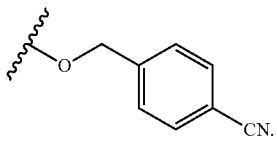 [SMILES: *OCc1ccc(C#N)cc1]

In embodiments, $R^{1.3}$ is independently

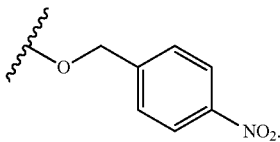

In embodiments, $R^{1.3}$ is independently a hydrogen.

In embodiments, $L^{1.3}$ is a bond, —S(O)$_2$—, —NH—, —O—, —S—, —C(O)—, —C(O)NH—, —NHC(O)—, —NHC(O)NH—, —C(O)O—, —OC(O)—, substituted or unsubstituted alkylene (e.g., $C_1$-$C_8$, $C_1$-$C_6$, or $C_1$-$C_4$), substituted or unsubstituted heteroalkylene (e.g., 2 to 8 membered, 2 to 6 membered, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8 membered, 3 to 6 membered, or 5 to 6 membered), substituted or unsubstituted arylene (e.g., $C_6$-$C_{10}$, $C_{10}$, or phenylene), or substituted or unsubstituted heteroarylene (e.g., 5 to 10 membered, 5 to 9 membered, or 5 to 6 membered). In embodiments, $L^{1.3}$ is a bond, —S(O)$_2$—, —NH—, —O—, —S—, —C(O)—, —C(O)NH—, —NHC(O)—, —NHC(O)NH—, —C(O)O—, —OC(O)—, substituted or unsubstituted alkylene, or substituted or unsubstituted heteroalkylene. In embodiments, $L^{1.3}$ is a bond, —O—, —C(O)—, —S—, —NH—, —NHC(O)—, —C(O)NH—, unsubstituted $C_1$-$C_4$ alkylene, or unsubstituted 2 to 4 membered heteroalkylene. In embodiments, $L^{1.3}$ is a bond. In embodiments, $L^{1.3}$ is —OCH$_2$—. In embodiments, $L^{1.3}$ is —NHC(O)—. In embodiments, $L^{1.3}$ is —S—. In embodiments, $L^{1.3}$ is —O—.

In embodiments, $R^{1.4}$ is independently hydrogen, halogen, —CX$^{1.4}_3$, —CHX$^{1.4}_2$, —CH$_2$X$^{1.4}$, —CN, —OH, —NH$_2$, —COOH, —CONH$_2$, —NO$_2$, —SH, —OCX$^{1.4}_3$, —OCHX$^{1.4}_2$, —OCH$_2$X$^{1.4}$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. $X^{1.4}$ is independently —F, —Cl, —Br, or —I. In embodiments, $R^{1.4}$ is independently hydrogen, halogen, —CX$^{1.4}_3$, —CHX$^{1.4}_2$, —CH$_2$X$^{1.4}$, —CN, —OH, —NH$_2$, —COOH, —CONH$_2$, —NO$_2$, —SH, —OCX$^{1.4}_3$, —OCHX$^{1.4}_2$, —OCH$_2$X$^{1.4}$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^{1.4}$ is independently —OCH$_3$. In embodiments, $R^{1.4}$ is independently unsubstituted phenyl. In embodiments, $R^{1.4}$ is independently —CF$_3$. In embodiments, $R^{1.4}$ is independently —NO$_2$. In embodiments, $R^{1.4}$ is independently —OCF$_3$. In embodiments, $R^{1.4}$ is independently —OCHF$_2$. In embodiments, $R^{1.4}$ is independently —OCH$_2$F. In embodiments, $R^{1.4}$ is independently halogen. In embodiments, $R^{1.4}$ is independently —F. In embodiments, $R^{1.4}$ is independently —Cl. In embodiments, $R^{1.4}$ is independently —Br. In embodiments, $R^{1.4}$ is independently —I. In embodiments, $R^{1.4}$ is independently —CH$_3$. In embodiments, $R^{1.4}$ is independently unsubstituted methyl. In embodiments, $R^{1.4}$ is independently unsubstituted ethyl. In embodiments, $R^{1.4}$ is independently unsubstituted propyl. In embodiments, $R^{1.4}$ is independently unsubstituted n-propyl. In embodiments, $R^{1.4}$ is independently unsubstituted isopropyl. In embodiments, $R^{1.4}$ is independently unsubstituted butyl. In embodiments, $R^{1.4}$ is independently unsubstituted n-butyl. In embodiments, $R^{1.4}$ is independently unsubstituted isobutyl. In embodiments, $R^{1.4}$ is independently unsubstituted tert-butyl. In embodiments, $R^{1.4}$ is independently unsubstituted pentyl. In embodiments, $R^{1.4}$ is independently unsubstituted hexyl. In embodiments, $R^{1.4}$ is independently unsubstituted heptyl. In embodiments, $R^{1.4}$ is independently unsubstituted octyl. In embodiments, $R^{1.4}$ is independently —CX$^{1.4}_3$. In embodiments, $R^{1.4}$ is independently —CHX$^{1.4}_2$. In embodiments, $R^{1.4}$ is independently —CH$_2$X$^{1.4}$. In embodiments, $R^{1.4}$ is independently —CN. In embodiments, $R^{1.4}$ is independently —OH. In embodiments, $R^{1.4}$ is independently —NH$_2$. In embodiments, $R^{1.4}$ is independently —COOH. In embodiments, $R^{1.4}$ is independently —CONH$_2$. In embodiments, $R^{1.4}$ is independently —SH. In embodiments, $R^{1.4}$ is independently —OCX$^{1.4}_3$. In embodiments, $R^{1.4}$ is independently —OCHX$^{1.4}_2$. In embodiments, $R^{1.4}$ is independently —OCH$_2$X$^{1.4}$. In embodiments, $R^{1.4}$ is independently unsubstituted $C_1$-$C_6$ alkyl. In embodiments, $R^{1.4}$ is independently unsubstituted 2 to 6 membered heteroalkyl. In embodiments, $R^{1.4}$ is independently unsubstituted $C_3$-$C_6$ cycloalkyl. In embodiments, $R^{1.4}$ is independently unsubstituted 3 to 6 membered heterocycloalkyl. In embodiments, $R^{1.4}$ is independently unsubstituted phenyl. In embodiments, $R^{1.4}$ is independently unsubstituted 5 to 6 membered heteroaryl. In embodiments, $R^{1.4}$ is independently —NHC(O)CH$_3$. In embodiments, $R^{1.4}$ is independently —OCH$_3$. In embodiments, $R^{1.4}$ is independently —SCH$_3$. In embodiments, $R^{1.4}$ is independently

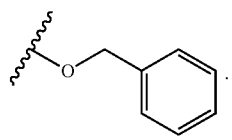 [SMILES: *OCc1ccccc1]

In embodiments, $R^{1.4}$ is independently

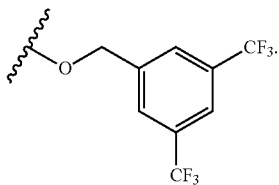

In embodiments, $R^{1.4}$ is independently

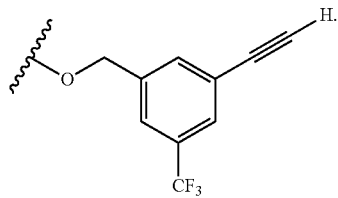

In embodiments, $R^{1.4}$ is independently

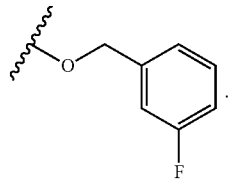 [SMILES: *OCc1cccc(F)c1]

In embodiments, $R^{1.4}$ is independently

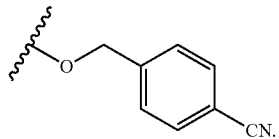 [SMILES: *OCc1ccc(C#N)cc1]

In embodiments, $R^{1.4}$ is independently

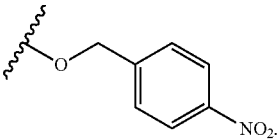

In embodiments, $R^{1.4}$ is independently a hydrogen.

In embodiments, $L^{1.4}$ is a bond, —S(O)$_2$—, —NH—, —O—, —S—, —C(O)—, —C(O)NH—, —NHC(O)—, —NHC(O)NH—, —C(O)O—, —OC(O)—, substituted or unsubstituted alkylene (e.g., $C_1$-$C_8$, $C_1$-$C_6$, or $C_1$-$C_4$), substituted or unsubstituted heteroalkylene (e.g., 2 to 8 membered, 2 to 6 membered, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8 membered, 3 to 6 membered, or 5 to 6 membered), substituted or unsubstituted arylene (e.g., $C_6$-$C_{10}$, $C_{10}$, or phenylene), or substituted or unsubstituted heteroarylene (e.g., 5 to 10 membered, 5 to 9 membered, or 5 to 6 membered). In embodiments, $L^{1.4}$ is a bond, —S(O)$_2$—, —NH—, —O—, —S—, —C(O)—, —C(O)NH—, —NHC(O)—, —NHC(O)NH—, —C(O)O—, —OC(O)—, substituted or unsubstituted alkylene, or substituted or unsubstituted heteroalkylene. In embodiments, $L^{1.4}$ is a bond, —O—, —C(O)—, —S—, —NH—, —NHC(O)—, —C(O)NH—, unsubstituted $C_1$-$C_4$ alkylene, or unsubstituted 2 to 4 membered heteroalkylene. In embodiments, $L^{1.4}$ is a bond. In embodiments, $L^{1.4}$ is —OCH$_2$—. In embodiments, $L^{1.4}$ is —NHC(O)—. In embodiments, $L^{1.4}$ is —S—. In embodiments, $L^{1.4}$ is —O—.

In embodiments, $R^{1.5}$ is independently hydrogen, halogen, —CX$^{1.5}_3$, —CHX$^{1.5}_2$, —CH$_2$X$^{1.5}$, —CN, —OH, —NH$_2$, —COOH, —CONH$_2$, —NO$_2$, —SH, —OCX$^{1.5}_3$, —OCHX$^{1.5}_2$, —OCH$_2$X$^{1.5}$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. $X^{1.5}$ is independently —F, —Cl, —Br, or —I. In embodiments, $R^{1.5}$ is independently hydrogen, halogen, —CX$^{1.5}_3$, —CHX$^{1.5}_2$, —CH$_2$X$^{1.5}$, —CN, —OH, —NH$_2$, —COOH, —CONH$_2$, —NO$_2$, —SH, —OCX$^{1.5}_3$, —OCHX$^{1.5}_2$, —OCH$_2$X$^{1.5}$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^{1.5}$ is independently —OCH$_3$. In embodiments, $R^{1.5}$ is independently unsubstituted phenyl. In embodiments, $R^{1.5}$ is independently —CF$_3$. In embodiments, $R^{1.5}$ is independently —NO$_2$. In embodiments, $R^{1.5}$ is independently —OCF$_3$. In embodiments, $R^{1.5}$ is independently —OCHF$_2$. In embodiments, $R^{1.5}$ is independently —OCH$_2$F. In embodiments, $R^{1.5}$ is independently halogen. In embodiments, $R^{1.5}$ is independently —F. In embodiments, $R^{1.5}$ is independently —Cl. In embodiments, $R^{1.5}$ is independently —Br. In embodiments, $R^{1.5}$ is independently —I. In embodiments, $R^{1.5}$ is independently —CH$_3$. In embodiments, $R^{1.5}$ is independently unsubstituted methyl. In embodiments, $R^{1.5}$ is independently unsubstituted ethyl. In embodiments, $R^{1.5}$ is independently unsubstituted propyl. In embodiments, $R^{1.5}$ is independently unsubstituted n-propyl. In embodiments, $R^{1.5}$ is independently unsubstituted isopropyl. In embodiments, $R^{1.5}$ is independently unsubstituted butyl. In embodiments, $R^{1.5}$ is independently unsubstituted n-butyl. In embodiments, $R^{1.5}$ is independently unsubstituted isobutyl. In embodiments, $R^{1.5}$ is independently unsubstituted tert-butyl. In embodiments, $R^{1.5}$ is independently unsubstituted pentyl. In embodiments, $R^{1.5}$ is independently unsubstituted hexyl. In embodiments, $R^{1.5}$ is independently unsubstituted heptyl. In embodiments, $R^{1.5}$ is independently unsubstituted octyl. In embodiments, $R^{1.5}$ is independently —$CX^{1.5}_3$. In embodiments, $R^{1.5}$ is independently —$CHX^{1.5}_2$. In embodiments, $R^{1.5}$ is independently —$CH_2X^{1.5}$. In embodiments, $R^{1.5}$ is independently —CN. In embodiments, $R^{1.5}$ is independently —OH. In embodiments, $R^{1.5}$ is independently —$NH_2$. In embodiments, $R^{1.5}$ is independently —COOH. In embodiments, $R^{1.5}$ is independently —$CONH_2$. In embodiments, $R^{1.5}$ is independently —SH. In embodiments, $R^{1.5}$ is independently —$OCX^{1.5}_3$. In embodiments, $R^{1.5}$ is independently —$OCHX^{1.5}_2$. In embodiments, $R^{1.5}$ is independently —$OCH_2X^{1.5}$. In embodiments, $R^{1.5}$ is independently unsubstituted $C_1$-$C_6$ alkyl. In embodiments, $R^{1.5}$ is independently unsubstituted 2 to 6 membered heteroalkyl. In embodiments, $R^{1.5}$ is independently unsubstituted $C_3$-$C_6$ cycloalkyl. In embodiments, $R^{1.5}$ is independently unsubstituted 3 to 6 membered heterocycloalkyl. In embodiments, $R^{1.5}$ is independently unsubstituted phenyl. In embodiments, $R^{1.5}$ is independently unsubstituted 5 to 6 membered heteroaryl. In embodiments, $R^{1.5}$ is independently —$NHC(O)CH_3$. In embodiments, $R^{1.5}$ is independently —$OCH_3$. In embodiments, $R^{1.5}$ is independently —$SCH_3$. In embodiments, $R^{1.5}$ is independently

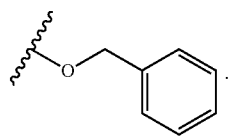 [SMILES: *OCc1ccccc1]

In embodiments, $R^{1.5}$ is independently

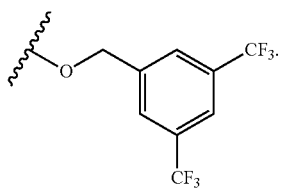 [SMILES: *OCc1cc(C(F)(F)F)cc(C(F)(F)F)c1]

In embodiments, $R^{1.5}$ is independently

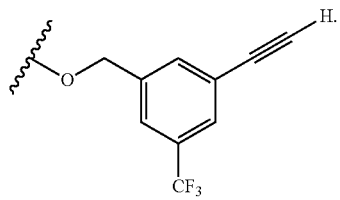

In embodiments, $R^{1.5}$ is independently

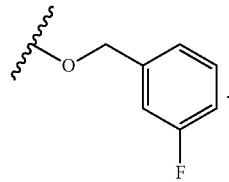 [SMILES: *OCc1cccc(F)c1]

In embodiments, $R^{1.5}$ is independently

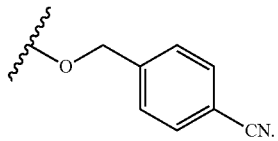 [SMILES: *OCc1ccc(C#N)cc1]

In embodiments, $R^{1.5}$ is independently

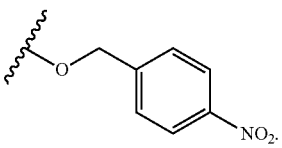 [SMILES: *OCc1ccc([N+](=O)[O-])cc1]

In embodiments, $R^{1.5}$ is independently a hydrogen.

In embodiments, $L^{1.5}$ is a bond, —$S(O)_2$—, —NH—, —O—, —S—, —C(O)—, —C(O)NH—, —NHC(O)—, —NHC(O)NH—, —C(O)O—, —OC(O)—, substituted or unsubstituted alkylene (e.g., $C_1$-$C_8$, $C_1$-$C_6$, or $C_1$-$C_4$), substituted or unsubstituted heteroalkylene (e.g., 2 to 8 membered, 2 to 6 membered, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8 membered, 3 to 6 membered, or 5 to 6 membered), substituted or unsubstituted arylene (e.g., $C_6$-$C_{10}$, $C_{10}$, or phenylene), or substituted or unsubstituted heteroarylene (e.g., 5 to 10 membered, 5 to 9 membered, or 5 to 6 membered). In embodiments, $L^{1.5}$ is a bond, —$S(O)_2$—, —NH—, —O—, —S—, —C(O)—, —C(O)NH—, —NHC(O)—, —NHC(O)NH—, —C(O)O—, —OC(O)—, substituted or unsubstituted alkylene, or substituted or unsubstituted heteroalkylene. In embodiments, $L^{1.5}$ is a bond, —O—, —C(O)—, —S—, —NH—, —NHC(O)—, —C(O)NH—, unsubstituted $C_1$-$C_4$ alkylene, or unsubstituted 2 to 4 membered heteroalkylene. In embodiments, $L^{1.5}$ is a bond. In embodiments, $L^{1.5}$ is —$OCH_2$—. In embodiments, $L^{1.5}$ is —NHC(O)—. In embodiments, $L^{1.5}$ is —S—. In embodiments, $L^{1.5}$ is —O—.

In embodiments, $R^{1.6}$ is independently hydrogen, halogen, —$CX^{1.6}_3$, —$CHX^{1.6}_2$, —$CH_2X^{1.6}$, —CN, —OH, —$NH_2$, —COOH, —$CONH_2$, —$NO_2$, —SH, —$OCX^{1.6}_3$, —$OCHX^{1.6}_2$, —$OCH_2X^{1.6}$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. $X^{1.6}$ is independently —F, —Cl, —Br, or —I. In embodiments, $R^{1.6}$ is independently hydrogen, halogen, —$CX^{1.6}_3$, —$CHX^{1.6}_2$, —$CH_2X^{1.6}$, —CN, —OH, —$NH_2$, —COOH, —$CONH_2$, —$NO_2$, —SH, —$OCX^{1.6}_3$, —$OCHX^{1.6}_2$, —$OCH_2X^{1.6}$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^{1.6}$ is independently —$OCH_3$. In embodiments, $R^{1.6}$ is independently unsubstituted phenyl. In embodiments, $R^{1.6}$ is independently —$CF_3$. In embodiments, $R^{1.6}$ is independently —$NO_2$. In embodiments, $R^{1.6}$ is independently —$OCF_3$. In embodiments, $R^{1.6}$ is independently —$OCHF_2$. In embodiments, $R^{1.6}$ is independently —$OCH_2F$. In embodiments, $R^{1.6}$ is independently halogen. In embodiments, $R^{1.6}$ is independently —F. In embodiments, $R^{1.6}$ is independently —Cl. In embodiments, $R^{1.6}$ is independently —Br. In embodiments, $R^{1.6}$ is independently —I. In embodiments, $R^{1.6}$ is independently —$CH_3$. In embodiments, $R^{1.6}$ is independently unsubstituted methyl. In embodiments, $R^{1.6}$ is independently unsubstituted ethyl. In embodiments, $R^{1.6}$ is independently unsubstituted propyl. In embodiments, $R^{1.6}$ is independently unsubstituted n-propyl. In embodiments, $R^{1.6}$ is independently unsubstituted isopropyl. In embodiments, $R^{1.6}$ is independently unsubstituted butyl. In embodiments, $R^{1.6}$ is independently unsubstituted n-butyl. In embodiments, $R^{1.6}$ is independently unsubstituted isobutyl. In embodiments, $R^{1.6}$ is independently unsubstituted tert-butyl. In embodiments, $R^{1.6}$ is independently unsubstituted pentyl. In embodiments, $R^{1.6}$ is independently unsubstituted hexyl. In embodiments, $R^{1.6}$ is independently unsubstituted heptyl. In embodiments, $R^{1.6}$ is independently unsubstituted octyl. In embodiments, $R^{1.6}$ is independently —$CX^{1.6}{}_3$. In embodiments, $R^{1.6}$ is independently —$CHX^{1.6}{}_2$. In embodiments, $R^{1.6}$ is independently —$CH_2X^{1.6}$. In embodiments, $R^{1.6}$ is independently —CN. In embodiments, $R^{1.6}$ is independently —OH. In embodiments, $R^{1.6}$ is independently —$NH_2$. In embodiments, $R^{1.6}$ is independently —COOH. In embodiments, $R^{1.6}$ is independently —$CONH_2$. In embodiments, $R^{1.6}$ is independently —SH. In embodiments, $R^{1.6}$ is independently —$OCX^{1.6}{}_3$. In embodiments, $R^{1.6}$ is independently —$OCHX^{1.6}{}_2$. In embodiments, $R^{1.6}$ is independently —$OCH_2X^{1.6}$. In embodiments, $R^{1.6}$ is independently unsubstituted $C_1$-$C_6$ alkyl. In embodiments, $R^{1.6}$ is independently unsubstituted 2 to 6 membered heteroalkyl. In embodiments, $R^{1.6}$ is independently unsubstituted $C_3$-$C_6$ cycloalkyl. In embodiments, $R^{1.6}$ is independently unsubstituted 3 to 6 membered heterocycloalkyl. In embodiments, $R^{1.6}$ is independently unsubstituted phenyl. In embodiments, $R^{1.6}$ is independently unsubstituted 5 to 6 membered heteroaryl. In embodiments, $R^{1.6}$ is independently —$NHC(O)CH_3$. In embodiments, $R^{1.6}$ is independently —$OCH_3$. In embodiments, $R^{1.6}$ is independently —$SCH_3$. In embodiments, $R^{1.6}$ is independently

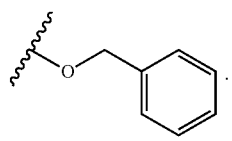 [SMILES: *OCc1ccccc1]

In embodiments, $R^{1.6}$ is independently

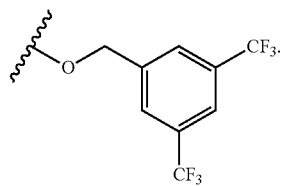 [SMILES: *OCc1cc(C(F)(F)F)cc(C(F)(F)F)c1]

In embodiments, $R^{1.6}$ is independently

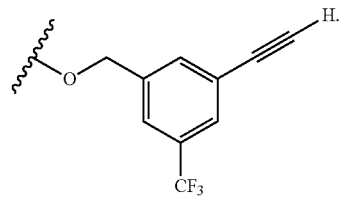

In embodiments, $R^{1.6}$ is independently

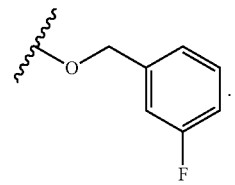 [SMILES: *OCc1cccc(F)c1]

In embodiments, $R^{1.6}$ is independently

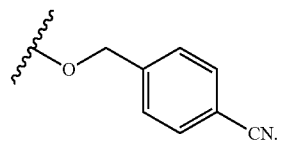 [SMILES: *OCc1ccc(C#N)cc1]

In embodiments, $R^{1.6}$ is independently

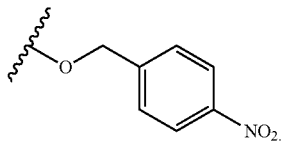

In embodiments, $R^{1.6}$ is independently a hydrogen.

In embodiments, $L^{1.6}$ is a bond, —$S(O)_2$—, —NH—, —O—, —S—, —C(O)—, —C(O)NH—, —NHC(O)—, —NHC(O)NH—, —C(O)O—, —OC(O)—, substituted or unsubstituted alkylene (e.g., $C_1$-$C_8$, $C_1$-$C_6$, or $C_1$-$C_4$), substituted or unsubstituted heteroalkylene (e.g., 2 to 8 membered, 2 to 6 membered, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8 membered, 3 to 6 membered, or 5 to 6 membered), substituted or unsubstituted arylene (e.g., $C_6$-$C_{10}$, $C_{10}$, or phenylene), or substituted or unsubstituted heteroarylene (e.g., 5 to 10 membered, 5 to 9 membered, or 5 to 6 membered). In embodiments, $L^{1.6}$ is a bond, —$S(O)_2$—, —NH—, —O—, —S—, —C(O)—, —C(O)NH—, —NHC(O)—, —NHC(O)NH—, —C(O)O—, —OC(O)—, substituted or unsubstituted alkylene, or substituted or unsubstituted heteroalkylene. In embodiments, $L^{1.6}$ is a bond, —O—, —C(O)—, —S—, —NH—, —NHC(O)—, —C(O)NH—, unsubstituted $C_1$-$C_4$ alkylene, or unsubstituted 2 to 4 membered heteroalkylene. In embodiments, $L^{1.6}$ is a bond. In embodiments, $L^{1.6}$ is —$OCH_2$—. In embodiments, $L^{1.6}$ is —NHC(O)—. In embodiments, $L^{1.6}$ is —S—. In embodiments, $L^{1.6}$ is —O—.

In some embodiments, the compound is any one of the compounds described herein (e.g., in an aspect, embodiment, claim, figure, table, or example). In embodiments, the compound is not a compound described herein (e.g., in an aspect, embodiment, claim, figure, table, or example).

In embodiments, the compound is

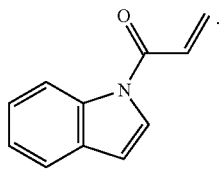

In embodiments, the compound is

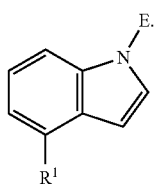

In embodiments, the compound is

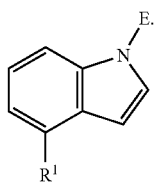

In embodiments, the compound is

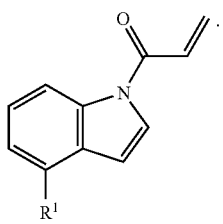

In embodiments, the compound is

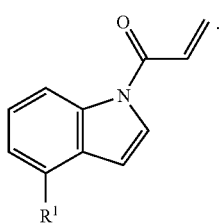

In embodiments, the compound is

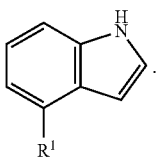

In embodiments, the compound is

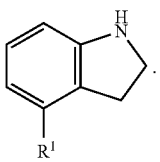

In embodiments, the compound is

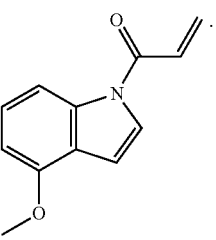

In embodiments, the compound is

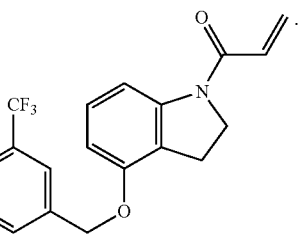

In embodiments, the compound is

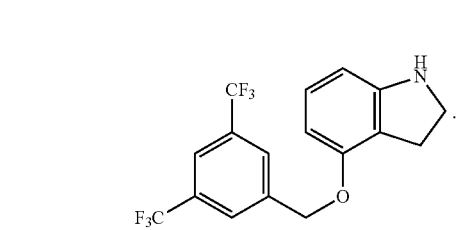

In embodiments, the compound is

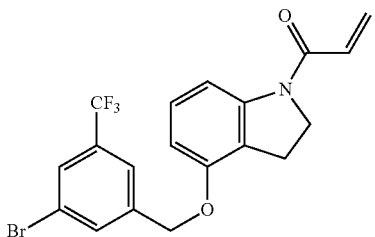

In embodiments, the compound is

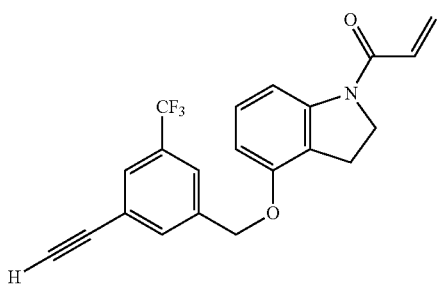

In embodiments, the compound is not

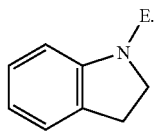

In embodiments, the compound is not

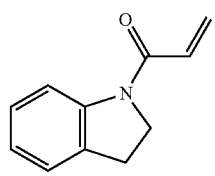

In embodiments, the compound is not

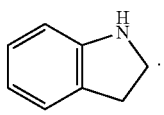

In some embodiments, a compound as described herein may include multiple instances of $R^1$ and/or other variables. In such embodiments, each variable may optional be different and be appropriately labeled to distinguish each group for greater clarity. For example, where each $R^1$ is different, they may be referred to, for example, as $R^{1.1}$, $R^{1.2}$, $R^{1.3}$, $R^{1.4}$, $R^{1.5}$, $R^{1.6}$, and $R^{1.7}$, respectively, wherein the definition of $R^1$ is assumed by $R^{1.1}$, $R^{1.2}$, $R^{1.3}$, $R^{1.4}$, $R^{1.5}$, $R^{1.6}$, and $R^{1.7}$. The variables used within a definition of $R^1$ and/or other variables that appear at multiple instances and are different may similarly be appropriately labeled to distinguish each group for greater clarity.

In an aspect is provided a compound having the formula:

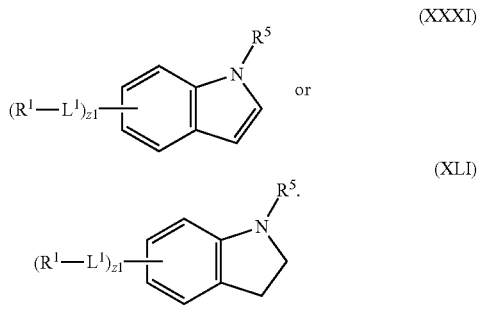

In embodiments, the compound has the formula:

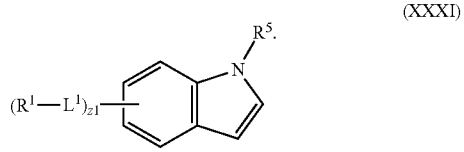

In embodiments, the compound has the formula:

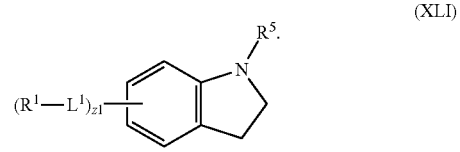

$L^1$, $R^1$, and z1 are as described herein, including in aspects and embodiments.

$R^5$ is independently hydrogen, $-CX^5_3$, $-CHX^5_2$, $-CH_2X^5$, $-CN$, $-OH$, $-COOH$, $-CONH_2$, $-OCX^5_3$, $-OCHX^5_2$, $-OCH_2X^5$, E, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $X^5$ is independently $-F$, $-Cl$, $-Br$, or $-I$.

E is as described herein.

In embodiments, $R^5$ is independently hydrogen, $-CX^5_3$, $-CHX^5_2$, $-CH_2X^5$, $-CN$, $-OH$, $-COOH$, $-CONH_2$, $-OCX^5_3$, $-OCHX^5_2$, $-OCH_2X^5$, E, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^5$ is independently hydrogen, $-CX^5_3$, $-CHX^5_2$, $-CH_2X^5$, $-CN$, $-COOH$, $-CONH_2$, E, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl In embodiments, $R^5$ is independently hydrogen, $-CX^5_3$, $-CHX^5_2$, $-CH_2X^5$, $-OCX^5_3$, $-OCH_2X^5$, $-OCHX^5_2$, $-CN$, $-OH$, $-COOH$, $-CONH_2$, E, $R^6$-substituted or unsubstituted alkyl (e.g., $C_1$-$C_8$, $C_1$-$C_6$, $C_1$-$C_4$, or $C_1$-$C_2$), $R^6$-substituted or unsubstituted heteroalkyl (e.g., 2 to 8 membered, 2 to 6 membered, 4 to 6 membered, 2 to 3 membered, or 4 to 5 membered), $R^6$-substituted or unsubstituted cycloalkyl (e.g., $C_3$-$C_8$, $C_3$-$C_6$, $C_4$-$C_6$, or $C_5$-$C_6$), $R^6$-substituted or unsubstituted heterocycloalkyl (e.g., 3 to 8 membered, 3 to 6 membered, 4 to 6 membered, 4 to 5 membered, or 5 to 6 membered), $R^6$-substituted or unsubstituted aryl (e.g., $C_6$-$C_{10}$ or phenyl), or $R^6$-substituted or unsubstituted heteroaryl (e.g., 5 to 10 membered, 5 to 9 membered, or 5 to 6 membered). In embodiments, $R^5$ is independently hydrogen, —$CX^5_3$, —$CHX^5_2$, —$CH_2X^5$, —$OCX^5_3$, —$OCH_2X^5$, —$OCHX^5_2$, —CN, —OH, —COOH, —$CONH_2$, E, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). In embodiments, $R^5$ is independently unsubstituted methyl. In embodiments, $R^5$ is independently unsubstituted ethyl. In embodiments, $R^5$ is independently hydrogen. In embodiments, $R^5$ is independently E.

$R^6$ is independently oxo, halogen, —$CX^6_3$, —$CHX^6_2$, —$CH_2X^6$, —$OCX^6_3$, —$OCH_2X^6$, —$OCHX^6_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$N_3$, $R^7$-substituted or unsubstituted alkyl (e.g., $C_1$-$C_8$, $C_1$-$C_6$, $C_1$-$C_4$, or $C_1$-$C_2$), $R^7$-substituted or unsubstituted heteroalkyl (e.g., 2 to 8 membered, 2 to 6 membered, 4 to 6 membered, 2 to 3 membered, or 4 to 5 membered), $R^7$-substituted or unsubstituted cycloalkyl (e.g., $C_3$-$C_8$, $C_3$-$C_6$, $C_4$-$C_6$, or $C_5$-$C_6$), $R^7$-substituted or unsubstituted heterocycloalkyl (e.g., 3 to 8 membered, 3 to 6 membered, 4 to 6 membered, 4 to 5 membered, or 5 to 6 membered), $R^7$-substituted or unsubstituted aryl (e.g., $C_6$-$C_{10}$ or phenyl), or $R^7$-substituted or unsubstituted heteroaryl (e.g., 5 to 10 membered, 5 to 9 membered, or 5 to 6 membered). In embodiments, $R^6$ is independently oxo, halogen, —$CX^6_3$, —$CHX^6_2$, —$CH_2X^6$, —$OCX^6_3$, —$OCH_2X^6$, —$OCHX^6_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^6$ is independently —F, —Cl, —Br, or —I. In embodiments, $R^6$ is independently unsubstituted methyl. In embodiments, $R^6$ is independently unsubstituted ethyl. In embodiments, $R^6$ is independently unsubstituted phenyl.

$R^7$ is independently oxo, halogen, —$CX^7_3$, —$CHX^7_2$, —$CH_2X^7$, —$OCX^7_3$, —$OCH_2X^7$, —$OCHX^7_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$N_3$, $R^8$-substituted or unsubstituted alkyl (e.g., $C_1$-$C_8$, $C_1$-$C_6$, $C_1$-$C_4$, or $C_1$-$C_2$), $R^8$-substituted or unsubstituted heteroalkyl (e.g., 2 to 8 membered, 2 to 6 membered, 4 to 6 membered, 2 to 3 membered, or 4 to 5 membered), $R^8$-substituted or unsubstituted cycloalkyl (e.g., $C_3$-$C_8$, $C_3$-$C_6$, $C_4$-$C_6$, or $C_5$-$C_6$), $R^8$-substituted or unsubstituted heterocycloalkyl (e.g., 3 to 8 membered, 3 to 6 membered, 4 to 6 membered, 4 to 5 membered, or 5 to 6 membered), $R^8$-substituted or unsubstituted aryl (e.g., $C_6$-$C_{10}$ or phenyl), or $R^8$-substituted or unsubstituted heteroaryl (e.g., 5 to 10 membered, 5 to 9 membered, or 5 to 6 membered). In embodiments, $R^7$ is independently oxo, halogen, —$CX^7_3$, —$CHX^7_2$, —$CH_2X^7$, —$OCX^7_3$, —$OCH_2X^7$, —$OCHX^7_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^7$ is independently —F, —Cl, —Br, or —I. In embodiments, $R^7$ is independently unsubstituted methyl. In embodiments, $R^7$ is independently unsubstituted ethyl.

$R^8$ is independently oxo, halogen, —$CX^8_3$, —$CHX^8_2$, —$CH_2X^8$, —$OCX^8_3$, —$OCH_2X^8$, —$OCHX^8_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^8$ is independently —F, —Cl, —Br, or —I. In embodiments, $R^8$ is independently unsubstituted methyl. In embodiments, $R^8$ is independently unsubstituted ethyl.

In embodiments, $R^5$ is independently —CN. In embodiments, $R^5$ is independently unsubstituted isopropyl. In embodiments, $R^5$ is independently —$OCH_3$. In embodiments, $R^5$ is independently unsubstituted cyclohexyl. In embodiments, $R^5$ is independently unsubstituted phenyl. In embodiments, $R^5$ is independently —$CF_3$. In embodiments, $R^5$ is independently —$OCF_3$. In embodiments, $R^5$ is independently —$OCHF_2$. In embodiments, $R^5$ is independently —$OCH_2F$. In embodiments, $R^5$ is independently unsubstituted cyclopropyl. In embodiments, $R^5$ is independently unsubstituted cyclobutyl. In embodiments, $R^5$ is independently unsubstituted cyclopentyl. In embodiments, $R^5$ is independently unsubstituted sec-butyl. In embodiments, $R^5$ is independently unsubstituted 2-butyl. In embodiments, $R^5$ is independently —CH(CH$_3$)(CH$_2$CH$_3$). In embodiments, $R^5$ is independently —CH$_2$CF$_3$. In embodiments, $R^5$ is independently —CH$_2$CX$^5_3$. In embodiments, $R^5$ is independently —CH(CH$_3$)(OCH$_3$). In embodiments, $R^5$ is independently unsubstituted butyl. In embodiments, $R^5$ is independently unsubstituted n-butyl. In embodiments, $R^5$ is independently unsubstituted n-pentyl. In embodiments, $R^5$ is independently unsubstituted n-hexyl. In embodiments, $R^5$ is independently unsubstituted n-heptyl. In embodiments, $R^5$ is independently unsubstituted n-octyl. In embodiments, $R^5$ is independently unsubstituted 1-pentyl. In embodiments, $R^5$ is independently unsubstituted 1-hexyl. In embodiments, $R^5$ is independently unsubstituted 1-heptyl. In embodiments, $R^5$ is independently unsubstituted 1-octyl. In embodiments, $R^5$ is independently —Br. In embodiments, $R^5$ is independently —CH$_3$. In embodiments, $R^5$ is independently —OCH(CH$_3$)$_2$.

In embodiments, the compound has the formula:

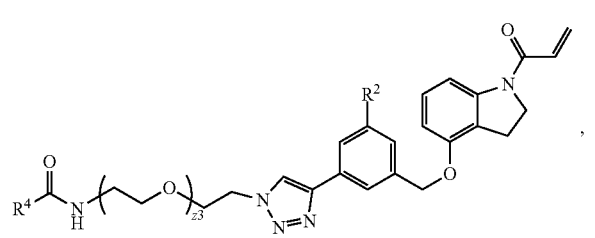

, is 5. In embodiments, z3 is 6. In embodiments, z3 is 7. In embodiments, z3 is 8.

In embodiments, the compound has the formula:

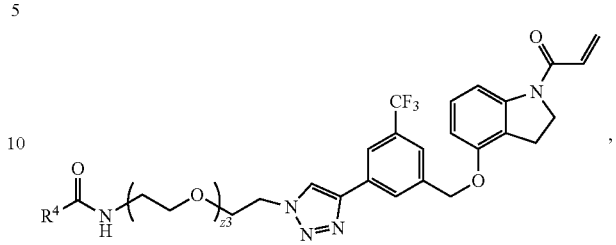

, wherein $R^4$ is as described herein.

In embodiments, the compound has the formula:

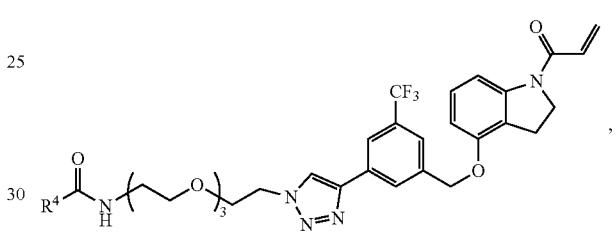

, wherein $R^4$ is as described herein.

In embodiments, the compound has the formula:

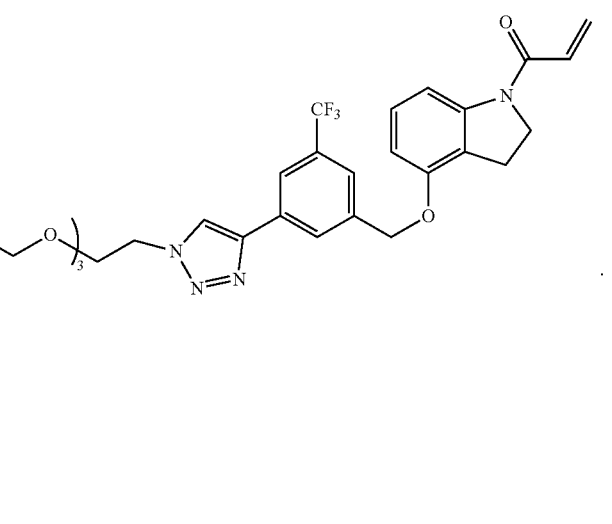

.

wherein $R^2$ and $R^4$ are as described herein. The symbol z3 is an integer from 0 to 8. In embodiments, z3 is 0. In embodiments, z3 is 1. In embodiments, z3 is 2. In embodiments, z3 is 3. In embodiments, z3 is 4. In embodiments, z3

In embodiments, compounds are referred to as followed: two letters, dash, one-digit number, dash, two-digit number. Compounds can alternatively be referred to with or without dashes (e.g. CC-1-44 or CC 1-44 or CC1-44).

III. Pharmaceutical Compositions

In an aspect is provided a pharmaceutical composition including a compound described herein and a pharmaceutically acceptable excipient.

In embodiments, the pharmaceutical composition includes an effective amount of the compound. In embodiments, the pharmaceutical composition includes a therapeutically effective amount of the compound. In embodiments, the pharmaceutical composition includes a second agent (e.g., an anti-cancer agent). In embodiments of the pharmaceutical compositions, the pharmaceutical composition includes a second agent in a therapeutically effective amount.

The pharmaceutical compositions may include optical isomers, diastereomers, or pharmaceutically acceptable salts of the modulators disclosed herein. The compound included in the pharmaceutical composition may be covalently attached to a carrier moiety. Alternatively, the compound included in the pharmaceutical composition is not covalently linked to a carrier moiety.

IV. Methods for Treating Diseases

In an aspect is provided a method for treating cancer, the method including administering to a subject in need thereof an effective amount of a compound described herein. In embodiments, the compound is included in a therapeutically effective amount.

In embodiments, the cancer is renal cell carcinoma. In embodiments, the cancer is follicular lymphoma. In embodiments, the cancer is glioblastoma. In embodiments, the cancer is colorectal cancer. In embodiments, the cancer is endometrial cancer. In embodiments, the cancer is lung cancer. In embodiments, the cancer is pancreatic cancer. In embodiments, the cancer is melanoma. In embodiments, the cancer is breast cancer. In embodiments, the cancer is acute myeloid leukemia. In embodiments, the cancer is endometrial cancer. In embodiments, the cancer is non-Hodgkin lymphoma. In embodiments, the cancer is mantle cell lymphoma. In embodiments, the method includes immunomodulation. In embodiments, the method includes cancer immunotherapy.

In an aspect is provided a method for treating a neurodegenerative disease, the method including administering to a subject in need thereof an effective amount of a compound described herein. In embodiments, the compound is included in a therapeutically effective amount. In embodiments, a method of treating nerve damage, the method including administering to a subject in need thereof an effective amount of a compound described herein. In embodiments, a method of treating a traumatic brain injury, the method including administering to a subject in need thereof an effective amount of a compound described herein. In embodiments, a method of treating a spinal cord injury, the method including administering to a subject in need thereof an effective amount of a compound described herein. In embodiments, a method of treating stroke, the method including administering to a subject in need thereof an effective amount of a compound described herein. In embodiments, the neurodegenerative disease is Huntington Disease, Alzheimer Disease, or Parkinson's Disease.

In an aspect is provided a method for treating a metabolic disease, the method including administering to a subject in need thereof an effective amount of a compound described herein. In embodiments, the compound is included in a therapeutically effective amount. In embodiments, the metabolic disease is diabetes. In embodiments, the metabolic disease is type 2 diabetes.

In an aspect is provided a method for treating an autoimmune disease, the method including administering to a subject in need thereof an effective amount of a compound described herein. In embodiments, the compound is included in a therapeutically effective amount. In embodiments, the autoimmune disease is systemic lupus erythematosus.

In an aspect is provided a method for treating a brain disorder, the method including administering to a subject in need thereof an effective amount of a compound described herein. In embodiments, the compound is included in a therapeutically effective amount. In embodiments, the brain disorder is epilepsy. In embodiments, the brain disorder is generalized epilepsy. In embodiments, the brain disorder is focal epilepsy. In embodiments, the brain disorder is autism spectrum disorder. In embodiments, the brain disorder is Asperger's syndrome. In embodiments, the brain disorder is pervasive developmental disorder. In embodiments, the brain disorder is autistic disorder. In embodiments, the brain disorder is childhood disintegrative disorder.

In an aspect is provided a method for treating a lysomal storage disorder, the method including administering to a subject in need thereof an effective amount of a compound described herein. In embodiments, the compound is included in a therapeutically effective amount. In embodiments, the lysomal storage disorder is Fabry disease. In embodiments, the lysomal storage disorder is Gaucher disease. In embodiments, the lysomal storage disorder is glycogenosis. In embodiments, the lysomal storage disorder is GM1 gangliosidosis. In embodiments, the lysomal storage disorder is mucopolysaccharidosis.

The compounds of the invention (i.e. compounds described herein, including in embodiments, examples, figures, tables) can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation or anti-cancer agents).

V. Methods of Modulating Activity

In an aspect is provided a method of reducing the level of activity of mTORC1 (e.g., reducing relative to a control), the method including contacting the mTORC1 with a compound described herein. In embodiments, the method includes contacting LAMTOR5 (e.g., SEQ ID NO:1).

In an aspect is provided a method of reducing the level of activity of a LAMTOR protein (e.g., reducing relative to a control), the method including contacting the LAMTOR protein with a compound described herein. In embodiments, the LAMTOR protein is LAMTOR5. In embodiments, the LAMTOR protein is human LAMTOR5.

In embodiments, the method includes inhibiting (e.g., reducing) the interaction of the Rag Guanosine Triphosphatases (GTPases) complex with the Ragulator complex. In embodiments, the method includes inhibiting (e.g., reducing) localization of mTORC1 to a lysosome (e.g., LAMP2-positive lysosome). In embodiments, the method includes inhibiting (e.g., reducing) interaction between the LAMTOR and the Ragulator complex (e.g., following amino acid stimulation of LAMTOR and Ragulator complex interaction). In embodiments, the method includes inhibiting the Guanine nucleotide exchange activity of LAMTOR (e.g., LAMTOR5). In embodiments, the method includes reducing the GTPase activity of RagA, RagB, RagC, or RagD. In embodiments, the method includes reducing the GTPase activity of the Ragulator complex. In embodiments, the method includes reducing the GTPase activity of a RagA/B dimer. In embodiments, the method includes reducing the GTPase activity of a RagC/D dimer. In embodiments, the method includes reducing the GTPase activity of a RagA/B-RagC/D heterodimeric GTPase. In embodiments, the method includes reducing the activity (e.g., GTPase activity) of a LAMTOR-Rag assembly (e.g., LAMTOR5-Rag assembly or the Ragulator complex).

In embodiments, the method includes reducing the activity of mTORC1 more than reducing the activity of mTORC2 (e.g., at least 1.1, 1.2, 1.3, 1.4, 1.5, 1.6, 1.7, 1.8, 1.9. 2, 3, 4, 5, 6, 7, 8, 9 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 100000, 1000000-fold more). In embodiments, the method includes reducing the activity of mTORC1 more than reducing the activity of mTORC2 (e.g., about 1.1, 1.2, 1.3, 1.4, 1.5, 1.6, 1.7, 1.8, 1.9. 2, 3, 4, 5, 6, 7, 8, 9 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 100000, 1000000-fold more). In embodiments, the method includes reducing the activity of mTORC1 more than reducing the activity of mTORC2 (e.g., 1.1, 1.2, 1.3, 1.4, 1.5, 1.6, 1.7, 1.8, 1.9. 2, 3, 4, 5, 6, 7, 8, 9 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 100000, 1000000-fold more).

In embodiments, the method includes reducing (e.g., reduced relative to a control) mTORC1 signaling by preventing mTORC1 localization to the lysosome. In embodiments, the method includes modulating (e.g., preventing the formation) of the Ragulator complex (e.g., Lamtor-Rag scaffold as described herein). In embodiments, the method includes reducing (e.g., reduced relative to a control) mTORC1 signaling by causing an accumulation of Ragulator complex in the lysosome. In embodiments, the method includes preventing the activation of the Ragulator complex (e.g., the Lamtor-Rag scaffold). In embodiments, the method includes preventing the binding of mTORC1 to the Ragulator complex. In embodiments, the method includes preventing the formation of the Ragulator complex. Additional insight into the Ragulator complex may be found in, for example, in Science. 2017 Oct. 20; 358(6361):377-381 and Cell. 2010; 141(2):290-303. PMCID: 3024592, each of which are incorporated herein by reference in their entirety.

VI. LAMTOR5 Protein

In an aspect is provided a LAMTOR5 protein covalently bonded to a compound described herein, which may be referred to herein as a LAMTOR5 protein-compound complex. In embodiments, the LAMTOR5 protein is a human LAMTOR5 protein. In embodiments, human LAMTOR5 protein has the sequence SEQ ID NO: 1. In embodiments, the compound is an oligonucleotide (e.g., DNA, RNA, or siRNA), protein (e.g., antibody, anti-LAMTOR5 antibody), or compound (e.g., compound described herein). In embodiments, the compound is provided in a therapeutically effective amount. In embodiments, the compound contacts one or more amino acids corresponding C23 and C148 of SEQ ID NO: 1. In embodiments, the compound covalently binds an amino acid corresponding to C23 in SEQ ID NO: 1. In embodiments, the compound covalently binds an amino acid corresponding to C148 in SEQ ID NO:1. In embodiments, compound contacts an amino acid corresponding to C23 and C148 of SEQ ID NO: 1. In embodiments, the compound contacts an amino acid corresponding to C23 of SEQ ID NO: 1. In embodiments, the compound contacts an amino acids corresponding to C148 of SEQ ID NO: 1.

In embodiments, the compound (e.g., the compound as described herein) is bonded to a cysteine residue of the LAMTOR5 protein. In embodiments, the compound is covalently bonded to a cysteine residue of the LAMTOR5 protein. In embodiments, the compound is reversibly covalently bonded to a cysteine residue of the LAMTOR5 protein. In embodiments, the compound is irreversibly covalently bonded to a cysteine residue of the LAMTOR5 protein. In embodiments, the compound is covalently bonded to a cysteine corresponding to C23 of human LAMTOR5 protein (e.g., SEQ ID NO: 1). In embodiments, the compound is irreversibly covalently bonded a cysteine corresponding to C23 of human LAMTOR5 protein (e.g., SEQ ID NO: 1). In embodiments, the compound is covalently bonded to a cysteine corresponding to C148 of human LAMTOR5 protein (e.g., SEQ ID NO: 1). In embodiments, the compound is irreversibly covalently bonded a cysteine corresponding to C148 of human LAMTOR5 protein (e.g., SEQ ID NO:1).

In an embodiment, human LAMTOR5 protein (e.g., SEQ ID NO: 1) is covalently bonded (e.g., reversibly or irreversibly) to a portion of a compound described herein.

In an aspect is provided a LAMTOR5 protein (e.g., human LAMTOR5 SEQ ID NO: 1) covalently bonded to a fragment (e.g., moiety, moiety of a fragment) of a compound described herein.

In embodiments, a LAMTOR5 protein (e.g., human LAMTOR5) is covalently bonded to a compound (e.g., compound described herein or a portion of a compound described herein). In embodiments, a LAMTOR5 protein (e.g., human LAMTOR5) is irreversibly covalently bonded to a compound (e.g., compound described herein or a portion of a compound described herein). In embodiments, the LAMTOR5 protein (e.g., human LAMTOR5) is reversibly covalently bonded to a compound (e.g., compound described herein or a portion of a compound described herein). In embodiments, the LAMTOR5 protein (e.g., human LAMTOR5) is covalently bonded to a portion of a compound (e.g., compound described herein). In embodiments, the LAMTOR5 protein (e.g., human LAMTOR5) is irreversibly covalently bonded to a portion of a compound described herein. In embodiments, the LAMTOR5 protein (e.g., human LAMTOR5) is reversibly covalently bonded to a portion of a compound described herein. In embodiments, the compound described herein is bonded to a cysteine residue (e.g., Cys23 of human LAMTOR5 or cysteine corresponding to Cys23 of human LAMTOR5) of the LAMTOR5 protein (e.g., human LAMTOR5). In embodiments, the portion of a compound described herein is bonded to a cysteine residue (e.g., Cys23 of SEQ ID NO: 1 or cysteine corresponding to Cys23 of SEQ ID NO: 1) of the LAMTOR5 protein (e.g., human LAMTOR5).

In embodiments, the LAMTOR5 protein covalently bonded to a compound described herein is the product of a reaction between the LAMTOR5 protein (e.g., SEQ ID NO: 1) and a compound described herein. It will be understood that the covalently bonded LAMTOR5 protein and compound described herein are the remnants of the reactant LAMTOR5 protein (e.g., SEQ ID NO: 1) and compound, wherein each reactant now participates in the covalent bond between the LAMTOR5 protein and or compound. In embodiments of the covalently bonded LAMTOR5 protein (e.g., SEQ ID NO: 1) and compound described herein, the remnant of the E substituent is a linker including a covalent bond between the LAMTOR5 protein (e.g., SEQ ID NO: 1) and the remainder of the compound described herein. It will be understood by a person of ordinary skill in the art that when a LAMTOR5 protein is covalently bonded to a compound described herein, the compound described herein forms a remnant of the pre-reacted compound wherein a bond connects the remnant of the compound to the remnant of the LAMTOR5 protein (e.g., cysteine sulfur, sulfur of amino acid corresponding to C23 of human LAMTOR5, sulfur of C23 of human LAMTOR5 having the sequence SEQ ID NO: 1). In embodiments, the remnant of the E substituent is a linker selected from a bond, $-S(O)_2-$, $-NH-$, $-O-$, $-S-$, $-C(O)-$, $-C(O)NH-$, $-NHC(O)-$, $-NHC(O)NH-$, $-NHC(O)NH-$, $-C(O)O-$, $-OC(O)-$, $-CH_2NH-$, substituted (e.g., substituted with a substituent group, a size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted arylene (e.g., $C_6$-$C_{10}$ or phenyl), or substituted (e.g., substituted with a substituent group, a size-limited substituent group, or lower substituent group) or unsubstituted heteroarylene (e.g., 5 to 10 membered, 5 to 9 membered, or 5 to 6 membered). As a non-limiting example, the LAMTOR5 protein covalently bonded to a compound may have the formula:

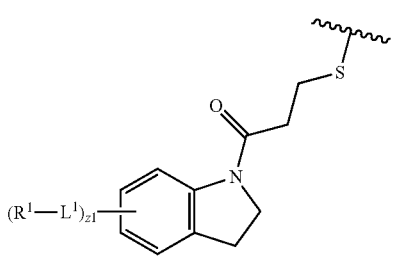

wherein S is the sulfur of a LAMTOR5 protein cysteine (e.g., corresponding to C23 of human LAMTOR5 (e.g., SEQ ID NO: 1)), which is bonded to the remainder of the LAMTOR5 protein and wherein $R^1$, $L^1$, and z1 are as described herein. As a non-limiting example, the LAMTOR5 protein covalently bonded to a compound may have the formula:

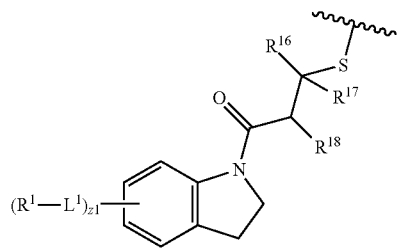

wherein S is the sulfur of a LAMTOR5 protein cysteine (e.g., corresponding to C23 of human LAMTOR5 (e.g., SEQ ID NO: 1)), which is bonded to the remainder of the LAMTOR5 protein and wherein $R^1$, $R^{16}$, $R^{17}$, $R^{18}$ $L^1$, and z1 are as described herein. As a non-limiting example, the LAMTOR5 protein covalently bonded to a compound may have the formula:

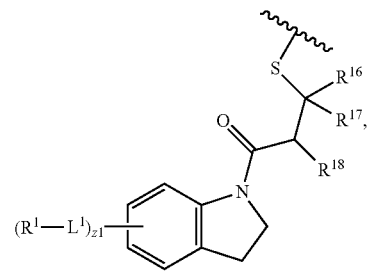

wherein S is the sulfur of a LAMTOR5 protein cysteine (e.g., corresponding to C23 of human LAMTOR5 (e.g., SEQ ID NO: 1)), which is bonded to the remainder of the LAMTOR5 protein and wherein $R^1$, $R^{16}$, $R^{17}$, $R^{18}$ $L^1$, and z1 are as described herein.

As a non-limiting example, the LAMTOR5 protein covalently bonded to a compound may have the formula:

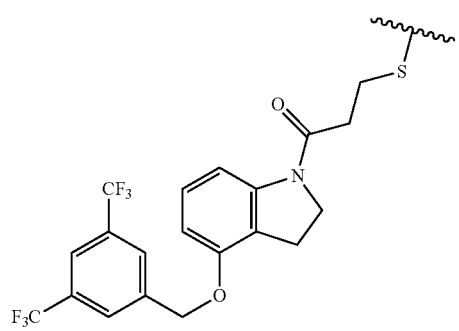

wherein S is the sulfur of a LAMTOR5 protein cysteine (e.g., corresponding to C23 of human LAMTOR5 (e.g., SEQ ID NO: 1)), which is bonded to the remainder of the LAMTOR5 protein.

VII. Embodiments

Embodiments S1

A compound having the formula:

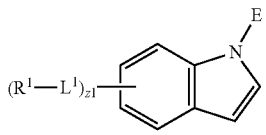
(I)

wherein, $L^1$ is independently a bond, —S(O)$_2$—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^1$ is independently halogen, —CX$^1$$_3$, —CHX$^1$$_2$, —CH$_2$X$^1$, —OCX$^1$$_3$, —OCH$_2$X$^1$, —OCHX$^1$$_2$, —CN, —SO$_{n1}$R$^{1D}$, —SO$_{v1}$NR$^{1A}$R$^{1B}$, —NHC(O)NR$^{1A}$R$^{1B}$, —N(O)$_{m1}$, —NR$^{1A}$R$^{1B}$, —C(O)R$^{1C}$, —C(O)—OR$^{1C}$, —C(O)NR$^{1A}$R$^{1B}$, —OR$^{1D}$, —NR$^{1A}$SO$_2$R$^{1D}$, —NR$^{1A}$C(O)R$^{1C}$, —NR$^{1A}$C(O)OR$^{1C}$, —NR$^{1A}$OR$^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent -L$^1$-R$^1$ substituents may optionally be joined to form a substituted or unsubstituted cycloalkyl, substituted or unsubstituted heterocycloalkyl, substituted or unsubstituted aryl, or substituted or unsubstituted heteroaryl;

E is an electrophilic moiety;

Each $R^{1A}$, $R^{1B}$, $R^{1C}$, and $R^{1D}$ is independently hydrogen, —CX$_3$, —CHX$_2$, —CH$_2$X, —CN, —OH, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl;

each X and X$^1$ is independently —F, —Cl, —Br, or —I;

n1 is independently an integer from 0 to 4;

m1 and v1 are independently 1 or 2; and z1 is independently an integer from 0 to 6.

Embodiments S2

The compound of embodiment S1, having the formula:

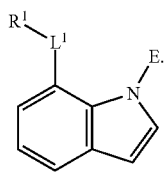
(Ia)

Embodiments S3

The compound of embodiment S1, having the formula:

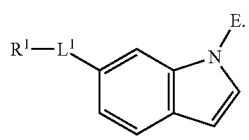
(Ib)

Embodiments S4

The compound of embodiment S1, having the formula:

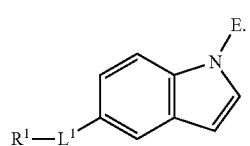
(Ic)

Embodiments S5

The compound of embodiment S1, having the formula:

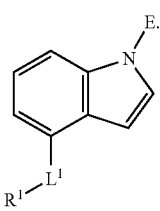
(Id)

Embodiments S6

The compound of embodiment Si, having the formula:

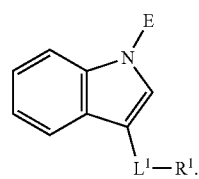
(Ie)

Embodiments S7

The compound of embodiment Si, having the formula:

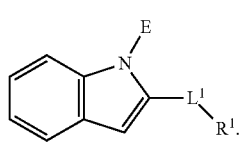
(If)

Embodiments S8

The compound of one of embodiments S1 to S7, wherein E is

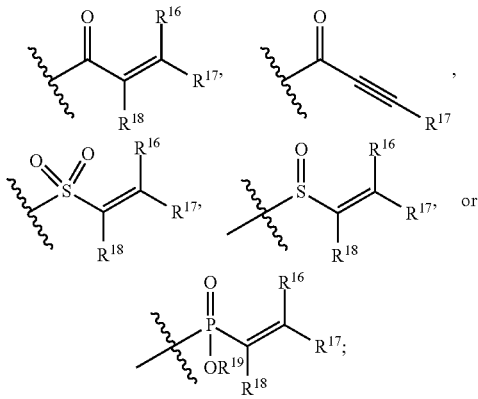

wherein $R^{16}$ is independently hydrogen, halogen, $-CX^{16}_3$, $-CHX^{16}_2$, $-CH_2X^{16}$, $-CN$, $-SO_{n16}R^{16A}$, $-SO_{v16}NR^{16A}R^{16B}$, $-NHNR^{16A}R^{16B}$, $-ONR^{16A}R^{16B}$, $-NHC(O)NHNR^{16A}R^{16B}$, $-NHC(O)NR^{16A}R^{16B}$, $-N(O)_{m16}$, $-NR^{16A}R^{16B}$, $-C(O)R^{16A}$, $-C(O)-OR^{16A}$, $-C(O)NR^{16A}R^{16B}$, $-OR^{16A}$, $-NR^{16A}SO_2R^{16B}$, $-NR^{16A}C(O)R^{16B}$, $-NR^{16A}C(O)OR^{16B}$, $-NR^{16A}OR^{16B}$, $-OCX^{16}_3$, $-OCHX^{16}_2$, $-OCH_2X^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{17}$ is independently hydrogen, halogen, $CX^{17}_3$, $-CHX^{17}_2$, $-CH_2X^{17}$, $-CN$, $-SO_{n17}R^{17A}$, $-SO_{v17}NR^{17A}R^{17B}$, $-NHNR^{17A}R^{17B}$, $-ONR^{17A}R^{17B}$, $-NHC(O)NHNR^{17A}R^{17B}$, $-NHC(O)NR^{17A}R^{17B}$, $-N(O)_{m17}$, $-NR^{17A}R^{17B}$, $-C(O)R^{17A}$, $-C(O)-OR^{17A}$, $-C(O)NR^{17A}R^{17B}$, $-OR^{17A}$, $-NR^{17A}SO_2R^{17B}$, $-NR^{17A}C(O)R^{17B}$, $-NR^{17A}C(O)OR^{17B}$, $-NR^{17A}OR^{17B}$, $-OCX^{17}_3$, $-OCHX^{17}_2$, $-OCH_2X^{17}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{18}$ is independently hydrogen, halogen, $CX^{18}_3$, $-CHX^{18}_2$, $-CH_2X^{18}$, $-CN$, $-SO_{n18}R^{18A}$, $-SO_{v18}NR^{18A}R^{18B}$, $-NHNR^{18A}R^{18B}$, $-ONR^{18A}R^{18B}$, $-NHC(O)NHNR^{18A}R^{18B}$, $-NHC(O)NR^{18A}R^{18B}$, $-N(O)_{m18}$, $-NR^{18A}R^{18B}$, $-C(O)R^{18A}$, $-C(O)-OR^{18A}$, $-C(O)NR^{18A}R^{18B}$, $-OR^{18A}$, $-NR^{18A}SO_2R^{18B}$, $-NR^{18A}C(O)R^{18B}$, $-NR^{18A}C(O)OR^{18B}$, $-NR^{18A}OR^{18B}$, $-OCX^{18}_3$, $-OCHX^{18}_2$, $-OCH_2X^{18}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{19}$ is independently hydrogen, halogen, $CX^{19}_3$, $-CHX^{19}_2$, $-CH_2X^{19}$, $-CN$, $-SO_{n19}R^{19A}$, $-SO_{v19}NR^{19A}R^{19B}$, $-NHNR^{19A}R^{19B}$, $-ONR^{19A}R^{19B}$, $-NHC(O)NHNR^{19A}R^{19B}$, $-NHC(O)NR^{19A}R^{19B}$, $-N(O)_{m19}$, $-NR^{19A}R^{19B}$, $-C(O)R^{19A}$, $-C(O)-OR^{19A}$, $-C(O)NR^{19A}R^{19B}$, $-OR^{19A}$, $-NR^{19A}SO_2R^{19B}$, $-NR^{19A}C(O)R^{19B}$, $-NR^{19A}C(O)OR^{19B}$, $-NR^{19A}OR^{19B}$, $-OCX^{19}_3$, $-OCHX^{19}_2$, $-OCH_2X^{19}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{16A}$, $R^{16B}$, $R^{17A}$, $R^{17B}$, $R^{18A}$, $R^{18B}$, $R^{19A}$, and $R^{19B}$ are independently hydrogen, $-CX_3$, $CHX_2$, $-CH_2X$, $-CN$, $-OH$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{16A}$ and $R^{16B}$ substituents bonded to the same nitrogen atom may optionally be joined to form a substituted or unsubstituted heterocycloalkyl or substituted or unsubstituted heteroaryl; $R^{17A}$ and $R^{17B}$ substituents bonded to the same nitrogen atom may optionally be joined to form a substituted or unsubstituted heterocycloalkyl or substituted or unsubstituted heteroaryl; $R^{18A}$ and $R^{18B}$ substituents bonded to the same nitrogen atom may optionally be joined to form a substituted or unsubstituted heterocycloalkyl or substituted or unsubstituted heteroaryl; $R^{19A}$ and $R^{19B}$ substituents bonded to the same nitrogen atom may optionally be joined to form a substituted or unsubstituted heterocycloalkyl or substituted or unsubstituted heteroaryl;

each X, $X^{16}$, $X^{17}$, $X^{18}$ and $X^{19}$ is independently $-F$, $-Cl$, $-Br$, or $-I$;

n16, n17, n18, and n19 are independently an integer from 0 to 4; and m16, m17, m18, m19, v16, v17, v18, and v19 are independently 1 or 2.

Embodiments S9

The compound of one of embodiments S1 to S7, wherein E is

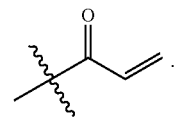

Embodiments S10

The compound of one of embodiments S1 to S9, wherein $L^1$ is a bond.

Embodiments S11

The compound of one of embodiments S1 to S9, wherein $L^1$ is $-OCH_2-$.

Embodiments S12

The compound of one of embodiments S1 to S9, wherein $L^1$ is $-NHC(O)-$.

Embodiments S13

The compound of one of embodiments S1 to S9, wherein $L^1$ is —S—.

Embodiments S14

The compound of one of embodiments S1 to S9, wherein $L^1$ is —O—.

Embodiments S15

The compound of one of embodiments S1 to S14, wherein $R^1$ is independently halogen, —$CX^1_3$, —$CHX^1_2$, —$CH_2X^1$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH$_2$, —NHC(O)NH$_2$, —NHSO$_2$H, —NHC(O)H, —NHC(O)OH, —NHOH, —$OCX^1_3$, —$OCHX^1_2$, —$OCH_2X^1$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl.

Embodiments S16

The compound of one of embodiments S1 to S14, wherein $R^1$ is independently halogen, —$CX^1_3$, —$CHX^1_2$, —$CH_2X^1$, —CN, —OH, —$NH_2$, —COOH, —$CONH_2$, —$NO_2$, —SH, —$OCX^1_3$, —$OCHX^1_2$, —$OCH_2X^1$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiments S17

The compound of one of embodiments S1 to S14, wherein $R^1$ is independently halogen, —$CX^1_3$, —$CHX^{12}$, —$CH_2X^1$, —CN, —OH, —$NH_2$, —COOH, —$CONH_2$, —$NO_2$, —SH, —$OCX^1_3$, —$OCHX^{12}$, —$OCH_2X^1$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

Embodiments S18

The compound of one of embodiments S1 to S14, wherein $R^1$ is independently halogen, —$CF_3$, —OH, —SH, —NHC(O)CH$_3$, —OCH$_3$, —SCH$_3$,

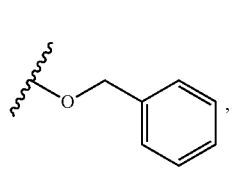
,
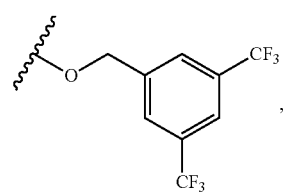
,

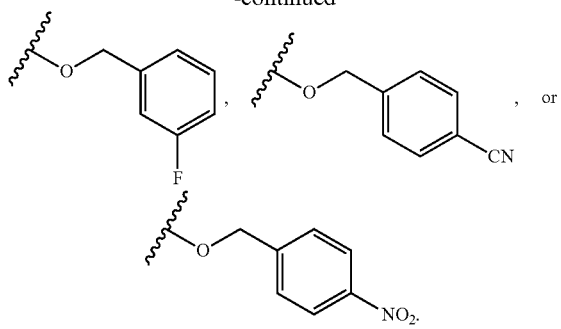

Embodiments S19

The compound of one of embodiments S1 to S18, wherein z1 is 2.

Embodiments S20

The compound of one of embodiments S1 to S18, wherein z1 is 1.

Embodiments S21

The compound of one of embodiments S1 to S18, wherein z1 is 0.

Embodiments S22

A pharmaceutical composition comprising a compound of one of embodiments S1 to S21 and a pharmaceutically acceptable excipient.

Embodiments S23

A method of reducing the level of activity of mTORC1, said method comprising contacting the mTORC1 with a compound of one of embodiments S1 to 521.

Embodiments S24

A method for treating cancer, said method comprising administering to a subject in need thereof a therapeutically effective amount of a compound of one of embodiments S1 to S21.

Embodiments S25

The method of embodiment S24, wherein said cancer is renal cell carcinoma, follicular lymphoma, glioblastoma, colorectal cancer, endometrial, or lung cancer.

Embodiments S26

A method for treating a neurodegenerative disease, said method comprising administering to a subject in need thereof a therapeutically effective amount of a compound of one of embodiments S1 to 521.

Embodiments S27

The method of embodiment S26, wherein said neurodegenerative disease is Huntington Disease, Alzheimer Disease, or Parkinson's Disease.

119

Embodiments S28

A method for treating a metabolic disease, said method comprising administering to a subject in need thereof a therapeutically effective amount of a compound of one of embodiments S1 to S21.

Embodiments S29

The method of embodiment S28, wherein said metabolic disease is type 2 diabetes.

Embodiments S30

A LAMTOR5 protein covalently bonded to a compound of one of embodiments S1 to S21.

Embodiments S31

The LAMTOR5 protein of embodiment S30, wherein the compound is covalently bonded to a cysteine residue of the protein.

Embodiments S32

The LAMTOR5 protein of embodiment S30, wherein the compound is irreversibly covalently bonded to a cysteine residue of the protein.

Embodiments S33

The LAMTOR5 protein of embodiment S30, wherein the compound is covalently bonded to a cysteine corresponding to C23 of human LAMTOR5 protein.

Embodiments S34

The LAMTOR5 protein of embodiment S30, wherein the compound is irreversibly covalently bonded a cysteine corresponding to C23 of human LAMTOR5 protein.

Embodiments S35

A LAMTOR5 protein covalently bonded to a fragment of a compound of one of embodiments S1 to S21.

Embodiment Q1

A compound having the formula:

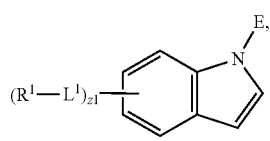
(I)

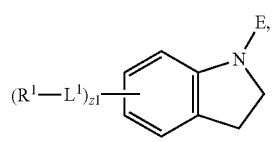
(VI)

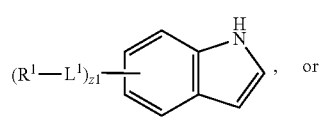
, or
(XI)

120

-continued

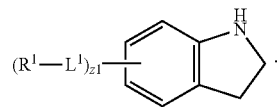
(XXI)

wherein, $L^1$ is independently a bond, —S(O)$_2$—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^1$ is independently halogen, —CX$^1_3$, —CHX$^1_2$, —CH$_2$X$^1$, —OCX$^1_3$, —OCH$_2$X$^1$, —OCHX$^1_2$, —CN, —SO$_{n1}$R$^{1D}$, —SO$_{v1}$NR$^{1A}$R$^{1B}$, —NHC(O)NR$^{1A}$R$^{1B}$, —N(O)$_{m1}$, —NR$^{1A}$R$^{1B}$, —C(O)R$^{1C}$, —C(O)—OR$^{1C}$, —C(O)NR$^{1A}$R$^{1B}$, —OR$^{1D}$, —NR$^{1A}$SO$_2$R$^{1D}$, —NR$^{1A}$C(O)R$^{1C}$, —NR$^{1A}$C(O)OR$^{1C}$, —NR$^{1A}$OR$^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent -L$^1$-R$^1$ substituents may optionally be joined to form a substituted or unsubstituted cycloalkyl, substituted or unsubstituted heterocycloalkyl, substituted or unsubstituted aryl, or substituted or unsubstituted heteroaryl;

E is an electrophilic moiety;

Each $R^{1A}$, $R^{1B}$, $R^{1C}$, and $R^{1D}$ is independently hydrogen, —CX$_3$, —CHX$_2$, —CH$_2$X, —CN, —OH, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl;

each X and $X^1$ is independently —F, —Cl, —Br, or —I;

n1 is independently an integer from 0 to 4;

m1 and v1 are independently 1 or 2; and z1 is independently an integer from 0 to 6.

Embodiment Q2

The compound of embodiment Q1, having the formula:

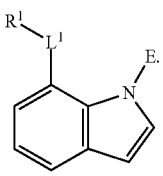
(Ia)

121
122

Embodiment Q3

The compound of embodiment Q1, having the formula:

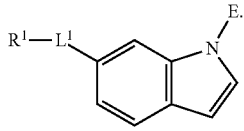

(Ib)

Embodiment Q4

The compound of embodiment Q1, having the formula:

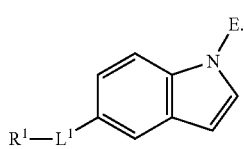

(Ic)

Embodiment Q5

The compound of embodiment Q1, having the formula:

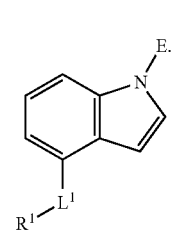

(Id)

Embodiment Q6

The compound of embodiment Q1, having the formula:

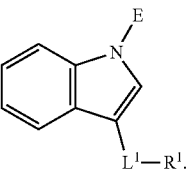

(Ie)

Embodiment Q7

The compound of embodiment Q1, having the formula:

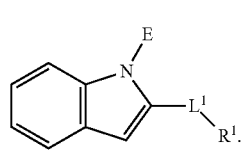

(If)

Embodiment Q8

The compound of embodiment Q1, having the formula:

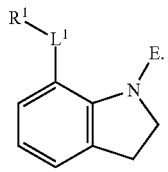

(VIa)

Embodiment Q9

The compound of embodiment Q1, having the formula:

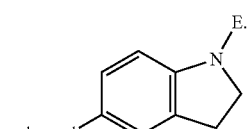

(VIb)

Embodiment Q10

The compound of embodiment Q1, having the formula:

(VIc)

Embodiment Q11

The compound of embodiment Q1, having the formula:

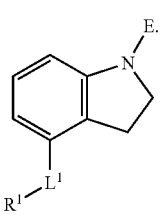

(VId)

Embodiment Q12

The compound of embodiment Q1, having the formula:

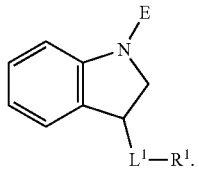

(VIe)

Embodiment Q13

The compound of embodiment Q1, having the formula:

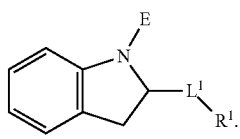

(VIf)

Embodiment Q14

The compound of one of embodiments Q1 to Q13, wherein E is

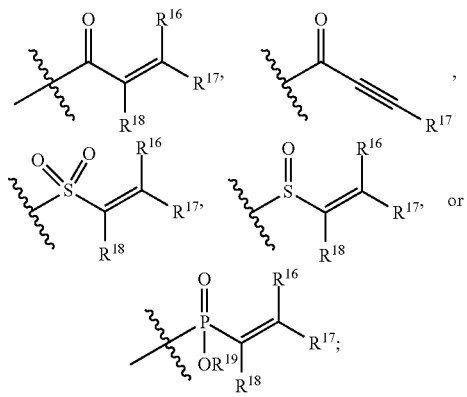

wherein $R^{16}$ is independently hydrogen, halogen, —$CX^{16}_3$, —$CHX^{16}_2$, —$CH_2X^{16}$, —CN, —$SO_{n16}R^{16A}$, —$SO_{v16}NR^{16A}R^{16B}$, —$NHNR^{16A}R^{16B}$, —$ONR^{16A}R^{16B}$, —$NHC(O)NHNR^{16A}R^{16B}$, —$NHC(O)NR^{16A}R^{16B}$, —$N(O)_{m16}$, —$NR^{16A}R^{16B}$, —$C(O)R^{16A}$, —$C(O)$—$OR^{16A}$, —$C(O)NR^{16A}R^{16B}$, —$OR^{16A}$, —$NR^{16A}SO_2R^{16B}$, —$NR^{16A}C(O)R^{16B}$, —$NR^{16A}C(O)OR^{16B}$, —$NR^{16A}OR^{16B}$, —$OCX^{16}_3$, —$OCHX^{16}_2$, —$OCH_2X^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{17}$ is independently hydrogen, halogen, $CX^{17}_3$, —$CHX^{17}_2$, —$CH_2X^{17}$, —CN, —$SO_{n17}R^{17A}$, —$SO_{v17}NR^{17A}R^{17B}$, —$NHNR^{17A}R^{17B}$, —$ONR^{17A}R^{17B}$, —$NHC(O)NHNR^{17A}R^{17B}$, —$NHC(O)NR^{17A}R^{17B}$, —$N(O)_{m17}$, —$NR^{17A}R^{17B}$, —$C(O)R^{17A}$, —$C(O)$—$OR^{17A}$, —$C(O)NR^{17A}R^{17B}$, —$OR^{17A}$, —$NR^{17A}SO_2R^{17B}$, —$NR^{17A}C(O)R^{17B}$, —$NR^{17A}C(O)OR^{17B}$, —$NR^{17A}OR^{17B}$, —$OCX^{17}_3$, —$OCHX^{17}_2$, —$OCH_2X^{17}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{18}$ is independently hydrogen, halogen, $CX^{18}_3$, —$CHX^{18}_2$, —$CH_2X^{18}$, —CN, —$SO_{n18}R^{18A}$, —$SO_{v18}NR^{18A}R^{18B}$, —$NHNR^{18A}R^{18B}$, —$ONR^{18A}R^{18B}$, —$NHC(O)NHNR^{18A}R^{18B}$, —$NHC(O)NR^{18A}R^{18B}$, —$N(O)_{m18}$, —$NR^{18A}R^{18B}$, —$C(O)R^{18A}$, —$C(O)$—$OR^{18A}$, —$C(O)NR^{18A}R^{18B}$, —$OR^{18A}$, —$NR^{18A}SO_2R^{18B}$, —$NR^{18A}C(O)R^{18B}$, —$NR^{18A}C(O)OR^{18B}$, —$NR^{18A}OR^{18B}$, —$OCX^{18}_3$, —$OCHX^{18}_2$, —$OCH_2X^{18}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{19}$ is independently hydrogen, halogen, $CX^{19}_3$, —$CHX^{19}_2$, —$CH_2X^{19}$, —CN, —$SO_{n19}R^{19A}$, —$SO_{v19}NR^{19A}R^{19B}$, —$NHNR^{19A}R^{19B}$, —$ONR^{19A}R^{19B}$, —$NHC(O)NHNR^{19A}R^{19B}$, —$NHC(O)NR^{19A}R^{19B}$, —$N(O)_{m19}$, —$NR^{19A}R^{19B}$, —$C(O)R^{19A}$, —$C(O)$—$OR^{19A}$, —$C(O)NR^{19A}R^{19B}$, —$OR^{19A}$, —$NR^{19A}SO_2R^{19B}$, —$NR^{19A}C(O)R^{19B}$, —$NR^{19A}C(O)OR^{19B}$, —$NR^{19A}OR^{19B}$, —$OCX^{19}_3$, —$OCHX^{19}_2$, —$OCH_2X^{19}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{16A}$, $R^{16B}$, $R^{17A}$, $R^{17B}$, $R^{18A}$, $R^{18B}$, $R^{19A}$, and $R^{19B}$ are independently hydrogen, —$CX_3$, $CHX_2$, —$CH_2X$, —CN, —OH, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{16A}$ and $R^{16B}$ substituents bonded to the same nitrogen atom may optionally be joined to form a substituted or unsubstituted heterocycloalkyl or substituted or unsubstituted heteroaryl; $R^{17A}$ and $R^{17B}$ substituents bonded to the same nitrogen atom may optionally be joined to form a substituted or unsubstituted heterocycloalkyl or substituted or unsubstituted heteroaryl; $R^{18A}$ and $R^{18B}$ substituents bonded to the same nitrogen atom may optionally be joined to form a substituted or unsubstituted heterocycloalkyl or substituted or unsubstituted heteroaryl; $R^{19A}$ and $R^{19B}$ substituents bonded to the same nitrogen atom may optionally be joined to form a substituted or unsubstituted heterocycloalkyl or substituted or unsubstituted heteroaryl;

each X, $X^{16}$, $X^{17}$, $X^{18}$ and $X^{19}$ is independently —F, —Cl, —Br, or —I;

n16, n17, n18, and n19 are independently an integer from 0 to 4; and m16, m17, m18, m19, v16, v17, v18, and v19 are independently 1 or 2.

Embodiment Q15

The compound of one of embodiments Q1 to Q13, wherein E is

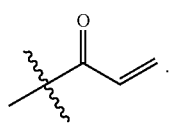 [SMILES: *C(=O)C=C]

Embodiment Q16

The compound of embodiment Q1, having the formula:

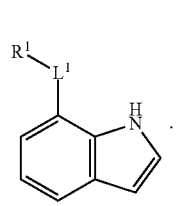 (XIa)

Embodiment Q17

The compound of embodiment Q1, having the formula:

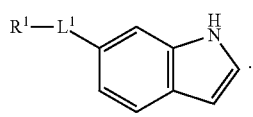 (XIb)

Embodiment Q18

The compound of embodiment Q1, having the formula:

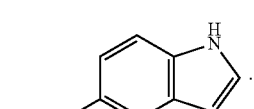 (XIc)

Embodiment Q19

The compound of embodiment Q1, having the formula:

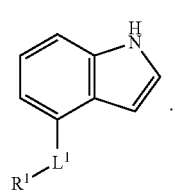 (XId)

Embodiment Q20

The compound of embodiment Q1, having the formula:

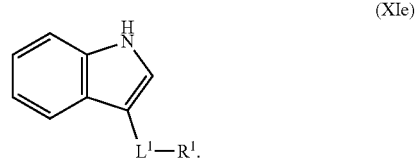 (XIe)

Embodiment Q21

The compound of embodiment Q1, having the formula:

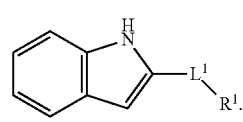 (XIf)

Embodiment Q22

The compound of embodiment Q1, having the formula:

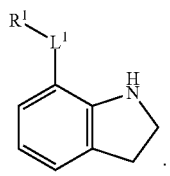 (XXIa)

Embodiment Q23

The compound of embodiment Q1, having the formula:

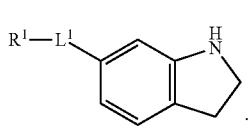 (XXIb)

Embodiment Q24

The compound of embodiment Q1, having the formula:

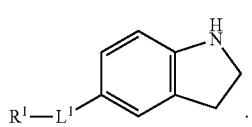 (XXIc)

Embodiment Q25

The compound of embodiment Q1, having the formula:

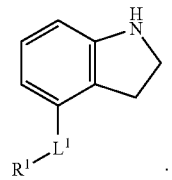

(XXId)

Embodiment Q26

The compound of embodiment Q1, having the formula:

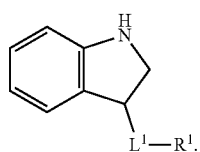

(XXIe)

Embodiment Q27

The compound of embodiment Q1, having the formula:

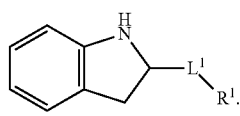

(XXIf)

Embodiment Q28

The compound of one of embodiments Q1 to Q27, wherein $L^1$ is a bond.

Embodiment Q29

The compound of one of embodiments Q1 to Q27, wherein $L^1$ is —OCH$_2$—.

Embodiment Q30

The compound of one of embodiment Rs Q1 to Q27, wherein $L^1$ is —NHC(O)—.

Embodiment Q31

The compound of one of embodiments Q1 to Q27, wherein $L^1$ is —S—.

Embodiment Q32

The compound of one of embodiments Q1 to Q27, wherein $L^1$ is —O—.

Embodiment Q33

The compound of one of embodiments Q1 to Q32, wherein $R^1$ is independently halogen, —CX$^1_3$, —CHX$^1_2$, —CH$_2$X$^1$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^1_3$, —OCHX$^1_2$, —OCH$_2$X$^1$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl.

Embodiment Q34

The compound of one of embodiments Q1 to Q32, wherein $R^1$ is independently halogen, —CX$^1_3$, —CHX$^1_2$, —CH$_2$X$^1$, —CN, —OH, —NH$_2$, —COOH, —CONH$_2$, —NO$_2$, —SH, —OCX$^1_3$, —OCHX$^1_2$, —OCH$_2$X$^1$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment Q35

The compound of one of embodiments Q1 to Q32, wherein $R^1$ is independently halogen, —CX$^1_3$, —CHX$^1_2$, —CH$_2$X$^1$, —CN, —OH, —NH$_2$, —COOH, —CONH$_2$, —NO$_2$, —SH, —OCX$^1_3$, —OCHX$^{12}$, —OCH$_2$X$^1$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

Embodiment Q36

The compound of one of embodiments Q1 to Q32, wherein $R^1$ is independently halogen, —CF$_3$, —OH, —SH, —NHC(O)CH$_3$, —OCH$_3$, —SCH$_3$,

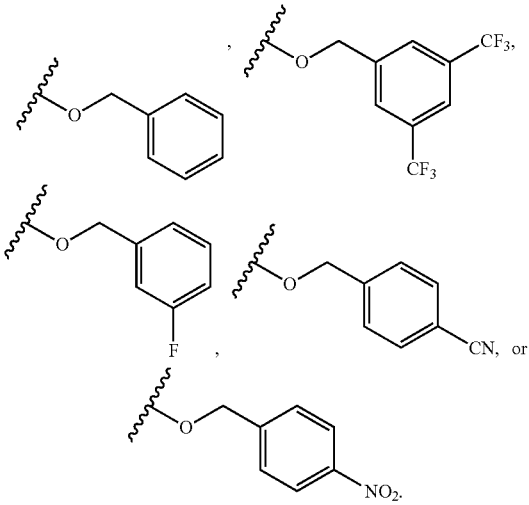

Embodiment Q37

The compound of one of embodiments Q1 to Q32, wherein -L$^1$-R$^1$ is independently —OCH$_3$.

Embodiment Q38

The compound of one of embodiments Q1 to Q32, wherein -L$^1$-R$^1$ is independently

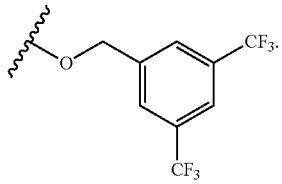 [SMILES: *OCc1cc(C(F)(F)F)cc(C(F)(F)F)c1]

Embodiment Q39

The compound of one of embodiments Q1 to Q38, wherein z1 is 2.

Embodiment Q40

The compound of one of embodiments Q1 to Q38, wherein z1 is 1.

Embodiment Q41

The compound of one of embodiments Q1 to Q38, wherein z1 is 0.

Embodiment Q42

The compound of embodiment Q41, wherein the compound is not

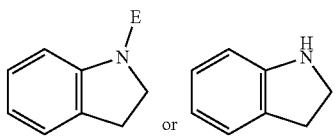

Embodiment Q43

The compound of embodiment Q41, wherein the compound is not

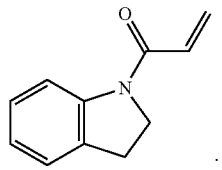

Embodiment Q44

The compound of embodiment Q1, having the formula:

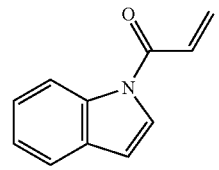

Embodiment Q45

The compound of embodiment Q1, having the formula:

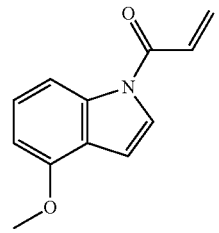

Embodiment Q46

The compound of embodiment Q1, having the formula:

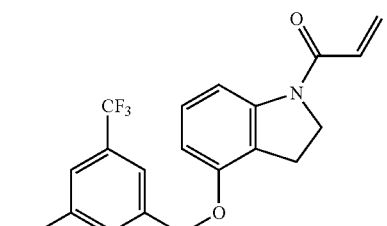

Embodiment Q47

The compound of embodiment Q1, having the formula:

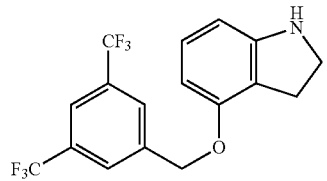 [SMILES: FC(F)(F)c1cc(COc2cccc3c2CCN3)cc(C(F)(F)F)c1]

Embodiment Q48

A pharmaceutical composition comprising a compound of one of embodiments Q1 to Q47 and a pharmaceutically acceptable excipient.

Embodiment Q49

A method of reducing the level of activity of mTORC1, said method comprising contacting the mTORC1 with a compound of one of embodiments Q1 to Q47.

Embodiment Q50

A method for treating cancer, said method comprising administering to a subject in need thereof a therapeutically effective amount of a compound of one of embodiments Q1 to Q47.

Embodiment Q51

The method of embodiment Q50, wherein said cancer is renal cell carcinoma, follicular lymphoma, glioblastoma, colorectal cancer, endometrial, or lung cancer.

Embodiment Q52

A method for treating a neurodegenerative disease, said method comprising administering to a subject in need thereof a therapeutically effective amount of a compound of one of embodiments Q1 to Q47.

Embodiment Q53

The method of embodiment Q52, wherein said neurodegenerative disease is Huntington Disease, Alzheimer Disease, or Parkinson's Disease.

Embodiment Q54

A method for treating a metabolic disease, said method comprising administering to a subject in need thereof a therapeutically effective amount of a compound of one of embodiments Q1 to Q47.

Embodiment Q55

The method of embodiment Q54, wherein said metabolic disease is type 2 diabetes.

Embodiment Q56

A LAMTOR5 protein covalently bonded to a compound of one of embodiments Q1 to Q15 and Q28 to Q46.

Embodiment Q57

The LAMTOR5 protein of embodiment Q56, wherein the compound is covalently bonded to a cysteine residue of the protein.

Embodiment Q58

The LAMTOR5 protein of embodiment Q56, wherein the compound is irreversibly covalently bonded to a cysteine residue of the protein.

Embodiment Q59

The LAMTOR5 protein of embodiment Q56, wherein the compound is covalently bonded to a cysteine corresponding to C23 of human LAMTOR5 protein.

Embodiment Q60

The LAMTOR5 protein of embodiment Q56, wherein the compound is irreversibly covalently bonded to a cysteine corresponding to C23 of human LAMTOR5 protein.

Embodiment Q61

The LAMTOR5 protein of embodiment Q56, wherein the compound is covalently bonded to a cysteine corresponding to C148 of human LAMTOR5 protein.

Embodiment Q62

The LAMTOR5 protein of embodiment Q56, wherein the compound is irreversibly covalently bonded to a cysteine corresponding to C148 of human LAMTOR5 protein.

Embodiment Q63

A LAMTOR5 protein covalently bonded to a fragment of a compound of one of embodiments Q1 to Q15 and Q28 to Q46.

Embodiment Q62

The LAMTOR5 protein of embodiment Q56, wherein the compound is irreversibly covalently bonded to a cysteine corresponding to C148 of human LAMTOR5 protein.

Embodiment P1

A compound having the formula:

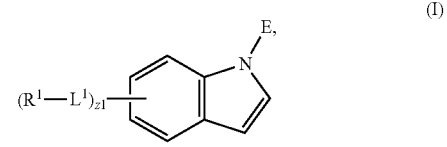

(I)

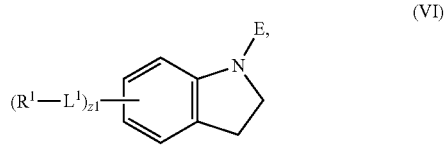

(VI)

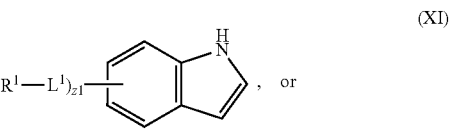

, or (XI)

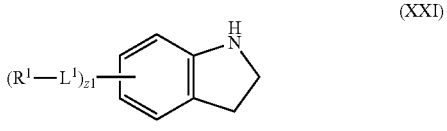

(XXI)

wherein, $L^1$ is independently a bond, $-S(O)_2-$, $-NH-$, $-O-$, $-S-$, $-C(O)-$, $-C(O)NH-$, $-NHC(O)-$, $-NHC(O)NH-$, $-C(O)O-$, $-OC(O)-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^1$ is independently halogen, $-CX^1{}_3$, $-CHX^1{}_2$, $-CH_2X^1$, $-OCX^1{}_3$, $-OCH_2X^1$, $-OCHX^1{}_2$, $-CN$, $-SO_{n1}R^{1D}$, $-SO_{v1}NR^{1A}R^{1B}$, $-NHC(O)NR^{1A}R^{1B}$, —N(O)$_{m1}$, —NR$^{1A}$R$^{1B}$, —C(O)R$^{1C}$, —C(O)—OR$^{1C}$, —C(O)NR$^{1A}$R$^{1B}$, —OR$^{1D}$, —NR$^{1A}$SO$_2$R$^{1D}$, —NR$^{1A}$C(O)R$^{1C}$, —NR$^{1A}$C(O)OR$^{1C}$, —NR$^{1A}$OR$^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent -L$^1$-R$^1$ substituents may optionally be joined to form a substituted or unsubstituted cycloalkyl, substituted or unsubstituted heterocycloalkyl, substituted or unsubstituted aryl, or substituted or unsubstituted heteroaryl; E is an electrophilic moiety; each R$^{1A}$, R$^{1B}$, R$^{1C}$, and R$^{1D}$ is independently hydrogen, —CX$_3$, —CHX$_2$, —CH$_2$X, —CN, —OH, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1A}$ and R$^{1B}$ substituents bonded to the same nitrogen atom may optionally be joined to form a substituted or unsubstituted heterocycloalkyl or substituted or unsubstituted heteroaryl; each X and X$^1$ is independently —F, —Cl, —Br, or —I; n1 is independently an integer from 0 to 4; m1 and v1 are independently 1 or 2; and z1 is independently an integer from 0 to 6.

Embodiment P2

The compound of embodiment P1, having the formula:

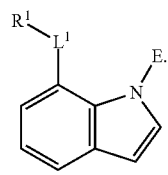

(Ia)

Embodiment P3

The compound of embodiment P1, having the formula:

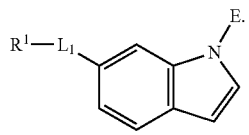

(Ib)

Embodiment P4

The compound of embodiment P1, having the formula:

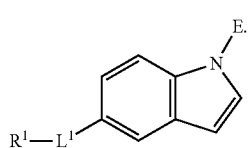

(Ic)

Embodiment P5

The compound of embodiment P1, having the formula:

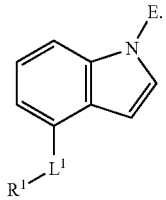

(Id)

Embodiment P6

The compound of embodiment P1, having the formula:

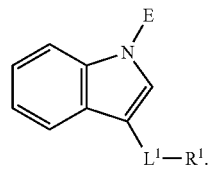

(Ie)

Embodiment P7

The compound of embodiment P1, having the formula:

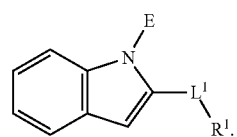

(If)

Embodiment P8

The compound of embodiment P1, having the formula:

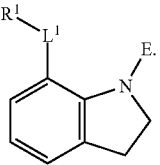

(VIa)

Embodiment P9

The compound of embodiment P1, having the formula:

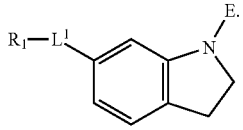

(VIb)

Embodiment P10

The compound of embodiment P1, having the formula:

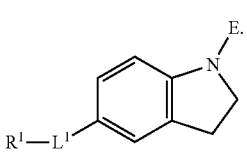

(VIc)

Embodiment P11

The compound of embodiment P1, having the formula:

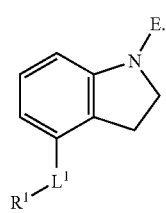

(VId)

Embodiment P12

The compound of embodiment P1, having the formula:

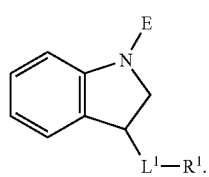

(VIe)

Embodiment P13

The compound of embodiment P1, having the formula:

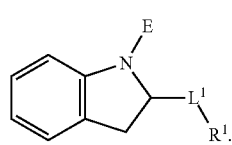

(VIf)

Embodiment P14

The compound of one of embodiments P1 to P13, wherein E is:

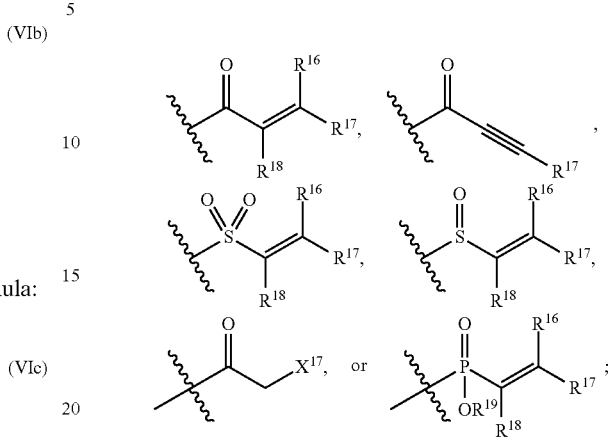

wherein $R^{16}$ is independently hydrogen, halogen, $-CX^{16}_3$, $-CHX^{16}_2$, $-CH_2X^{16}$, $-CN$, $-SO_{n16}R^{16A}$, $-SO_{v16}NR^{16A}R^{16B}$, $-NHNR^{16A}R^{16B}$, $-ONR^{16A}R^{16B}$, $-NHC(O)NHNR^{16A}R^{16B}$, $-NHC(O)NR^{16A}R^{16B}$, $-N(O)_{m16}$, $-NR^{16A}R^{16B}$, $-C(O)R^{16A}$, $-C(O)-OR^{16A}$, $-C(O)NR^{16A}R^{16B}$, $-OR^{16A}$, $-NR^{16A}SO_2R^{16B}$, $-NR^{16A}C(O)R^{16B}$, $-NR^{16A}C(O)OR^{16B}$, $-NR^{16A}OR^{16B}$, $-OCX^{16}_3$, $-OCHX^{16}_2$, $-OCH_2X^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^{17}$ is independently hydrogen, halogen, $CX^{17}_3$, $-CHX^{17}_2$, $-CH_2X^{17}$, $-CN$, $-SO_{n17}R^{17A}$, $-SO_{v17}NR^{17A}R^{17B}$, $-NHNR^{17A}R^{17B}$, $-ONR^{17A}R^{17B}$, $-NHC(O)NHNR^{17A}R^{17B}$, $-NHC(O)NR^{17A}R^{17B}$, $-N(O)_{m7}$, $-NR^{17A}R^{17B}$, $-C(O)R^{17A}$, $-C(O)-OR^{17A}$, $-C(O)NR^{17A}R^{17B}$, $-OR^{17A}$, $-NR^{17A}SO_2R^{17B}$, $-NR^{17A}C(O)R^{17B}$, $-NR^{17A}C(O)OR^{17B}$, $-NR^{17A}OR^{17B}$, $-OCX^{17}_3$, $-OCHX^{17}_2$, $-OCH_2X^{17}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^{18}$ is independently hydrogen, halogen, $CX^{18}_3$, $-CHX^{18}_2$, $-CH_2X^{18}$, $-CN$, $-SO_{n18}R^{18A}$, $-SO_{v1}NR^{18A}R^{18B}$, $-NHNR^{18A}R^{18B}$, $-ONR^{18A}R^{18B}$, $-NHC(O)NHNR^{18A}R^{18B}$, $-NHC(O)NR^{18A}R^{18B}$, $-N(O)_{m18}$, $-NR^{18A}R^{18B}$, $-C(O)R^{18A}$, $-C(O)-OR^{18A}$, $-C(O)NR^{18A}R^{18B}$, $-OR^{18A}$, $-NR^{18A}SO_2R^{18B}$, $-NR^{18A}C(O)R^{18B}$, $-NR^{18A}C(O)OR^{18B}$, $-NR^{18A}OR^{18B}$, $-OCX^{18}_3$, $-OCHX^{18}_2$, $-OCH_2X^{18}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^{19}$ is independently hydrogen, halogen, $CX^{19}_3$, $-CHX^{19}_2$, $-CH_2X^{19}$, $-CN$, $-SO_{n19}R^{19A}_9$, $-SO_{v19}NR^{19A}R^{19B}$, $-NHNR^{19A}R^{19B}$, $-ONR^{19A}R^{19B}$, $-NHC(O)NHNR^{19A}R^{19B}$, $-NHC(O)NR^{19A}R^{19B}$, $-N(O)_{m19}$, $-NR^{19A}R^{19B}$, $-C(O)R^{19A}$, $-C(O)-OR^{19A}$, $-C(O)NR^{19A}R^{19B}$, $-OR^{19A}$, $-NR^{19A}SO_2R^{19B}$, $-NR^{19A}C(O)R^{19B}$, $-NR^{19A}C(O)OR^{19B}$, $-NR^{19A}OR^{19B}$, $-OCX^{19}_3$, $-OCHX^{19}_2$, $-OCH_2X^{19}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^{16A}$, $R^{16B}$, $R^{17A}$, $R^{17B}$, $R^{18A}$, $R^{18B}$, $R^{19A}$, and $R^{19B}$ are independently hydrogen, —$CX_3$, $CHX_2$, —$CH_2X$, —CN, —OH, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{16A}$ and $R^{16B}$ substituents bonded to the same nitrogen atom may optionally be joined to form a substituted or unsubstituted heterocycloalkyl or substituted or unsubstituted heteroaryl; $R^{17A}$ and $R^{17B}$ substituents bonded to the same nitrogen atom may optionally be joined to form a substituted or unsubstituted heterocycloalkyl or substituted or unsubstituted heteroaryl; $R^{18A}$ and $R^{18B}$ substituents bonded to the same nitrogen atom may optionally be joined to form a substituted or unsubstituted heterocycloalkyl or substituted or unsubstituted heteroaryl; $R^{19A}$ and $R^{19B}$ substituents bonded to the same nitrogen atom may optionally be joined to form a substituted or unsubstituted heterocycloalkyl or substituted or unsubstituted heteroaryl; each X, $X^{16}$, $X^{17}$, $X^{18}$ and $X^{19}$ is independently —F, —Cl, —Br, or —I; n16, n17, n18, and n19 are independently an integer from 0 to 4; and m16, m17, m18, m19, v16, v17, v18, and v19 are independently 1 or 2.

Embodiment P15

The compound of one of embodiments P1 to P13, wherein E is

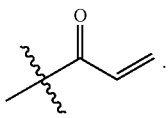

Embodiment P16

The compound of embodiment P1, having the formula:

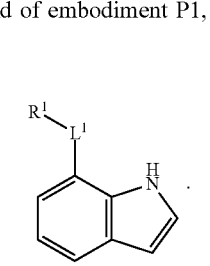

(XIa)

Embodiment P17

The compound of embodiment P1, having the formula:

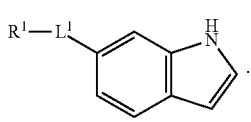

(XIb)

Embodiment P18

The compound of embodiment P1, having the formula:

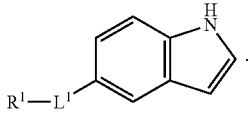

(XIc)

Embodiment P19

The compound of embodiment P1, having the formula:

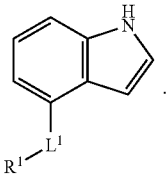

(XId)

Embodiment P20

The compound of embodiment P1, having the formula:

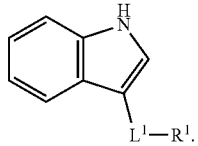

(XIe)

Embodiment P21

The compound of embodiment P1, having the formula:

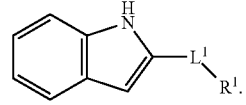

(XIf)

Embodiment P22

The compound of embodiment P1, having the formula:

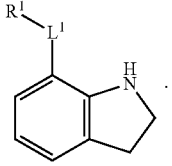

(XXIa)

Embodiment P23

The compound of embodiment P1, having the formula:

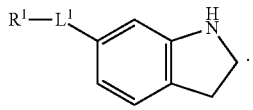

(XXIb)

Embodiment P24

The compound of embodiment P1, having the formula:

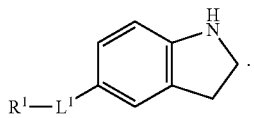

(XXIc)

Embodiment P25

The compound of embodiment P1, having the formula:

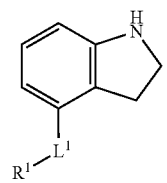

(XXId)

Embodiment P26

The compound of embodiment P1, having the formula:

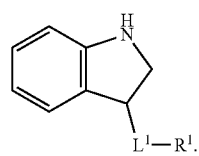

(XXIe)

Embodiment P27

The compound of embodiment P1, having the formula:

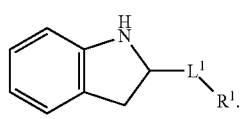

(XXIf)

Embodiment P28

The compound of one of embodiments P1 to P27, wherein $L^1$ is a bond.

Embodiment P29

The compound of one of embodiments P1 to P27, wherein $L^1$ is —OCH$_2$—.

Embodiment P30

The compound of one of embodiments P1 to P27, wherein $L^1$ is —NHC(O)—.

Embodiment P31

The compound of one of embodiments P1 to P27, wherein $L^1$ is —S—.

Embodiment P32

The compound of one of embodiments P1 to P27, wherein $L^1$ is —O—.

Embodiment P33

The compound of one of embodiments P1 to P32, wherein $R^1$ is independently halogen, —CX$^1_3$, —CHX$^1_2$, —CH$_2$X$^1$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^1_3$, —OCHX$^1_2$, —OCH$_2$X$^1$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl.

Embodiment P34

The compound of one of embodiments P1 to P32, wherein $R^1$ is independently halogen, —CX$^1_3$, —CHX$^1_2$, —CH$_2$X$^1$, —CN, —OH, —NH$_2$, —COOH, —CONH$_2$, —NO$_2$, —SH, —OCX$^1_3$, —OCHX$^1_2$, —OCH$_2$X$^1$, substituted or unsubstituted C$_1$-C$_6$ alkyl, substituted or unsubstituted 2 to 6 membered heteroalkyl, substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl.

Embodiment P35

The compound of one of embodiments P1 to P32, wherein $R^1$ is independently halogen, —CX$^1_3$, —CHX$^1_2$, —CH$_2$X$^1$, —CN, —OH, —NH$_2$, —COOH, —CONH$_2$, —NO$_2$, —SH, —OCX$^1_3$, —OCHX$^1_2$, —OCH$_2$X$^1$, unsubstituted C$_1$-C$_6$ alkyl, unsubstituted 2 to 6 membered heteroalkyl, unsubstituted C$_3$-C$_6$ cycloalkyl, unsubstituted 3 to 6 membered heterocycloalkyl, unsubstituted phenyl, or unsubstituted 5 to 6 membered heteroaryl.

Embodiment P36

The compound of one of embodiments P1 to P32, wherein $R^1$ is independently halogen, —$CF_3$, —OH, —SH, —NHC(O)$CH_3$, —O$CH_3$, —S$CH_3$,

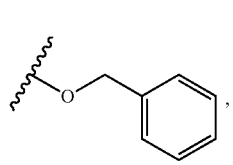 , 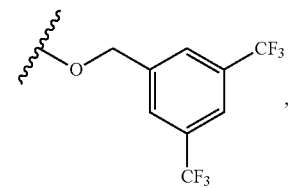 [SMILES: *OCc1cc(C(F)(F)F)cc(C(F)(F)F)c1] ,

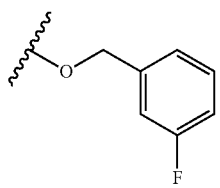 , 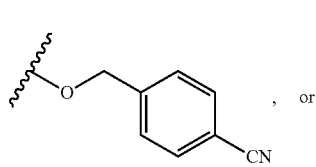 , or

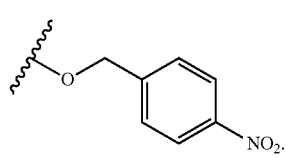.

Embodiment P37

The compound of one of embodiments P1 to P32, wherein -$L^1$-$R^1$ is independently —O$CH_3$.

Embodiment P38

The compound of one of embodiments P1 to P32, wherein -$L^1$-$R^1$ is independently

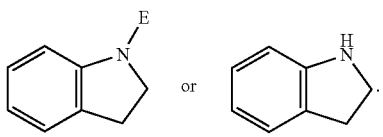

Embodiment P39

The compound of one of embodiments P1 to P38, wherein z1 is 2.

Embodiment P40

The compound of one of embodiments P1 to P38, wherein z1 is 1.

Embodiment P41

The compound of one of embodiments P1 to P38, wherein z1 is 0.

Embodiment P42

The compound of embodiment P41, wherein the compound is not

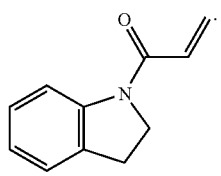

Embodiment P43

The compound of embodiment P41, wherein the compound is not

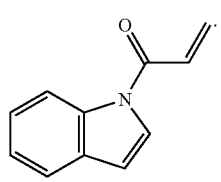

Embodiment P44

The compound of embodiment P1, having the formula:

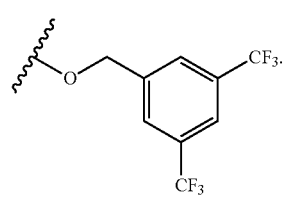

Embodiment P45

The compound of embodiment P1, having the formula:

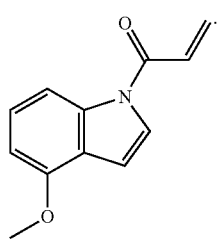

Embodiment P46

The compound of embodiment P1, having the formula:

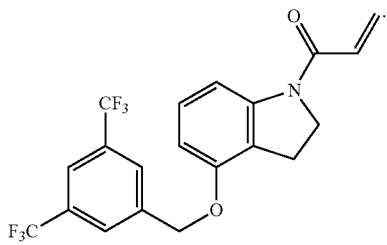 [SMILES: C=CC(=O)N1CCc2c(OCc3cc(C(F)(F)F)cc(C(F)(F)F)c3)cccc21]

Embodiment P47

The compound of embodiment P1, having the formula:

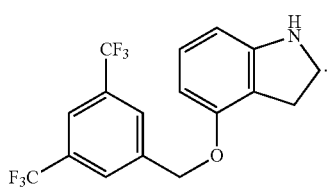 [SMILES: FC(F)(F)c1cc(COc2cccc3c2CCN3)cc(C(F)(F)F)c1]

Embodiment P48

A pharmaceutical composition comprising a compound of one of embodiments P1 to P47 and a pharmaceutically acceptable excipient.

Embodiment P49

A method of reducing the level of activity of mTORC1, said method comprising contacting the mTORC1 with a compound of one of embodiments P1 to P47.

Embodiment P50

A method for treating cancer, said method comprising administering to a subject in need thereof a therapeutically effective amount of a compound of one of embodiments P1 to P47.

Embodiment P51

The method of embodiment P50, wherein said cancer is renal cell carcinoma, follicular lymphoma, glioblastoma, colorectal cancer, endometrial, or lung cancer.

Embodiment P52

A method for treating a neurodegenerative disease, said method comprising administering to a subject in need thereof a therapeutically effective amount of a compound of one of embodiments P1 to P47.

Embodiment P53

The method of embodiment P52, wherein said neurodegenerative disease is Huntington Disease, Alzheimer Disease, or Parkinson's Disease.

Embodiment P54

A method for treating a metabolic disease, said method comprising administering to a subject in need thereof a therapeutically effective amount of a compound of one of embodiments P1 to P47.

Embodiment P55

The method of embodiment P54, wherein said metabolic disease is type 2 diabetes.

Embodiment P56

A LAMTOR5 protein covalently bonded to a compound of one of embodiments P1 to P15 and P28 to P46.

Embodiment P57

The LAMTOR5 protein of embodiment P56, wherein the compound is covalently bonded to a cysteine residue of the protein.

Embodiment P58

The LAMTOR5 protein of embodiment P56, wherein the compound is irreversibly covalently bonded to a cysteine residue of the protein.

Embodiment P59

The LAMTOR5 protein of embodiment P56, wherein the compound is covalently bonded to a cysteine corresponding to C23 of human LAMTOR5 protein.

Embodiment P60

The LAMTOR5 protein of embodiment P56, wherein the compound is irreversibly covalently bonded to a cysteine corresponding to C23 of human LAMTOR5 protein.

Embodiment P61

The LAMTOR5 protein of embodiment P56, wherein the compound is covalently bonded to a cysteine corresponding to C148 of human LAMTOR5 protein.

Embodiment P62

The LAMTOR5 protein of embodiment P56, wherein the compound is irreversibly covalently bonded to a cysteine corresponding to C148 of human LAMTOR5 protein.

Embodiment P63

A LAMTOR5 protein covalently bonded to a fragment of a compound of one of embodiments P1 to P15 and P28 to P46.

Embodiment 1

A compound having the formula:

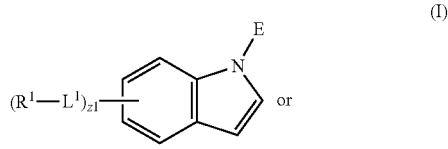

or

-continued

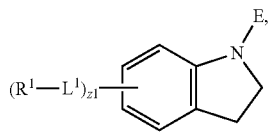

(VI)

wherein,
L¹ is independently substituted or unsubstituted heteroalkylene, a bond, —S(O)₂—, —NH—, —O—, —S—, —C(O)—, —C(O)NH—, —NHC(O)—, —NHC(O)NH—, —C(O)O—, —OC(O)—, or substituted or unsubstituted alkylene;
R¹ is independently substituted or unsubstituted aryl, halogen, —CX¹₃, —CHX¹₂, —CH₂X¹, —OH, —SH, substituted or unsubstituted alkyl, substituted or unsubstituted heteroalkyl, substituted or unsubstituted cycloalkyl, substituted or unsubstituted heterocycloalkyl, or substituted or unsubstituted heteroaryl;
E is

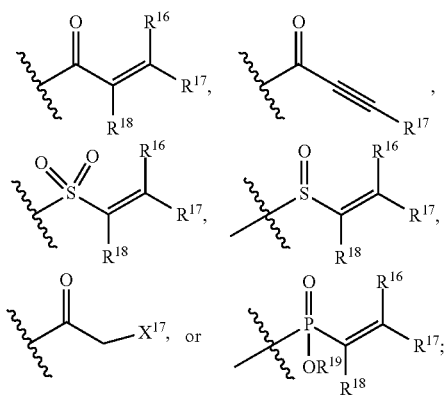

wherein R¹⁶ is independently hydrogen, halogen, —CX¹⁶₃, —CHX¹⁶₂, —CH₂X¹⁶, —CN, —SO_{n16}R¹⁶ᴬ, —SO_{v16}NR¹⁶ᴬR¹⁶ᴮ, —NHNR¹⁶ᴬR¹⁶ᴮ, —ONR¹⁶ᴬR¹⁶ᴮ, —NHC(O)NHNR¹⁶ᴬR¹⁶ᴮ, —NHC(O)NR¹⁶ᴬR¹⁶ᴮ, —N(O)_{m16}, —NR¹⁶ᴬR¹⁶ᴮ, —C(O)R¹⁶ᴬ, —C(O)—OR¹⁶ᴬ, —C(O)NR¹⁶ᴬR¹⁶ᴮ, —OR¹⁶ᴬ, —NR¹⁶ᴬSO₂R¹⁶ᴮ, —NR¹⁶ᴬC(O)R¹⁶ᴮ, —NR¹⁶ᴬC(O)OR¹⁶ᴮ, —NR¹⁶ᴬOR¹⁶ᴮ, —OCX¹⁶₃, —OCHX¹⁶₂, —OCH₂X¹⁶, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;
R¹⁷ is independently hydrogen, halogen, CX¹⁷₃, —CHX¹⁷₂, —CH₂X¹⁷, —CN, —SO_{n17}R¹⁷ᴬ, —SO_{v17}NR¹⁷ᴬR¹⁷ᴮ, —NHNR¹⁷ᴬR¹⁷ᴮ, —ONR¹⁷ᴬR¹⁷ᴮ, —NHC(O)NHNR¹⁷ᴬR¹⁷ᴮ, —NHC(O)NR¹⁷ᴬR¹⁷ᴮ, —N(O)_{m17}, —NR¹⁷ᴬR¹⁷ᴮ, —C(O)R¹⁷ᴬ, —C(O)—OR¹⁷ᴬ, —C(O)NR¹⁷ᴬR¹⁷ᴮ, —OR¹⁷ᴬ, —NR¹⁷ᴬSO₂R¹⁷ᴮ, —NR¹⁷ᴬC(O)R¹⁷ᴮ, —NR¹⁷ᴬC(O)OR¹⁷ᴮ, —NR¹⁷ᴬOR¹⁷ᴮ—OCX¹⁷₃, —OCHX¹⁷₂, —OCH₂X¹⁷, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;
R¹⁸ is independently hydrogen, halogen, CX¹⁸₃, —CHX¹⁸₂, —CH₂X¹⁸, —CN, —SO_{n18}R¹⁸ᴬ, —SO_{v18}NR¹⁸ᴬR¹⁸ᴮ, —NHNR¹⁸ᴬR¹⁸ᴮ, —ONR¹⁸ᴬR¹⁸ᴮ, —NHC(O)NHNR¹⁸ᴬR¹⁸ᴮ, —NHC(O)NR¹⁸ᴬR¹⁸ᴮ, —N(O)_{m18}, —NR¹⁸ᴬR¹⁸ᴮ, —C(O)R¹⁸ᴬ, —C(O)—OR¹⁸ᴬ, —C(O)NR¹⁸ᴬR¹⁸ᴮ, —OR¹⁸ᴬ, —NR¹⁸ᴬSO₂R¹⁸ᴮ, —NR¹⁸ᴬC(O)R¹⁸ᴮ, —NR¹⁸ᴬC(O)OR¹⁸ᴮ, —NR¹⁸ᴬOR¹⁸ᴮ, —OCX¹⁸₃, —OCHX¹⁸₂, —OCH₂X¹⁸, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;
R¹⁹ is independently hydrogen, halogen, CX¹⁹₃, —CHX¹⁹₂, —CH₂X¹⁹, —CN, —SO_{n19}R¹⁹ᴬ, —SO_{v19}NR¹⁹ᴬR¹⁹ᴮ, —NHNR¹⁹ᴬR¹⁹ᴮ, —ONR¹⁹ᴬR¹⁹ᴮ, —NHC(O)NHNR¹⁹ᴬR¹⁹ᴮ, —NHC(O)NR¹⁹ᴬR¹⁹ᴮ, —N(O)_{m19}, —NR¹⁹ᴬR¹⁹ᴮ, —C(O)R¹⁹ᴬ, —C(O)—OR¹⁹ᴬ, —C(O)NR¹⁹ᴬR¹⁹ᴮ, —OR¹⁹ᴬ, —NR¹⁹ᴬSO₂R¹⁹ᴮ, —NR¹⁹ᴬC(O)R¹⁹ᴮ, —NR¹⁹ᴬC(O)OR¹⁹ᴮ, —NR¹⁹ᴬOR¹⁹ᴮ, —OCX¹⁹₃, —OCHX¹⁹₂, —OCH₂X¹⁹, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;
R¹⁶ᴬ, R¹⁶ᴮ, R¹⁷ᴬ, R¹⁷ᴮ, R¹⁸ᴬ, R¹⁸ᴮ, R¹⁹ᴬ, and R¹⁹ᴮ are independently hydrogen, —CX₃, CHX₂, —CH₂X, —CN, —OH, —COOH, —CONH₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R¹⁶ᴬ and R¹⁶ᴮ substituents bonded to the same nitrogen atom may optionally be joined to form a substituted or unsubstituted heterocycloalkyl or substituted or unsubstituted heteroaryl; R¹⁷ᴬ and R¹⁷ᴮ substituents bonded to the same nitrogen atom may optionally be joined to form a substituted or unsubstituted heterocycloalkyl or substituted or unsubstituted heteroaryl; R¹⁸ᴬ and R¹⁸ᴮ substituents bonded to the same nitrogen atom may optionally be joined to form a substituted or unsubstituted heterocycloalkyl or substituted or unsubstituted heteroaryl; R¹⁹ᴬ and R¹⁹ᴮ substituents bonded to the same nitrogen atom may optionally be joined to form a substituted or unsubstituted heterocycloalkyl or substituted or unsubstituted heteroaryl;
each X, X¹, X¹⁶, X¹⁷, X¹⁸ and X¹⁹ is independently —F, —Cl, —Br, or —I;
n16, n17, n18, and n19 are independently an integer from 0 to 4; and
m16, m17, m18, m19, v16, v17, v18, and v19 are independently 1 or 2; and
z1 is independently an integer from 0 to 6.

Embodiment 2

The compound of embodiment 1, having the formula:

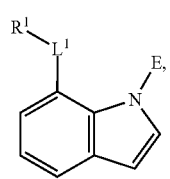

(Ia)

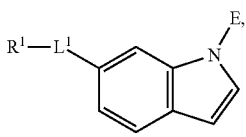 (Ib)

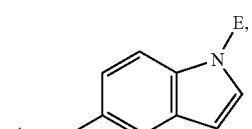 (Ic)

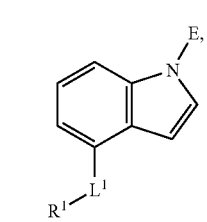 (Id)

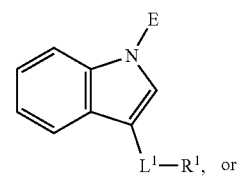 (Ie)

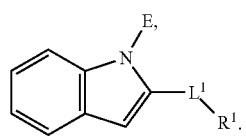 (If)

Embodiment 3

The compound of embodiment 1, having the formula:

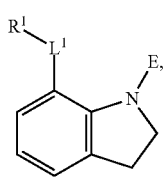 (VIa)

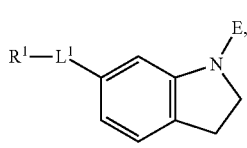 (VIb)

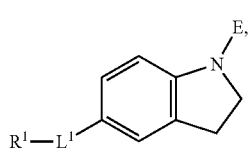 (VIc)

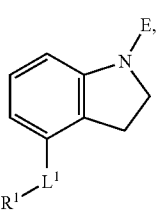 (VId)

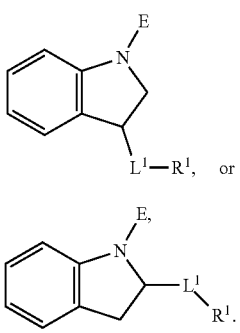 (VIe)

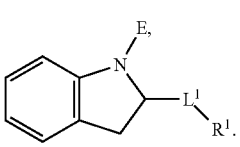 (VIf)

Embodiment 4

The compound of embodiment 1, having the formula:

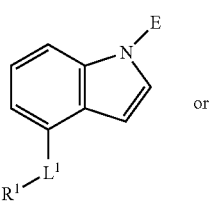 (Id)

or

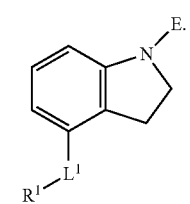 (VId)

Embodiment 5

The compound of one of embodiments 1 to 4, wherein E is

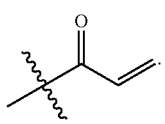

Embodiment 6

The compound of one of embodiments 1 to 5, wherein $L^1$ is a substituted or unsubstituted alkylene, or substituted or unsubstituted heteroalkylene.

Embodiment 7

The compound of one of embodiments 1 to 5, wherein $L^1$ is —OCH$_2$— or —O—.

Embodiment 8

The compound of one of embodiments 1 to 7, wherein $R^1$ is independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 9

The compound of one of embodiments 1 to 7, wherein $R^1$ is independently substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment 10

The compound of one of embodiments 1 to 7, wherein $R^1$ is independently substituted or unsubstituted phenyl.

Embodiment 11

The compound of one of embodiments 1 to 7, wherein $R^1$ is independently halogen, —CF$_3$, —OH, —SH, —NHC(O)CH$_3$, —OCH$_3$, —SCH$_3$,

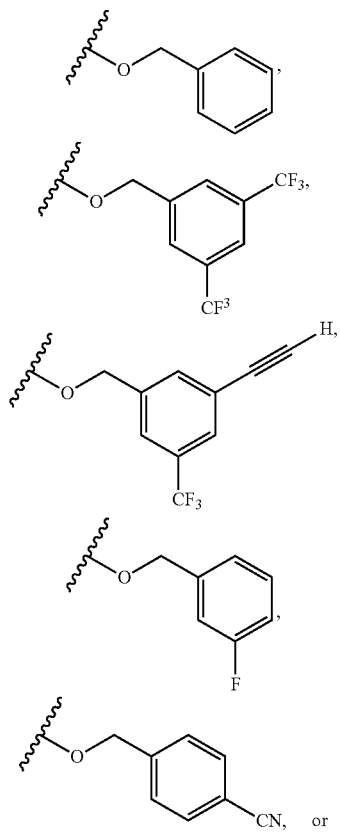

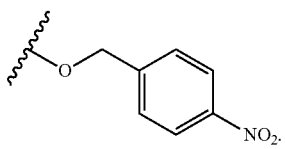

Embodiment 12

The compound of one of embodiments 1 to 11, wherein z1 is 0 or 1.

Embodiment 13

The compound of embodiment 1, having the formula:

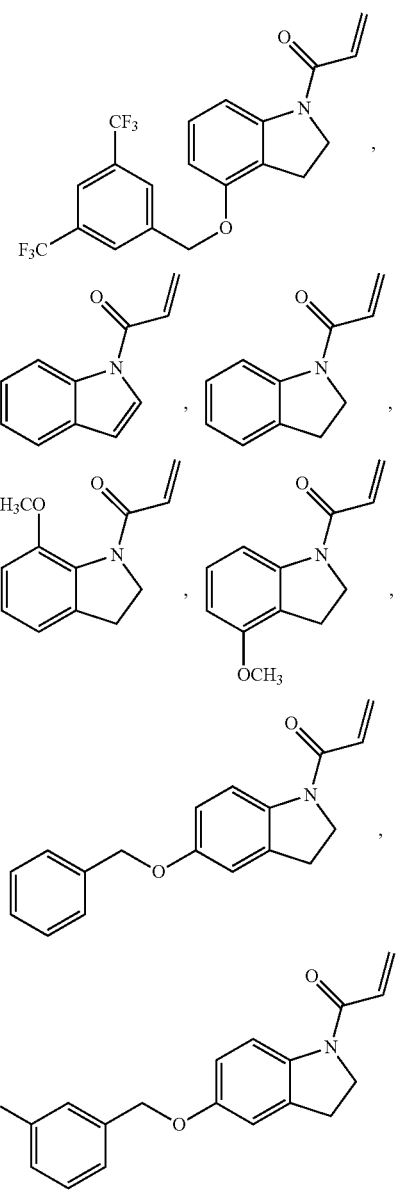

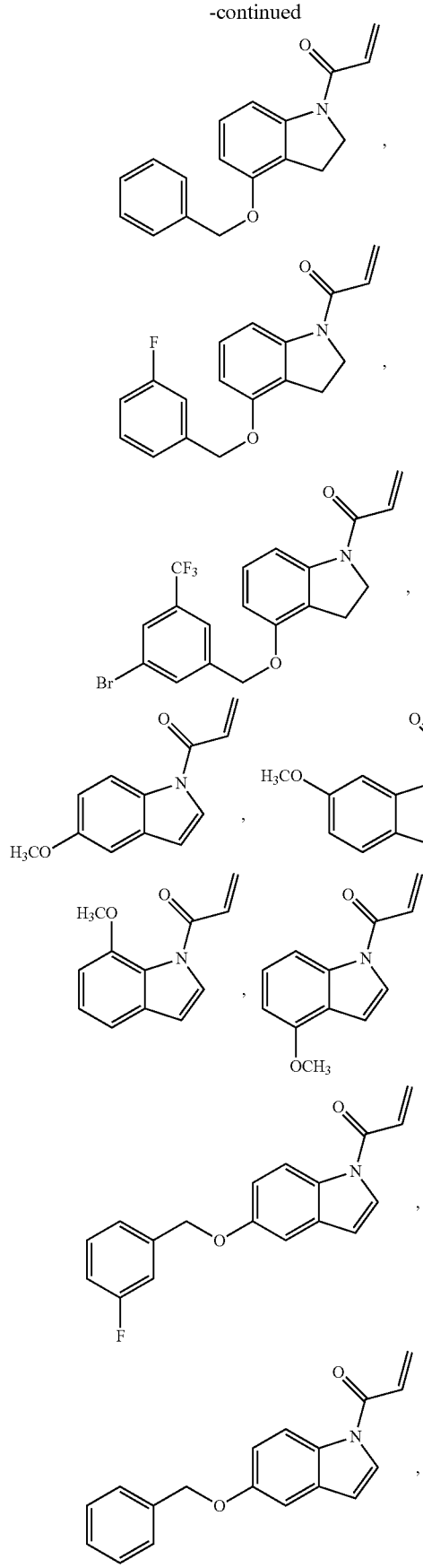
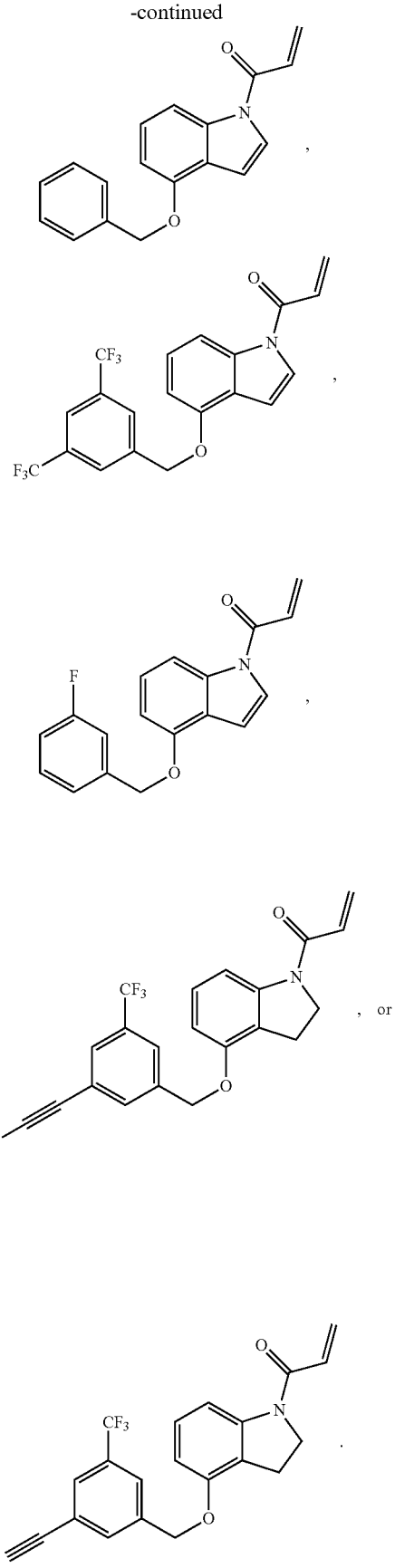

Embodiment 14

The compound of embodiment 1, having the formula:

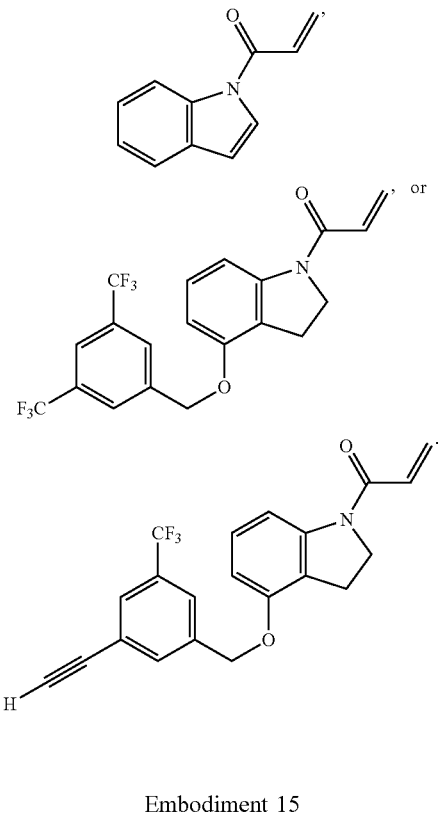

Embodiment 15

A pharmaceutical composition comprising a compound of one of embodiments 1 to 14 and a pharmaceutically acceptable excipient.

Embodiment 16

A method for treating cancer, a neurodegenerative disease, or a metabolic disease, said method comprising administering to a subject in need thereof a therapeutically effective amount of a compound of one of embodiments 1 to 14.

Embodiment 17

The method of embodiment 16, wherein said cancer is renal cell carcinoma, follicular lymphoma, glioblastoma, colorectal cancer, endometrial, or lung cancer.

Embodiment 18

The method of embodiment 16, wherein said neurodegenerative disease is Huntington Disease, Alzheimer Disease, or Parkinson's Disease.

Embodiment 19

The method of embodiment 16, wherein said metabolic disease is type 2 diabetes.

Embodiment 20

A LAMTOR5 protein covalently bonded to a compound of one of embodiments 1 to 14.

VIII. Examples

Growth, the process of mass accumulation that precedes cell division, is key to the function of all organisms, from yeast to humans. Aberrant growth enables the unbridled proliferation of cancer cells, and is emerging as a driver in a wide spectrum of pathological conditions, from diabetes to age-related cognitive decline (1, 22, 29). Thus, identifying novel treatments and drugs to precisely control growth programs inside the human body will significantly impact human health and society.

In every cell, growth is under the control of sophisticated 'master regulators', which sense the presence of external nutrients and hormones. A prominent example is the large protein kinase mechanistic Target of Rapamycin, mTOR (1, 22, 29). As part of a multiprotein complex known as as mTOR Complex 1 (mTORC1), mTOR drives the production of cellular building blocks such as proteins, lipids and nucleotides in response to amino acids, insulin and energy. At the same time, mTORC1 actively suppresses autophagy, a cellular 'self-eat' process that opposes growth (3, 8).

Overwhelming evidence indicates that aberrant mTORC1 activity underlies the growth advantage that many cancer types display over the surrounding healthy tissue (1, 13, 39). Moreover, recent work strongly suggests that chronic mTORC1 activation may compromise cellular housekeeping and accelerate proteotoxic stress in neurodegenerative diseases (1, 17, 29, 42). Thus, there is enormous interest in identifying and developing novel strategies to inhibit mTORC1 activity in the context of many human diseases.

Current therapeutic investigations in cancer and other mTORC1-related diseases focus on the naturally available allosteric inhibitor, rapamycin (44-46). This macrolide suppresses the kinase activity of mTORC1 by causing its dimerization to the small cytosolic protein FKBP12. Rapamycin is potent (Kd in the low nM range) and has a good bioavailability. However, rapamycin suffers from significant limitations that have so far hampered its effectiveness. Most importantly, this drug only blocks a subset of the many activities regulated by mTORC1. For instance, stimulation of protein synthesis by mTORC1 is largely resistant to rapamycin treatment (16, 34). Thus, a new class of 'ATP-competitive' compounds was recently developed. These drugs block the kinase activity of mTOR toward virtually all substrates (31, 34, 35). The higher potency and broader range of ATP-competitive mTOR inhibitors has led to promising results in cancer clinical trials (25, 26); however, these compounds are not devoid of limitations and significant side effects, including high toxicity and metabolic imbalance (1, 23, 40). Moreover, the bioavailability of some ATP competitive inhibitors is poorer than rapamycin. Thus, renewed efforts must be directed toward identifying new ways to block mTORC1 selectively and safely.

Recent findings on the mechanisms of mTORC1 by nutrients regulation have opened up novel avenues to control its activity in cells as well as in organisms. Amino acids, carbohydrates and lipids (collectively referred to as 'nutrients') activate mTORC1 with high potency and specificity by inducing its recruitment to the surface of a specific organelle, the lysosome (1, 2, 15, 24, 30). At the lysosome, mTORC1 acquires the ability to phosphorylate its substrates and promote growth and proliferation. Importantly, blocking nutrient inputs renders mTORC1 unresponsive to cancer-promoting signals that are relayed by various oncogenes (4, 11, 15). Thus, blocking key protein-protein interactions in the nutrient-mTORC1 axis represents a promising but still largely unexplored avenue for drug development in cancer and possibly other mTOR-related diseases.

Drugging protein-protein interaction is notoriously arduous and expensive. Current high-throughput approaches include yeast-two-hybrid (Y2H), which can detect PPIs in living cells. However, Y2H screens suffer from several limitations, including variability in the concentration, localization and stability of the genetically expressed protein reporters, as well as the fact that potentially effective compounds may not be able to cross the plasma membrane (18, 27). Another approach often used in cells is Forster resonance energy transfer (FRET). FRET assays require that the interacting proteins be tagged with donor and acceptor fluorophores according to an optimal geometry, which is not always attainable or may result in signals that have a small dynamic range (14, 27, 43). In vitro approaches are also severely limited for a variety of reasons. Enzyme-linked immunoadsorbent (ELISA)-based screens require antibodies that recognize the target multi-protein complex, making it unsuitable for the vast majority of protein-protein interactions (27). Fluorescence polarization (FP) is only applicable when the masses of the interacting proteins differ by a factor of 10 or higher. Finally, surface-plasmon resonance (SPR), although capable of providing kinetic information, suffers from low throughput and thus only enables the exploration of a very small chemical space (14, 27). Moreover, several of these techniques require expensive reagents, surface derivatization and special detectors.

Described herein is the development of a coupled platform to rapidly discover small-molecule modulators that target unique druggable hotspots to disrupt protein-protein interactions. The present approach overcomes many limitations of prior methods, and it does so with a simple, easily constructed platform that can be screened in a high throughput manner using inexpensive microscopes and readily available image analysis software. Through using this approach, a unique druggable hotspot that can be targeted with covalent ligands to disrupt the TORC1 complex and inhibit TORC1 signaling and lysosomal localization has been identified.

A major challenge in drug development is the identification of compounds that can disrupt the physical interaction between two proteins. Decades of technological development have yielded robust assays for inhibitors of enzymatic activities such as kinases, dehydrogenases, etc. (14, 19, 32). These assays are made possible by the ability of the target protein to convert the substrates or products of enzymatic reactions into chemiluminescent molecules that can be read in a high-throughput manner on microplates (14, 27). However, this type of readout cannot be used when the binding of two proteins to each other does not result in the conversion of a reactant into a product. Yet, protein-protein interactions (PPIs) are of fundamental importance in most biological processes, including signal transduction, genome replication and repair, and are prime targets for drug development. For example, current approaches to drug the mTORC1 kinase, a driver of human cancer, diabetes and neurodegeneration, rely on chemical inhibitors known as 'rapalogues', which target the kinase activity of mTORC1 (22, 29). Rapalogues suffer from major limitations, including inability to block several of mTORC1 substrates, along with significant off-target effects such as immunosuppression and disruption of glucose homeostasis (23, 40). We and others discovered recently that mTORC1 activation depends on physical interactions between two protein complexes known as the Rag Guanosine Triphosphatases (GTPases) and the Ragulator (22, 30, 36, 37). Breaking the interaction between these two protein complexes would lead to complete inactivation of the pathway and could therefore be a superior approach to rapalogues in clinical settings (22, 30, 36, 37), but currently there are no available small molecules that can interfere with Rag GTPase-Ragulator binding. Described herein are two main aspects of general utility. First, it will lead to the identification of novel drugs that modulate the mTORC1 pathway and therefore lead to therapeutics in multiple disease settings linked to aberrant mTORC1 activity. These include cancers in which activating mutations in the PI3K-mTORC1 pathway have been identified, such as renal cell carcinoma, follicular lymphoma, glioblastoma, along with colorectal, endometrial and lung cancer (9, 10, 13, 15). Additionally, as excessive mTORC1 activity is found in obese and insulin-resistant subjects, the compounds described here could find application in the context of type-2 diabetes (20, 28, 33). mTORC1 was shown to be hyperactive in autodomal dominant polycystic kidney disease (ADPKD) and rapamycin has been considered as a potential therapeutic avenue. The mechanism of action of CC 1-44 and its derivatives makes this class of compounds well-suited for ADPKD. Furthermore, pharmacological mTORC1 inhibition is a promising avenue to activate autophagy in order to restore proteostasis and cellular quality control in the context of neurodegenerative diseases such as Huntington, Alzheimer, Parkinson, fronto-temporal dementia (FTD) and spinocerebellar ataxia (SCA) (8, 21, 38, 41, 42). The ability of CC 1-44 to activate autophagy both in cells and in mice with superior potency to rapamycin (FIGS. 7A-C) makes this compound and its derivatives especially attractive for these neurodegenerative disorders. Second, the technology described herein provides a rapid, robust, and inexpensive platform for drugging any PPI for drug discovery efforts through coupling Visual IP with screening of covalent ligands and isoTOP-ABPP-enabled target identification platforms.

Example 1. Identification of Inhibitor

Figure 1B:
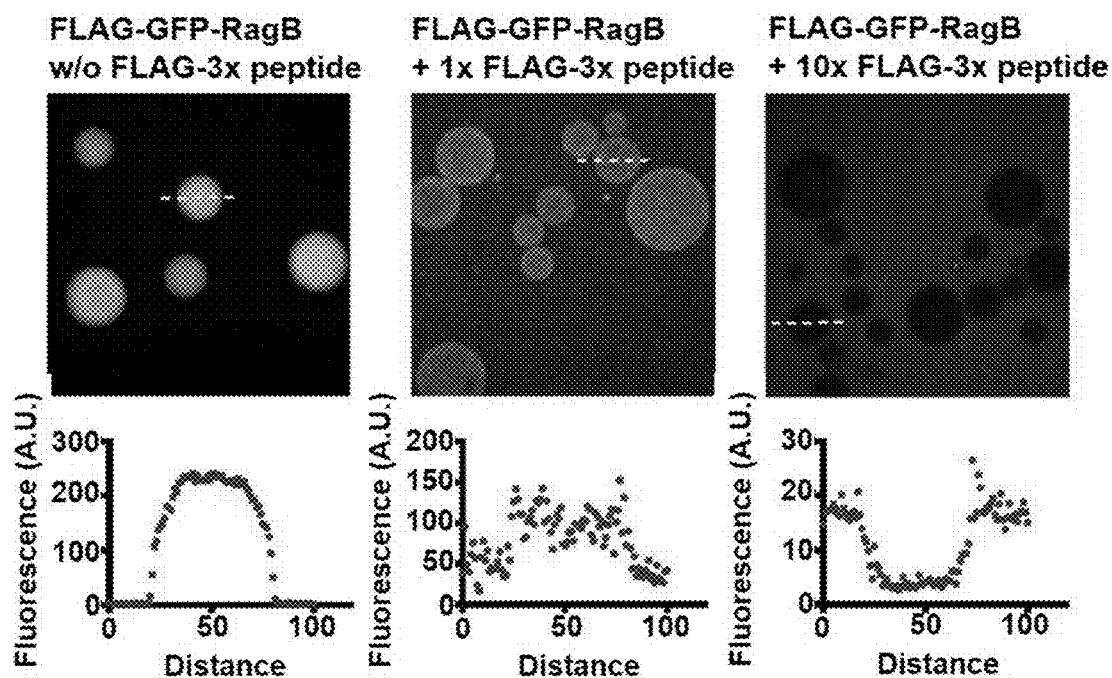
Figure 1C:
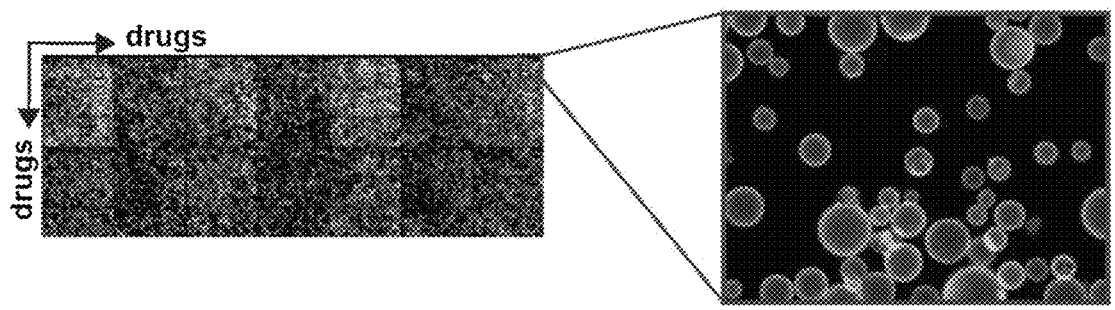

To assay for mTORC1-inhibiting compounds, we in vitro-reconstituted the interaction between the Lamtor (a.k.a. Ragulator) and Rag GTPase protein complexes, which are essential for amino acid-driven mTORC1 recruitment (and thus activation) to the lysosome (24, 30, 36, 37). We sequentially coated agarose beads with RFP-tagged Ragulator and with GFP-tagged Rag GTPases, resulting in Rag binding to the beads via their interaction with Lamtor. This method, which we call 'Visual co-immunoprecipitation' (Visual-IP) is essentially a binding reaction at equilibrium, in which the interaction between the two binding partners can be easily scored as color overlap between the bead-bound, red-tagged Lamtor and the soluble, green-fluorescent Rag GTPases. Interaction between the two proteins results in red-green color overlap ('yellow beads'), whereas when the interaction is disrupted, partial or complete dispersion of the green signal in the surrounding buffer is observed ('red beads') (FIG. 1A and FIG. 1B). This assay could easily be scaled up and implemented in 384-well plates, which were imaged with the aid of an automated fluorescence microscope (FIG. 1C).

Figure 2A:
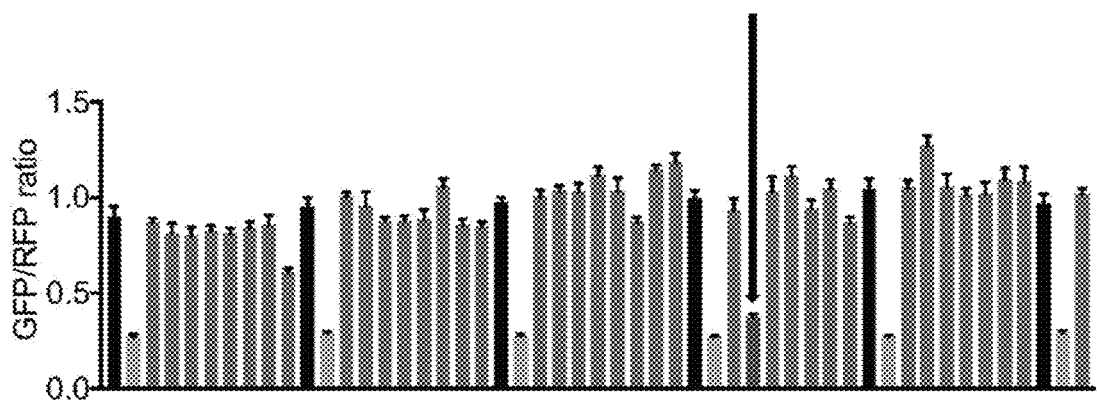
FIGS. 2A-2F. Identification of an inhibitor of Rag GTPase-Lamtor interaction by Visual IP.
Figure 2B:
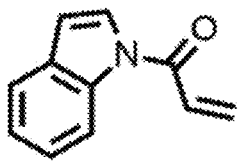
Figure 2C:
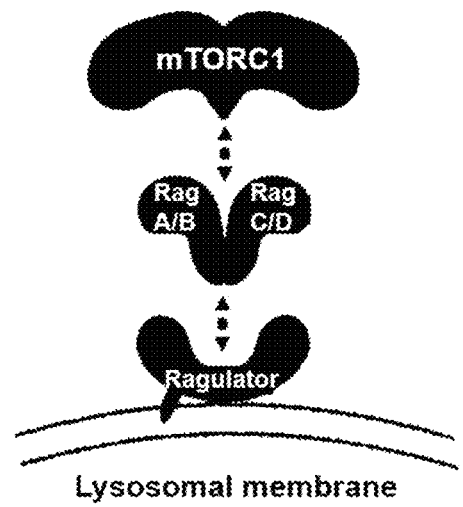
Figure 2D:
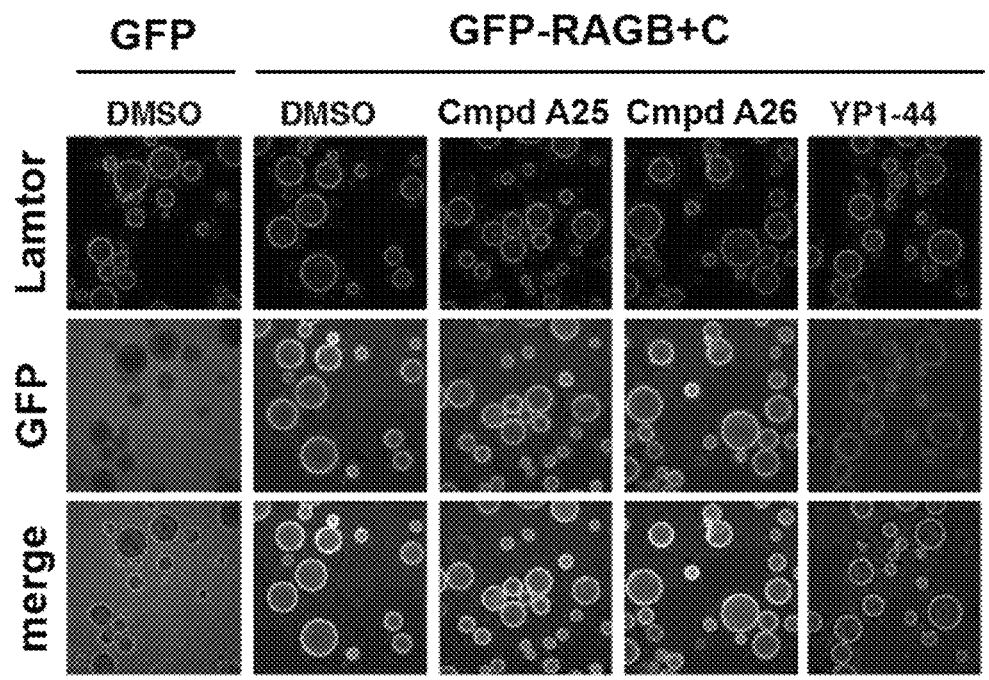
Figure 2E:
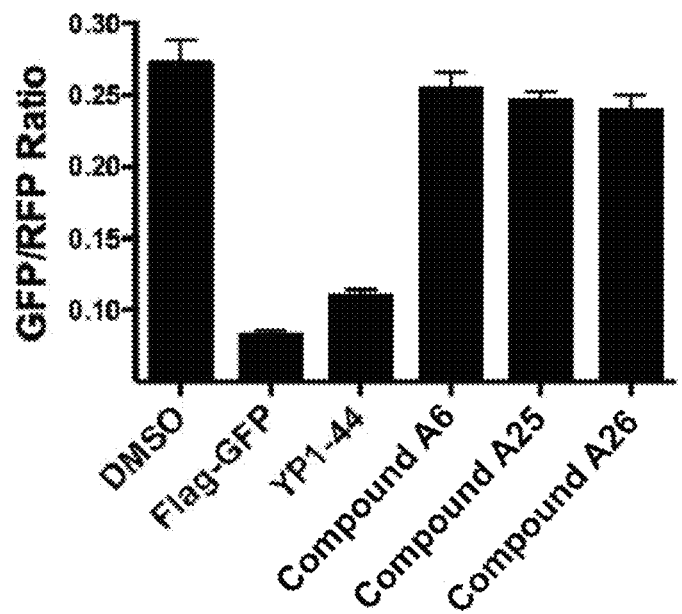
Figure 2F:
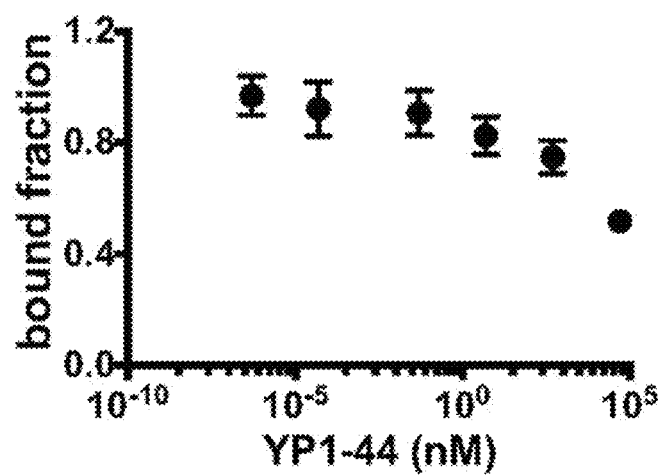

We screened a fragment-based cysteine-reactive covalent ligand library using Visual IP to identify small-molecules that could disrupt the interactions of Lamtor and Rag proteins, towards developing a selective strategy to disrupt TORC1 recruitment to the lysosome (FIG. 2A). This library consisted of acrylamides and chloroacetamides that are known to be cysteine-reactive. We and others have previously shown that these reactive scaffolds can be tempered to confer selectivity for specific cysteines through appendage of appropriate R groups (6, 7, 12). Through this screen, we identified a hit—a cysteine-reactive acrylamide lead YP 1-44 (FIG. 2B). We confirmed that this hit disrupted the interaction between Lamtor and Ragulator complex, which is essential to recruit mTORC1 to the lysosomal surface (FIG. 2C) by microscopy methods showing that Rag B and Rag C no longer localized with Lamtor upon YP 1-44 treatment (FIG. 2D). We also showed that compounds that were negative in our screen, such as compound A25 and compound A26 did not disrupt Rag and Lamtor interactions (FIG. 2D and FIG. 2E). We further reproduced these findings showing that YP 1-44 was able to disrupt protein interactions and show that YP 1-44 at 10 µM displaces Rag and Lamtor interactions by ~50% in a dose-responsive manner (FIG. 2F).

Small-Scale Compound Screens.

HEK293T cells were plated on 15 cm plates at 10 million cells per plate. 24 hours later, the cells were transfected using 500 µL OptiMEM transfection media, 60 µL polyethyleneimine (PEI, Sigma) and 10 µg total DNA. The transfection mix was incubated for 15 minutes and then added directly to the cell media. 48 hours later, the media was removed, and the cells were washed three times with PBS. The cells were scraped from the plate and collected in 10 mL PBS. The samples were centrifuged for 5 minutes at 1500 g at 4° C. The cell pellets were then resuspended in 1 mL Triton lysis buffer (1% Triton X-100, 130 mM NaCl, 2 mM EGTA, 2.5 mM $MgCl_2$, 25 mM HEPES, pH 7.4, 10% glycerol, protease inhibitor (Pierce)), and allowed to rotate at 4° C. for 20 minutes. The samples were then centrifuged at 13000 g for 2 minutes, and the supernatant was separated for immunoprecipitation. 50 µL of washed anti-FLAG affinity beads (Sigma) were added to the supernatant and the sample was rotated at 4° C. for 2 hours. After immunoprecipitation, the samples were washed twice in Triton lysis buffer, once in high salt (500 mM NaCl) lyso sucrose buffer, and once in normal salt lyso sucrose buffer (250 mM sucrose, 10 mM KCl, 2 mM EGTA, 2.5 mM $MgCl_2$, 25 mM HEPES, pH 7.4, 10% glycerol, protease inhibitor (Pierce)). Each wash consisted of rotating with the wash buffer for 5 minutes at 4° C. and subsequent centrifugation at 2000 g for 1 minute. For elution off FLAG beads, 3×-FLAG peptide in Phosphate Buffered Saline (PBS) was added to the sample, [RL2] and the sample was allowed to rotate overnight at 4° C. The sample was then centrifuged at 3000 g for 3 minutes and the proteins used for subsequent experiments were present in the supernatant fraction. Samples were assembled with 10 µL bead suspension with bound protein 1, 15 µL cytosol preparation, 20 µL lyso sucrose buffer, and 3 µL FLAG elution of protein 2. Ragulator and Rags were incubated at room temperature for 15 minutes in the presence of 50 µM compound or an equivalent volume of DMSO. 20 µL of the sample was mounted onto a glass slide, and the coverslip was sealed with nail polish. Images were acquired on a Nikon Ti microscope equipped with Yokogawa spinning disk module at 488 nm and 561 nm excitation, using 10× or 40× air objectives.

Large-Scale Compound Screens, Protein Preparation/Immunoprecipitation.

HEK293F cells were grown in suspension to a density of 2 million cells per mL. For transfection of suspension cells, 1 mg total DNA was used per liter of cells. The DNA was heated to 70° C. and mixed with 3 mL polyethyleneimine (1 mg/mL PEI, Sigma) and Hybridoma Media (Gibco). The transfection mix was incubated for 20 minutes and then added directly to the cell suspension. 72 hours later, the cells were pelleted and collected by centrifugation at 1500 g at 4° C. for 15 minutes. The cell pellets were then resuspended in 50 mL Triton lysis buffer (phosphate buffered saline, 1% Triton X-100, 2 mM $MgCl_2$, 0.5 mM TCEP, protease inhibitor (Pierce)), and allowed to rotate at 4° C. for 20 minutes. The samples were then centrifuged at 13000 g for 2 minutes, and the supernatant was separated for immunoprecipitation. For purification of GST-fusion Ragulator complex, the supernatant was incubated with 5 mL of washed glutathione-conjugated beads (Pierce) for 2 hours and then washed with washing buffer (phosphate buffered saline, 2 mM $MgCl_2$, 0.5 mM TCEP, protease inhibitor (Pierce)). For the preparation of FLAG-fusion Rag GTPases, 50 mL of washed anti-FLAG affinity beads (Sigma) were added to the supernatant and the sample was rotated at 4° C. for 2 hours. After immunoprecipitation, the samples were washed with washing buffer (phosphate buffered saline, 2 mM $MgCl_2$, 0.5 mM TCEP, protease inhibitor (Pierce)). For elution off FLAG beads, 3×-FLAG peptide in Phosphate Buffered Saline (PBS) was added to the sample, and the sample was allowed to rotate overnight at 4° C. The sample was then centrifuged at 3000 g for 3 minutes and the proteins used for subsequent experiments were present in the supernatant fraction.

Sample Preparation.

Samples were injected onto Polystyrene 384-well plates (Greiner) using a Beckman-Coulter BioMek NX system. Samples were prepared such that the final volume per well was 50 jµL, having glutathione beads conjugated with GST-RFP-fusion Ragulator complex at a final concentration of 2% slurry, incubated with 100 ng FLAG-GFP-fusion Rag GTPases. The samples were mixed and test compounds were added at the appropriate concentrations. The samples were allowed to equilibrate for 30 minutes at room temperature.

Image Acquisition and Analysis.

Figure 3A:
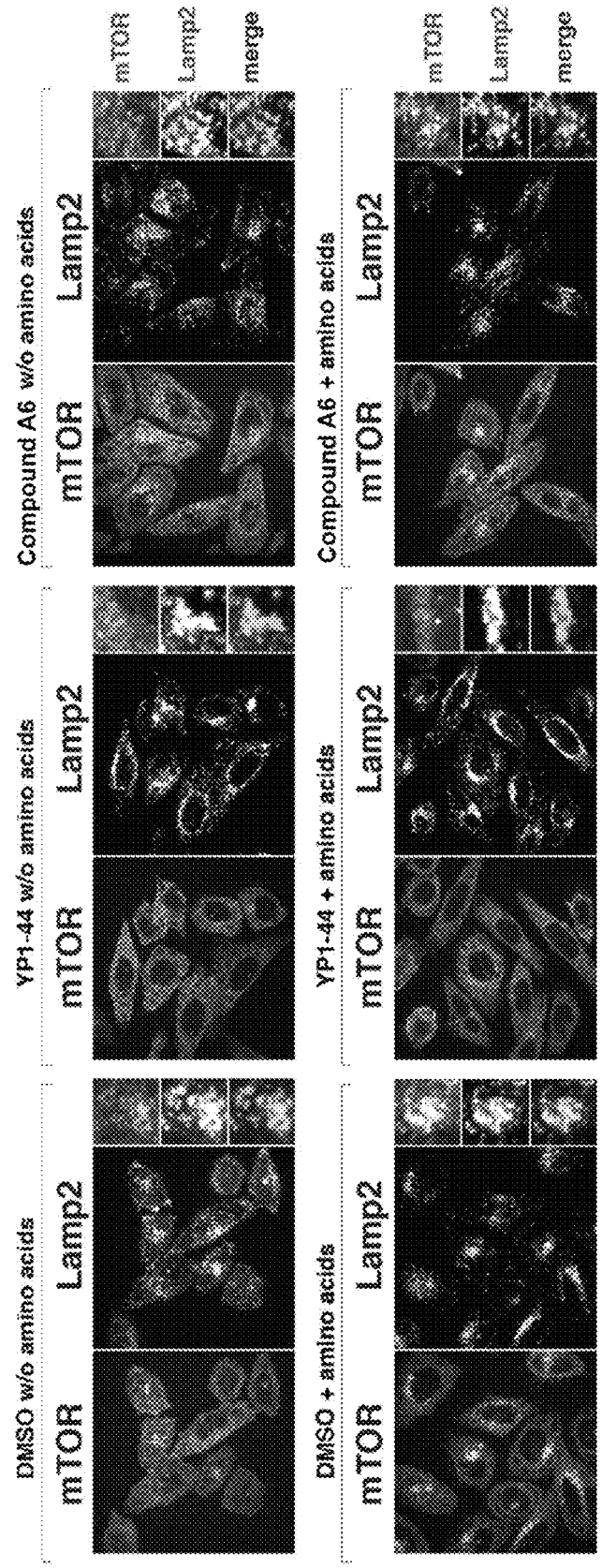
FIGS. 3A-3D. Validation of YP1-44 mediated mTORC1 inhibition in cells.
Figure 3B:
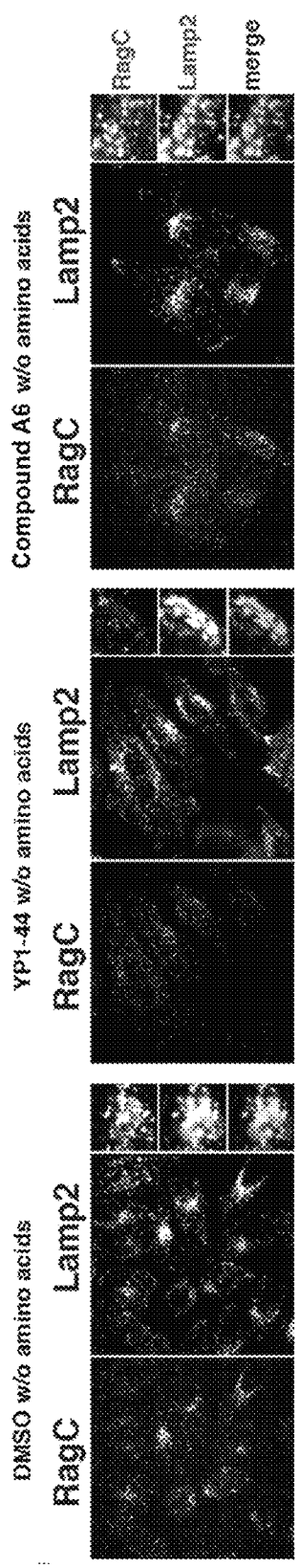
Figure 3C:
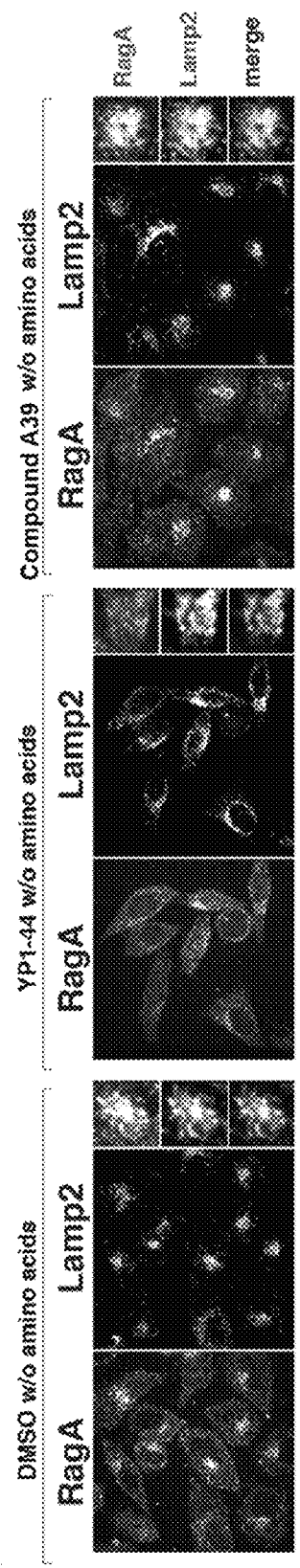
Figure 3D:
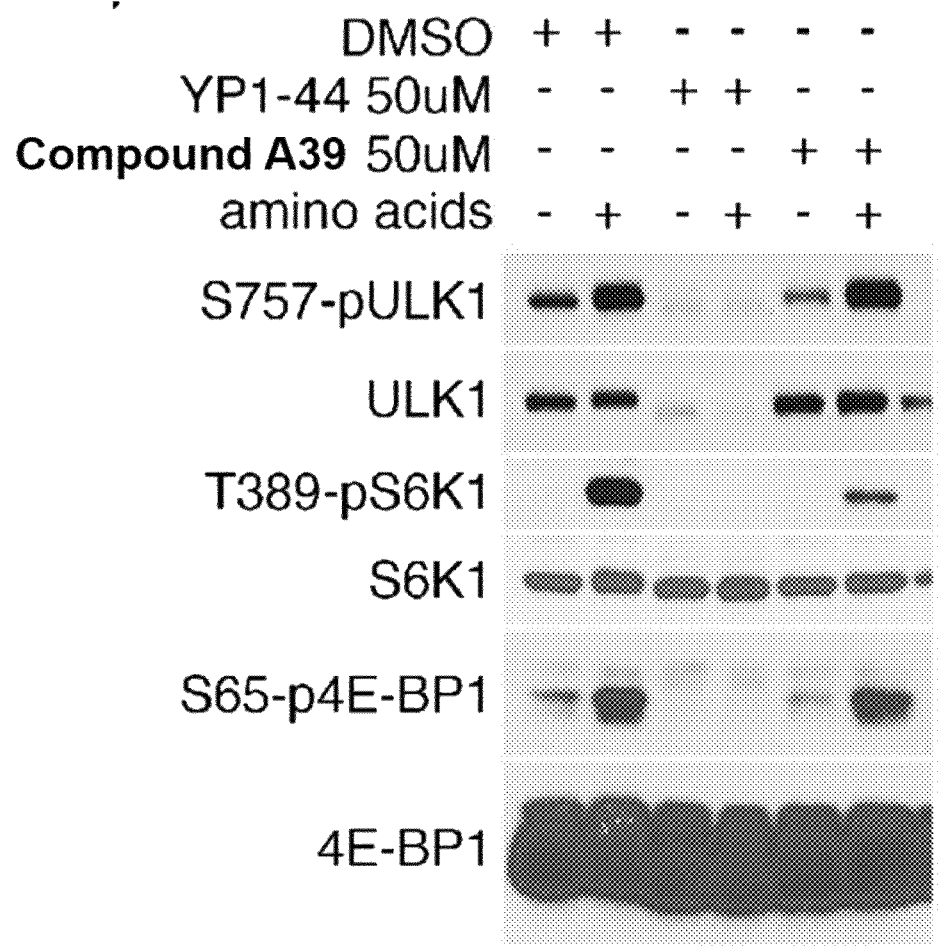

Samples were imaged using an ImageXpress Micro XLS Widefield High-Content Analysis automated microscope system (Molecular Devices). Samples were imaged at 4× magnification using FITC and TRITC filter sets Example 2. Cellular Characterization of Inhibitor Next, we sought to determine whether YP 1-44 had expected cellular effects in disrupting the TORC1 complex, recruitment of TORC1 to the lysosome, and TORC1 signaling. We treated Hela cells with YP 1-44 for 1 h with and without amino acid stimulation. We show that amino acid stimulation expectedly causes mTOR to localize to LAMP2-positive lysosomes, and that YP 1-44, but not the negative control compound A6, disrupts amino acid-induced mTOR localization (FIG. 3A). We similarly show that both RagC and RagA are no longer localized to the lysosome upon treatment with YP 1-44 treatment, but not compound A6 (FIG. 3B, FIG. 3C). This finding is consistent with the role of Lamtor as an obligate scaffold not only for mTORC1 but also for the Rag GTPases at the lysosome. We further show that mTORC1-mediated signaling pathways, represented by p-ULK1, pS6K1, and p-4E-BP1, were completely inhibited by YP 1-44 in Hela cells, but much less so with a negative control compounds compound A39 (FIG. 3D). Thus, our results establish that YP 1-44 abolishes mTORC1 signaling both in vitro and in live cells by preventing mTORC1 localization to the lysosome, and that this action occurs via disruption of the Lamtor-Rag scaffold.

Compound Validation in Cells. Microscopy.

HeLa cells were plated on fibronectin-coated glass coverslips in 6-well plates (35 mm diameter/well), at 300,000-500,000 cells/well. 12-16 hours later, cells were subjected to amino acid depletion for 1 h in the presence of 50 uM compounds or an equivalent volume of DMSO, restimulated with a complete amino acid mix for 10 minutes, and fixed in 4% paraformaldehyde (in PBS) for 15 min at RT. The coverslips were rinsed twice with PBS and cells were permeabilized with 0.1% (w/v) Saponin in PBS for 10 min. After rinsing twice with PBS, the slides were incubated with primary antibody in 5% normal donkey serum for 1 hr at room temperature, rinsed four times with PBS, and incubated with fluorophore-conjugated secondary antibodies produced in goat or donkey (Life Technologies, diluted 1:1000 in 5% normal donkey serum) for 45 min at room temperature in the dark, washed four times with PBS. Coverslips were mounted on glass slides using Vectashield (Vector Laboratories) and imaged on a spinning disk confocal system (Andor Revolution on a Nikon Eclipse Ti microscope).

Western Blotting.

HeLa cells were subjected to starvation/refeeding protocols as described in the previous section, then lysed in ice-cold lysis buffer (150 mM NaCl, 20 mM HEPES [pH 7.4], 2 mM EDTA, 0.3% CHAPS or 1% Triton X-100, and one tablet of EDTA-free protease inhibitors per 50 ml). Cell lysates were cleared by centrifugation at 13,000 rpm for 10 minutes in a microfuge. Samples were normalized to a total concentration of 1 mg/mL protein and prepared using sample buffer at 1×, then boiled for 5 minutes at 95 C. Samples were loaded onto 10% or 12% SDS-Page gels, and analyzed by immunoblotting.

Example 3. Identification of Binding Location

Figure 4A:
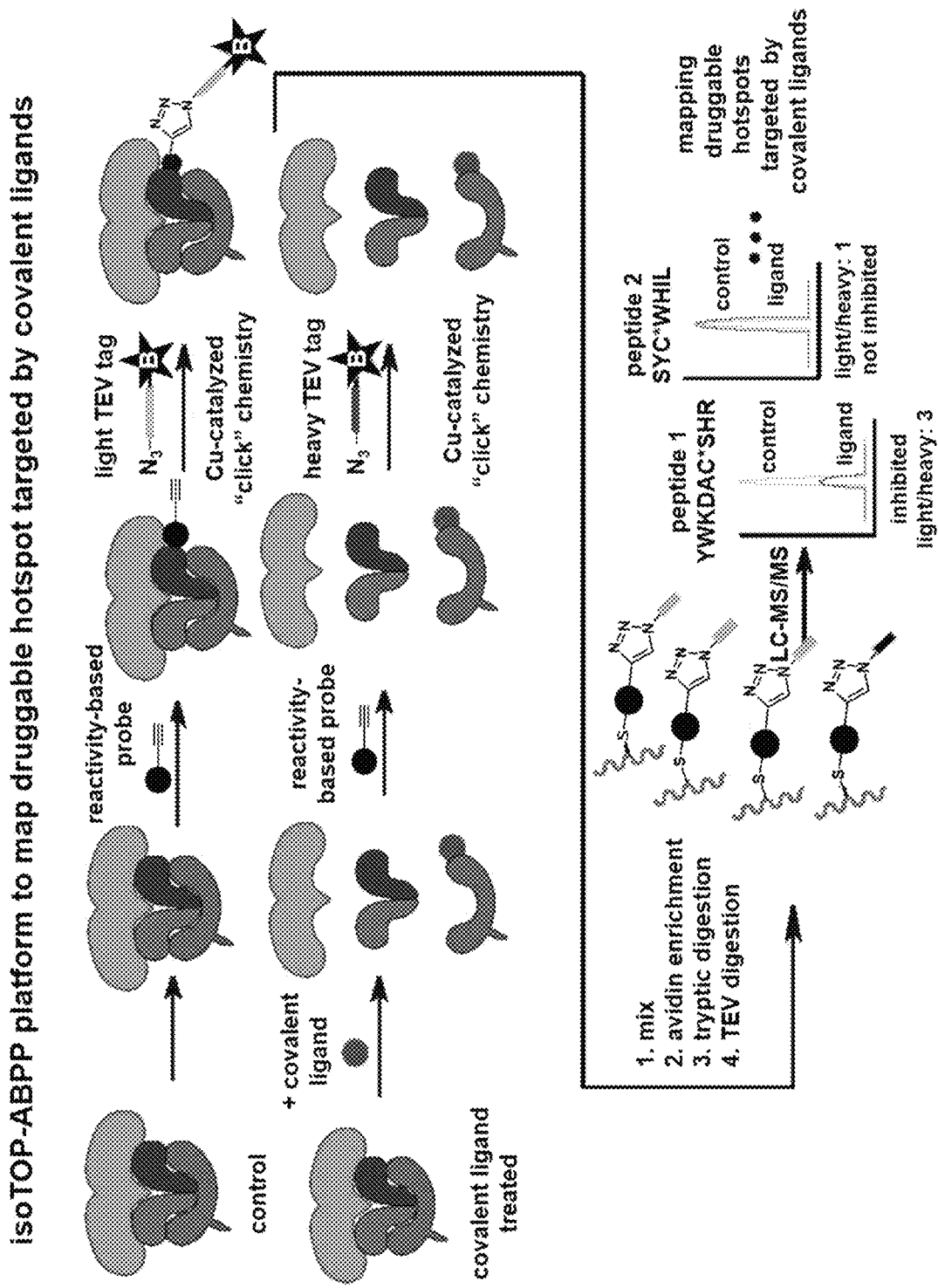
FIGS. 4A-4B. Competitive isoTOP-ABPP analysis of YP 1-44 with the TORC1 Complex Proteins.
Figure 4B:
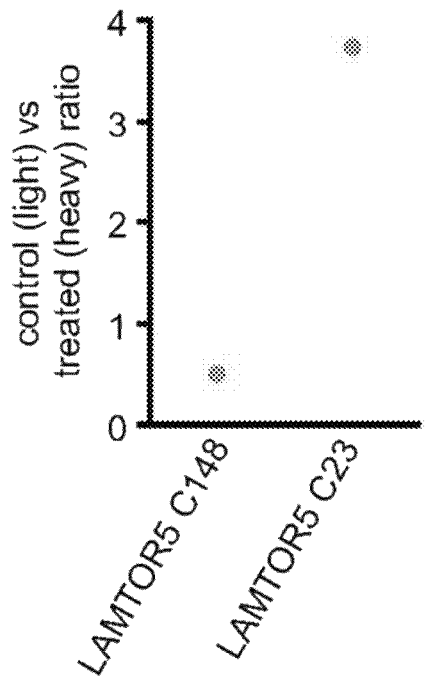
Figure 4B:
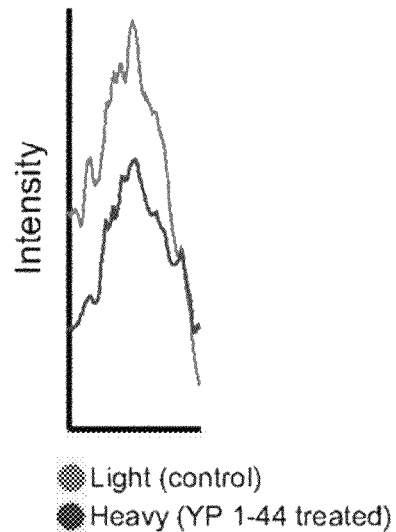

To identify the specific druggable hotspot targeted by YP 1-44 within the TORC1 complex, we performed a chemoproteomic study using isotopic tandem orthogonal proteolysis-enabled activity-based protein profiling (isoTOP-ABPP). IsoTOP-ABPP uses reactivity-based chemical probes to profile proteome-wide reactive, functional, and druggable hotspots directly in complex proteomes. When used in a competitive manner, small-molecule covalent ligands can be competed against the binding of reactivity-based probes to facilitate the identification of druggable hotspots targeted by lead covalent ligands (5-7) (FIG. 4A). Here, we pre-treated human purified mTORC1, Rag GTPase and Lamtor complexes with either vehicle or YP 1-44, and subsequently labeled this reconstituted system with a broad cysteine-reactive probe iodoacetamide-alkyne (IA-alkyne). Any accessible cysteine druggable hotspot would be labeled with the IA-alkyne probe in the vehicle-treated control, but the site bound by YP 1-44 would no longer accessible to IA-alkyne binding. Subsequently, we used copper-catalyzed azide-alkyne cycloaddition to append an isotopically light (for control) or heavy (for YP 1-44-treated) biotin-azide tag bearing a TEV protease recognition peptide onto probe-labeled proteins, upon which we combined the control and treated proteomes in a 1:1 ratio, followed by avidin-enrichment, tryptic digestion, and elution of probe-modified tryptic peptides by TEV protease. The resulting peptides were analyzed by LC-LC/MS/MS and light-to-heavy ratios of probe-modified peptides were quantified. We identified two cysteines within LAMTOR5, C148 and C23 that were labeled with ratios of 0.51 and 3.7, respectively. If YP 1-44 bound to a particular cysteine, we would expect a higher (>2) light-to-heavy ratio. We thus interpreted our results to indicate that C23 of LAMTOR5 was the primary site targeted by YP 1-44 (FIG. 4B).

Figure 5A:
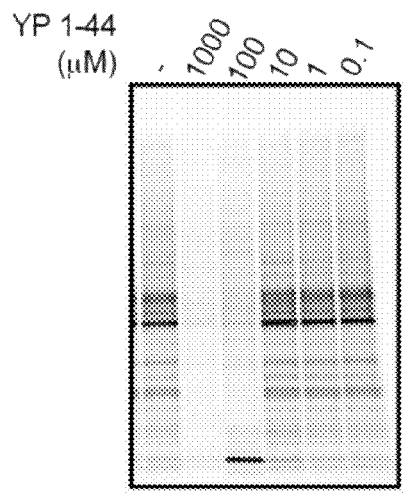
FIGS. 5A-5F. Improving potency and selectivity of mTORC1 inhibitors.
Figure 5B:
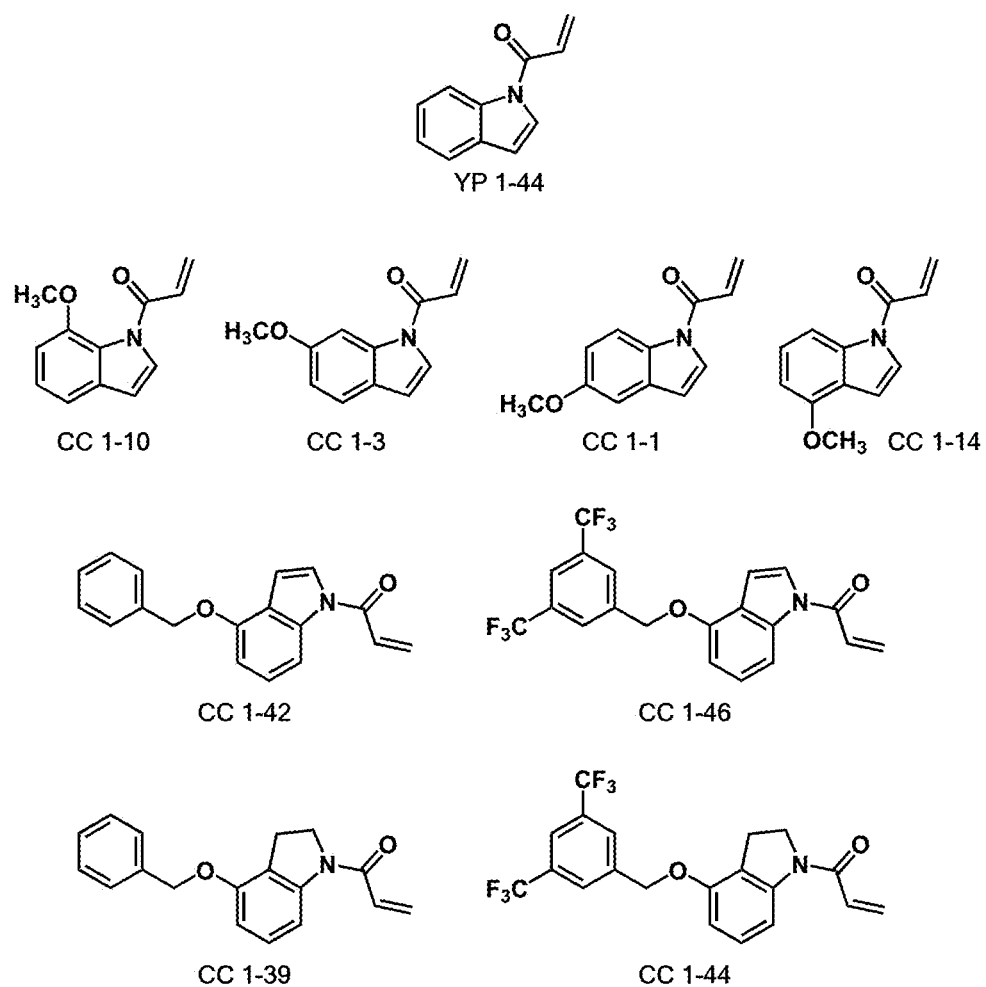
Figure 5C:
Figure 5D:
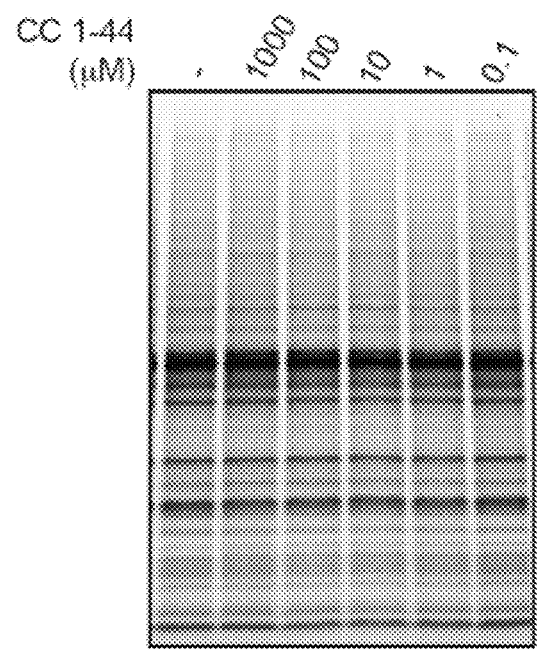
Figure 9A:
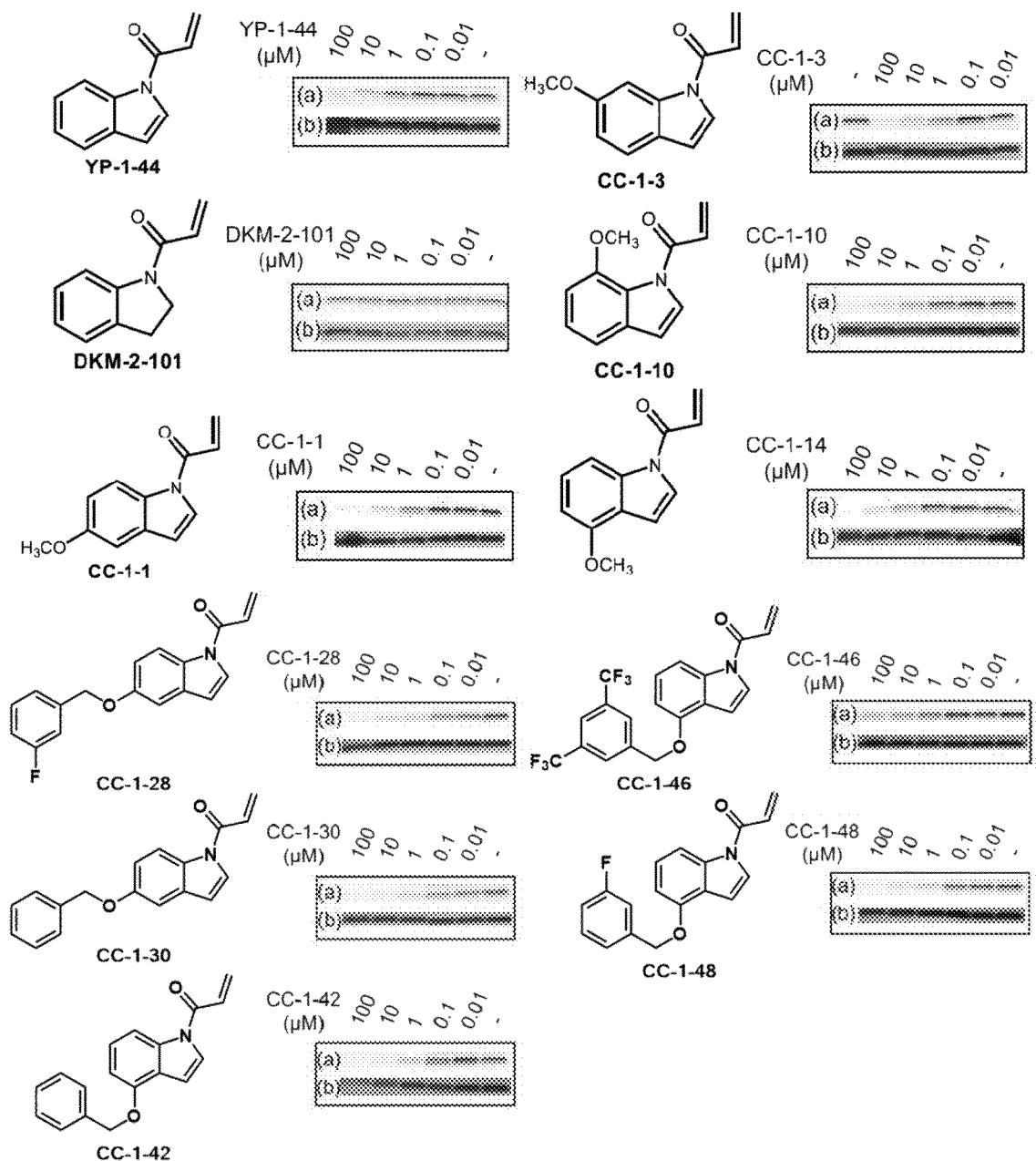
FIGS. 9A-9C. Potency and selectivity of YP 1-44 analogs.
Figure 9B:
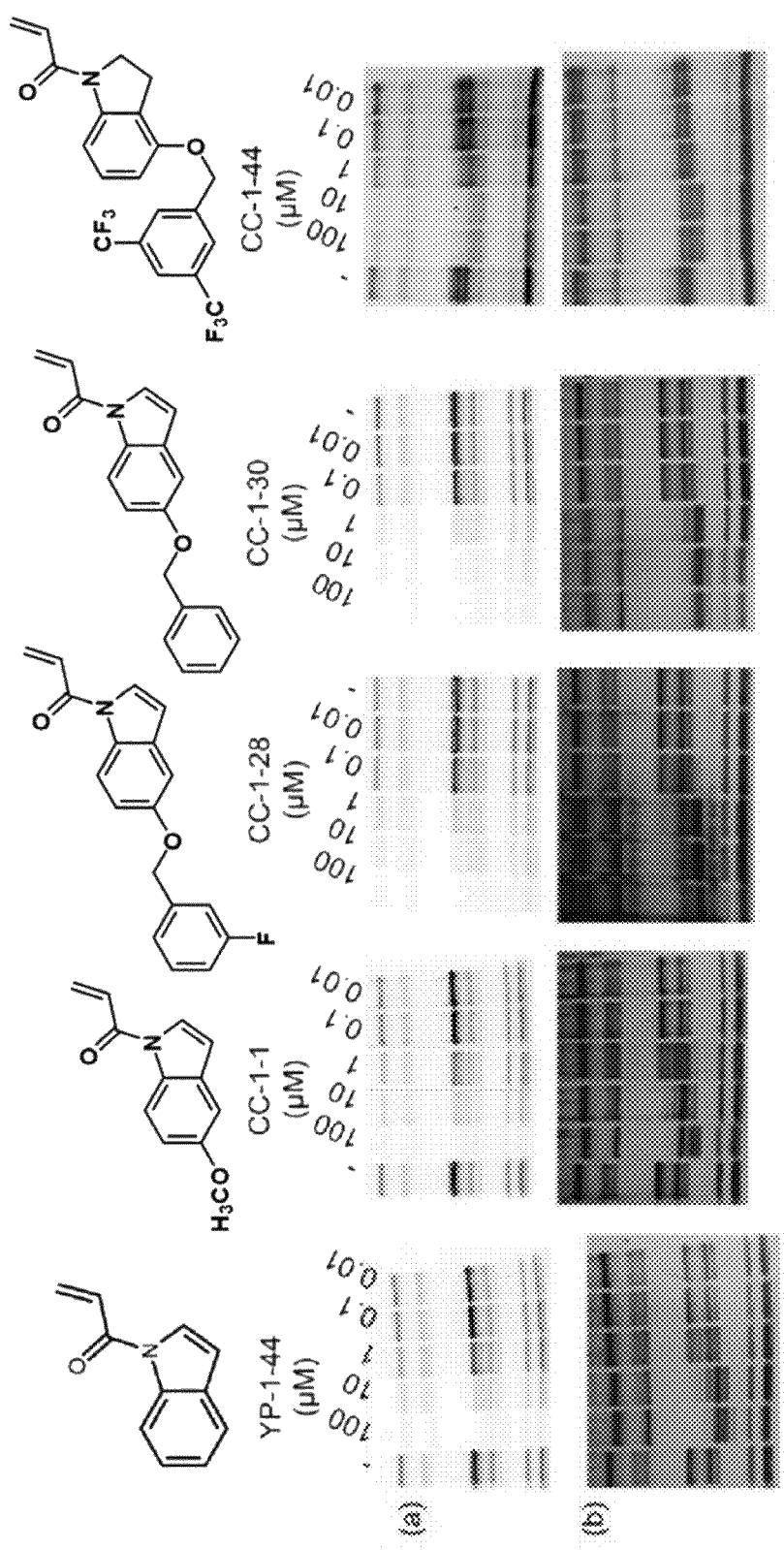
Figure 9C:
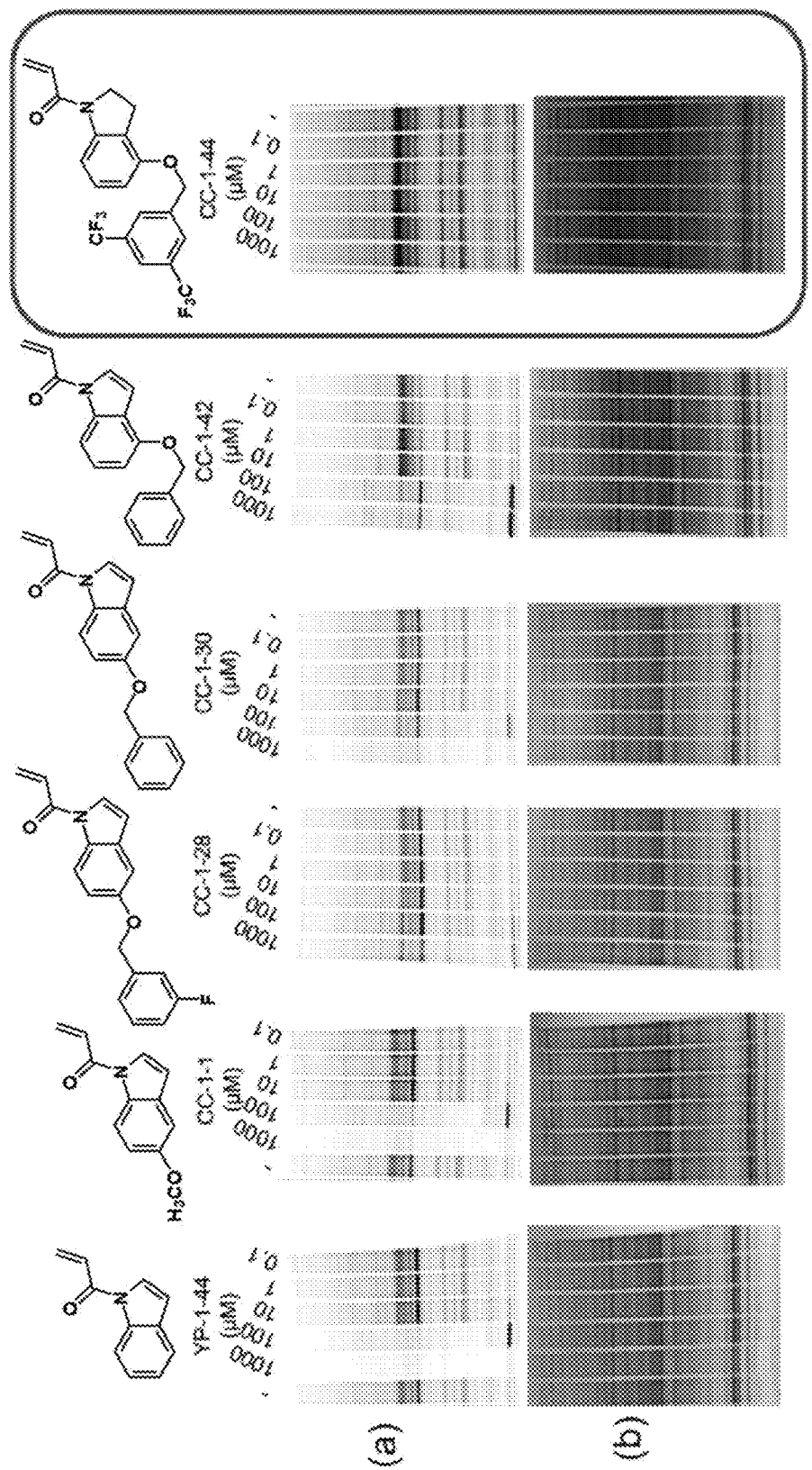

Further investigation showed that YP 1-44 was not sufficiently selective at higher concentrations (>100 µM) showing broad displacement of IA-alkyne cysteine reactivity in Hela whole cell proteome (FIG. 5A; FIGS. 9A-9C). Thus, we performed medicinal chemistry to optimize the potency and selectivity of our initial hits by addition of further bulk to the core YP 1-44 scaffold (FIGS. 9A-9C; FIG. 5B). We initially screened these compounds against both LAMTOR5 and the Ragulator complex using gel-based ABPP methods competing the binding of these YP 1-44 analogs against IA-alkyne labeling of these proteins (FIG. 5C, FIG. 9). We also tested these compounds against Hela cell whole proteome cysteine reactivity to get initial read-outs of proteome-wide selectivity (FIGS. 9A-9C, FIG. 5D). Among the various YP 1-44 analogs, CC 1-44 showed both desirable potency and apparent selectivity up to 1 mM (FIG. 5D; FIGS. 9A-9C).

Figure 5E:
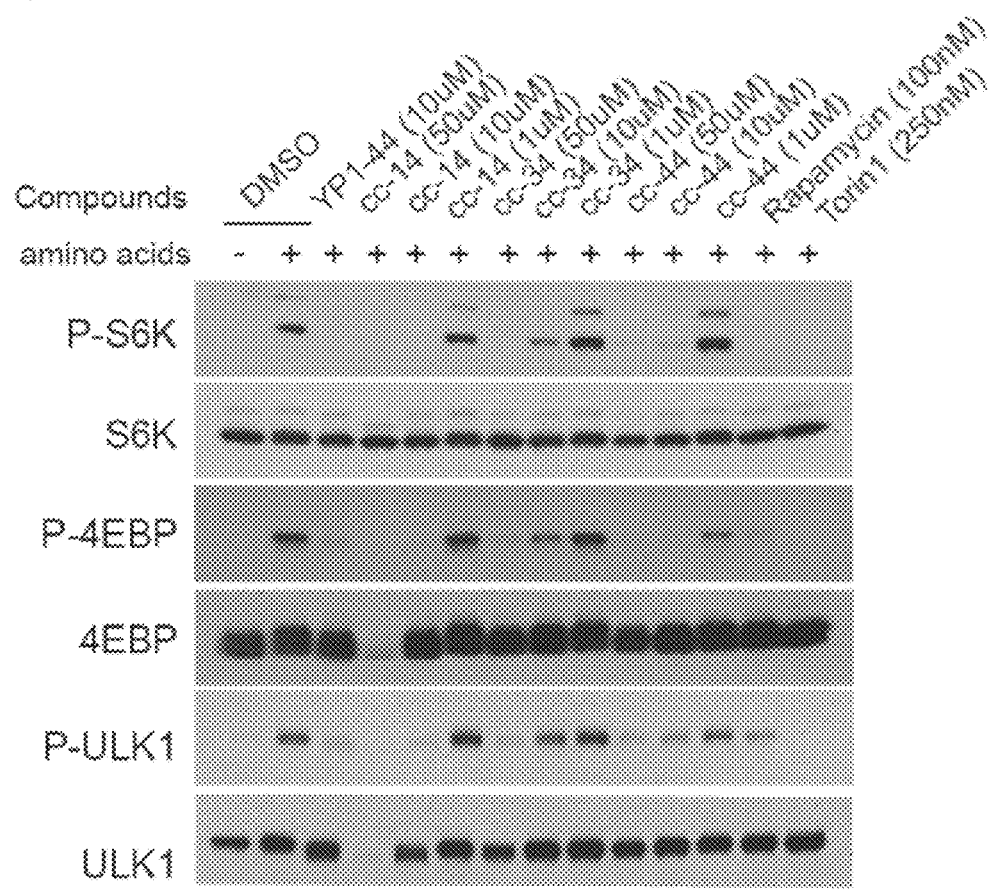
Figure 5F:
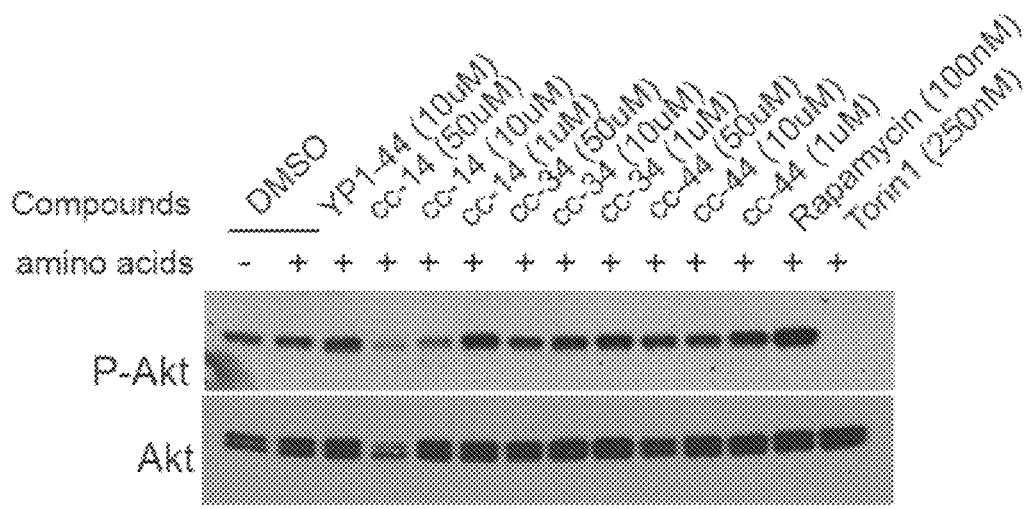

Several of these compounds were also directly tested for their ability to inhibit mTORC1 signaling in immunoblotting-based assays. Three of them: CC 1-14, CC 1-34 and CC 1-44, blocked mTORC1 with potency comparable to YP 1-44 (FIG. 5E). In particular, when used at 10 µM they completely inhibited phosphorylation of canonical mTORC1 substrates S6K1, 4E-BP1 and ULK1. Moreover, unlike the other two compounds, CC 1-44 did not affect the canonical mTORC2 substrate, pAKT, when used at up to 50 µM (FIG. 5F). Thus, we pursued CC 1-44 for further characterization.

Figure 6A:
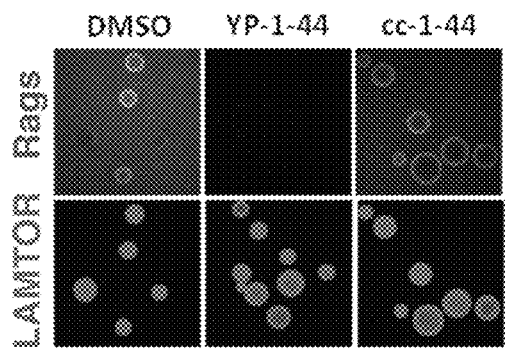
FIGS. 6A-6D. CC 1-44 inhibits mTORC1 signaling and activates autophagy.
Figure 6B:
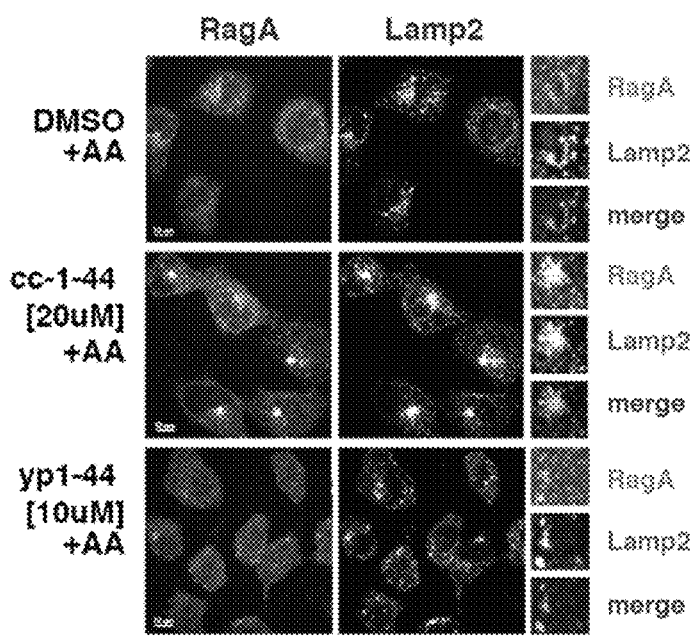
Figure 6C:
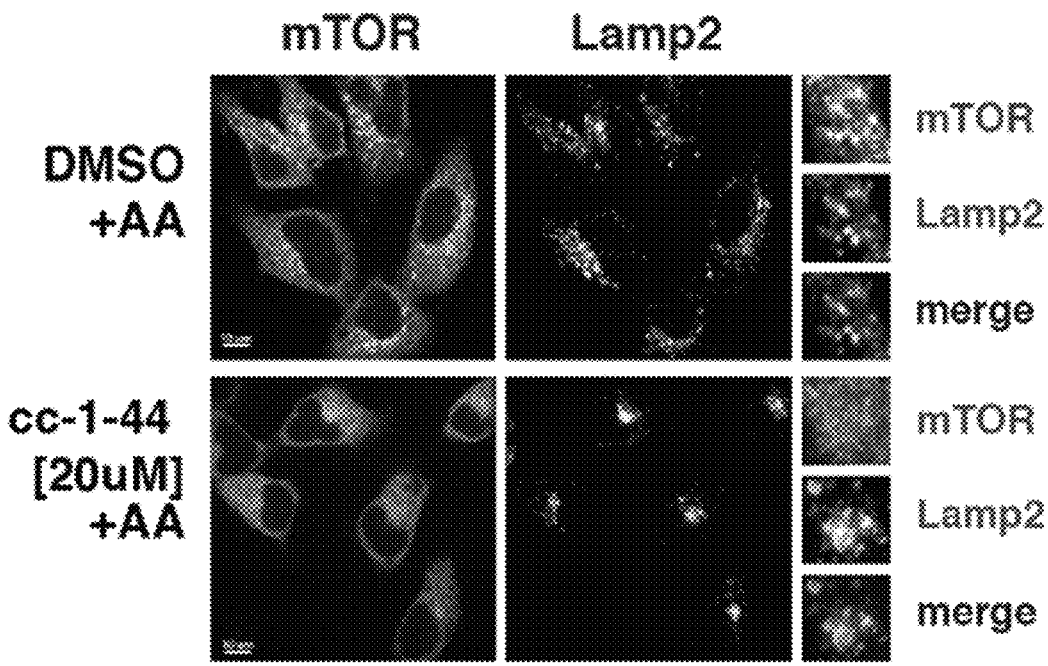

Next, we investigated the mechanism of mTORC1 inhibition by CC-1-44 using visual IP and immunofluorescence. Surprisingly, unlike YP 1-44, CC 1-44 did not break the LAMTOR-Rag interaction in vitro (FIG. 6A). Indeed, when we visualized RagA and RagC localization in CC 1-44-treated cells, their localization to LAMP2-positive lysosomes was increased, not decreased as for YP 1-44 (FIG. 6B). This observation pointed to a different mechanism for mTORC1 inactivation by CC 1-44. Rather than disrupting the integrity of the LAMTOR-Rag assembly, CC 1-44 prevents its activation, causing it to strongly accumulate at the lysosome in a conformation that is unable to bind to mTORC1. Consistent with this interpretation, mTORC1 was completely dispersed from lysosomes in cells treated with CC 1-44, as observed with YP 1-44 (FIG. 6C). This interpretation is also consistent with numerous reports in the literature, showing that in the inactive state the Rags and LAMTOR complexes bind to each other more tightly than in the active state.

The reasons for the different mechanism of action of CC 1-44 and YP 1-44 remain to be determined. IsoTOP-ABPP indicated that, similar to YP 1-44, CC 1-44 modified C23 and C148 in LAMTOR5. However, given the selectivity profile of YP 1-44, we suspect that this compound may modify additional cysteine residues that were not detected by initial isotope-ABPP experiments. A more widespread cysteine modification could indeed lead to complete disassembly of the LAMTOR-Rag complex that was observed both with visual IP and immunofluorescence.

Figure 6D:
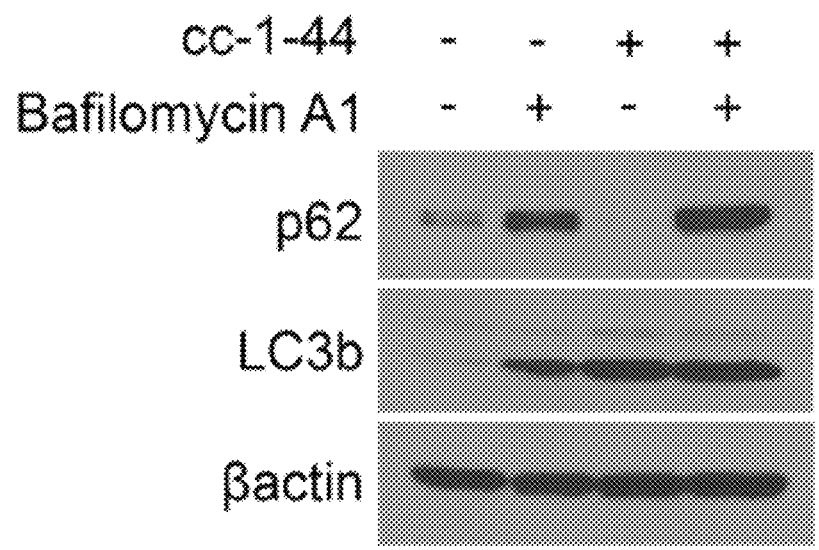

In cells treated with CC 1-44, autophagy becomes activated within 1 h, as judged by accumulation of cleaved LC3b and increased degradation of p62 (FIG. 6D). Thus, CC 1-44 fits two requirements that have not been found in a single chemical so far: 1-specific suppression of mTORC1 without inhibiting mTORC2 and 2-efficient activation of autophagy.

Figure 7A:
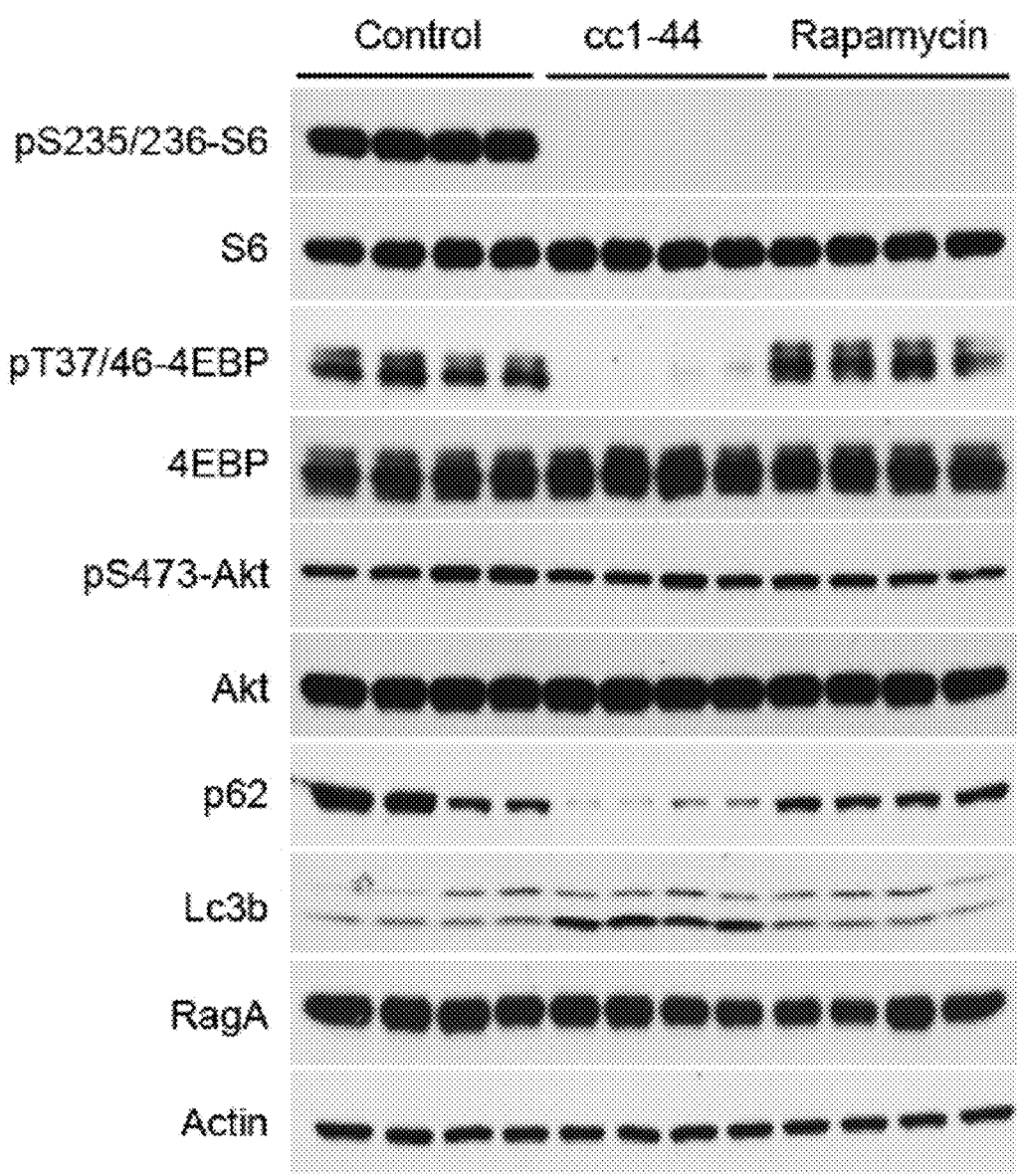
FIG. 7A-C. Efficacy of CC 1-44 in living mice in various tissues: heart (FIG. 7A), skeletal muscle (FIG. 7B), and kidney (FIG. 7C). Mice (4 animals/group) injected with CC 1-44 (100 mg/kg) show dramatic inhibition of mTORC1 signaling as assessed by phospho-S6 and 4EBP1, whereas rapamycin injection (10 mg/kg) only leads to pS6 but not p-4EBP1 inhibition. C 1-44 also results in much stronger autophagy induction as compared to rapamycin in various tissues tested, including heart and skeletal muscle (FIG. 7A, FIG. 7B). Similar results are observed in kidney (FIG. 7C).
Figure 7B:
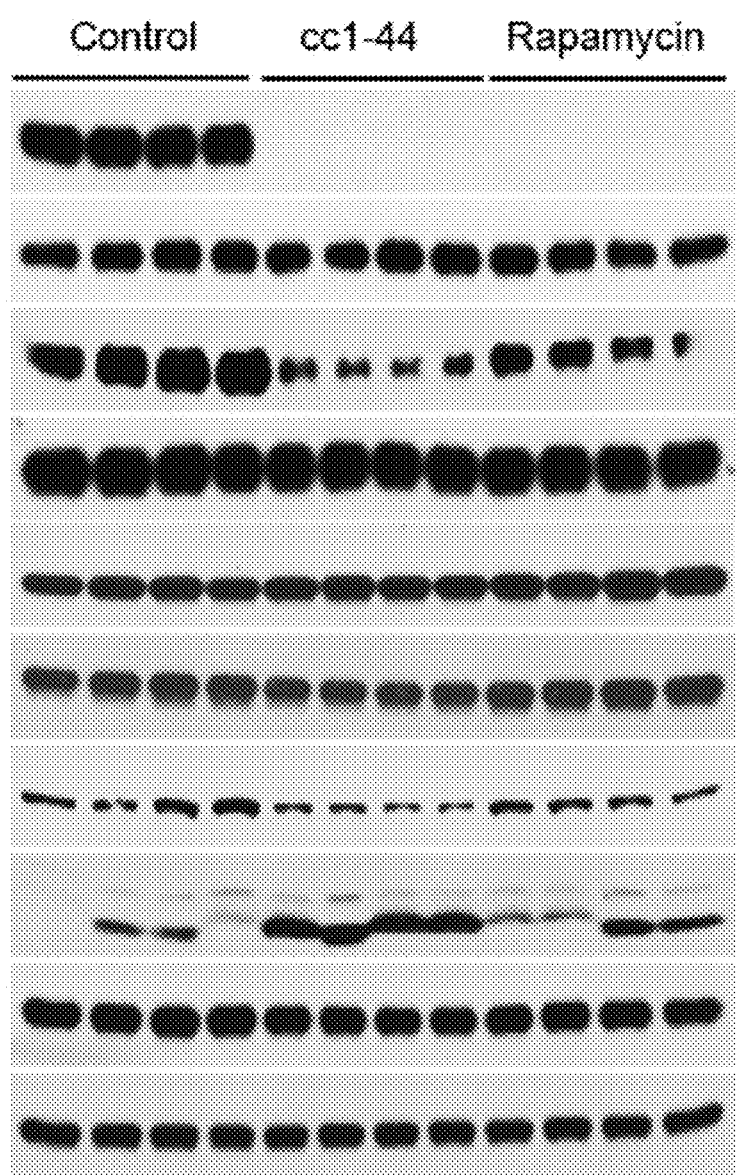
Figure 7C:
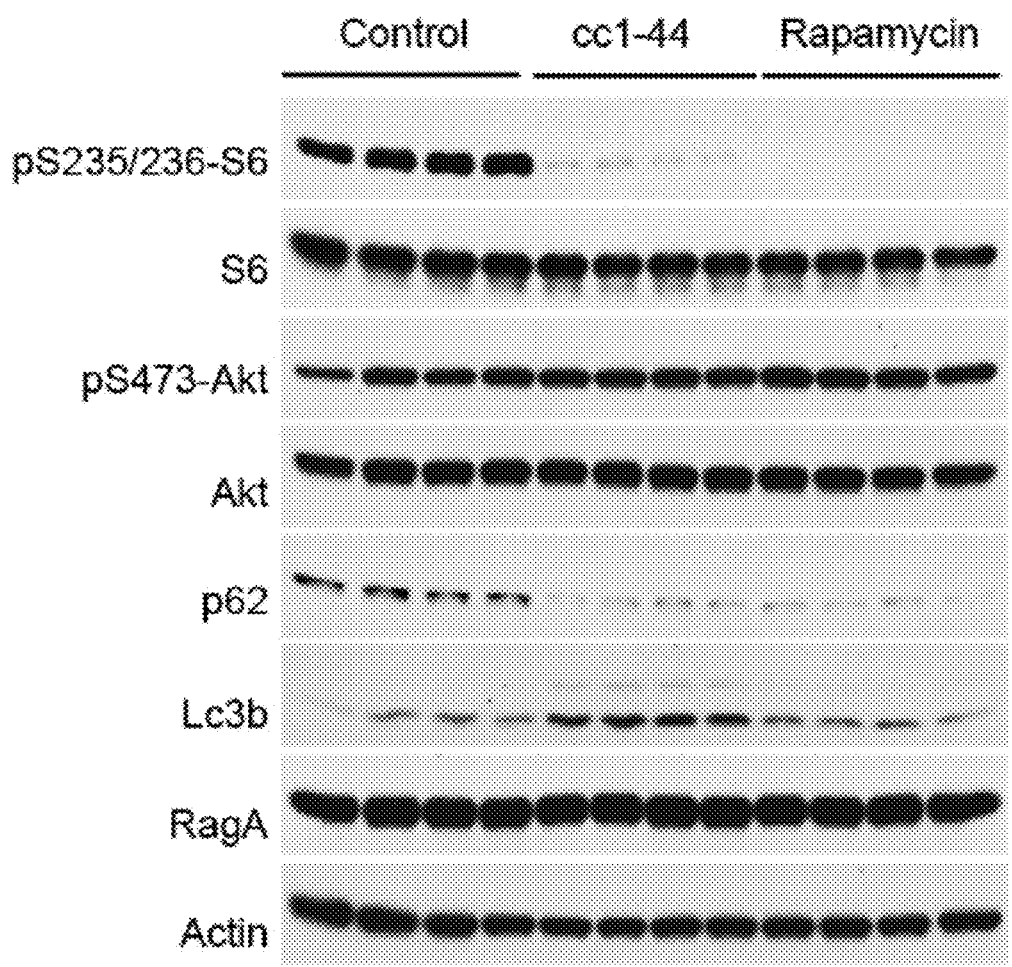

We next tested the efficacy of CC 1-44 in living mice. Mice (4 animals/group) injected with CC 1-44 (100 mg/kg) showed dramatic inhibition of mTORC1 signaling as assessed by phospho-S6 and 4EBP1, whereas rapamycin injection (10 mg/kg) only led to pS6 but not p-4EBP1 inhibition. C 1-44 also resulted in much stronger autophagy induction as compared to rapamycin in various tissues tested, including heart and skeletal muscle (FIG. 7A, FIG. 7B). Similar results were observed in kidney (FIG. 7C).

Figure 8A:
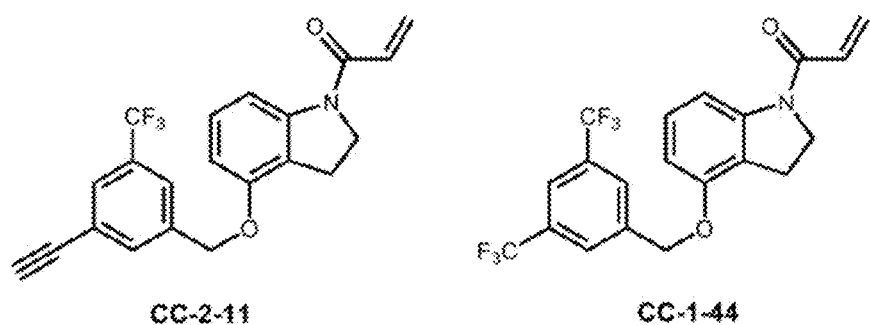
FIGS. 8A-8B.
Figure 8B:
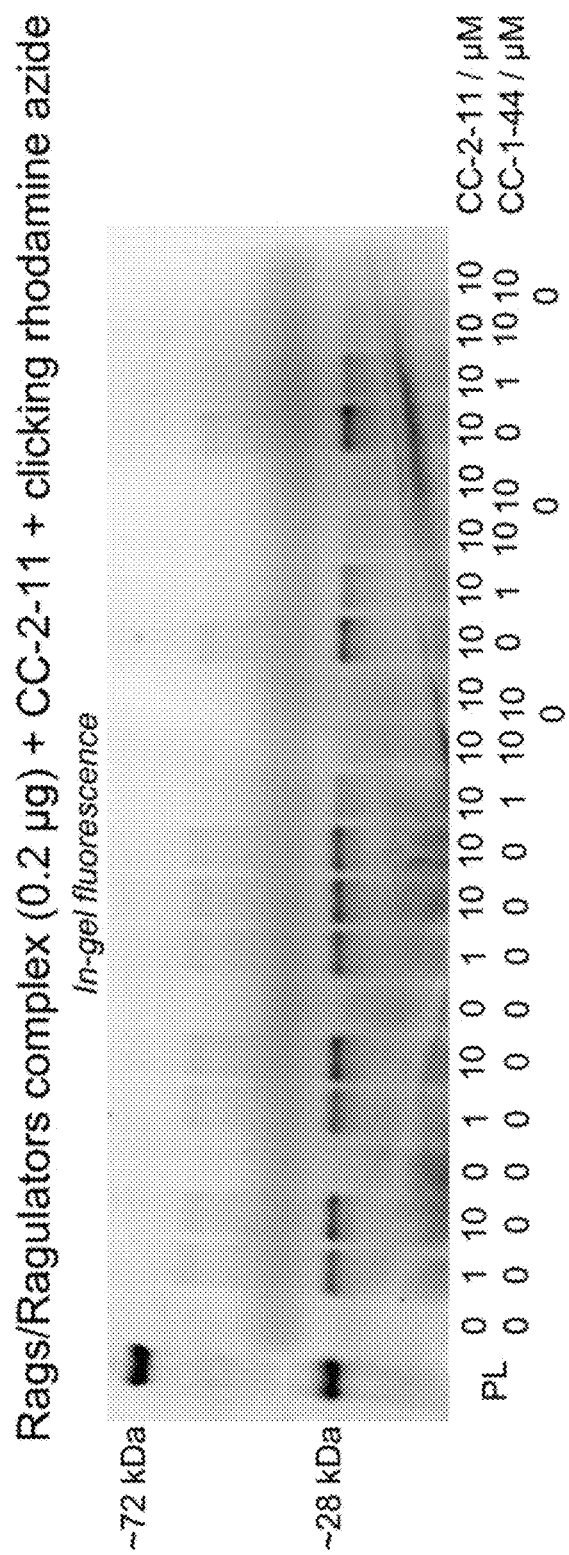

We also synthesized a CC 1-44 derivative, named CC 2-11, which bears an alkyne group on a separate ring from the cysteine-reactive warhead (FIG. 8A). The presence of the alkyne group enables us to directly label the modified target protein (e.g. Lamtor5) with biotin or rhodamine groups, either in gels or in complex proteomes. In preliminary experiments with purified Lamtor-Rag complexes, CC 2-11 enabled rhodamine labeling of a 28 KDa band corresponding to Lamtor5, and the signal was competed by incubation with excess unlabeled CC 1-44 (FIG. 8B). Thus, CC 2-11 will allow precise mapping of the target cysteines as well as accurate identification of the off-targets.

In summary, our results thus reveal three novel covalent ligands YP 1-44, CC-1-44, and CC 2-11, that disrupt the TORC1 complex protein interactions to impair lysosomal localization and signaling of mTOR. We show that both YP 1-44 and CC-1-44 target C23 and C148 of LAMTOR5, revealing these sites as unique druggable hotspots that can be targeted to impair mTOR activity and to trigger autophagy activation both in cells and in vivo. Our findings also highlight how the Visual IP technology can be coupled with chemoproteomics-enabled covalent ligand screening to rapidly discover druggable hotspots that can be targeted by small-molecules to disrupt protein-protein interactions.

IsoTOP-ABPP Analysis.

IsoTOP-ABPP analyses were performed using a modified version of our previously reported method (PMID 28352901, 28186401). We pre-treated human purified mTORC1, Rag GTPase and Lamtor complexes (5 micrograms each) with DMSO vehicle or YP 1-44 (50 µM) for 30 min at 37° C. in phosphate-buffered saline (PBS), and then labeled with IA-alkyne (100 µM) for 1 h at room temperature. They were subsequently treated with isotopically light (control) or heavy (treated) TEV-biotin (100 µM) and copper-catalyzed azide-alkyne cycloaddition (CuAAC). For analysis of cysteine reactivity in primary colorectal tumor tissue, tumors were pooled and incubated with either 100 µM IA-alkyne and isotopically heavy TEV-biotin or 10 µM IA-alkyne and isotopically light TEV-biotin followed by CuAAC. Proteins were precipitated over one hour and pelleted by centrifugation at 6500×g. Proteins were washed 3 times with cold methanol then denatured and resolubilized by heating in 1.2% SDS/PBS to 85° C. for 5 min. Insoluble components were precipitated by centrifugation at 6500×g and soluble proteome was diluted in 5 ml PBS, for a final concentration of 0.2% SDS. Labeled proteins were bound to avidin-agarose beads (170 µL resuspended beads/sample, Thermo Pierce) while rotating overnight at 4° C. Bead-linked proteins were enriched by washing three times each in PBS and water, then resuspended in 6 M urea/PBS (Sigma-Aldrich) and reduced with dithiothreitol (1 mM, Sigma-Aldrich), alkylated with iodoacetamide (18 mM, Sigma-Aldrich), then washed and resuspended in 2 M urea/PBS with 1 mM calcium chloride and trypsinized overnight with 0.5 µg/µl sequencing grade trypsin (Promega). Tryptic peptides were discarded and beads were washed three times each in PBS and water, then washed with one wash of TEV buffer containing 1 µM DTT. TEV-biotin tag was digested overnight in TEV buffer containing 1 µM DTT and 5 µL Ac-TEV protease at 29° C. Peptides were diluted in water and acidified with final concentration of 5% formic acid (1.2 M, Spectrum). Peptides from all proteomic experiments were pressure-loaded onto a 250 mm inner diameter fused silica capillary tubing packed with 4 cm of Aqua C18 reverse-phase resin (Phenomenex #04A-4299) which was previously equilibrated on an Agilent 600 series HPLC using gradient from 100% buffer A to 100% buffer B over 10 min, followed by a 5 min wash with 100% buffer B and a 5 min wash with 100% buffer A. The samples were then attached using a MicroTee PEEK 360 µm fitting (Thermo Fisher Scientific # p-888) to a 13 cm laser pulled column packed with 10 cm Aqua C18 reverse-phase resin and 3 cm of strong-cation exchange resin for isoTOP-ABPP studies. Samples were analyzed using an Q Exactive Plus mass spectrometer (Thermo Fisher Scientific) using a 5-step Multidimensional Protein Identification Technology (MudPIT) program, using 0%, 25%, 50%, 80%, and 100% salt bumps of 500 mM aqueous ammonium acetate and using a gradient of 5-55% buffer B in buffer A (buffer A: 95:5 water: acetonitrile, 0.1% formic acid; buffer B 80:20 acetonitrile: water, 0.1% formic acid). Data was collected in data-dependent acquisition mode with dynamic exclusion enabled (60 s). One full MS (MS1) scan (400-1800 m/z) was followed by 15 MS2 scans (ITMS) of the nth most abundant ions. Heated capillary temperature was set to 200° C. and the nanospray voltage was set to 2.75 kV. Data was extracted in the form of MS1 and MS2 files using Raw Extractor 1.9.9.2 (Scripps Research Institute) and searched against the Uniprot mouse database using ProLuCID search methodology in IP2 v.3 (Integrated Proteomics Applications, Inc). Cysteine residues were searched with a static modification for carboxyaminomethylation (+57.02146) and up to two differential modifications for methionine oxidation and either the light or heavy TEV tags (+464.28596 or +470.29977, respectively). Peptides were required to have at least one tryptic end and to contain the TEV modification. ProLUCID data was filtered through DTASelect to achieve a peptide false-positive rate below 1%.

Example 4. Synthesis and Characterization of Compound

Scheme 1. Synthetic route of YP-1-44

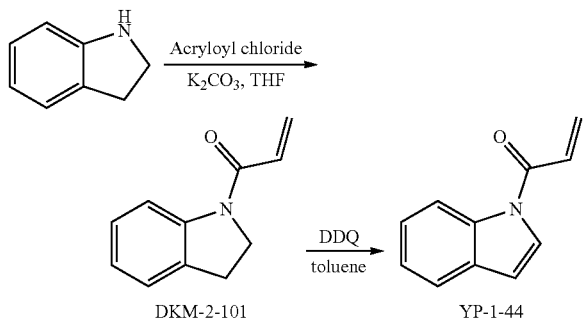

Synthesis of DKM-2-101.

K$_2$CO$_3$ (2.32 g, 16.8 mmol) was added to indoline (1 g, 8.4 mmol) in dry THF (20 mL). At 0 OC, acryloyl chloride (0.79 mL, 9.2 mmol) in dry THF (10 mL) was added dropwise to the solution mixture with vigorous stirring. The solution mixture was further stirred at 0° C. for 30 min, and then the reaction was quenched by addition of water. Any organic volatile was removed by evaporation under reduced pressure, and the aqueous layer was extracted with ethyl acetate. The ethyl acetate layer was then washed by saturated NaCl solution, dried by MgSO$_4$ and filtered. Volatile organic solvent was evaporated under reduced pressure, and the crude product was purified by column chromatography on silica gel using hexane/ethyl acetate (5:1, v/v) as eluent, yielding the desired product as a white solid (1.1 g, 76%). $^1$H NMR (CDCl$_3$, 400 MHz): δ=8.24 (1H, d, J=7.9 Hz), 7.05-7.14 (2H, m), 6.94 (1H, t, J=7.5 Hz), 6.38-6.44 (2H, m), 5.69 (1H, m), 3.97 (1H, t, J=8.4 Hz), 3.04 (1H, t, J=8.4 Hz). $^{13}$C{$^1$H} NMR (CDCl$_3$, 100 MHz) δ=163.4, 142.5, 131.4, 128.9, 128.4, 127.1, 124.3, 123.7, 117.0, 47.6, 27.6.

Synthesis of YP-1-44.

2,3-Dichloro-5,6-dicyano-p-benzoquinone (DDQ; 1.6 g, 7.0 mmol) was added to DKM-2-101 (0.94 g, 5.4 mmol) in dry toluene (30 mL), and the solution mixture was heated to reflux with vigorous stirring overnight. The reaction mixture was then diluted by ethyl acetate and washed by water and saturated NaCl solution. The organic layer was dried by MgSO$_4$, filtered and evaporated under reduced pressure. The crude product was purified by column chromatography on silica gel using hexane/ethyl acetate (19:1, v/v) as eluent, yielding the desired product as off-white white solid (0.8 g, 87%). $^1$H NMR (CDCl$_3$, 300 MHz): δ=8.62 (1H, d, J=8.2 Hz), 7.59 (1H, d, J=7.6 Hz), 7.29-7.43 (3H, m), 6.79-6.88 (1H, m), 6.59-6.68 (2H, m), 5.92 (1H, dd, J=10.2 and 1.7 Hz). $^{13}$C{$^1$H} NMR (CDCl$_3$, 75 MHz) 3=163.6, 135.5, 131.7, 130.4, 127.5, 124.8, 124.5, 123.7, 120.7, 116.6, 109.

Example 5. Additional Compounds

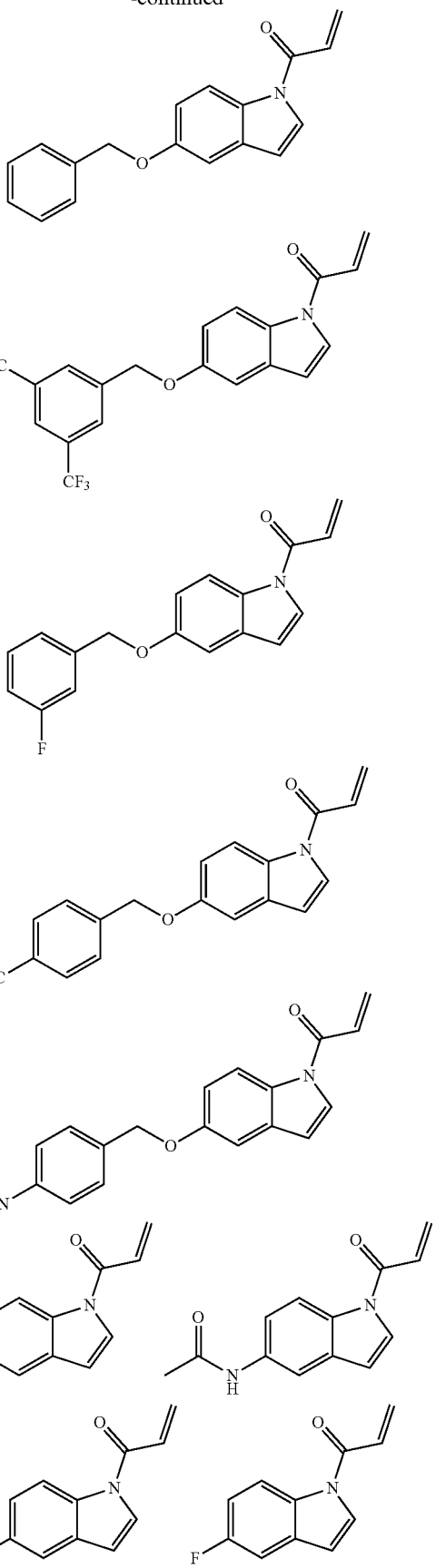

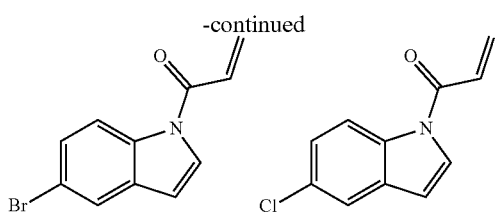

Example 6. General Method for Syntheses of Substituted Indole Compounds

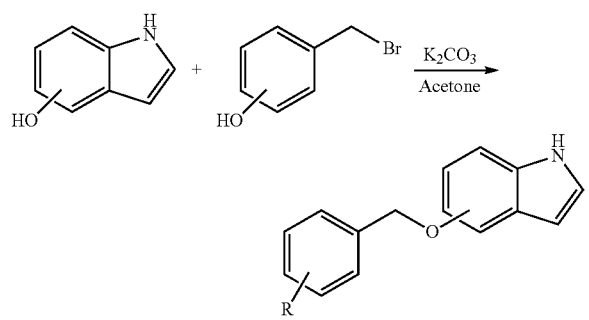

K$_2$CO$_3$ (1.56 g, 11.3 mmol) was added to indoline (3.8 mmol) and benzyl bromide (5.6 mmol) in acetone (50 mL). The solution was heated under reflux overnight. After the reaction, undissolved solid was filtered off, and the filtrate was evaporated under reduced pressure. The crude product was purified by column chromatography on silica gel using hexane/ethyl acetate (10:1, v/v) as eluent.

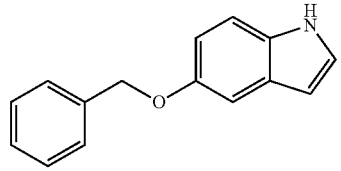

CC-1-17

Yield=68%. $^1$H NMR (CDCl$_3$, 400 MHz): δ=8.04 (1H, br), 7.53 (2H, d, J=7.4 Hz), 7.22-7.47 (5H, m), 7.16 (1H, t, J=2.7 Hz), 7.00 (1H, dd, J=2.2 and 8.8 Hz), 6.51 (1H, m), 5.15 (2H, s). $^{13}$C{$^1$H} NMR (CDCl$_3$, 100 MHz) δ=153.4, 137.8, 131.2, 128.6, 128.3, 127.9, 127.7, 125.0, 113.1, 111.8, 104.0, 102.4, 71.0

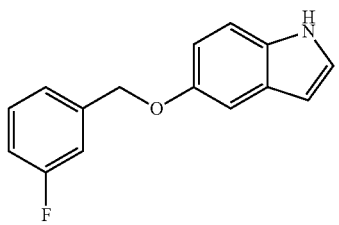

CC-1-23

Yield=64%. $^1$H NMR (CDCl$_3$, 400 MHz): δ=8.11 (1H, br), 7.40-7.47 (1H, m), 7.32-7.40 (3H, m), 7.30 (1H, d, J=8.8 Hz), 7.09-7.18 (3H, m), 6.63 (1H, m), 5.19 (2H, s). $^{13}$C{$^1$H}NMR (CDCl$_3$, 100 MHz) δ=164.4, 162.0, 153.2, 140.6, 140.5, 131.5, 130.4, 130.3, 128.5, 125.5, 123.2, 123.1, 114.9, 114.7, 114.6, 114.4, 113.1, 112.9, 104.3, 102.4, 70.3. $^{19}$F{$^1$H} NMR (CDCl$_3$, 376 MHz) δ=−111.8.

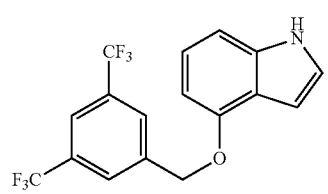

CC-1-32

Yield=70%. $^1$H NMR (CDCl$_3$, 400 MHz): δ=8.21 (1H, br), 7.99 (2H, s), 7.87 (1H, s). 7.07-7.19 (3H, m), 6.73 (1H, t, J=2.7 Hz), 6.58 (1H, d), 5.32 (2H, s). $^{13}$C{$^1$H} NMR (CDCl$_3$, 100 MHz) δ=151.9, 140.4, 137.6, 132.1, 131.8, 127.3, 124.8, 123.2, 122.8, 122.1, 121.9, 119.0, 105.6, 101.3, 100.0, 68.7. $^{19}$F{$^1$H} NMR (CDCl$_3$, 376 MHz) δ=−62.0.

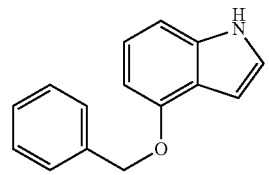

CC-1-33

Yield=74%. $^1$H NMR (CDCl$_3$, 400 MHz): δ=8.21 (1H, br), 7.71 (2H, d, J=7.1 Hz), 7.49-7.62 (3H, m), 7.31 (1H, t, J=8.0 Hz), 7.05-7.12 (2H, m), 6.95 (1H, t, J=2.2 Hz), 6.81 (1H, d, J=7.8 Hz), 5.40 (2H, s). $^{13}$C{$^1$H} NMR (CDCl$_3$, 100 MHz) δ=152.4, 137.5, 137.3, 128.5, 127.7, 127.4, 123.0 122.5, 118.8, 104.9, 101.0, 99.6, 69.9.

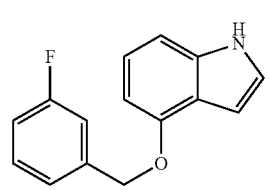

CC-1-43

Yield=66%. $^1$H NMR (CDCl$_3$, 400 MHz): δ=8.08 (1H, br), 7.39-7.53 (3H, m), 7.34 (1H, t, J=8.0 Hz), 7.22 (1H, m), 7.07-7.14 (2H, m), 6.99 (1H, t, J=2.2 Hz), 6.78 (1H, d, J=7.8 Hz), 5.34 (2H, s). $^{13}$C{$^1$H} NMR (CDCl$_3$, 100 MHz) δ=164.1, 161.7, 152.1, 140.2, 140.1, 137.3, 130.1, 130.0, 123.1, 122.7, 122.7, 122.6, 118.8, 114.6, 114.4, 114.2, 113.9, 105.1, 101.1, 99.6, 69.0. $^{19}$F{$^1$H} NMR (CDCl$_3$, 376 MHz) δ=−111.6.

CC-2-7

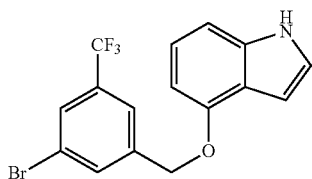

Yield=46%. ¹H NMR (CDCl₃, 400 MHz): δ=8.12 (1H, br), 7.87 (1H, s), 7.80 (1H, s), 7.74 (1H, s), 7.05-7.20 (3H, m), 6.80 (1H, t, J=2.1 Hz), 6.59 (1H, d, J=7.7 Hz), 5.20 (2H, s). ¹³C{¹H} NMR (CDCl₃, 100 MHz) δ=151.9, 141.1, 137.4, 133.5, 132.6, 132.3, 127.8, 124.6, 123.2, 122.9, 122.8, 122.6, 121.9, 118.8, 105.4, 101.2, 99.9, 68.4. ¹⁹F{¹H} NMR (CDCl₃, 376 MHz) δ=−61.8.

General Method for Syntheses of Acrylamide-Functionalized Indoline and Indole Compounds

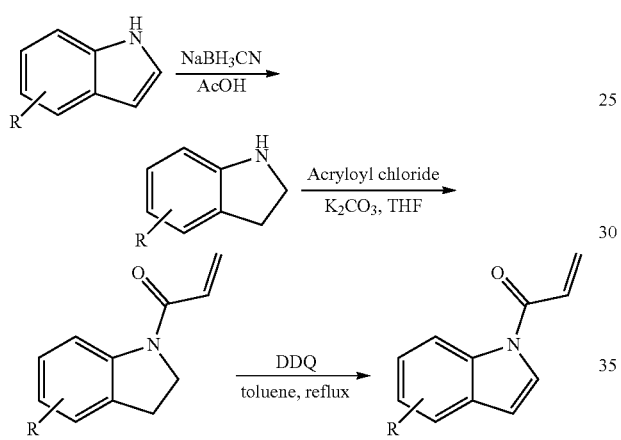

Syntheses for Substituted Indoline Compounds

The indole compound (2 mmol) was dissolved in acetic acid (20 mL). NaBH₃CN (627 mg, 10 mmol) was added to the solution mixture portionwise at 10° C. The solution mixture was then stirred at 10° C. for 4 h, and then water was added to quench the reaction. Any organic volatile was removed by evaporation under reduced pressure, and the aqueous layer was extracted with dichloromethane. The dichloromethane layer was washed by dilute NaOH solution and then saturated NaCl solution, dried by MgSO₄ and filtered. Volatile organic solvent was evaporated under reduced pressure, and the crude product was purified by column chromatography on silica gel using hexane/ethyl acetate (10:1, v/v) as eluent, yielding the indoline compound.

CC-1-8

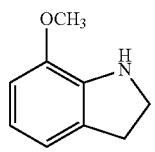

Yield=66%. ¹H NMR (CDCl₃, 400 MHz): δ=6.87-6.91 (1H, m), 6.80 (1H, t, J=8.0 Hz), 6.72-6.76 (1H, m), 3.89-3.91 (1H, br), 3.89 (3H, s), 3.63 (2H, t, J=8.4 Hz), 3.13 (2H, t, J=8.4 Hz). ¹³C{¹H} NMR (CDCl₃, 100 MHz) δ=145.3, 140.5, 130.1, 119.0, 117.0, 109.0, 55.1, 47.5, 30.3.

CC-1-11

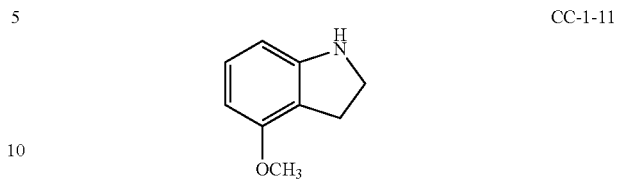

Yield=72%. ¹H NMR (CDCl₃, 400 MHz): δ=7.03 (1H, t, J=8.0 Hz), 6.31-6.39 (2H, m), 4.78 (1H, s), 3.84 (3H, s), 3.58 (2H, t, J=8.5 Hz), 3.02 (2H, t, J=8.4 Hz). ¹³C{¹H} NMR (CDCl₃, 100 MHz) δ=156.5, 153.1, 128.6, 116.0, 103.5, 101.9, 55.2, 47.4, 26.9.

CC-1-22

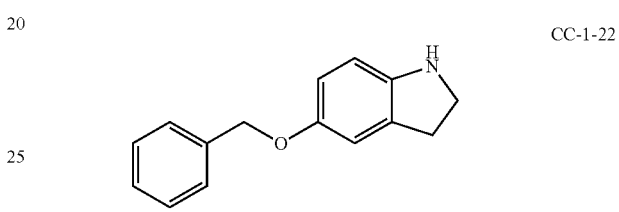

Yield=90%. ¹H NMR (CDCl₃, 400 MHz): δ=7.28-7.46 (5H, m), 6.84 (1H, s), 6.65-6.70 (1H, m), 6.60 (1H, d, J=8.4 Hz), 5.00 (2H, s), 3.54 (2H, t, J=8.3 Hz), 3.01 (2H, t, J=8.3 Hz). ¹³C{¹H} NMR (CDCl₃, 100 MHz) δ=153.0, 145.5, 137.8, 131.3, 128.6, 127.9, 127.6, 113.6, 112.8, 110.3, 71.1, 47.9, 30.5.

CC-1-24

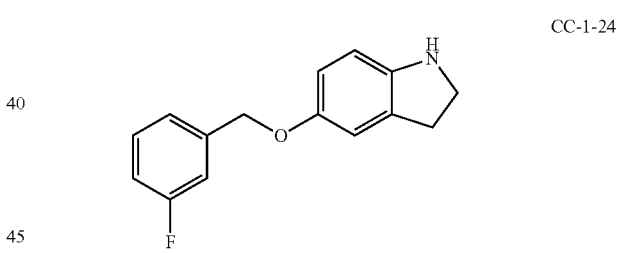

Yield=81%. ¹H NMR (CDCl₃, 400 MHz): δ=7.32-7.39 (1H, m), 7.22 (1H, d, J=7.6 Hz), 7.19 (1H, s), 7.03 (1H, dt, J=2.2 and 8.9 Hz), 6.87 (1H, d, J=2.1 Hz), 6.67-6.73 (1H, m), 6.60 (1H, d, J=8.4 Hz), 5.00 (2H, s), 3.86 (1H, s), 3.53 (2H, t, J=8.3 Hz), 3.03 (2H, t, J=8.3 Hz). ¹³C{¹H} NMR (CDCl₃, 100 MHz)=164.1, 161.7, 152.3, 145.7, 140.4, 140.3, 131.1, 130.0, 129.9, 122.7, 122.6, 114.5, 114.3, 114.2, 114.0, 113.3, 112.6, 110.0, 70.0, 47.7, 30.3. ¹⁹F{¹H} NMR (CDCl₃, 376 MHz) δ=−112.

CC-1-34

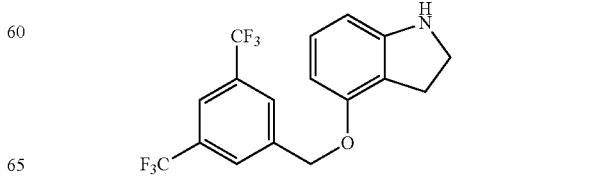

Yield=66%. ¹H NMR (CDCl₃, 400 MHz): δ=7.94 (2H, s), 7.89 (1H, s), 7.03 (1H, s), 6.37 (2H, dd, J=6.9 and 10.7 Hz), 5.19 (2H, s), 3.76 (1H, s), 3.63 (2H, t, J=7.6 Hz), 3.10 (2H, t, J=7.5 Hz). ¹³C{¹H} NMR (CDCl₃, 100 MHz) δ=155.1, 153.9, 140.4, 132.4, 132.1, 131.8, 131.4, 128.9, 127.1, 124.8, 122.1, 121.8, 116.5, 104.0, 102.8, 68.4, 47.5, 27. ¹⁹F{¹H} NMR (CDCl₃, 376 MHz) δ=−62.1.

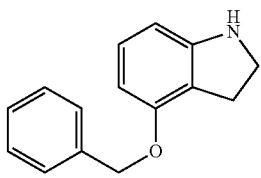

CC-1-36

Yield=74%. ¹H NMR (CDCl₃, 400 MHz): δ=7.34-7.56 (5H, m), 7.09 (1H, t, J=10.6 Hz), 7.01 (1H, s), 6.44-6.52 (2H, m), 5.14 (2H, s), 3.60 (2H, t, J=11.2 Hz), 3.13 (2H, t, J=11.1 Hz). ¹³C{¹H} NMR (CDCl₃, 100 MHz) δ=155.5, 152.2, 137.3, 128.4, 128.3, 127.6, 127.0, 116.9, 104.1, 103.7, 69.6, 60.3, 47.0, 26.9.

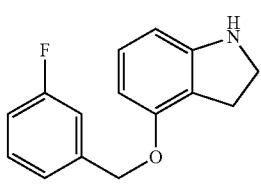

CC-1-45

Yield=78%. ¹H NMR (CDCl₃, 400 MHz): δ=7.40-7.48 (1H, m), 7.26-7.34 (2H, m), 7.12 (2H, t, J=8.0 Hz), 6.42-6.51 (2H, m), 5.16 (2H, s), 5.03 (1H, s), 3.66 (2H, t, J=8.5 Hz), 3.18 (2H, t, J=8.4 Hz). ¹³C{¹H} NMR (CDCl₃, 100 MHz) δ=164.1, 161.6, 155.3, 153.2, 140.2, 140.1, 129.9, 129.9, 128.5, 122.4, 122.4, 116.5, 114.5, 114.3, 113.9, 113.7, 103.7, 103.0, 68.7, 68.7, 47.2, 26.9. ¹⁹F{¹H} NMR (CDCl₃, 376 MHz)=−111.9.

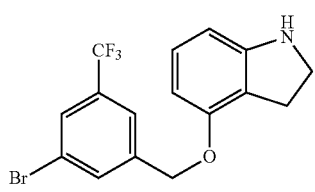

CC-2-8

Yield=89%. ¹H NMR (CDCl₃, 300 MHz): δ=7.79 (1H, s), 7.75 (1H, s), 7.66 (1H, s), 7.20 (1H, t, J=8.0 Hz), 6.38 (1H, d, J=7.7 Hz), 6.30 (1H, d, J=8.2 Hz), 5.09 (2H, s), 3.61 (2H, t, J=8.5 Hz), 3.09 (2H, t, J=8.5 Hz). ¹³C{¹H} NMR (CDCl₃, 75 MHz) δ=155.1, 153.8, 141.0, 133.3, 133.2, 132.7, 132.3, 131.9, 128.8, 127.8, 125.0, 122.9, 122.5, 122.4, 121.4, 116.4, 103.8, 102.7, 68.3, 47.5, 27. ¹⁹F{¹H} NMR (CDCl₃, 376 MHz) δ=−61.9.

Syntheses for Acrylamide-Functionalized Indoline Compounds

K₂CO₃ (2.32 g, 16.8 mmol) was added to indoline compound (8.4 mmol) in dry THF (20 mL). At 0 OC, acryloyl chloride (0.79 mL, 9.2 mmol) in dry THF (10 mL) was added dropwise to the solution mixture with vigorous stirring. The solution mixture was further stirred at 0° C. for 30 min, and then the reaction was quenched by addition of water. Any organic volatile was removed by evaporation under reduced pressure, and the aqueous layer was extracted with ethyl acetate. The ethyl acetate layer was then washed by saturated NaCl solution, dried by MgSO₄ and filtered. Volatile organic solvent was evaporated under reduced pressure, and the crude product was purified by column chromatography on silica gel using hexane/ethyl acetate (10:1, v/v) as eluent, yielding acrylamide-functionalized indoline compound.

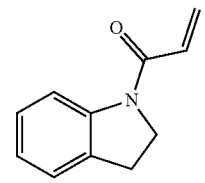

DKM-2-101

¹H NMR (CDCl₃, 400 MHz): δ=8.24 (1H, d, J=7.9 Hz), 7.05-7.14 (2H, m), 6.94 (1H, t, J=7.5 Hz), 6.38-6.44 (2H, m), 5.69 (1H, m), 3.97 (1H, t, J=8.4 Hz), 3.04 (1H, t, J=8.4 Hz). ¹³C{¹H} NMR (CDCl₃, 100 MHz) δ=163.4, 142.5, 131.4, 128.9, 128.4, 127.1, 124.3, 123.7, 117.0, 47.6, 27.6.

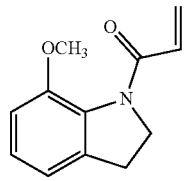

CC-1-9

Yield=73%. ¹H NMR (CDCl₃, 400 MHz): δ=7.08 (1H, t, J=7.9 Hz), 6.88-6.93 (1H, m), 6.82-6.86 (1H, m), 6.35-6.51 (2H, m), 5.65 (1H, dd, J=2.3 and 5.0 Hz), 4.24 (2H, t, J=7.6 Hz), 3.84 (3H, s), 3.01 (2H, t, J=7.6 Hz). ¹³C{¹H} NMR (CDCl₃, 100 MHz) δ=165.3, 148.9, 137.2, 130.6, 130.4, 126.0, 125.9, 117.6, 111.5, 55.4, 51.5, 29.4.

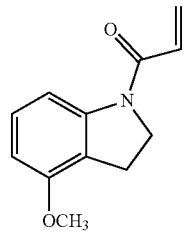

CC-1-12

Yield=65%. ¹H NMR (CDCl₃, 400 MHz): =7.92 (1H, d, J=7.6 Hz), 7.18 (1H, t, J=8.1 Hz), 6.43-6.60 (3H, m), 5.77 (1H, dd, J=3.0 and 9.2 Hz), 4.15 (2H, t, J=8.4 Hz), 3.82 (3H, s), 3.10 (2H, t, J=8.0 Hz). ¹³C{¹H} NMR (CDCl₃, 100 MHz) δ=163.9, 155.7, 144.2, 129.2, 129.0, 128.9, 118.8, 110.6, 106.3, 55.4, 48.6, 25.1.

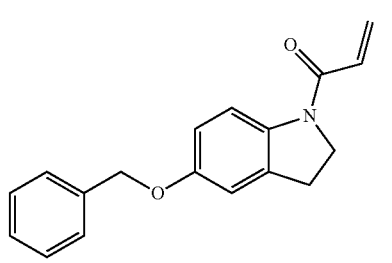
CC-1-26

Yield=93%. ¹H NMR (CDCl₃, 400 MHz): δ=8.23 (1H, d, J=8.4 Hz), 7.29-7.44 (5H, m), 6.78-6.85 (2H, m), 6.47-6.53 (2H, m), 5.75 (1H, dd, J=3.6 and 4.3 Hz), 5.01 (2H, s), 4.10 (2H, t, J=8.4 Hz), 3.13 (2H, t, J=8.4 Hz). ¹³C{¹H} NMR (CDCl₃, 100 MHz) δ=163.2, 155.7, 137.1, 136.8, 133.3, 129.0, 128.6, 128.5, 127.9, 127.5, 118.2, 113.2, 111.8, 70.4, 48.1, 28.1.

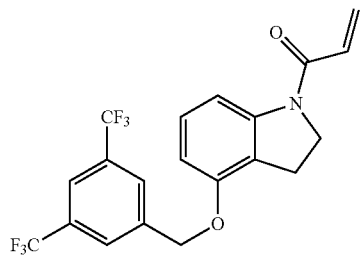
CC-1-44

Yield=86%. ¹H NMR (CDCl₃, 400 MHz): δ=7.97 (1H, br), 7.89 (2H, s), 7.85 (1H, s), 7.16 (1H, t, J=8.2 Hz), 6.60 (1H, d, J=8.2 Hz), 6.42-6.56 (2H, m), 5.72-5.80 (1H, m), 5.17 (2H, s), 4.16 (2H, t, J=8.4 Hz), 3.16 (2H, t, J=7.4 Hz). ¹³C{¹H} NMR (CDCl₃, 100 MHz) δ=163.9, 154.2, 144.6, 139.9, 132.5, 132.1, 131.8, 131.5, 129.2, 129.0, 127.4, 127.1, 124.7, 122.0, 121.9, 121.8, 119.4, 119.2, 111.4, 107.4, 68.4, 48.5, 25.1. ¹⁹F{¹H} NMR (CDCl₃, 376 MHz)=−62.1.

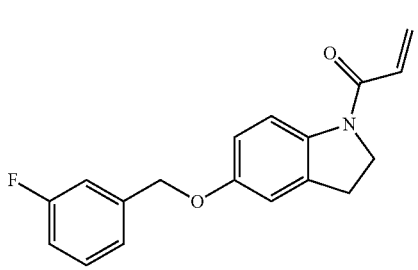
CC-1-27

Yield=92%. ¹H NMR (CDCl₃, 400 MHz): δ=8.24 (1H, d, J=8.4 Hz), 7.33 (1H, q, J=7.4 Hz), 7.10-7.20 (2H, m), 7.00 (1H, t, J=8.0 Hz), 6.73-6.82 (2H, m), 6.45-6.52 (2H, m), 5.74 (1H, dd, J=2.8 and 4.3 Hz), 4.98 (2H, s), 4.06 (2H, t, J=8.1 Hz), 3.10 (2H, t, J=8.2 Hz). ¹³C{¹H} NMR (CDCl₃, 100 MHz) δ=164.0, 163.0, 161.6, 155.2, 139.7, 139.6, 136.8, 133.3, 130.0, 129, 128.9, 128.3, 122.6, 122.6, 117.9, 114.7, 114.5, 114.1, 113.9, 112.9, 111.6, 69.3, 48.0, 27.9. ¹⁹F{¹H} NMR (CDCl₃, 376 MHz) δ=−111.9.

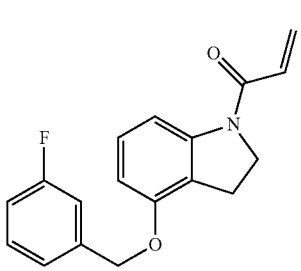
CC-1-47

Yield=79%. ¹H NMR (CDCl₃, 400 MHz): δ=7.93 (1H, d, J=7.7 Hz), 7.23-7.31 (1H, m), 7.03-7.13 (3H, m), 6.95 (1H, dt, J=2.1 and 4.2 Hz), 6.50 (1H, d, J=8.2 Hz), 6.43 (2H, d, J=5.7 Hz), 5.69 (1H, t, J=6.0 Hz), 4.92 (2H, s), 3.98 (2H, t, J=8.2 Hz), 3.01 (2H, t, J=8.3 Hz). ¹³C{¹H} NMR (CDCl₃, 100 MHz) δ=163.9, 163.4, 161.4, 154.3, 144.1, 139.6, 139.5, 129.9, 129.8, 128.9, 128.6, 128.4, 122.2, 122.2, 119.1, 118.7, 114.5, 114.3, 113.7, 113.4, 110.6, 110.0, 107.2, 68.5, 48.1, 39.0, 38.4, 24.8. ¹⁹F{¹H} NMR (CDCl₃, 376 MHz)=−111.9.

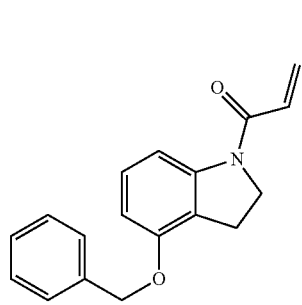
CC-1-39

Yield=90%. ¹H NMR (CDCl₃, 400 MHz): δ=7.98 (1H, d, J=7.6 Hz), 7.28-7.43 (4H, m), 7.15 (1H, t, J=8.1 Hz), 6.61 (1H, d, J=8.2 Hz), 6.49 (2H, d, J=5.4 Hz), 5.75 (2H, t, J=6.0 Hz), 5.02 (2H, s), 4.05 (2H, t, J=8.1 Hz), 3.08 (2H, t, J=8.1 Hz). ¹³C{¹H} NMR (CDCl₃, 100 MHz)=163.6, 154.7, 144.1, 136.9, 129.0, 128.7, 128.6, 128.4, 127.7, 127.0, 119.2, 110.6, 107.5, 69.6, 48.3, 25.0

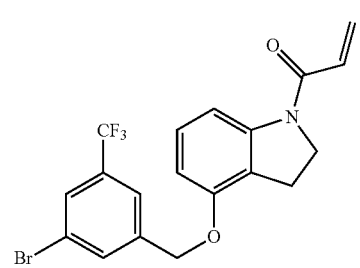
CC-2-9

Yield=90%. ¹H NMR (CDCl₃, 400 MHz): δ=797 (1H, br), 7.78 (1H, s), 7.72 (1H, s), 7.61 (1H, s), 7.18 (1H, t, J=8.1 Hz), 6.47-6.63 (3H, m), 5.77-5.83 (1H, m), 5.10 (2H, s), 4.20 (2H, t, J=8.4 Hz), 3.19 (2H, t, J=8.5 Hz). ¹⁹F{¹H} NMR (CDCl₃, 376 MHz) δ=−62.0.

Syntheses for Acrylamide-Functionalized Indole Compounds 2,3-Dichloro-5,6-dicyano-p-benzoquinone (DDQ; 1.6 g, 7.0 mmol) was added to acrylamide-functionalized indoline (5.4 mmol) in dry toluene (30 mL), and the solution mixture was heated to reflux with vigorous stirring overnight. The reaction mixture was then diluted by ethyl acetate and washed by water and saturated NaCl solution. The organic layer was dried by MgSO$_4$, filtered and evaporated under reduced pressure. The crude product was purified by column chromatography on silica gel using hexane/ethyl acetate (19:1, v/v) as eluent, yielding acrylamide-functionalized indole compound.

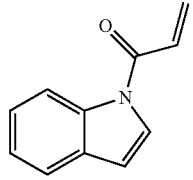

YP-1-44

Yield=87%. $^1$H NMR (CDCl$_3$, 300 MHz): δ=8.62 (1H, d, J=8.2 Hz), 7.59 (1H, d, J=7.6 Hz), 7.29-7.43 (3H, m), 6.79-6.88 (1H, m), 6.59-6.68 (2H, m), 5.92 (1H, dd, J=1.7 and 5.1 Hz). $^{13}$C{$^1$H} NMR (CDCl$_3$, 75 MHz) δ=163.6, 135.5, 131.7, 130.4, 127.5, 124.8, 124.5, 123.7, 120.7, 116.6, 109.0.

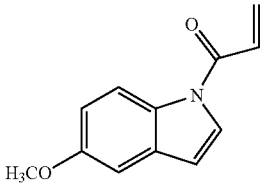

CC-1-1

Yield=84%. $^1$H NMR (CDCl$_3$, 400 MHz): δ=8.41 (1H, d, J=9.0 Hz), 7.49 (1H, d, J=3.8 Hz), 6.91-7.06 (3H, m), 6.59-6.69 (2H, m), 6.03 (1H, dd, J=1.3 and 5.2 Hz), 3.87 (3H, s).

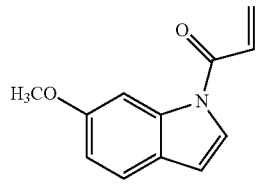

CC-1-3

Yield=87%. $^1$H NMR (CDCl$_3$, 400 MHz): δ=8.14 (1H, d, J=2.2 Hz), 7.38-7.46 (2H, m), 6.91-7.00 (2H, m), 6.59-6.70 (2H, m), 6.04 (1H, dd, J=1.4 and 5.2 Hz), 3.90 (3H, s).

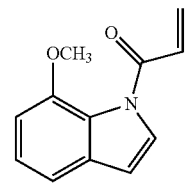

CC-1-10

Yield=81%. $^1$H NMR (CDCl$_3$, 400 MHz): δ=7.65 (1H, d, J=3.6 Hz), 7.22-7.30 (2H, m), 6.83-6.93 (2H, m), 6.56-6.66 (2H, m), 5.94 (1H, dd, J=1.3 and 5.2 Hz), 3.95 (3H, s). $^{13}$C{$^1$H} NMR (CDCl$_3$, 100 MHz) δ=164.8, 148.0, 134.0, 131.4, 129.6, 127.8, 124.4, 124.3, 114.1, 108.0, 106.7, 55.5.

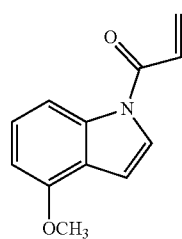

CC-1-14

Yield=90%. $^1$H NMR (CDCl$_3$, 400 MHz): δ=8.11 (1H, d, J=8.4 Hz), 7.42 (1H, d, J=3.8 Hz), 7.31 (1H, t, J=8.2 Hz), 6.92-7.00 (1H, m), 6.81 (1H, d, J=3.8 Hz), 6.74 (1H, d, J=8.0 Hz), 6.64-6.67 (1H, m), 6.03 (1H, dd, J=1.4 and 5.2 Hz), 3.95 (3H, s). $^{13}$C{$^1$H} NMR (CDCl$_3$, 100 MHz)=164.2, 152.9, 137.1, 132.2, 128.1, 126.2, 123.2, 120.9, 110.0, 106.5, 104.5, 55.5.

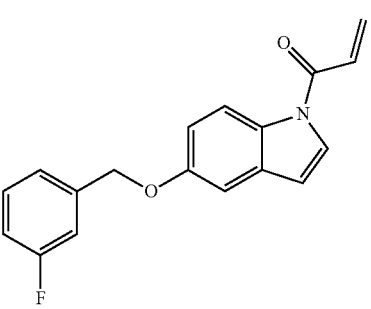

CC-1-28

Yield=87%. $^1$H NMR (CDCl$_3$, 400 MHz): δ=8.43 (1H, d, J=9.0 Hz), 7.49 (1H, d, J=3.7 Hz), 7.31-7.39 (1H, m), 7.16-7.25 (2H, m), 6.98-7.10 (2H, m), 6.97 (1H, d, J=10.4 Hz), 6.92 (1H, d, J=10.4 Hz), 6.63-6.70 (1H, m), 6.59 (1H, d, J=3.7 Hz), 6.03 (1H, dd, J=1.4 and 5.2 Hz), 5.11 (2H, s). $^{13}$C{$^1$H} NMR (CDCl$_3$, 100 MHz) δ=164.3, 163.6, 161.9, 155.7, 140.0, 139.9, 132.0, 131.7, 130.9, 130.3, 130.2, 127.8, 125.4, 122.8, 122.8, 117.9, 115.0, 114.8, 114.4, 114.3, 114.2, 109.4, 105.2, 69.8. $^{19}$F{$^1$H} NMR (CDCl$_3$, 376 MHz)=−112.0.

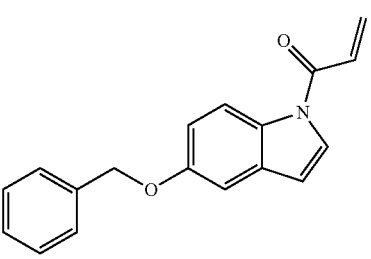

CC-1-30

Yield=81%. $^1$H NMR (CDCl$_3$, 400 MHz): δ=8.45 (1H, d, J=8.7 Hz), 7.31-7.53 (6H, m), 7.01-7.15 (2H, m), 6.87-6.98 (1H, m), 6.56-6.71 (2H, m), 6.01 (1H, d, J=10.1 Hz), 5.13

(2H, s). $^{13}C\{^1H\}$ NMR (CDCl$_3$, 100 MHz) δ=163.5, 155.9, 137.2, 131.9, 131.7, 130.7, 128.6, 128.0, 127.8, 127.6, 125.3, 117.7, 114.3, 109.4, 105.1, 70.5.

CC-1-42

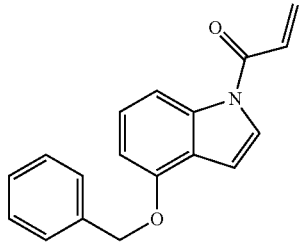

Yield=91%. $^1H$ NMR (CDCl$_3$, 400 MHz): δ=8.18 (1H, d, J=8.4 Hz), 7.49-7.54 (2H, m), 7.35-7.47 (4H, m), 7.32 (1H, t, J=8.2 Hz), 6.80-6.98 (3H, m), 6.66-6.72 (1H, m), 6.02 (1H, dd, J=1.5 and 5.2 Hz), 5.22 (2H, s). $^{13}C\{^1H\}$ NMR (CDCl$_3$, 100 MHz) δ=164.1, 152.0, 137.1, 132.1, 128.6, 128.0, 127.9, 127.4, 126.1, 123.2, 121.2, 110.2, 106.6, 105.9, 70.1.

CC-1-46

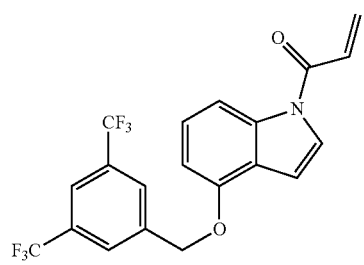

Yield=87%. $^1H$ NMR (CDCl$_3$, 400 MHz): δ=8.18 (1H, d, J=8.4 Hz), 7.96 (2H, s), 7.88 (1H, s), 7.47 (1H, d, J=3.8 Hz), 7.31 (1H, t, J=8.2 Hz), 6.94-7.02 (1H, m), 6.85 (1H, d, J=3.4 Hz), 6.78 (1H, d, J=8.0 Hz), 6.66-6.73 (1H, m), 6.06 (1H, dd, J=1.3 and 5.3 Hz), 5.30 (2H, s). $^{13}C\{^1H\}$ NMR (CDCl$_3$, 100 MHz) δ=164.2, 151.3, 139, 137.4, 132.5, 132.2, 131.9, 128.0, 127.4, 126.2, 124.7, 123.7, 122.1, 122.0, 121.2, 111.0, 106.3, 105.8, 68.8. $^{19}F\{^1H\}$ NMR (CDCl$_3$, 376 MHz) δ=−62.0.

CC-1-48

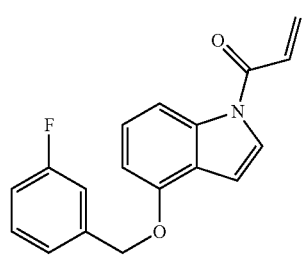

Yield=89%. $^1H$ NMR (CDCl$_3$, 400 MHz): δ=8.16 (1H, d, J=8.4 Hz), 7.43 (1H, d, J=3.8 Hz), 7.32-7.40 (1H, m), 7.20-7.31 (3H, m), 7.03 (1H, dt, J=2.1 and 8.9 Hz), 6.91-6.99 (1H, m), 6.86-6.88 (1H, m), 6.76 (1H, d, J=8.0 Hz), 6.65-6.71 (1H, m), 6.03 (1H, d, J=1.5 and 5.2 Hz), 5.18 (2H, s). $^{13}C\{^1H\}$ NMR (CDCl$_3$, 100 MHz) δ=164.3, 164.1, 161.8, 151.7, 139.8, 139.7, 137.2, 132.2, 130.2, 130.1, 128.0, 126.1, 123.3, 122.7, 121.2, 114.9, 114.7, 114.3, 114.0, 110.4, 106.5, 105.9, 69.3. $^{19}F\{^1H\}$ NMR (CDCl$_3$, 376 MHz) δ=−111.9.

Synthesis of Alkyne Probe of CC-2-11

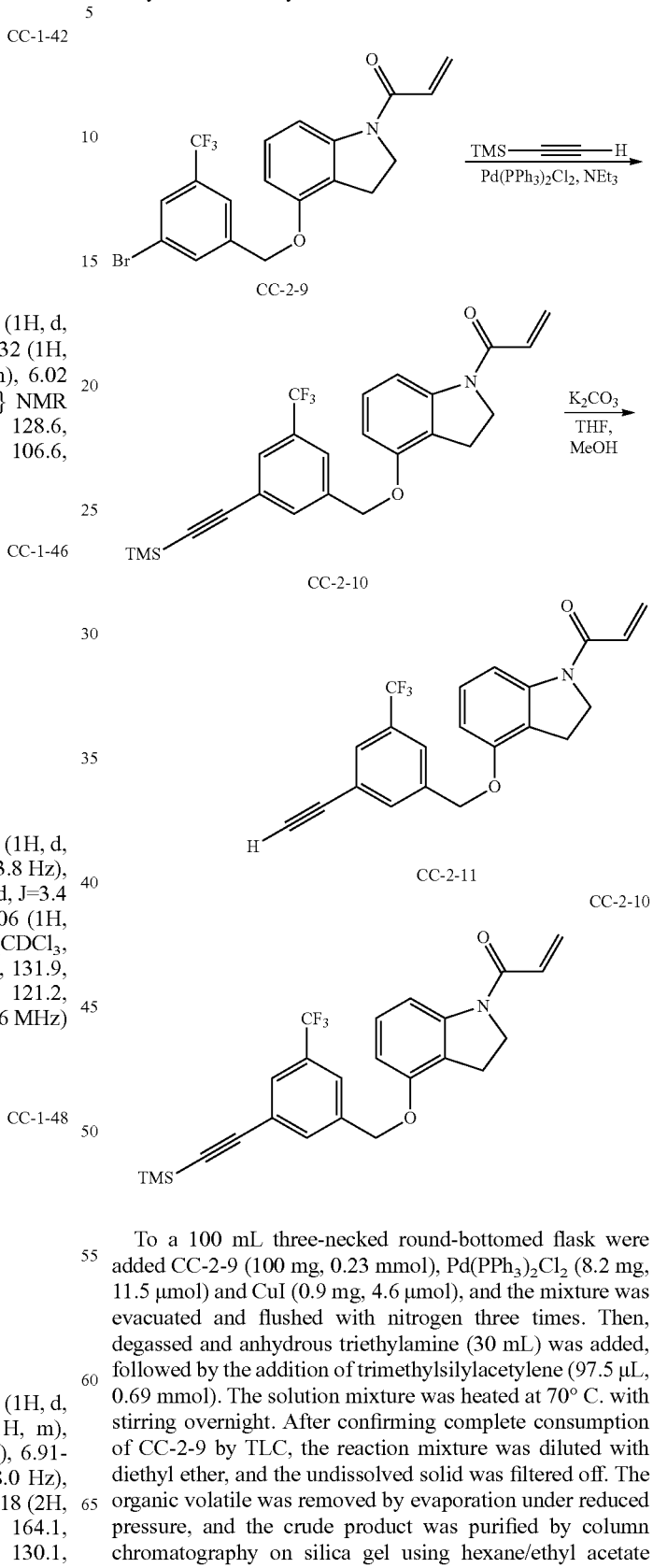

To a 100 mL three-necked round-bottomed flask were added CC-2-9 (100 mg, 0.23 mmol), Pd(PPh$_3$)$_2$Cl$_2$ (8.2 mg, 11.5 µmol) and CuI (0.9 mg, 4.6 µmol), and the mixture was evacuated and flushed with nitrogen three times. Then, degassed and anhydrous triethylamine (30 mL) was added, followed by the addition of trimethylsilylacetylene (97.5 µL, 0.69 mmol). The solution mixture was heated at 70° C. with stirring overnight. After confirming complete consumption of CC-2-9 by TLC, the reaction mixture was diluted with diethyl ether, and the undissolved solid was filtered off. The organic volatile was removed by evaporation under reduced pressure, and the crude product was purified by column chromatography on silica gel using hexane/ethyl acetate (9:1, v/v) as eluent, yielding CC-2-10 as a white crystalline solid. Yield=55%. $^1$H NMR (CDCl$_3$, 400 MHz): δ=7.97 (1H, d, J=7.2 Hz), 7.68 (1H, s), 7.67 (1H, s), 7.62 (1H, s), 718 (1H, t, J=8.1 Hz), 6.47-6.63 (3H, m), 5.80 (1H, m), 5.10 (2H, s), 4.22 (2H, t, J=8.3 Hz), 3.20 (2H, t, J=8.1 Hz), 0.26 (9H, s). $^{19}$F{$^1$H} NMR (CDCl$_3$, 376 MHz) δ=−62.1.

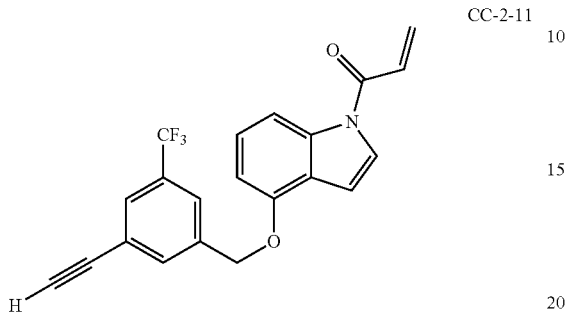

CC-2-11

K$_2$CO$_3$ (36.9 mg, 0.27 mmol) was added to CC-2-10 (58.4 mg, 0.13 mmol) in tetrahydrofuran-methanol mixture (4 mL), and the solution mixture was stirred at room temperature for 2 h. The reaction mixture was then quenched by water, and the organic volatile was removed by evaporation under reduced pressure. The remaining aqueous solution was extracted with dichloromethane, and the organic layer was washed with saturated NaCl(aq), dried by MgSO$_4$, filtered and evaporated under reduced pressure. The crude product was purified by column chromatography on silica gel using hexane/ethyl acetate (5:1, v/v) as eluent, yielding CC-2-11 as a white solid. Yield=61%. $^1$H NMR (CDCl$_3$, 300 MHz): δ=6=7.97 (1H, d, J=6.3 Hz), 7.71 (2H, s), 7.66 (1H, s), 7.19 (1H, t, J=8.2 Hz), 6.45-6.65 (3H, m), 5.80 (1H, m), 5.12 (2H, s), 4.22 (2H, t, J=8.3 Hz), 3.20 (2H, t, J=7.9 Hz), 3.18 (1H, s). $^{19}$F{$^1$H} NMR (CDCl$_3$, 376 MHz) δ=−62.1.

REFERENCES

1. Saxton R A, Sabatini D M. mTOR Signaling in Growth, Metabolism, and Disease. Cell. 2017; 169(2):361-71. 2. Castellano B M, Thelen A M, Moldavski O, Feltes M, van der Welle R E, Mydock-McGrane L, Jiang X, van Eijkeren R J, Davis O B, Louie S M, Perera R M, Covey D F, Nomura D K, Ory D S, Zoncu R. Lysosomal cholesterol activates mTORC1 via an SLC38A9-Niemann-Pick C1 signaling complex. Science. 2017; 355(6331):1306-11. 3. Hurley J H, Young L N. Mechanisms of Autophagy Initiation. Annu Rev Biochem. 2017; 86:225-44. 4. Di Malta C, Siciliano D, Calcagni A, Monfregola J, Punzi S, Pastore N, Eastes A N, Davis O, De Cegli R, Zampelli A, Di Giovannantonio L G, Nusco E, Platt N, Guida A, Ogmundsdottir M H, Lanfrancone L, Perera R M, Zoncu R, Pelicci P G, Settembre C, Ballabio A. Transcriptional activation of RagD GTPase controls mTORC1 and promotes cancer growth. Science. 2017; 356(6343):1188-92. 5. Roberts A M, Ward C C, Nomura D K. Activity-based protein profiling for mapping and pharmacologically interrogating proteome-wide ligandable hotspots. Curr Opin Biotechnol. 2017; 43:25-33. PMCID: PMC5305418. 6. Roberts A M, Miyamoto D K, Huffman T R, Bateman L A, Ives A N, Akopian D, Heslin M J, Contreras C M, Rape M, Skibola C F, Nomura D K. Chemoproteomic Screening of Covalent Ligands Reveals UBAS As a Novel Pancreatic Cancer Target. ACS Chem Biol. 2017; 12(4):899-904. 7. Bateman L A, Nguyen T B, Roberts A M, Miyamoto D K, Ku W M, Huffman T R, Petri Y, Heslin M J, Contreras C M, Skibola C F, Olzmann J A, Nomura D K. Chemoproteomics-enabled covalent ligand screen reveals a cysteine hotspot in reticulon 4 that impairs E R morphology and cancer pathogenicity. Chem Commun (Camb). 2017; 53(53):7234-7. PMCID: PMC5491356. 8. Perera R M, Zoncu R. The Lysosome as a Regulatory Hub. Annual review of cell and developmental biology. 2016; 32:223-53. 9. Rodrik-Outmezguine V S, Okaniwa M, Yao Z, Novotny C J, McWhirter C, Banaji A, Won H, Wong W, Berger M, de Stanchina E, Barratt D G, Cosulich S, Klinowska T, Rosen N, Shokat K M. Overcoming mTOR resistance mutations with a new-generation mTOR inhibitor. Nature. 2016; 534 (7606):272-6. PMCID: PMC4902179. 10. Okosun J, Wolfson R L, Wang J, Araf S, Wilkins L, Castellano B M, Escudero-Ibarz L, Al Seraihi A F, Richter J, Bernhart S H, Efeyan A, Iqbal S, Matthews J, Clear A, Guerra-Assuncao J A, Bodor C, Quentmeier H, Mansbridge C, Johnson P, Davies A, Strefford J C, Packham G, Barrans S, Jack A, Du M Q, Calaminici M, Lister T A, Auer R, Montoto S, Gribben J G, Siebert R, Chelala C, Zoncu R, Sabatini D M, Fitzgibbon J. Recurrent mTORC1-activating RRAGC mutations in follicular lymphoma. Nature genetics. 2016; 48(2):183-8. PMCID: PMC4731318. 11. Sahu N, Dela Cruz D, Gao M, Sandoval W, Haverty P M, Liu J, Stephan J P, Haley B, Classon M, Hatzivassiliou G, Settleman J. Proline Starvation Induces Unresolved E R Stress and Hinders mTORC1-Dependent Tumorigenesis. Cell Metab. 2016; 24(5):753-61. 12. Backus K M, Correia B E, Lum K M, Forli S, Homing B D, Gonzalez-Paez G E, Chatterjee S, Lanning B R, Teijaro J R, Olson A J, Wolan D W, Cravatt B F. Proteome-wide covalent ligand discovery in native biological systems. Nature. 2016; 534 (7608):570-4. PMCID: PMC4919207. 13. Grabiner B C, Nardi V, Birsoy K, Possemato R, Shen K, Sinha S, Jordan A, Beck A H, Sabatini D M. A diverse array of cancer-associated MTOR mutations are hyperactivating and can predict rapamycin sensitivity. Cancer Discov. 2014; 4(5): 554-63. PMCID: PMC4012430. 14. Gul S, Hadian K. Protein-protein interaction modulator drug discovery: past efforts and future opportunities using a rich source of low- and high-throughput screening assays. Expert Opin Drug Discov. 2014; 9(12):1393-404. 15. Bar-Peled L, Chantranupong L, Chemiack A D, Chen W W, Ottina K A, Grabiner B C, Spear E D, Carter S L, Meyerson M, Sabatini D M. A Tumor suppressor complex with GAP activity for the Rag GTPases that signal amino acid sufficiency to mTORC1. Science. 2013; 340(6136):1100-6. PMCID: 3728654. 16. Kang S A, Pacold M E, Cervantes C L, Lim D, Lou H J, Ottina K, Gray N S, Turk B E, Yaffe M B, Sabatini D M. mTORC1 phosphorylation sites encode their sensitivity to starvation and rapamycin. Science. 2013; 341(6144):1236566. PMCID: 3771538. 17. Johnson S C, Rabinovitch P S, Kaeberlein M. mTOR is a key modulator of ageing and age-related disease. Nature. 2013; 493(7432):338-45. PMCID: 3687363. 18. Hamdi A, Colas P. Yeast two-hybrid methods and their applications in drug discovery. Trends Pharmacol Sci. 2012; 33(2):109-18. 19. Hoelder S, Clarke P A, Workman P. Discovery of small molecule cancer drugs: successes, challenges and opportunities. Mol Oncol. 2012; 6(2): 155-76. PMCID: PMC3476506. 20. Laplante M, Horvat S, Festuccia W T, Birsoy K, Prevorsek Z, Efeyan A, Sabatini D M. DEPTOR cell-autonomously promotes adipogenesis, and its expression is associated with obesity. Cell Metab. 2012; 16(2):202-12. PMCID: PMC3463374. 21. Efeyan A, Zoncu R, Sabatini D M. Amino acids and mTORC1: from lysosomes to disease. Trends Mol Med. 2012; 18(9):524-33. PMCID: 3432651. 22. Laplante M, Sabatini D M. mTOR signaling in growth control and disease. Cell. 2012; 149(2):274-93. PMCID: 3331679. 23. Lamming D W, Ye L, Katajisto P, Goncalves M D, Saitoh M, Stevens D M, Davis J G, Salmon A B, Richardson A, Ahima R S, Guertin D A, Sabatini D M, Baur J A. Rapamycin-induced insulin resistance is mediated by mTORC2 loss and uncoupled from longevity. Science. 2012; 335(6076):1638-43. PMCID: 3324089. 24. Zoncu R, Bar-Peled L, Efeyan A, Wang S, Sancak Y, Sabatini D M. mTORC1 senses lysosomal amino acids through an inside-out mechanism that requires the vacuolar H(+)-ATPase. Science. 2011; 334(6056):678-83. PMCID: 3211112. 25. Wander S A, Hennessy B T, Slingerland J M. Next-generation mTOR inhibitors in clinical oncology: how pathway complexity informs therapeutic strategy. The Journal of clinical investigation. 2011; 121 (4): 1231-41. PMCID: 3069769. 26. Benjamin D, Colombi M, Moroni C, Hall M N. Rapamycin passes the torch: a new generation of mTOR inhibitors. Nature reviews Drug discovery. 2011; 10(11): 868-80. 27. Heeres J T, Hergenrother P J. High-throughput screening for modulators of protein-protein interactions: use of photonic crystal biosensors and complementary technologies. Chem Soc Rev. 2011; 40(8):4398-410. 28. Peterson T R, Sengupta S S, Harris T E, Carmack A E, Kang S A, Balderas E, Guertin D A, Madden K L, Carpenter A E, Finck B N, Sabatini D M. mTOR complex 1 regulates lipin 1 localization to control the SREBP pathway. Cell. 2011; 146(3):408-20. PMCID: 3336367. 29. Zoncu R, Efeyan A, Sabatini D M. mTOR: from growth signal integration to cancer, diabetes and ageing. Nat Rev Mol Cell Biol. 2011; 12(1):21-35. PMCID: 3390257. 30. Sancak Y, Bar-Peled L, Zoncu R, Markhard A L, Nada S, Sabatini D M. Ragulator-Rag complex targets mTORC1 to the lysosomal surface and is necessary for its activation by amino acids. Cell. 2010; 141(2):290-303. PMCID: 3024592. 31. Feldman M E, Shokat K M. New inhibitors of the PI3K-Akt-mTOR pathway: insights into mTOR signaling from a new generation of Tor Kinase Domain Inhibitors (TORKinibs). Curr Top Microbiol Immunol. 2010; 347:241-62. 32. Dixon S J, Stockwell B R. Drug discovery: engineering drug combinations. Nat Chem Biol. 2010; 6(5):318-9. PMCID: PMC3048766. 33. Laplante M, Sabatini D M. An emerging role of mTOR in lipid biosynthesis. Current biology: C B. 2009; 19(22): R1046-52. PMCID: 3390254. 34. Thoreen C C, Kang S A, Chang J W, Liu Q, Zhang J, Gao Y, Reichling L J, Sim T, Sabatini D M, Gray N S. An ATP-competitive mammalian target of rapamycin inhibitor reveals rapamycin-resistant functions of mTORC1. J Biol Chem. 2009; 284(12):8023-32. PMCID: PMC2658096. 35. Feldman M E, Apsel B, Uotila A, Loewith R, Knight Z A, Ruggero D, Shokat K M. Active-site inhibitors of mTOR target rapamycin-resistant outputs of mTORC1 and mTORC2. PLoS Biol. 2009; 7(2):e38. PMCID: PMC2637922 owned by UCSF related to PP242 and licensed to Intellikine. ZAK and KMS are consultants to Intellikine. 36. Sancak Y, Peterson T R, Shaul Y D, Lindquist R A, Thoreen C C, Bar-Peled L, Sabatini D M. The Rag GTPases bind raptor and mediate amino acid signaling to mTORC1. Science. 2008; 320(5882):1496-501. PMCID: 2475333. 37. Kim E, Goraksha-Hicks P, Li L, Neufeld T P, Guan K L. Regulation of TORC1 by Rag GTPases in nutrient response. Nature cell biology. 2008; 10(8):935-45. PMCID: 2711503. 38. Settembre C, Fraldi A, Jahreiss L, Spampanato C, Venturi C, Medina D, de Pablo R, Tacchetti C, Rubinsztein D C, Ballabio A. A block of autophagy in lysosomal storage disorders. Hum Mol Genet. 2008; 17(1):119-29. 39. Guertin D A, Sabatini D M. Defining the role of mTOR in cancer. Cancer Cell. 2007; 12(1):9-22. 40. Sarbassov D D, Ali S M, Sengupta S, Sheen J H, Hsu P P, Bagley A F, Markhard A L, Sabatini D M. Prolonged rapamycin treatment inhibits mTORC2 assembly and Akt/PKB. Mol Cell. 2006; 22(2):159-68. 41. Komatsu M, Waguri S, Chiba T, Murata S, Iwata J, Tanida I, Ueno T, Koike M, Uchiyama Y, Kominami E, Tanaka K. Loss of autophagy in the central nervous system causes neurodegeneration in mice. Nature. 2006; 441(7095):880-4. 42. Ravikumar B, Vacher C, Berger Z, Davies J E, Luo S, Oroz L G, Scaravilli F, Easton D F, Duden R, O'Kane C J, Rubinsztein D C. Inhibition of mTOR induces autophagy and reduces toxicity of polyglutamine expansions in fly and mouse models of Huntington disease. Nature genetics. 2004; 36(6):585-95. 43. Berg T, Cohen S B, Desharnais J, Sonderegger C, Maslyar D J, Goldberg J, Boger D L, Vogt P K. Small-molecule antagonists of Myc/Max dimerization inhibit Myc-induced transformation of chicken embryo fibroblasts. Proc Natl Acad Sci USA. 2002; 99(6):3830-5. PMCID: PMC122609. 44. Sabatini D M, Erdjument-Bromage H, Lui M, Tempst P, Snyder S H. RAFT1: a mammalian protein that binds to FKBP12 in a rapamycin-dependent fashion and is homologous to yeast TORs. Cell. 1994; 78(1):35-43. 45. Brown E J, Albers M W, Shin T B, Ichikawa K, Keith C T, Lane W S, Schreiber S L. A mammalian protein targeted by Gi-arresting rapamycin-receptor complex. Nature. 1994; 369(6483):756-8. 46. Heitman J, Movva N R, Hall M N. Targets for cell cycle arrest by the immunosuppressant rapamycin in yeast. Science. 1991; 253(5022):905-9.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound having the formula:

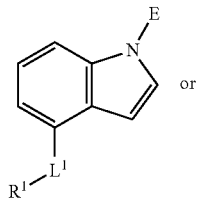
(Id)

or

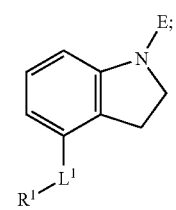
(VId)

wherein,

L¹ is independently —OCH₂—, —S(O)₂—, —NH—, —O—, —S—, —C(O)—, —C(O)NH—, —NHC(O)—, —NHC(O)NH—, or —OC(O)—;

R¹ is independently R²-substituted or unsubstituted aryl, halogen, —CX¹₃, —CHX¹₂—, —CH₂X¹, —OH, —SH, R²-substituted or unsubstituted alkyl, R²-substituted or unsubstituted heteroalkyl, R²-substituted or unsubstituted cycloalkyl, or R²-substituted or unsubstituted heterocycloalkyl;

R² is independently oxo, halogen, —CX²₃, —CHX²₂, —CH²X², —OCX²₃, —OCH₂X², —OCHX²₂, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —N₃, R³-substituted or unsubstituted alkyl, R³-substituted or unsubstituted heteroalkyl, R³-substituted or unsubstituted cycloalkyl, R³-substituted or unsubstituted heterocycloalkyl, R³-substituted or unsubstituted aryl, or R³-substituted or unsubstituted heteroaryl;

R³ is Independently oxo, halogen, —CX³₃, —CHX³₂, —CR₂X³, —OCX³₃, —OCH₂X³, —OCHX³₂, —CN, —OH, —NH₂, —COOH, —CONH₂, —NO₂, —SH, —SO₃H, —SO₄H, —SO₂NH, —NHNH₂, —ONH₂, —NHC(O)NHNH₂, —NHC(O)NH₂, —NHSO₂H, —NHC(O)H, —NHC(O)OH, —NHOH, —N₃, R⁴-substituted or unsubstituted alkyl, R⁴-substituted or unsubstituted heteroalkyl, R⁴-substituted or unsubstituted cycloalkyl, R⁴-substituted or unsubstituted heterocycloalkyl, R⁴-substituted or unsubstituted aryl, or R⁴-substituted or unsubstituted heteroaryl;

R⁴ is independently oxo, halogen, —CX⁴₃, —CHX⁴₂, —CH₂X⁴, —OCX⁴₃, —OCH₂X⁴, —OCHX⁴₂, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —N₃, unsubstituted alkyl, unsubstituted heteroalkyl, unsubstituted cycloalkyl, unsubstituted heterocycloalkyl unsubstituted aryl, or unsubstituted heteroaryl;

E is

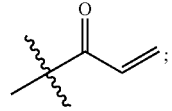 [SMILES: *C(=O)C=C]

X¹, X², X³, and X⁴ are independently —F, —Cl, —Br, or —I;

wherein each heteroalkyl Independently comprises at least one carbon atom and at least one heteroatom selected from O, N, P, Si, and S, and wherein the heteroatom may be placed at any interior position of the heteroalkyl or at the position at which the heteroalkyl is attached to the remainder of the molecule;

each heterocycloalkyl is independently a cyclic group which comprises at least one carbon atom and at least one heteroatom selected from O, N, P, Si, and S;

each heteroaryl is Independently an aromatic group which comprises at least one heteroatom selected from O, N, P, St, and S;

provided when L¹ is —C(O)—, R¹ is not —OCH₃; and provided when L¹ is —OC(O)—, R¹ is not —CH₃.

2. The compound of claim 1, wherein L¹ is —OCH₂— or —O—.

3. The compound of claim 1, wherein R¹ is independently R²-substituted or unsubstituted aryl, R²-substituted or unsubstituted heteroalkyl, R²-substituted or unsubstituted cycloalkyl, R²-substituted or unsubstituted heterocycloalkyl, or R²-substituted or unsubstituted alkyl.

4. The compound of claim 1, wherein R¹ is independently R²-substituted or unsubstituted phenyl, R²-substituted or unsubstituted 2 to 6 membered heteroalkyl, R²-substituted or unsubstituted C₃-C₆ cycloalkyl, R²-substituted or unsubstituted 3 to 6 membered heterocycloalkyl, or R²-substituted or unsubstituted C₁-C₆ alkyl.

5. The compound of claim 1, wherein R¹ is independently R²-substituted or unsubstituted phenyl.

6. The compound of claim 1, wherein R¹ is independently

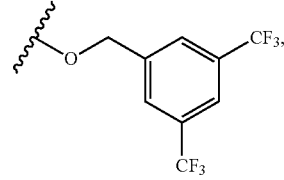 [SMILES: *OCc1cc(C(F)(F)F)cc(C(F)(F)F)c1]

halogen, —CF₃, —OH, —SH, —NHC(O)CH₃, —OCH₃, —SCH₃,

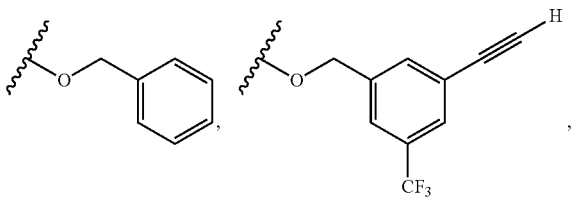

197
-continued
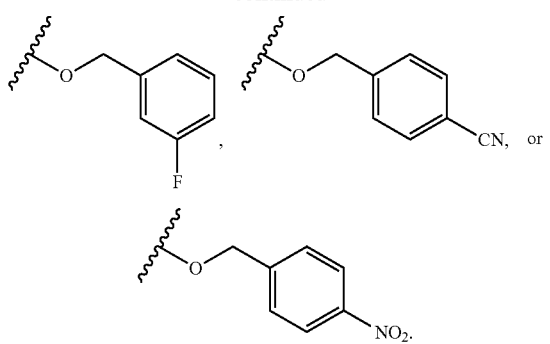
7. The compound of claim 1, having the formula:
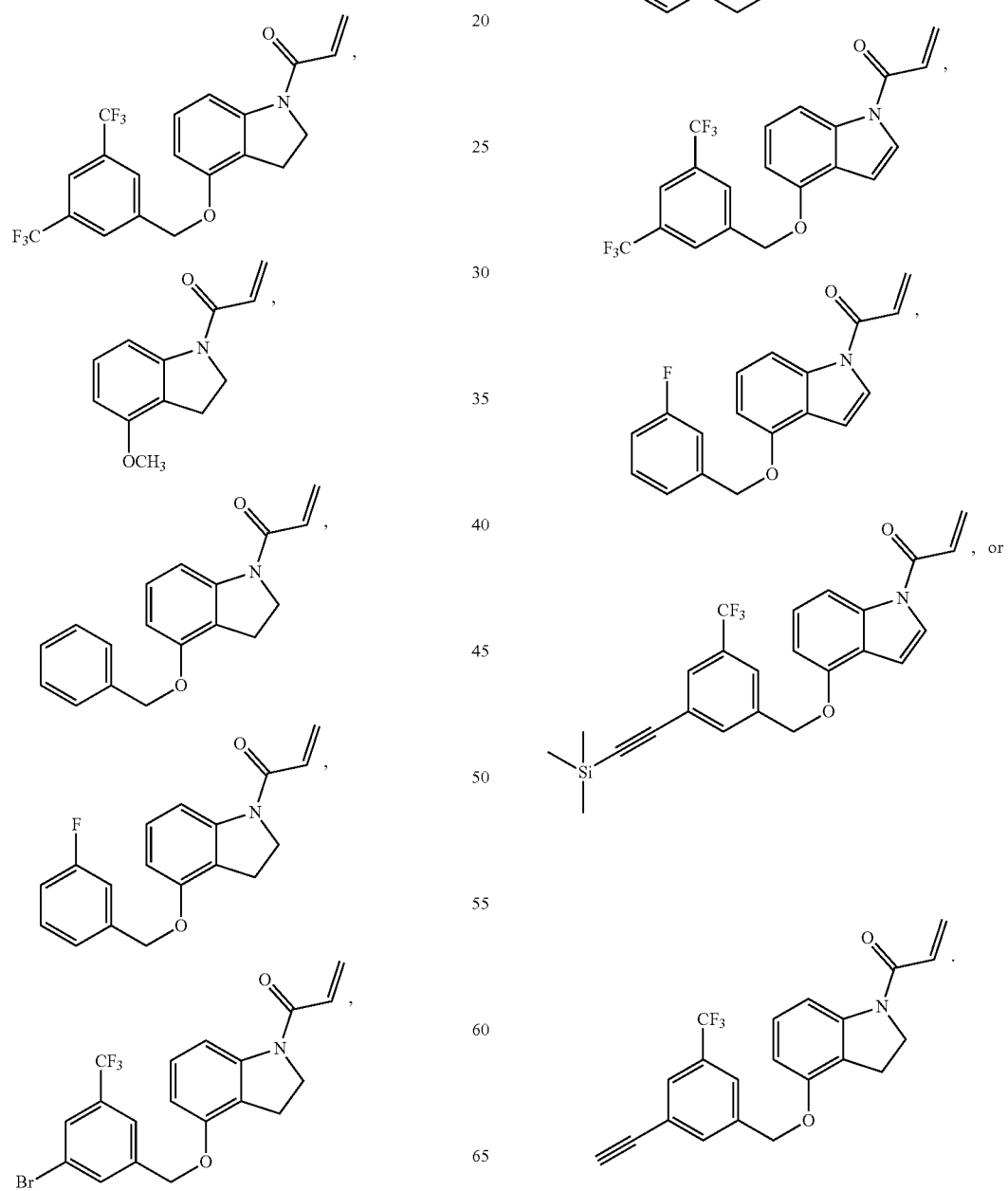
198
-continued
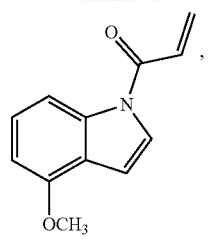
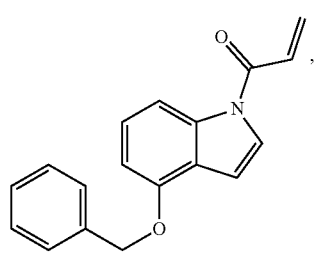
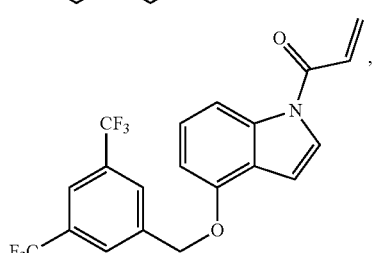
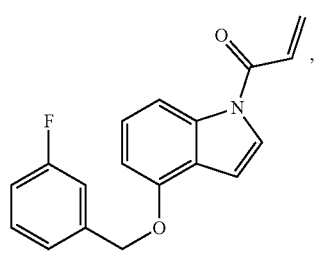
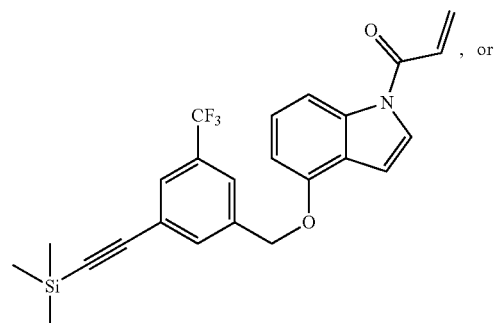, or
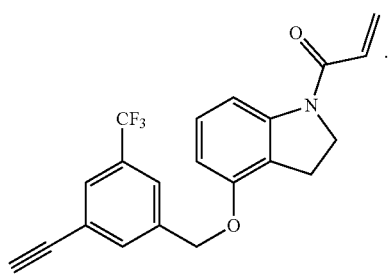

8. The compound of claim 1, having the formula:

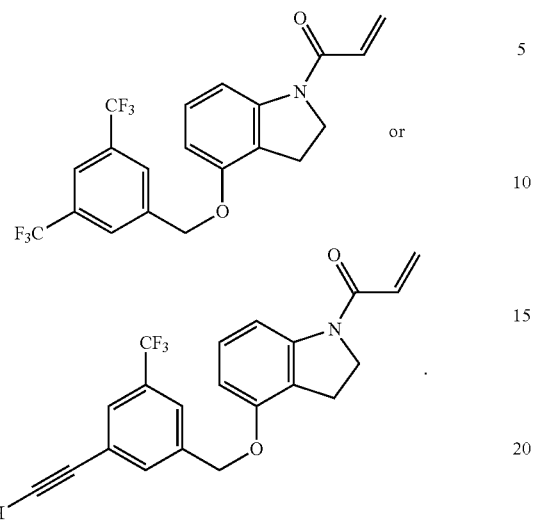

or

9. A pharmaceutical composition comprising a compound of claim 1 and a pharmaceutically acceptable excipient.

10. A method for treating renal cell carcinoma, pancreatic cancer, breast cancer, or non-Hodgkin lymphoma, said method comprising administering to a subject in need thereof a therapeutically effective amount of a compound of claim 1.

* * * * *

SEQUENCE LISTING

```
<160> NUMBER OF SEQ ID NOS: 2

<210> SEQ ID NO 1
<211> LENGTH: 173
<212> TYPE: PRT
<213> ORGANISM: Artificial sequence
<220> FEATURE:
```

<223> OTHER INFORMATION: Synthetic polypeptide

<400> SEQUENCE: 1

```
Met Glu Pro Gly Ala Gly His Leu Asp Gly His Arg Ala Gly Ser Pro
1               5                   10                  15

Ser Leu Arg Gln Ala Leu Cys Asp Gly Ser Ala Val Met Phe Ser Ser
            20                  25                  30

Lys Glu Arg Gly Arg Cys Thr Val Ile Asn Phe Val Pro Leu Glu Ala
        35                  40                  45

Pro Leu Arg Ser Thr Pro Arg Ser Arg Gln Val Thr Glu Ala Cys Gly
    50                  55                  60

Gly Glu Gly Arg Ala Val Pro Leu Gly Ser Glu Pro Glu Trp Ser Val
65                  70                  75                  80

Gly Gly Met Glu Ala Thr Leu Glu Gln His Leu Glu Asp Thr Met Lys
                85                  90                  95

Asn Pro Ser Ile Val Gly Val Leu Cys Thr Asp Ser Gln Gly Leu Asn
            100                 105                 110

Leu Gly Cys Arg Gly Thr Leu Ser Asp Glu His Ala Gly Val Ile Ser
        115                 120                 125

Val Leu Ala Gln Gln Ala Ala Lys Leu Thr Ser Asp Pro Thr Asp Ile
    130                 135                 140

Pro Val Val Cys Leu Glu Ser Asp Asn Gly Asn Ile Met Ile Gln Lys
145                 150                 155                 160

His Asp Gly Ile Thr Val Ala Val His Lys Met Ala Ser
                165                 170
```

<210> SEQ ID NO 2
<211> LENGTH: 2549
<212> TYPE: PRT
<213> ORGANISM: Artificial sequence
<220> FEATURE:
<223> OTHER INFORMATION: Synthetic polypeptide

<400> SEQUENCE: 2

```
Met Leu Gly Thr Gly Pro Ala Ala Ala Thr Thr Ala Ala Thr Thr Ser
1               5                   10                  15

Ser Asn Val Ser Val Leu Gln Gln Phe Ala Ser Gly Leu Lys Ser Arg
            20                  25                  30

Asn Glu Glu Thr Arg Ala Lys Ala Ala Lys Glu Leu Gln His Tyr Val
        35                  40                  45

Thr Met Glu Leu Arg Glu Met Ser Gln Glu Glu Ser Thr Arg Phe Tyr
    50                  55                  60

Asp Gln Leu Asn His His Ile Phe Glu Leu Val Ser Ser Ser Asp Ala
65                  70                  75                  80

Asn Glu Arg Lys Gly Gly Ile Leu Ala Ile Ala Ser Leu Ile Gly Val
                85                  90                  95

Glu Gly Gly Asn Ala Thr Arg Ile Gly Arg Phe Ala Asn Tyr Leu Arg
            100                 105                 110

Asn Leu Leu Pro Ser Asn Asp Pro Val Val Met Glu Met Ala Ser Lys
        115                 120                 125

Ala Ile Gly Arg Leu Ala Met Ala Gly Asp Thr Phe Thr Ala Glu Tyr
    130                 135                 140

Val Glu Phe Glu Val Lys Arg Ala Leu Glu Trp Leu Gly Ala Asp Arg
145                 150                 155                 160

Asn Glu Gly Arg Arg His Ala Ala Val Leu Val Leu Arg Glu Leu Ala
                165                 170                 175
```

```
Ile Ser Val Pro Thr Phe Phe Gln Gln Val Gln Pro Phe Phe Asp
            180                 185                 190

Asn Ile Phe Val Ala Val Trp Asp Pro Lys Gln Ala Ile Arg Glu Gly
            195                 200                 205

Ala Val Ala Ala Leu Arg Ala Cys Leu Ile Leu Thr Thr Gln Arg Glu
            210                 215                 220

Pro Lys Glu Met Gln Lys Pro Gln Trp Tyr Arg His Thr Phe Glu Glu
225                 230                 235                 240

Ala Glu Lys Gly Phe Asp Glu Thr Leu Ala Lys Glu Lys Gly Met Asn
            245                 250                 255

Arg Asp Asp Arg Ile His Gly Ala Leu Leu Ile Leu Asn Glu Leu Val
            260                 265                 270

Arg Ile Ser Ser Met Glu Gly Glu Arg Leu Arg Glu Glu Met Glu Glu
            275                 280                 285

Ile Thr Gln Gln Gln Leu Val His Asp Lys Tyr Cys Lys Asp Leu Met
            290                 295                 300

Gly Phe Gly Thr Lys Pro Arg His Ile Thr Pro Phe Thr Ser Phe Gln
305                 310                 315                 320

Ala Val Gln Pro Gln Gln Ser Asn Ala Leu Val Gly Leu Leu Gly Tyr
            325                 330                 335

Ser Ser His Gln Gly Leu Met Gly Phe Gly Thr Ser Pro Ser Pro Ala
            340                 345                 350

Lys Ser Thr Leu Val Glu Ser Arg Cys Cys Arg Asp Leu Met Glu Glu
            355                 360                 365

Lys Phe Asp Gln Val Cys Gln Trp Val Leu Lys Cys Arg Asn Ser Lys
            370                 375                 380

Asn Ser Leu Ile Gln Met Thr Ile Leu Asn Leu Leu Pro Arg Leu Ala
385                 390                 395                 400

Ala Phe Arg Pro Ser Ala Phe Thr Asp Thr Gln Tyr Leu Gln Asp Thr
            405                 410                 415

Met Asn His Val Leu Ser Cys Val Lys Lys Glu Lys Glu Arg Thr Ala
            420                 425                 430

Ala Phe Gln Ala Leu Gly Leu Leu Ser Val Ala Val Arg Ser Glu Phe
            435                 440                 445

Lys Val Tyr Leu Pro Arg Val Leu Asp Ile Ile Arg Ala Ala Leu Pro
            450                 455                 460

Pro Lys Asp Phe Ala His Lys Arg Gln Lys Ala Met Gln Val Asp Ala
465                 470                 475                 480

Thr Val Phe Thr Cys Ile Ser Met Leu Ala Arg Ala Met Gly Pro Gly
            485                 490                 495

Ile Gln Gln Asp Ile Lys Glu Leu Leu Glu Pro Met Leu Ala Val Gly
            500                 505                 510

Leu Ser Pro Ala Leu Thr Ala Val Leu Tyr Asp Leu Ser Arg Gln Ile
            515                 520                 525

Pro Gln Leu Lys Lys Asp Ile Gln Asp Gly Leu Leu Lys Met Leu Ser
            530                 535                 540

Leu Val Leu Met His Lys Pro Leu Arg His Pro Gly Met Pro Lys Gly
545                 550                 555                 560

Leu Ala His Gln Leu Ala Ser Pro Gly Leu Thr Thr Leu Pro Glu Ala
            565                 570                 575

Ser Asp Val Gly Ser Ile Thr Leu Ala Leu Arg Thr Leu Gly Ser Phe
            580                 585                 590
```

-continued

```
Glu Phe Glu Gly His Ser Leu Thr Gln Phe Val Arg His Cys Ala Asp
            595                 600                 605
His Phe Leu Asn Ser Glu His Lys Glu Ile Arg Met Glu Ala Ala Arg
            610                 615                 620
Thr Cys Ser Arg Leu Leu Thr Pro Ser Ile His Leu Ile Ser Gly His
625                 630                 635                 640
Ala His Val Val Ser Gln Thr Ala Val Gln Val Val Ala Asp Val Leu
                645                 650                 655
Ser Lys Leu Leu Val Val Gly Ile Thr Asp Pro Asp Pro Asp Ile Arg
            660                 665                 670
Tyr Cys Val Leu Ala Ser Leu Asp Glu Arg Phe Asp Ala His Leu Ala
            675                 680                 685
Gln Ala Glu Asn Leu Gln Ala Leu Phe Val Ala Leu Asn Asp Gln Val
            690                 695                 700
Phe Glu Ile Arg Glu Leu Ala Ile Cys Thr Val Gly Arg Leu Ser Ser
705                 710                 715                 720
Met Asn Pro Ala Phe Val Met Pro Phe Leu Arg Lys Met Leu Ile Gln
                725                 730                 735
Ile Leu Thr Glu Leu Glu His Ser Gly Ile Gly Arg Ile Lys Glu Gln
            740                 745                 750
Ser Ala Arg Met Leu Gly His Leu Val Ser Asn Ala Pro Arg Leu Ile
            755                 760                 765
Arg Pro Tyr Met Glu Pro Ile Leu Lys Ala Leu Ile Leu Lys Leu Lys
            770                 775                 780
Asp Pro Asp Pro Asp Pro Asn Pro Gly Val Ile Asn Asn Val Leu Ala
785                 790                 795                 800
Thr Ile Gly Glu Leu Ala Gln Val Ser Gly Leu Glu Met Arg Lys Trp
                805                 810                 815
Val Asp Glu Leu Phe Ile Ile Met Asp Met Leu Gln Asp Ser Ser
            820                 825                 830
Leu Leu Ala Lys Arg Gln Val Ala Leu Trp Thr Leu Gly Gln Leu Val
            835                 840                 845
Ala Ser Thr Gly Tyr Val Val Glu Pro Tyr Arg Lys Tyr Pro Thr Leu
850                 855                 860
Leu Glu Val Leu Leu Asn Phe Leu Lys Thr Glu Gln Asn Gln Gly Thr
865                 870                 875                 880
Arg Arg Glu Ala Ile Arg Val Leu Gly Leu Leu Gly Ala Leu Asp Pro
                885                 890                 895
Tyr Lys His Lys Val Asn Ile Gly Met Ile Asp Gln Ser Arg Asp Ala
            900                 905                 910
Ser Ala Val Ser Leu Ser Glu Ser Lys Ser Ser Gln Asp Ser Ser Asp
            915                 920                 925
Tyr Ser Thr Ser Glu Met Leu Val Asn Met Gly Asn Leu Pro Leu Asp
930                 935                 940
Glu Phe Tyr Pro Ala Val Ser Met Val Ala Leu Met Arg Ile Phe Arg
945                 950                 955                 960
Asp Gln Ser Leu Ser His His His Thr Met Val Val Gln Ala Ile Thr
                965                 970                 975
Phe Ile Phe Lys Ser Leu Gly Leu Lys Cys Val Gln Phe Leu Pro Gln
            980                 985                 990
Val Met Pro Thr Phe Leu Asn Val Ile Arg Val Cys Asp Gly Ala Ile
            995                 1000                1005
Arg Glu Phe Leu Phe Gln Gln Leu Gly Met Leu Val Ser Phe Val
```

```
        1010                1015                1020

Lys Ser His Ile Arg Pro Tyr Met Asp Glu Ile Val Thr Leu Met
    1025                1030                1035

Arg Glu Phe Trp Val Met Asn Thr Ser Ile Gln Ser Thr Ile Ile
    1040                1045                1050

Leu Leu Ile Glu Gln Ile Val Ala Leu Gly Gly Glu Phe Lys
    1055                1060                1065

Leu Tyr Leu Pro Gln Leu Ile Pro His Met Leu Arg Val Phe Met
    1070                1075                1080

His Asp Asn Ser Pro Gly Arg Ile Val Ser Ile Lys Leu Leu Ala
    1085                1090                1095

Ala Ile Gln Leu Phe Gly Ala Asn Leu Asp Asp Tyr Leu His Leu
    1100                1105                1110

Leu Leu Pro Pro Ile Val Lys Leu Phe Asp Ala Pro Glu Ala Pro
    1115                1120                1125

Leu Pro Ser Arg Lys Ala Ala Leu Glu Thr Val Asp Arg Leu Thr
    1130                1135                1140

Glu Ser Leu Asp Phe Thr Asp Tyr Ala Ser Arg Ile Ile His Pro
    1145                1150                1155

Ile Val Arg Thr Leu Asp Gln Ser Pro Glu Leu Arg Ser Thr Ala
    1160                1165                1170

Met Asp Thr Leu Ser Ser Leu Val Phe Gln Leu Gly Lys Lys Tyr
    1175                1180                1185

Gln Ile Phe Ile Pro Met Val Asn Lys Val Leu Val Arg His Arg
    1190                1195                1200

Ile Asn His Gln Arg Tyr Asp Val Leu Ile Cys Arg Ile Val Lys
    1205                1210                1215

Gly Tyr Thr Leu Ala Asp Glu Glu Asp Pro Leu Ile Tyr Gln
    1220                1225                1230

His Arg Met Leu Arg Ser Gly Gln Gly Asp Ala Leu Ala Ser Gly
    1235                1240                1245

Pro Val Glu Thr Gly Pro Met Lys Lys Leu His Val Ser Thr Ile
    1250                1255                1260

Asn Leu Gln Lys Ala Trp Gly Ala Ala Arg Arg Val Ser Lys Asp
    1265                1270                1275

Asp Trp Leu Glu Trp Leu Arg Arg Leu Ser Leu Glu Leu Leu Lys
    1280                1285                1290

Asp Ser Ser Pro Ser Leu Arg Ser Cys Trp Ala Leu Ala Gln
    1295                1300                1305

Ala Tyr Asn Pro Met Ala Arg Asp Leu Phe Asn Ala Ala Phe Val
    1310                1315                1320

Ser Cys Trp Ser Glu Leu Asn Glu Asp Gln Gln Asp Glu Leu Ile
    1325                1330                1335

Arg Ser Ile Glu Leu Ala Leu Thr Ser Gln Asp Ile Ala Glu Val
    1340                1345                1350

Thr Gln Thr Leu Leu Asn Leu Ala Glu Phe Met Glu His Ser Asp
    1355                1360                1365

Lys Gly Pro Leu Pro Leu Arg Asp Asp Asn Gly Ile Val Leu Leu
    1370                1375                1380

Gly Glu Arg Ala Ala Lys Cys Arg Ala Tyr Ala Lys Ala Leu His
    1385                1390                1395

Tyr Lys Glu Leu Glu Phe Gln Lys Gly Pro Thr Pro Ala Ile Leu
    1400                1405                1410
```

```
Glu Ser Leu Ile Ser Ile Asn Asn Lys Leu Gln Gln Pro Glu Ala
    1415                1420                1425

Ala Ala Gly Val Leu Glu Tyr Ala Met Lys His Phe Gly Glu Leu
    1430                1435                1440

Glu Ile Gln Ala Thr Trp Tyr Glu Lys Leu His Glu Trp Glu Asp
    1445                1450                1455

Ala Leu Val Ala Tyr Asp Lys Lys Met Asp Thr Asn Lys Asp Asp
    1460                1465                1470

Pro Glu Leu Met Leu Gly Arg Met Arg Cys Leu Glu Ala Leu Gly
    1475                1480                1485

Glu Trp Gly Gln Leu His Gln Cys Cys Glu Lys Trp Thr Leu
    1490                1495                1500

Val Asn Asp Glu Thr Gln Ala Lys Met Ala Arg Met Ala Ala Ala
    1505                1510                1515

Ala Ala Trp Gly Leu Gly Gln Trp Asp Ser Met Glu Glu Tyr Thr
    1520                1525                1530

Cys Met Ile Pro Arg Asp Thr His Asp Gly Ala Phe Tyr Arg Ala
    1535                1540                1545

Val Leu Ala Leu His Gln Asp Leu Phe Ser Leu Ala Gln Gln Cys
    1550                1555                1560

Ile Asp Lys Ala Arg Asp Leu Leu Asp Ala Glu Leu Thr Ala Met
    1565                1570                1575

Ala Gly Glu Ser Tyr Ser Arg Ala Tyr Gly Ala Met Val Ser Cys
    1580                1585                1590

His Met Leu Ser Glu Leu Glu Val Ile Gln Tyr Lys Leu Val
    1595                1600                1605

Pro Glu Arg Arg Glu Ile Ile Arg Gln Ile Trp Trp Glu Arg Leu
    1610                1615                1620

Gln Gly Cys Gln Arg Ile Val Glu Asp Trp Gln Lys Ile Leu Met
    1625                1630                1635

Val Arg Ser Leu Val Val Ser Pro His Glu Asp Met Arg Thr Trp
    1640                1645                1650

Leu Lys Tyr Ala Ser Leu Cys Gly Lys Ser Gly Arg Leu Ala Leu
    1655                1660                1665

Ala His Lys Thr Leu Val Leu Leu Leu Gly Val Asp Pro Ser Arg
    1670                1675                1680

Gln Leu Asp His Pro Leu Pro Thr Val His Pro Gln Val Thr Tyr
    1685                1690                1695

Ala Tyr Met Lys Asn Met Trp Lys Ser Ala Arg Lys Ile Asp Ala
    1700                1705                1710

Phe Gln His Met Gln His Phe Val Gln Thr Met Gln Gln Gln Ala
    1715                1720                1725

Gln His Ala Ile Ala Thr Glu Asp Gln Gln His Lys Gln Glu Leu
    1730                1735                1740

His Lys Leu Met Ala Arg Cys Phe Leu Lys Leu Gly Glu Trp Gln
    1745                1750                1755

Leu Asn Leu Gln Gly Ile Asn Glu Ser Thr Ile Pro Lys Val Leu
    1760                1765                1770

Gln Tyr Tyr Ser Ala Ala Thr Glu His Asp Arg Ser Trp Tyr Lys
    1775                1780                1785

Ala Trp His Ala Trp Ala Val Met Asn Phe Glu Ala Val Leu His
    1790                1795                1800
```

```
Tyr Lys His Gln Asn Gln Ala Arg Asp Glu Lys Lys Lys Leu Arg
    1805                1810                1815

His Ala Ser Gly Ala Asn Ile Thr Asn Ala Thr Thr Ala Ala Thr
    1820                1825                1830

Thr Ala Ala Thr Ala Thr Thr Ala Ser Thr Glu Gly Ser Asn
    1835                1840                1845

Ser Glu Ser Glu Ala Glu Ser Thr Glu Asn Ser Pro Thr Pro Ser
    1850                1855                1860

Pro Leu Gln Lys Lys Val Thr Glu Asp Leu Ser Lys Thr Leu Leu
    1865                1870                1875

Met Tyr Thr Val Pro Ala Val Gln Gly Phe Phe Arg Ser Ile Ser
    1880                1885                1890

Leu Ser Arg Gly Asn Asn Leu Gln Asp Thr Leu Arg Val Leu Thr
    1895                1900                1905

Leu Trp Phe Asp Tyr Gly His Trp Pro Asp Val Asn Glu Ala Leu
    1910                1915                1920

Val Glu Gly Val Lys Ala Ile Gln Ile Asp Thr Trp Leu Gln Val
    1925                1930                1935

Ile Pro Gln Leu Ile Ala Arg Ile Asp Thr Pro Arg Pro Leu Val
    1940                1945                1950

Gly Arg Leu Ile His Gln Leu Leu Thr Asp Ile Gly Arg Tyr His
    1955                1960                1965

Pro Gln Ala Leu Ile Tyr Pro Leu Thr Val Ala Ser Lys Ser Thr
    1970                1975                1980

Thr Thr Ala Arg His Asn Ala Ala Asn Lys Ile Leu Lys Asn Met
    1985                1990                1995

Cys Glu His Ser Asn Thr Leu Val Gln Gln Ala Met Met Val Ser
    2000                2005                2010

Glu Glu Leu Ile Arg Val Ala Ile Leu Trp His Glu Met Trp His
    2015                2020                2025

Glu Gly Leu Glu Glu Ala Ser Arg Leu Tyr Phe Gly Glu Arg Asn
    2030                2035                2040

Val Lys Gly Met Phe Glu Val Leu Glu Pro Leu His Ala Met Met
    2045                2050                2055

Glu Arg Gly Pro Gln Thr Leu Lys Glu Thr Ser Phe Asn Gln Ala
    2060                2065                2070

Tyr Gly Arg Asp Leu Met Glu Ala Gln Glu Trp Cys Arg Lys Tyr
    2075                2080                2085

Met Lys Ser Gly Asn Val Lys Asp Leu Thr Gln Ala Trp Asp Leu
    2090                2095                2100

Tyr Tyr His Val Phe Arg Arg Ile Ser Lys Gln Leu Pro Gln Leu
    2105                2110                2115

Thr Ser Leu Glu Leu Gln Tyr Val Ser Pro Lys Leu Leu Met Cys
    2120                2125                2130

Arg Asp Leu Glu Leu Ala Val Pro Gly Thr Tyr Asp Pro Asn Gln
    2135                2140                2145

Pro Ile Ile Arg Ile Gln Ser Ile Ala Pro Ser Leu Gln Val Ile
    2150                2155                2160

Thr Ser Lys Gln Arg Pro Arg Lys Leu Thr Leu Met Gly Ser Asn
    2165                2170                2175

Gly His Glu Phe Val Phe Leu Leu Lys Gly His Glu Asp Leu Arg
    2180                2185                2190

Gln Asp Glu Arg Val Met Gln Leu Phe Gly Leu Val Asn Thr Leu
```

```
            2195                2200                2205

Leu Ala Asn Asp Pro Thr Ser Leu Arg Lys Asn Leu Ser Ile Gln
        2210                2215                2220

Arg Tyr Ala Val Ile Pro Leu Ser Thr Asn Ser Gly Leu Ile Gly
    2225                2230                2235

Trp Val Pro His Cys Asp Thr Leu His Ala Leu Ile Arg Asp Tyr
2240                2245                2250

Arg Glu Lys Lys Lys Ile Leu Leu Asn Ile Glu His Arg Ile Met
    2255                2260                2265

Leu Arg Met Ala Pro Asp Tyr Asp His Leu Thr Leu Met Gln Lys
    2270                2275                2280

Val Glu Val Phe Glu His Ala Val Asn Asn Thr Ala Gly Asp Asp
    2285                2290                2295

Leu Ala Lys Leu Leu Trp Leu Lys Ser Pro Ser Ser Glu Val Trp
    2300                2305                2310

Phe Asp Arg Arg Thr Asn Tyr Thr Arg Ser Leu Ala Val Met Ser
    2315                2320                2325

Met Val Gly Tyr Ile Leu Gly Leu Gly Asp Arg His Pro Ser Asn
    2330                2335                2340

Leu Met Leu Asp Arg Leu Ser Gly Lys Ile Leu His Ile Asp Phe
    2345                2350                2355

Gly Asp Cys Phe Glu Val Ala Met Thr Arg Glu Lys Phe Pro Glu
    2360                2365                2370

Lys Ile Pro Phe Arg Leu Thr Arg Met Leu Thr Asn Ala Met Glu
    2375                2380                2385

Val Thr Gly Leu Asp Gly Asn Tyr Arg Ile Thr Cys His Thr Val
    2390                2395                2400

Met Glu Val Leu Arg Glu His Lys Asp Ser Val Met Ala Val Leu
    2405                2410                2415

Glu Ala Phe Val Tyr Asp Pro Leu Leu Asn Trp Arg Leu Met Asp
    2420                2425                2430

Thr Asn Thr Lys Gly Asn Lys Arg Ser Arg Thr Arg Thr Asp Ser
    2435                2440                2445

Tyr Ser Ala Gly Gln Ser Val Glu Ile Leu Asp Gly Val Glu Leu
    2450                2455                2460

Gly Glu Pro Ala His Lys Lys Thr Gly Thr Thr Val Pro Glu Ser
    2465                2470                2475

Ile His Ser Phe Ile Gly Asp Gly Leu Val Lys Pro Glu Ala Leu
    2480                2485                2490

Asn Lys Lys Ala Ile Gln Ile Ile Asn Arg Val Arg Asp Lys Leu
    2495                2500                2505

Thr Gly Arg Asp Phe Ser His Asp Asp Thr Leu Asp Val Pro Thr
    2510                2515                2520

Gln Val Glu Leu Leu Ile Lys Gln Ala Thr Ser His Glu Asn Leu
    2525                2530                2535

Cys Gln Cys Tyr Ile Gly Trp Cys Pro Phe Trp
    2540                2545
```